US009376489B2

(12) United States Patent
Bardroff et al.

(10) Patent No.: US 9,376,489 B2
(45) Date of Patent: Jun. 28, 2016

(54) IL-18 BINDING MOLECULES

(71) Applicants: Michael Otto Bardroff, Loerrach (DE); Barbara Brannetti, Basel (CH); Emma Michelle Campbell, Surrey (GB); Beate Diefenbach-Streiber, Windach (DE); Adina Eberth, Munich (DE); Christian Carsten Silvester Kunz, Munich (DE); Sylwia Marshall, Epsom (GB); Jean-Michel Rene Rondeau, Rixheim (FR); Jean-Marc Alfred Schlaeppi, Allschil (CH); Gino Anselmus Van Heeke, Upper Beeding (GB)

(72) Inventors: Michael Otto Bardroff, Loerrach (DE); Barbara Brannetti, Basel (CH); Emma Michelle Campbell, Surrey (GB); Beate Diefenbach-Streiber, Windach (DE); Adina Eberth, Munich (DE); Christian Carsten Silvester Kunz, Munich (DE); Sylwia Marshall, Epsom (GB); Jean-Michel Rene Rondeau, Rixheim (FR); Jean-Marc Alfred Schlaeppi, Allschil (CH); Gino Anselmus Van Heeke, Upper Beeding (GB)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/017,561

(22) Filed: Sep. 4, 2013

(65) Prior Publication Data

US 2014/0112915 A1 Apr. 24, 2014

Related U.S. Application Data

(60) Provisional application No. 61/697,981, filed on Sep. 7, 2012.

(51) Int. Cl.
*C07K 16/24* (2006.01)
*G01N 33/68* (2006.01)

(52) U.S. Cl.
CPC .......... *C07K 16/244* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 7,491,803 B2 | 2/2009 | Sugimura et al. |
| 7,968,684 B2 | 6/2011 | Ghayur et al. |
| 2002/0128450 A1 | 9/2002 | Nishida |
| 2004/0141964 A1 | 7/2004 | Abdel-Meguid |
| 2005/0100965 A1 | 5/2005 | Ghayur |
| 2005/0147610 A1 | 7/2005 | Ghayur et al. |
| 2005/0221433 A1 | 10/2005 | Karow |
| 2006/0287678 A1 | 12/2006 | Shafer |
| 2006/0292145 A1 | 12/2006 | Sugimura |
| 2007/0003981 A1 | 1/2007 | Chandler et al. |
| 2007/0292432 A1 | 12/2007 | Ellis |
| 2009/0202557 A1 | 8/2009 | Argiriadi |
| 2009/0215992 A1 | 8/2009 | Wu et al. |
| 2010/0104563 A1 | 4/2010 | Ghayer |
| 2010/0291088 A1 | 11/2010 | Ghayur et al. |
| 2011/0008357 A1 | 1/2011 | Ghayer et al. |

FOREIGN PATENT DOCUMENTS

| | | |
|---|---|---|
| EP | 0 712 931 A2 | 5/1996 |
| EP | 0850952 A1 | 7/1998 |
| EP | 0974600 A2 | 1/2000 |
| EP | 1047781 A1 | 11/2000 |
| EP | 1101772 A1 | 5/2001 |
| EP | 1487541 A2 | 12/2004 |
| EP | 1705191 A2 | 9/2006 |
| EP | 2 221 317 A2 | 8/2010 |
| JP | 3-230220 B2 | 11/2001 |
| JP | 2005-052021 A | 3/2005 |
| JP | 2007-121310 A | 5/2007 |
| JP | 2009-047705 A | 3/2009 |
| JP | 4673068 B2 | 4/2011 |
| JP | 4728785 B2 | 7/2011 |
| WO | 00/56771 A1 | 9/2000 |
| WO | 01/58956 A2 | 8/2001 |
| WO | 01/85201 A2 | 11/2001 |
| WO | 02/32374 A2 | 4/2002 |
| WO | 02/060479 A1 | 8/2002 |
| WO | 03/057821 A2 | 7/2003 |
| WO | 03/084979 A2 | 10/2003 |
| WO | 2004/101617 A1 | 11/2004 |
| WO | 2005/047307 A2 | 5/2005 |
| WO | 2005/075648 A1 | 8/2005 |
| WO | 2005/079766 A2 | 9/2005 |
| WO | 2007/024715 A2 | 3/2007 |
| WO | 2007/137984 A2 | 12/2007 |
| WO | 2009/025846 A2 | 2/2009 |
| WO | 2009/099545 A1 | 8/2009 |
| WO | 2009/149185 A2 | 12/2009 |

(Continued)

OTHER PUBLICATIONS

Bowie et al. (Science, 1990, 247:1306-1310).*

(Continued)

*Primary Examiner* — Brian J Gangle
*Assistant Examiner* — Andrea McCollum

(57) ABSTRACT

Interleukin 18 (IL-18) participates in both innate and acquired immunity. The bioactivity of IL-18 is negatively regulated by the IL-18 binding protein (IL18BP), a naturally occurring and highly specific inhibitor. This soluble protein forms a complex with free IL-18 preventing its interaction with the IL-18 receptor, thus neutralizing and inhibiting its biological activity. The present invention discloses binding molecules, in particular antibodies or fragments thereof, which bind IL-18 and do not bind IL-18 bound to IL-18BP (IL-18/IL-18BP complex). Apart from its physiological role, IL-18 has been shown to mediate a variety of autoimmune and inflammatory diseases. The binding molecules of the inventions may be used as therapeutic molecules for treating IL-18-related autoimmune and inflammatory diseases or as diagnostic tools for characterizing, detecting and/or measuring IL-18 not bound to IL-18BP as component of the total IL-18 pool.

25 Claims, 38 Drawing Sheets

(56) References Cited

FOREIGN PATENT DOCUMENTS

| WO | 2010/006060 | A2 | 1/2010 | | |
|---|---|---|---|---|---|
| WO | 2010/020593 | A1 | 2/2010 | | |
| WO | 2010/040736 | | 4/2010 | | |
| WO | 2010/040736 | A2 | 4/2010 | | |
| WO | 2010/048183 | A1 | 4/2010 | | |
| WO | 2010/048192 | A2 | 4/2010 | | |
| WO | 2010/073199 | A1 | 7/2010 | | |
| WO | 2010/127294 | A2 | 11/2010 | | |
| WO | 2011/098424 | A2 | 8/2011 | | |
| WO | WO 2012/085015 | A1 | * | 6/2012 | ............ C07K 16/24 |

OTHER PUBLICATIONS

Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Vajdos et al. (J Mol Biol. Jul. 5, 2002;320(2):415-28 at 416).*
Brown et al. (J Immunol. May 1996;156(9):3285-91).*
Dinarello et al., "Interleukin-18 Treatment Options for Inflammatory Diseases"; Expert Review Clinical Immunology, vol. 4: 619-632 (Sep. 2005).
Born et al., "A Poxvirus Protein That Binds to and Inactivates IL-18, and Inhibits NK Cell Response"; The Journal of Immunology, vol. 164: 3246-3254 (2000).
Dirk E. Smith, "The Biological Paths of IL-1 Family Members IL-18 and IL-33" Journal of Leukocyte Biology, vol. 89: 383-392 (Mar. 2011).
Aizawa et al., "Cloning and Expression of Interleukin-18 Binding Protein" FEBS Letters, vol. 445, Issues 2-3: 338-342 (Feb. 26, 1999).
Novick et al., "Interleukin-18 Binding Protein: A Novel Modulator of the Th1 Cytokine Response" Immunity, vol. 10, Issue 1: 127-136 (Jan. 1, 1999).
Xiang et al., "Determination of the Functional Epitopes of Human Interleukin-18-binding Proteins by Site-directed Mutagenesis" J. Biology Chemistry 2001, vol. 276: 17380-17386 (2001).
Faggioni et al., "IL-18-Binding Protein Protects Against Lipopolysaccharide-Induced Lethality and Prevents the Development of Fas/Fas ligand-Mediated Models of Liver Disease in Mice" The Journal of Immunology, vol. 167: 5913-5920 (2001).
Plitz et al., "IL-18 Binding Proteins Protects Against Contact Hypersensitivity" J Immunol, vol. 171: 1164-1171 (2003).
Calderara et al., "Orthopoxvirus IL-18 Binding Proteins: Affinities and Antagonist Activites" Virology, vol. 279, Issue.1: 22-26 (Jan. 5, 2001).
Meng et al. "Variola Virus IL-18 Binding Protein Interacts with Three Human IL-18 Residues that are Part of a Binding Site for Human IL-18 Receptor Alpha Subunit" Virology, vol. 358, Issue 1: 211-220 (Feb. 5, 2007).
Nakamura et al., "Endotoxin-induced Serum Factor that Stimulates Gamma Interferon Production" Infection and Immunity, vol. 57, No. 2: 590-595 (1989).
Kato et al ., "The Structure and Binding Mode of Interleukin-18" Nature Structural Biology, vol. 10, No. 11: 966-971 (Nov. 2003).
Ushio et al., "Cloning of the cDNA for Human IFN-y-Inducing Factor, Expression in *Escherichia coli*, and Studies on the Biologic Activities of the Protein" The Journal of Immunology, vol. 145: 4274-4279 (1996).
Dinarello et al., "Overview of Interleukin-18: More than an Interferon-y-inducing Factor" Journal of Leukocyte Biology, vol. 63: 658-664 (Jun. 1998).
Kikkawa et al., "A Comparative Analysis of the Antigenic, Structural, and Functional Properties of Three Different Preparations of Recombinant Human Interleukin-18" Journal of Interferon and Cytokine Research, vol. 20: 179-185 (2000).
Taniguchi et al., "Characterization of Anti-Human Interleukin-18 (IL-18)/interferon-y-inducing factor (IGIF) Monoclonal Antibodies and their Application in the Measurement of Human IL-18 by ELISA" Journal of Immunological Methods, vol. 206, issue 1-2; 107-113 (Aug. 1997).
Wu et al., "IL-18 Receptor Beta-Induced Changes in the Presentation of IL-18 Binding Sites Affect Ligand Binding and Signal Transduction" J Immunol, vol. 170: 5571-5577 ( 2003).
Hamasaki et al., "Human Anti-Human IL-18 Antibody Recognizing the IL-18-Binding Site 3 with IL-18 Signaling Blocking Activity" J. Biochem, vol. 138: 433-442 (2005).
Torigoe et al., "Purification and Characterizations of the Human Interleukin-18 Receptor" The Journal of Biological Chemistry, vol. 272; 25737-25742 (1997).
Shida et al., "An Alternative Form of IL-18 in Human Blood Plasma: Complex Formation with IgM Defined by Monoclonal Antibodies" J Immunol vol. 166: 6671-6679 (2001).
Schmid et al., "Neutralization of IFNy Defects Haemophagocytosis in LCMV-infected Perforin- and Rab27a-deficient Mice" EMBO Mol. Med., vol. 1: 112-124 (2009).
Takada et al., "Oversecretion of IL-18 in Haemophagocytic Lymphohistiocytosis: A novel Marker of Disease Activity" British Journal of Haematology, vol. 106: 182-189 (1999).
Takada et al., "Increased Serum Levels of Interferon-y-inducible Protein 10 and Monokine Induced by Gamma Interferon in Patients with Haemophagocytic Lymphohistiocytosis" Clin Exp Immunol, vol. 133: 448-453 (2003).
Billiau et al., "Macrophage Activation Syndrome: Characteristic Findings on Liver Biopsy Illustrating the Key Role of Activated, IFN-y-producing Lymphocytes and IL-6- and TNF-alpha-producing Macrophanges" Blood Journal, vol. 105: 1648-1651 (2005).
Tang et al., "Early Diagnostic and Prognostic Significance of a Specific Th1/Th2 Cytokine Pattern in Children with Haemophagocytic Syndrome" British Journal of Haematology, vol. 143, Issue 1: 84-91 (2008).
Mazodier et al.. "Severe Imbalance of IL-18/IL-18BP in Patients with Secondary Hemophagocytic Syndrome" Blood Journal, vol. 106: 3483-3489 (2005).
Nold-Petry et al., "Failure of Interferon y to Induce the Anti-Inflammatory Interleukin 18 Binding Protein in Familial Hemophagocytosis" PLoS One, vol. 5: 1-6 (2010).
Osugi et al., "Cytokine Production Regulating Th1 and Th2 Cytokines in Hemophagocytic Lymphohistiocytosis" Blood Journal, vol. 89: 4100-4103 (1997).
Jordan et al., "An Animal Model of Hemophagocytic Lymphohistiocytosis (HLH): CD8+T Cells and Interferon Gamma are Essential for the Disorder" Blood Journal, vol. 104: 735-743 (2004).
Behrans, "Macrophage Activation Syndrome in Rheumatic Disease: What is the Role of the Antigen Presenting Cell?" Autoimmunity Reviews, vol. 7: 305-308 (2008).
Jordan et al., "Role of IL-18 in Acute Lung Inflammation" The Journal of Immunology, vol. 167: 7060-7068 (2001).
Barnes, "Novel Approaches and Targets for Treatment of Chronic Obstructive Pulmonary Disease" American Journal of Respir Crit Care Med, vol. 160: S72-S79 (1999).
Pauwles et al., "Global Strategy for the Diagnosis, Managment, and Prevention of Chronic Obstructive Pulmonary Disease" American Journal of Resp Crit Care Med., vol. 163: 1256-1276 (2001).
Wang et al., "Interferon y Induction of Pulmonary Emphysema in the Adult Murine Lung" Journal of Exp Med., vol. 192, No. 11: 1587-1599 (2000).
Kang et al., "IL-18 is Induced and IL-18 Receptor Alpha Plays a Critical Role in the Pathogenesis of Cigarette Smoke-Induced Pulmonary Emphysema and Inflammation" J Immunol, vol. 178: 1948-1959 (2007).
Hogg et al., "The Nature of Small-Airway Obstruction in Chronic Obstructive Pulmonary Disease" The New England Journal of Medicine, vol. 350, No. 26: 2645-2653 (Jun. 24, 2004).
Rovina et al., "Interleukin-18 in Induced Sputum: Association with Lung Function in Chronic Obstructive Pulmonary Disease" Respiratory Medicine, vol. 103: 1056-1062 (2009).
Lee et al., "Both E6 and E7 Oncoproteins of Human Papillomavirus 16 Inhibit IL-18-Induced IFN-y Production in Human Peripheral Blood Mononuclear and NK Cells" J Immunol, vol. 167: 497-504 (2001).
Imaoka et al., "Interleukin-18 Production and Pulmonary Fucntion in COPD" European Respiratory Journal, vol. 31: 287-297 (2008).

(56) References Cited

OTHER PUBLICATIONS

McKay et al., "Interleukin-18 Levels in Induced Sputum are Reduced in Asthmatic and Normal Smokers" Clin Exp Allergy, vol. 34: 904-910 (2004).

Jordan et al., "Role of IL-18 in Acute Lung Inflammation" J Immunol, vol. 167: 7060-7068 (2001).

Braddock et al., "Therapeutic Potential of Targeting IL-1 and IL-18 in Inflammation" Expert Opin. Biol. Ther., vol. 4, No. 6: 847-860 (2004).

Okamoto et al., "Interleukin 18 (IL-18) in Synergy with IL-2 Induces Lethal Lung Injury in Mice: A Potential Role for Cytokines, Chemokines, and Natural Killer Cells in the Pathogenesis of Interstitial Pneumonia" Blood Journal, vol. 99: 1289-1298 (2002).

Kitasato et al., "Enhanced Expression of Interleukin-18 and its Receptor in Idoiopathic Pulmonary Fibrosis" American Journal of Respiratory Cell and Molecular Biology, vol. 31: 619-625.

Wakankar et al., "Aspartate Isomerization in the Complementarity-Determining Regions of Two Closely Related Monoclonal Antibodies" Biochemistry, vol. 46: 1534-1544 (2007).

Geiger et al., "Deamidation, Isomerization, and Racemization at Asparaginyl and Aspartyl Residues in Peptides" The Journal of Biological Chemistry, vol. 262, No. 2: 785-794 (Jan. 15, 1987).

Walsh et al., "Post-translational Modifications in the Context of Therapeutic Proteins" Nature Biotechnology, vol. 24, No. 10: 1241-1252 (Oct. 2006).

Vlasak et al., "Identification and Characterization of Asparagine Deamidation in the Light Chain CDR1 of a Humanized IgG1 Antibody" Analytical Biochemistry, vol. 392: 145-154 (2009).

Hamasaki et al., "Human Anti-Human IL-18 Antibody Recognizing the IL-18 Binding Site 3 with IL-18 Signaling Blocking Activity" J Biochem, vol. 138: 433-442 (2005).

Kimura et al., "Expression, Purification and Structural Analysis of human IL-18 Binding Protein: A Potent Therapeutic Molecule for Allergy" Allergology International, vol. 57: 367-376 (2008).

Argiriadi et al., Unusual water-mediated antigenic recognition of the proinflammatory cytokine interleukin-18. J Biol Chem. Sep. 4, 2009;284(36):24478-89.

Dinarello, Interleukin-18. Methods. Sep. 1999;19(1):121-32.

Dinarello, Targeting interleukin 18 with interleukin 18 binding protein. Ann Rheum Dis. Nov. 2000;59 Suppl 1:i17-20.

Eisenhardt et al., Subtractive single-chain antibody (scFv) phage-display: tailoring phage-display for high specificity against function-specific conformations of cell membrane molecules. Nat Protoc. 2007;2(12):3063-73.

Janka, Hemophagocytic lymphohistiocytosis: when the immune system runs amok. Klin Padiatr. Sep. 2009;221(5):278-85. Epub Aug. 25, 2009.

Janka, Familial and acquired hemophagocytic lymphohistiocytosis. Eur J Pediatr. Feb. 2007;166(2):95-109. Epub Dec. 7, 2006.

Kim et al., Identification of amino acid residues critical for biological activity in human interleukin-18. J Biol Chem. Mar. 29, 2002;277(13):10998-1003. Epub Jan. 14, 2002.

Kim et al., Structural requirements of six naturally occurring isoforms of the IL-18 binding protein to inhibit IL-18. Proc Natl Acad Sci U S A. Feb. 1, 2000;97(3):1190-5.

Kim et al., Site-specific mutations in the mature form of human IL-18 with enhanced biological activity and decreased neutralization by IL-18 binding protein. Proc Natl Acad Sci U S A. Mar. 13, 2001;98(6):3304-9.

Krumm et al., Structural basis for antagonism of human interleukin 18 by poxvirus interleukin 18-binding protein. Proc Natl Acad Sci U S A. Dec. 30, 2008;105(52):20711-5. Epub Dec. 22, 2008.

Lowell et al., Chronic Obstructive Pulmonary Emphysema: A Disease of Smokers. Annals Internal Med. 1956;45(2):268-274.

Novick et al., High circulating levels of free interleukin-18 in patients with active SLE in the presence of elevated levels of interleukin-18 binding protein. J Autoimmun. Mar. 2010;34(2):121-6. Epub Aug. 22, 2009.

Okamura et al., Cloning of a new cytokine that induces IFN-gamma production by T cells. Nature. Nov. 2, 1995;378(6552):88-91.

Petersen et al., Elevated levels of IL-18 in plasma and skeletal muscle in chronic obstructive pulmonary disease. Lung. May-Jun. 2007;185(3):161-71. Epub Apr. 10, 2007.

Reeves et al., IL-8 dictates glycosaminoglycan binding and stability of IL-18 in cystic fibrosis. J Immunol. Feb. 1, 2010;184(3):1642-52.

Wild et al., Interleukin-18 and allergic asthma. Isr Med Assoc J. Dec. 2000;2 Suppl:16-8.

Xiang et al., Correspondence of the functional epitopes of poxvirus and human interleukin-18-binding proteins. J Virol. Oct. 2001;75(20):9947-54.

Xiang et al., IL-18 binding and inhibition of interferon gamma induction by human poxvirus-encoded proteins. Proc Natl Acad Sci U S A. Sep. 28, 1999;96(20):11537-42.

Yellayi et al., Cloning and characterization of rhesus IL-18 binding protein, a natural antagonist to IL-18. Cytokine. Sep. 2010;51(3):232-9.

Zhong et al., Biological Insights into Therapeutic Protein Modifications throughout Trafficking and Their Biopharmaceutical Applications. Int J Cell Biol. 2013;2013:273086. Epub Apr. 18, 2013.

\* cited by examiner

Figure 1

| | H-CDR1 | H-CDR2 | H-CDR3 |
|---|---|---|---|
| MOR9464 | SYAIS (SEQ ID NO:3) | NIIP-MTGQTYYAQKFQG (SEQ ID NO:9) | AAYHPLVFDN (SEQ ID NO: 5) |
| MOR9464N30K | SYAIS (SEQ ID NO:3) | NIIP-MTGQTYYAQKFQG (SEQ ID NO:9) | AAYHPLVFDN (SEQ ID NO: 5) |
| MOR10222N30SM54I | SYAIS (SEQ ID NO:3) | NIIP-ITGQTYYAQKFQG (SEQ ID NO:13) | AAYHPLVFDN (SEQ ID NO: 5) |
| MOR8775 | SYAIS (SEQ ID NO:3) | GIIP-TYGTANYAQKFQG (SEQ ID NO:4) | AAYHPLVFDN (SEQ ID NO: 5) |
| MOR9465 | SYAIS (SEQ ID NO:3) | NIIP-HYGFAYYAQKFQG (SEQ ID NO:11) | AAYHPLVFDN (SEQ ID NO: 5) |
| MOR9466 | SYAIS (SEQ ID NO:3) | NIIP-YSGFAYYAQKFQG (SEQ ID NO:12) | AAYHPLVFDN (SEQ ID NO: 5) |
| MOR10222 | SYAIS (SEQ ID NO:3) | NIIP-MTGQTYYAQKFQG (SEQ ID NO:9) | AAYHPLVFDN (SEQ ID NO: 5) |
| MOR9441 | SYAIS (SEQ ID NO:3) | WINPFYIGETFYAQKFQG (SEQ ID NO:10) | AAYHPLVFDN (SEQ ID NO: 5) |
| MOR10579 | SYAIS (SEQ ID NO:3) | WINPFYIGETFYAQKFQG (SEQ ID NO:10) | AAYHPLVFDN (SEQ ID NO: 5) |
| MOR13363 | SYAIH (SEQ ID NO:106) | VISGEGSNTYYADSVKG (SEQ ID NO:107) | VMIGYGFDY (SEQ ID NO:108) |
| MOR13361 | SYAIH (SEQ ID NO:106) | TIQSSGENKFYADSVKG (SEQ ID NO:122) | VMIGYGFDY (SEQ ID NO:108) |
| MOR13341 | TFSIS (SEQ ID NO:120) | GIIP-IFGTANYAQKFQG (SEQ ID NO:121) | GGYGGYYYFDY (SEQ ID NO:123) |
| MOR13342 | TFSIS (SEQ ID NO:120) | GIIP-IFGTANYAQKFQG (SEQ ID NO:121) | GGYGGYYYFDY (SEQ ID NO:123) |
| MOR13347 | TFSIS (SEQ ID NO:120) | GIIP-IFGTANYAQKFQG (SEQ ID NO:121) | GGYGGYYYFDY (SEQ ID NO:123) |
| MOR8776 | TGSYYWN (SEQ ID NO:74) | EINHMGITYYNPSLKG (SEQ ID NO:75) | TTRYWMSHILAYGMDY (SEQ ID NO: 79) |
| MOR10497 | TGSYYWN (SEQ ID NO:74) | EIQSPGYTFYNPSLKS (SEQ ID NO:78) | TTRYWMSHILAYGMDY (SEQ ID NO: 79) |
| MOR10501 | TGSYYWN (SEQ ID NO:74) | EIWHSGPTFYNPSLKS (SEQ ID NO:76) | TTRYWMSHILAYGMDY (SEQ ID NO: 79) |
| MOR10502 | TGSYYWN (SEQ ID NO:74) | EIHGHGFTFYNPSLKS (SEQ ID NO:77) | TTRYWMSHILAYGMDY (SEQ ID NO: 79) |

Figure 2

| | L-CDR1 | | L-CDR2 | | L-CDR3 | |
|---|---|---|---|---|---|---|
| MOR9464 | SGSSSNIGNHYVN | (SEQ ID NO:6) | RNNHRPS | (SEQ ID NO:7) | QSWDYSGFSTV | (SEQ ID NO:8) |
| MOR9464N30K | SGSSSNIGNHYVN | (SEQ ID NO:6) | RNNHRPS | (SEQ ID NO:7) | QSWDYSGFSTV | (SEQ ID NO:8) |
| MOR10222N30SM54I | SGSSSNIGNHYVN | (SEQ ID NO:6) | RNNHRPS | (SEQ ID NO:7) | QSWDYSGFSTV | (SEQ ID NO:8) |
| MOR8775 | SGSSSNIGNHYVN | (SEQ ID NO:6) | RNNHRPS | (SEQ ID NO:7) | QSWDYSGFSTV | (SEQ ID NO:8) |
| MOR9465 | SGSSSNIGNHYVN | (SEQ ID NO:6) | RNNHRPS | (SEQ ID NO:7) | QSWDYSGFSTV | (SEQ ID NO:8) |
| MOR9466 | SGSSSNIGNHYVN | (SEQ ID NO:6) | RNNHRPS | (SEQ ID NO:7) | QSWDYSGFSTV | (SEQ ID NO:8) |
| MOR10579 | SGSSSNIGNHYVN | (SEQ ID NO:6) | RNNHRPS | (SEQ ID NO:7) | QSWDYSGFSTV | (SEQ ID NO:8) |
| MOR10222 | SGSSSNIGNHYVN | (SEQ ID NO:6) | RNNHRPS | (SEQ ID NO:7) | QSWDYSGFSTV | (SEQ ID NO:8) |
| MOR9441 | SGSSSNIGNHYVN | (SEQ ID NO:6) | RNNHRPS | (SEQ ID NO:7) | QSWDYSGFSTV | (SEQ ID NO:8) |
| MOR13363 | RASQSIFNYLN | (SEQ ID NO:109) | DSSTLQS | (SEQ ID NO:110) | LQYSGFLFT | (SEQ ID NO:111) |
| MOR13361 | RASQSIFNYLN | (SEQ ID NO:109) | DSSTLQS | (SEQ ID NO:110) | HQYSGLLFT | (SEQ ID NO:126) |
| MOR13341 | RASQSISNRLN | (SEQ ID NO:124) | KGSTLQS | (SEQ ID NO:125) | QQHKVWLTT | (SEQ ID NO:127) |
| MOR13342 | RASQSISNRLN | (SEQ ID NO:124) | KGSTLQS | (SEQ ID NO:125) | QQHYVWSTT | (SEQ ID NO:128) |
| MOR13347 | RASQSISNRLN | (SEQ ID NO:124) | KGSTLQS | (SEQ ID NO:125) | QQHYQWLTT | (SEQ ID NO:129) |
| MOR8776 | SGSSSNIGNHYVS | (SEQ ID NO:80) | ANTKRPS | (SEQ ID NO:81) | SSYDGSQSIV | (SEQ ID NO:82) |
| MOR10497 | SGSSSNIGNHYVS | (SEQ ID NO:80) | ANTKRPS | (SEQ ID NO:81) | SSYDGSQSIV | (SEQ ID NO:82) |
| MOR10501 | SGSSSNIGNHYVS | (SEQ ID NO:80) | ANTKRPS | (SEQ ID NO:81) | SSYDGSQSIV | (SEQ ID NO:82) |
| MOR10502 | SGSSSNIGNHYVS | (SEQ ID NO:80) | ANTKRPS | (SEQ ID NO:81) | SSYDGSQSIV | (SEQ ID NO:82) |

Figure 3(A)
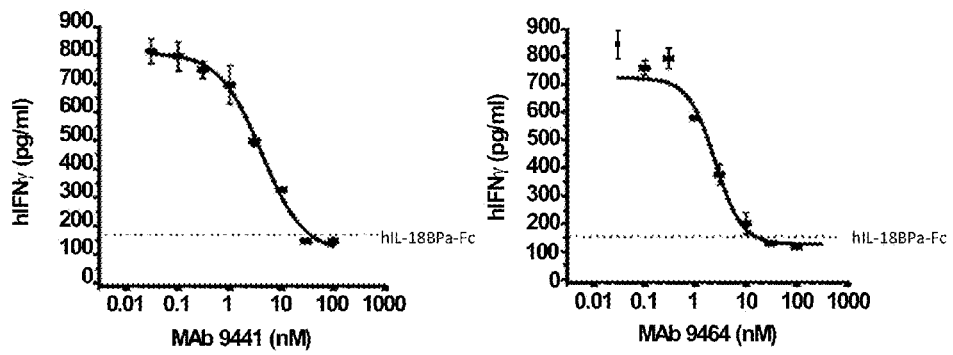
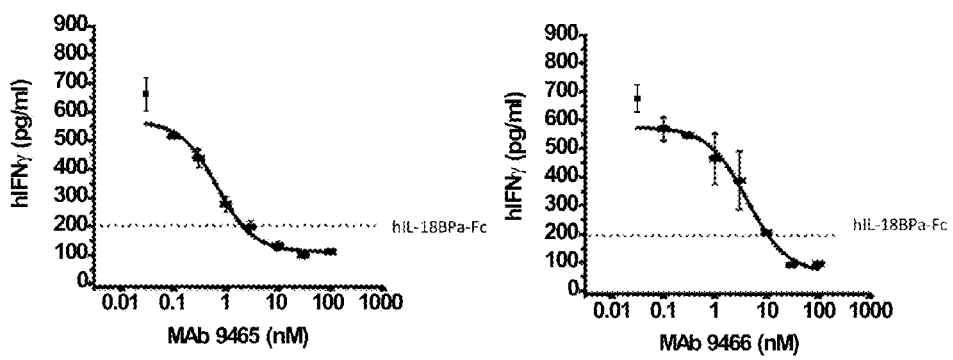
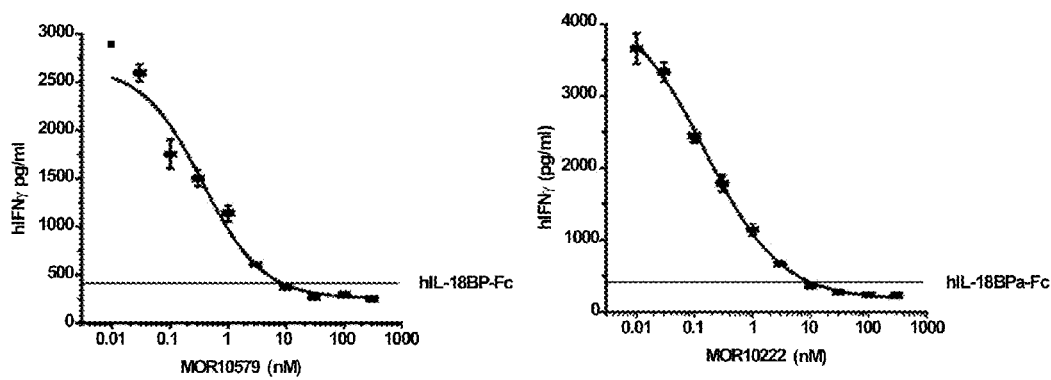

Figure 3(D)
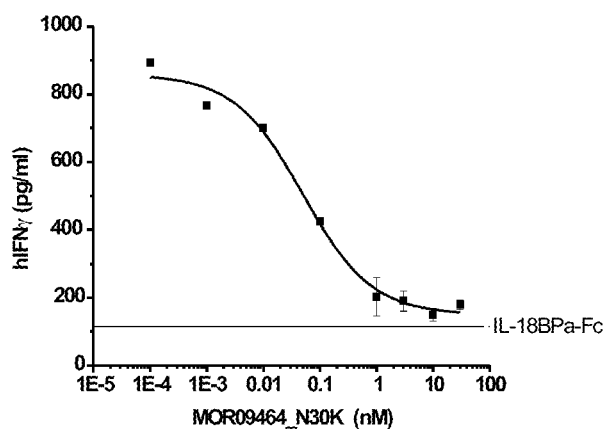
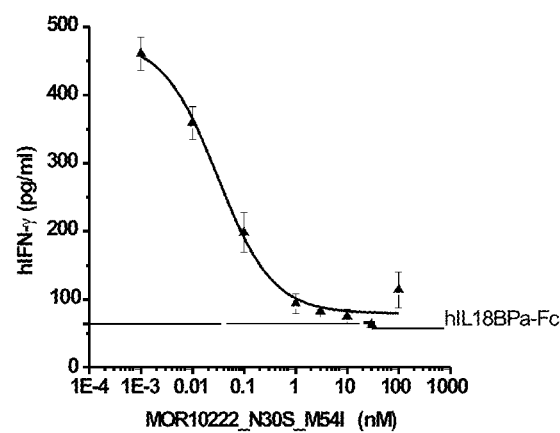

Figure 5(C)
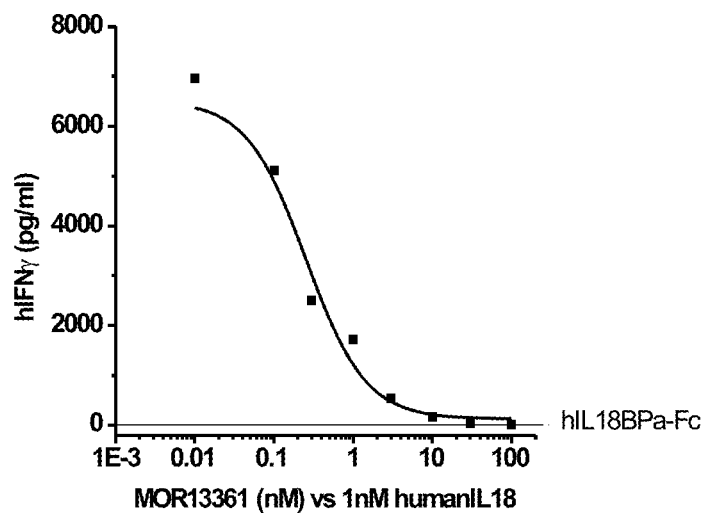
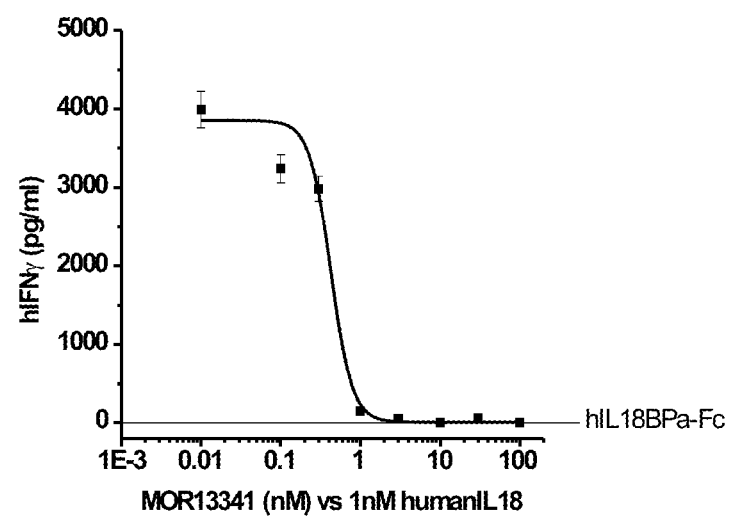

Figure 6(B)
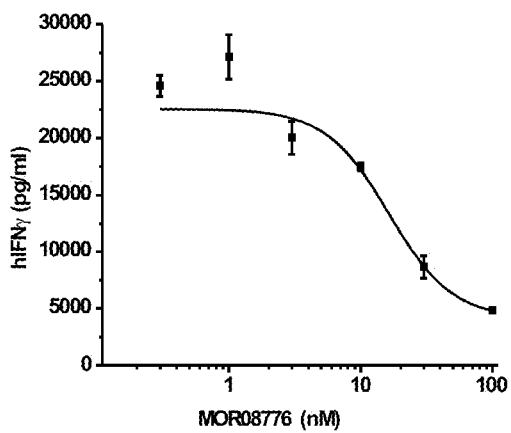
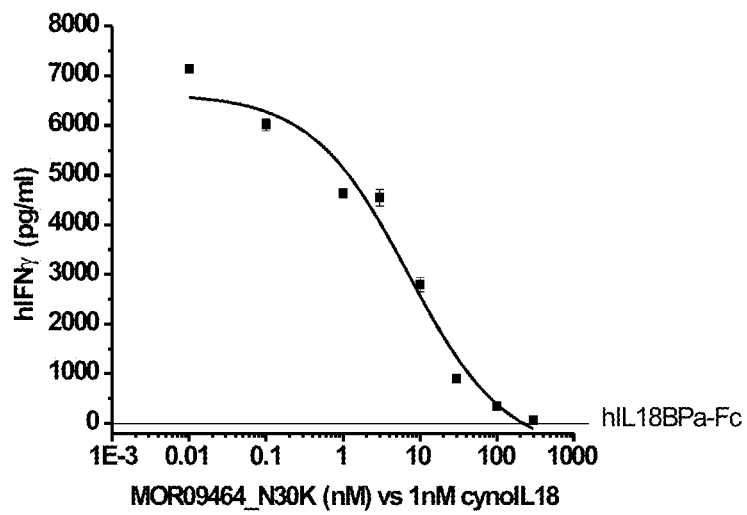
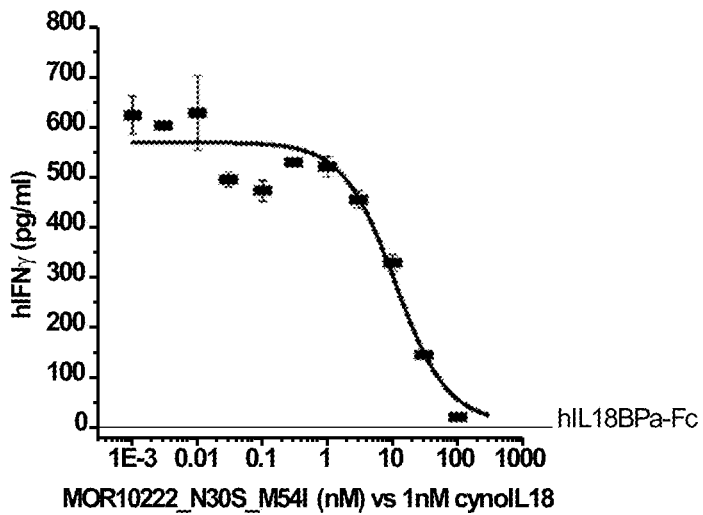

Figure 6(C)
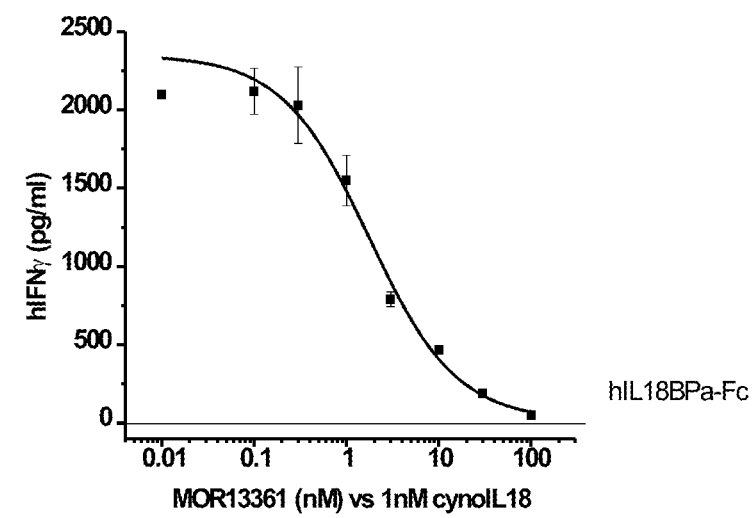
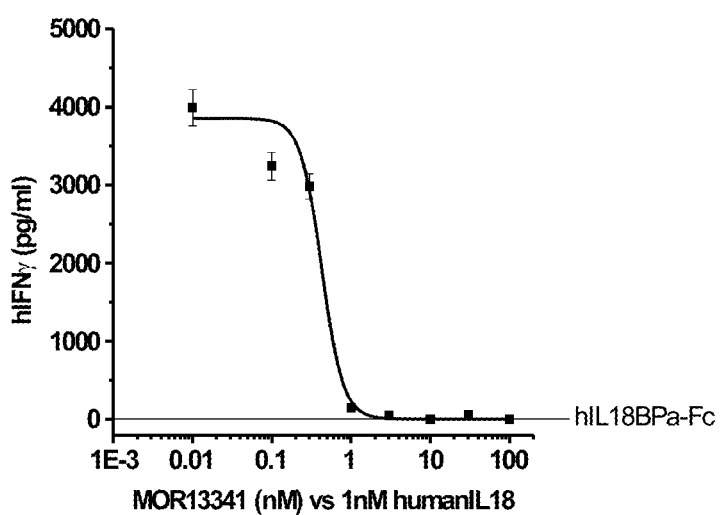

Figure 7(C)
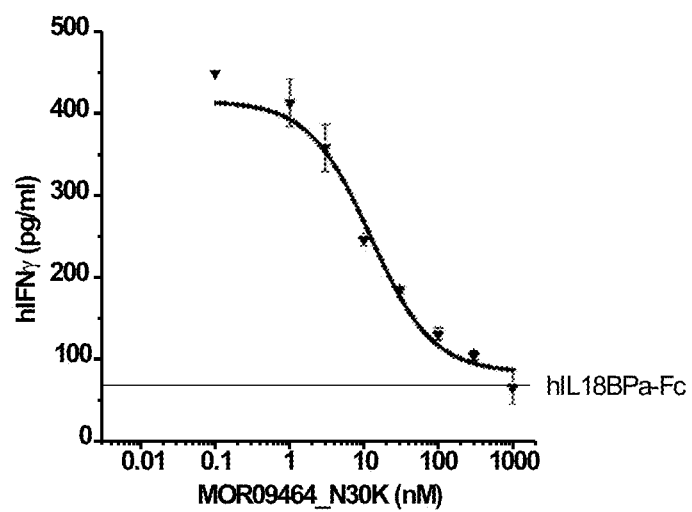
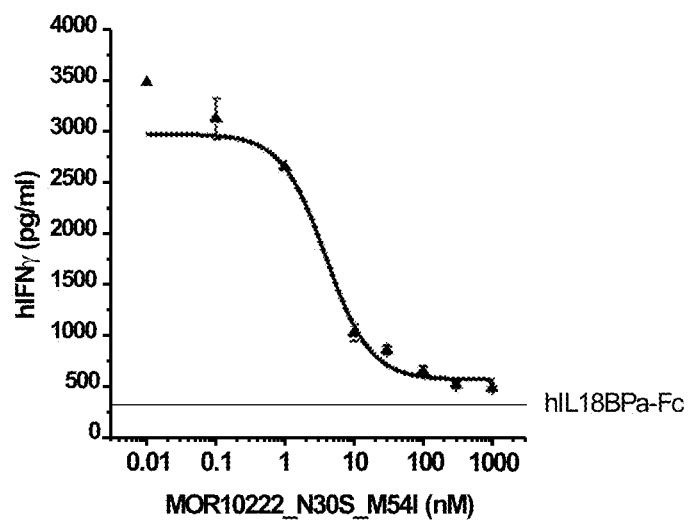

Figure 7(D)
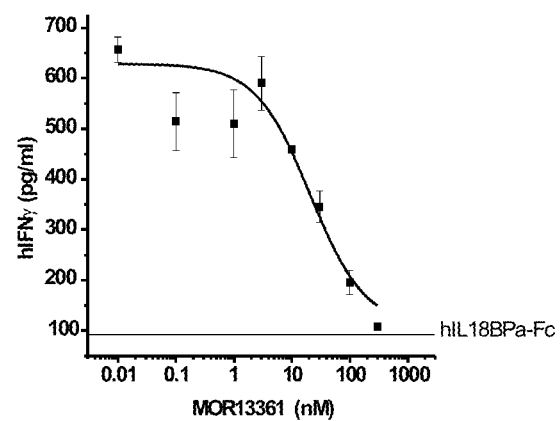
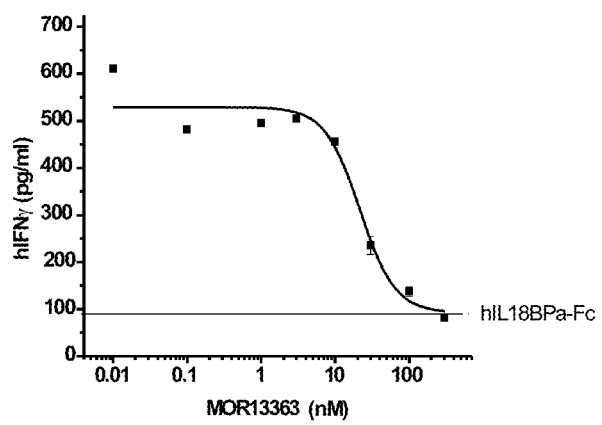
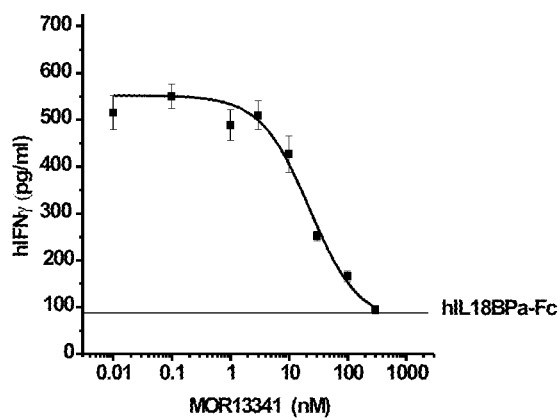

Figure 7(E)
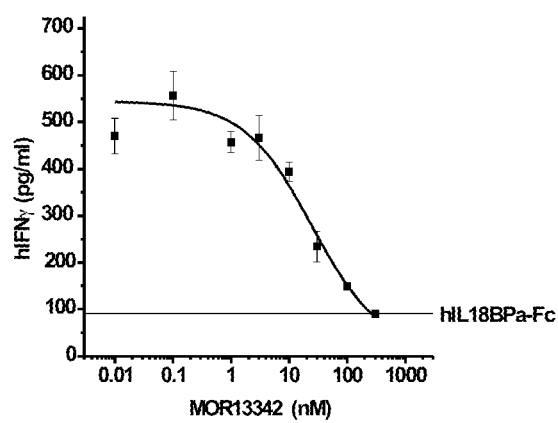
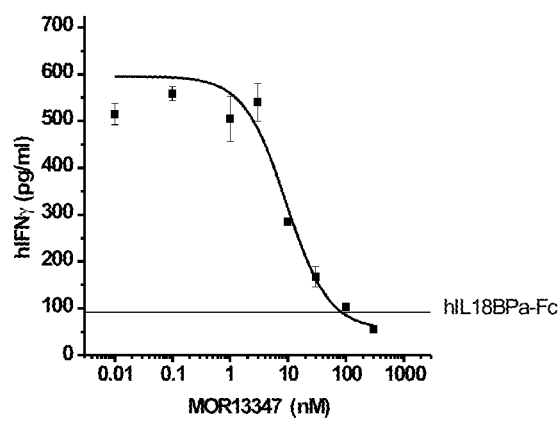

Figure 8(C)
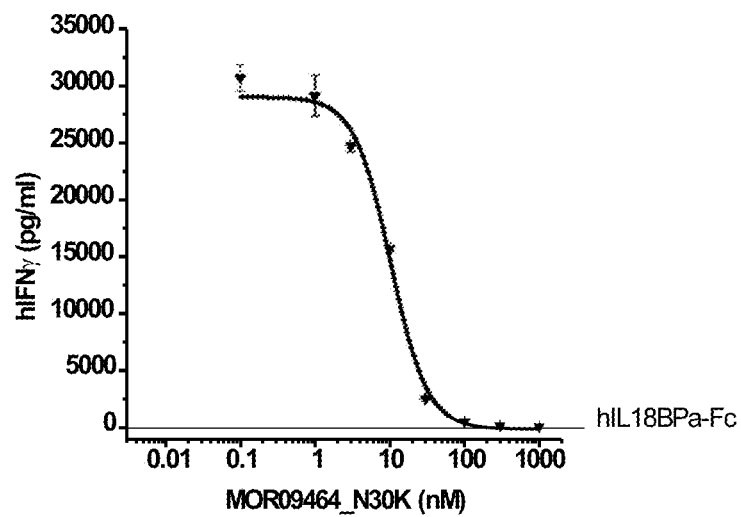
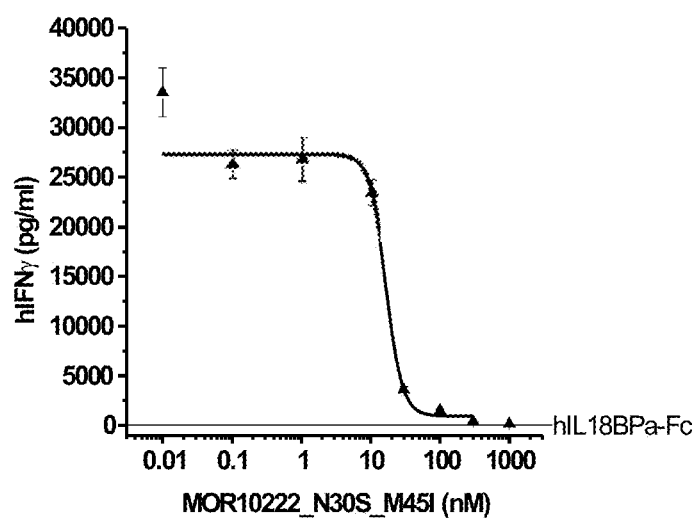

Figure 8(D)
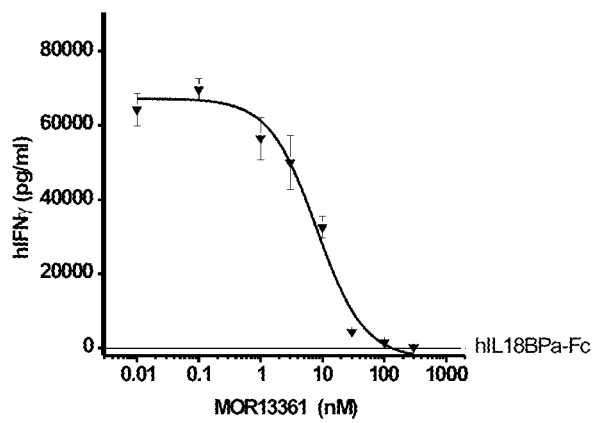
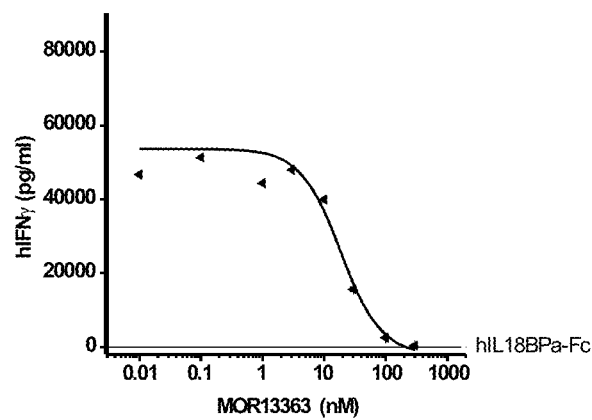
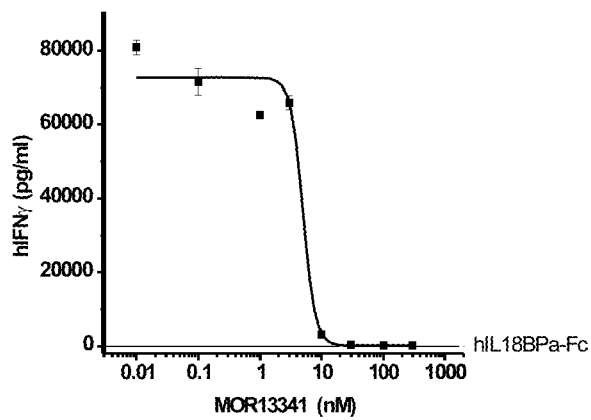

Figure 8(E)
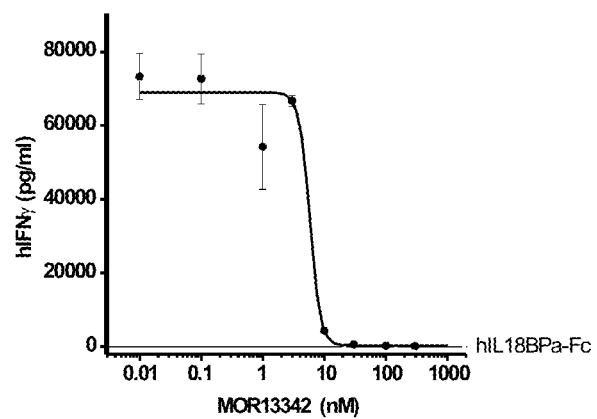
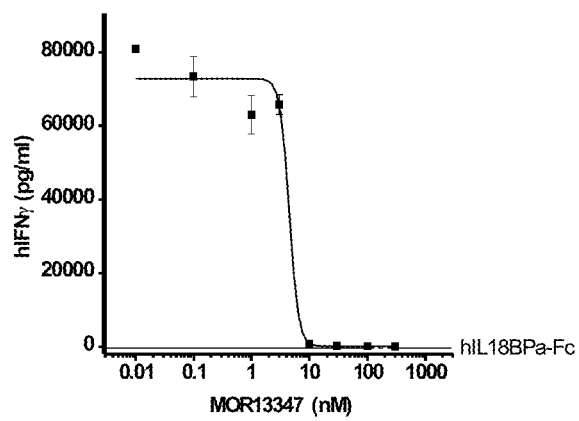

Figure 10(A)

|         | ABT325 | 125-2H | IL18-BP | MOR08776 | MOR08775 | MOR08775 |
|---------|--------|--------|---------|----------|----------|----------|
| ABT325  | ■      |        |         |          |          |          |
| 125-2H  |        | ■      | ■       |          | ■        |          |
| IL18-BP |        |        | ■       | ■        | ■        |          |
| MOR08776|        |        | ■       | ■        |          | ▨        |
| MOR08775|        | ■      | ■       | ▨        | ■        |          |
| MOR09066|        |        |         |          |          |          |

Figure 10(B)

| | ABT325 | 125-2H | IL18-BP | MOR9464_N30K | MOR10222_N30S_M54I | MOR13341 | MOR9464 |
|---|---|---|---|---|---|---|---|
| ABT325 | ■ | | | | | | |
| 125-2H | | | ■ | | | | |
| IL18-BP | | ■ | | | | | |
| MOR9464_N30K | | ■ | ■ | ■ | ■ | ■ | ■ |
| MOR10222_N30S_M54I | | ■ | ■ | ■ | ■ | ■ | ■ |
| MOR13341 | | ■ | ■ | ■ | ■ | ■ | ■ |
| MOR9464 | | ■ | ■ | ■ | ■ | ■ | ■ |

Figure 12

```
1) Human IL-18     YFGK⁴⁰LESKLSVIRN⁵⁰LNDQVLFIDQ⁶⁰GNRPLFEDMT⁷⁰DSDCRDNAPR⁸⁰TIFIISMYKD⁹⁰SQPRGMAVTI¹⁰⁰SVKCEKI
2) Kim et all                       E                                                I M K         M
3) Krumm et all    YFG  L  K                                                       I MYKD⁹⁰S PRGMAV
4) IL-18Rα         K⁴⁰L  K                           R          D                               R M
5) H/DxMS                                       M     D                                  MYKD⁹⁰SQPRGMAVT
```

```
1) Human IL-18     STL¹¹⁰SCENKIISFK¹²⁰EMNPPDNIKD¹³⁰TKSDIIFFQR¹⁴⁰SVPGHDNKMQ¹⁵⁰FESSSYEGYF¹⁶⁰LACEKERDLF¹⁷⁰KLILK
2) Kim et all                    N                 QR¹⁴⁰S      DNKM
3) Krumm et all                  N                 QR¹⁴⁰S      DN M
4) IL-18Rα                                              R                                            D
5) H/DxMS                   FK¹²⁰EMNPPDNIKD¹³⁰TKSDIIFFQR¹⁴⁰SVPGHDNKMQ¹⁵⁰FESSSYEGYF
```

```
1) Human IL-18     KEDEL¹⁸⁰GDRSIMFTVQ¹⁹⁰NED
2) Kim et all                 V    N
3) Krumm et all               V
4) IL-18Rα
5) H/DxMS
```

Figure 14(A)

| | 47 | 86 | 99 |
|---|---|---|---|
| Human IL-18 | YFGKLESKLSVIRNLNDQVLFIDQGNRPLFEDMTDSDCRDNAPRTIFIISSMYKDSQPRGMAVTISVKCEKISTLSCE |
| Cyno. IL-18 | YFGKLESKLSIIIRNLNDQVLFIDQGNRPLFEDMTDSDCRDNAPRTIFIISNMYKDSQPRGMAVAISVKCEKISTLSCE |

| | 115 | 170 177 |
|---|---|---|
| Human IL-18 | NKIISFKEMNPPDNIKDTKSDIIFFQRSVPGHDNKMQFESSSYEGYFLACEKERDLFKLILKKEDELGDRSIMFTVQNED |
| Cyno. IL-18 | NRIISFKEMNPPDNIKDTKSDIIFFQRSVPGHDNKMQFESSSYEGYFLACEKERDLYKLILKKKDELGDRSIMFTVQNED |

Figure 14(B)

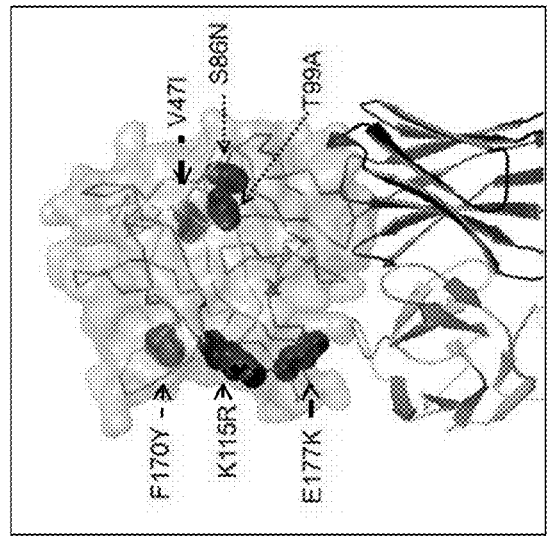

Figure 15

IL-18 receptor

D1

IL-18

D3

MOR9464_N30K

SEQUENCE LISTING

<160> NUMBER OF SEQ ID NOS: 264

<210> SEQ ID NO 1
<211> LENGTH: 193
<212> TYPE: PRT
<213> ORGANISM: Homo sapiens

<400> SEQUENCE: 1

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 2
<211> LENGTH: 193
<212> TYPE: PRT
<213> ORGANISM: Macaca sp.

<400> SEQUENCE: 2

Met Ala Ala Glu Pro Ala Glu Asp Asn Cys Ile Asn Phe Val Ala Met
1               5                   10                  15

Lys Pro Ile Asp Ser Thr Leu Tyr Phe Ile Ala Glu Asp Asp Glu Asn
            20                  25                  30

Leu Glu Ser Asp Tyr Phe Gly Lys Leu Glu Ser Lys Leu Ser Ile Ile
        35                  40                  45

Arg Asn Leu Asn Asp Gln Val Leu Phe Ile Asp Gln Gly Asn Arg Pro
50                  55                  60

Leu Phe Glu Asp Met Thr Asp Ser Asp Cys Arg Asp Asn Ala Pro Arg
65                  70                  75                  80

Thr Ile Phe Ile Ile Asn Met Tyr Lys Asp Ser Gln Pro Arg Gly Met
                85                  90                  95

Ala Val Ala Ile Ser Val Lys Cys Glu Lys Ile Ser Thr Leu Ser Cys
            100                 105                 110

Glu Asn Arg Ile Ile Ser Phe Lys Glu Met Asn Pro Pro Asp Asn Ile
        115                 120                 125

```
Lys Asp Thr Lys Ser Asp Ile Ile Phe Phe Gln Arg Ser Val Pro Gly
            130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Tyr Lys Leu Ile Leu Lys Lys
                165                 170                 175

Lys Asp Glu Leu Gly Asp Arg Ser Ile Met Phe Thr Val Gln Asn Glu
            180                 185                 190

Asp

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Ala Ile Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Ile Pro Ile Tyr Gly Thr Ala Asn Tyr Ala Gln Lys Phe Gln
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Tyr His Pro Leu Val Phe Asp Asn
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Ser Ser Ser Asn Ile Gly Asn His Tyr Val Asn
1               5                   10

<210> SEQ ID NO 7
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Arg Asn Asn His Arg Pro Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ser Trp Asp Tyr Ser Gly Phe Ser Thr Val
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Ile Ile Pro Met Thr Gly Gln Thr Tyr Tyr Ala Gln Lys Phe Gln
1               5                   10                  15

Gly

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Ile Asn Pro Phe Tyr Ile Gly Glu Thr Phe Tyr Ala Gln Lys Phe
1               5                   10                  15

Gln Gly

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Ile Ile Pro His Tyr Gly Phe Ala Tyr Tyr Ala Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 12

Asn Ile Ile Pro Tyr Ser Gly Phe Ala Tyr Tyr Ala Gln Lys Phe Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ile Ile Pro Ile Thr Gly Gln Thr Tyr Tyr Ala Gln Lys Phe Gln
1               5                   10                  15

Gly

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser
        115

<210> SEQ ID NO 15
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gaggtgcagc tggtgcagtc aggcgccgaa gtgaagaaac ccggctctag cgtgaaagtc      60
agctgtaaag ctagtggcgg caccttcaag tcctacgcta ttagctgggt cagacaggcc     120
ccaggtcagg gcctggagtg gatgggcaat attatcccta tgaccggtca gacctactac     180
gctcagaaat ttcagggtag agtgactatc accgccgacg agtctactag caccgcctat     240
atggaactgt ctagcctgag atcagaggac accgccgtct actactgcgc tagagccgcc     300
tatcaccccc tggtgttcga taactggggt cagggcaccc tggtcaccgt gtctagc    357

<210> SEQ ID NO 16
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu
            100                 105                 110

<210> SEQ ID NO 17
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gatatcgtcc tgactcagcc ccctagcgtc agcggcgctc ccggtcagag agtgactatt    60
agctgtagcg gctctagctc taatatcggt aatcactacg tgaactggta tcagcagctg    120
cccggcaccg cccctaagct gctgatctat agaaacaatc accggcctag cggcgtgccc    180
gataggttta gcggatctaa gtcaggcact agcgctagtc tggctatcac cggactgcag    240
tcagaggacg aggccgacta ctactgtcag tcctgggact atagcggctt tagcaccgtg    300
ttcggcggag gcactaagct gaccgtgctg                                     330

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Asn Ile Ile Pro Ile Thr Gly Gln Thr Tyr Tyr Ala Gln Lys Phe
    50                  55                  60

```
Gln Gly Arg Val Thr Ile Thr Ala Asp Glu Ser Thr Ser Thr Ala Tyr
 65                 70                  75                  80

Met Glu Leu Ser Ser Leu Arg Ser Glu Asp Thr Ala Val Tyr Tyr Cys
                 85                  90                  95

Ala Arg Ala Ala Tyr His Pro Leu Val Phe Asp Asn Trp Gly Gln Gly
            100                 105                 110

Thr Leu Val Thr Val Ser Ser
        115
```

```
<210> SEQ ID NO 19
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtgcagtc aggcgccgaa gtgaagaaac ccggctctag cgtgaaagtc      60
agctgtaaag ctagtggcgg caccttctct agctacgcta ttagctgggt cagacaggcc    120
ccaggtcagg gcctggagtg gatgggcaat attatcccta tcaccggtca gacctactac    180
gctcagaaat ttcagggtag agtgactatc accgccgacg agtctactag caccgcctat    240
atggaactgt ctagcctgag atcagaggac accgccgtct actactgcgc tagagccgcc    300
tatcaccccc tggtgttcga taactggggt cagggcaccc tggtcaccgt gtctagc       357
```

```
<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Asn His
                 20                  25                  30

Tyr Val Asn Trp Tyr Gln Gln Leu Pro Gly Thr Ala Pro Lys Leu Leu
             35                  40                  45

Ile Tyr Arg Asn Asn His Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gln Ser Trp Asp Tyr Ser Gly
                 85                  90                  95

Phe Ser Thr Val Phe Gly Gly Gly Thr Lys Leu Thr Val Leu
            100                 105                 110
```

```
<210> SEQ ID NO 21
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
```
cagtcagtcc tgactcagcc ccctagcgct agtggcaccc ctggtcagag agtgactatt      60
agctgtagcg gctctagctc taatatcggt aatcactacg tgaactggta tcagcagctg     120
cccggcaccg cccctaagct gctgatctat agaaacaatc accggcctag cggcgtgccc     180
gataggttta gcggatctaa gtcagggact agcgctagtc tggctattag cggcctgcag     240
tcagaggacg aggccgacta ctactgtcag tcctgggact atagcggctt tagcaccgtg     300
ttcggcggag gcactaagct gaccgtgctg                                      330

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Tyr Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser
        115

<210> SEQ ID NO 23
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caggtgcaat tggttcagtc tggcgcggaa gtgaaaaaac cgggcagcag cgtgaaagtg      60
agctgcaaag cctccggagg cacttttaat tcttatgcta tttcttgggt gcgccaagcc     120
cctgggcagg gtctcgagtg gatgggcggt atcattccga tttatggcac tgcgaattac     180
gcgcagaagt tcagggccg ggtgaccatt accgcggatg aaagcaccag caccgcgtat     240
atggaactga gcagcctgcg tagcgaagat acggccgtgt attattgcgc gcgtgctgct     300
tatcatcctc ttgtttttga taattgggc caaggcaccc tggtgacggt tagctca        357

<210> SEQ ID NO 24
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gatatcgtgc tgacccagcc gccttcagtg agtggcgcac caggtcagcg tgtgaccatc    60
tcgtgtagcg gcagcagcag caacattggt aatcattatg tgaattggta ccagcagttg   120
cccgggacgg cgccgaaact tctgatttat cgtaataatc atcgtccctc aggcgtgccg   180 gatcgttttta gcggatccaa aagcggcacc agcgcgagcc ttgcgattac gggcctgcaa   240
agcgaagacg aagcggatta ttattgccag tcttgggatt attctggttt ttctactgtg   300
tttggcggcg gcacgaagtt aaccgtccta                                     330
```

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Trp Ile Asn Pro Phe Tyr Ile Gly Glu Thr Phe Tyr Ala Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Ala Tyr His Pro Leu Val Phe Asp Asn Trp Gly Gln
            100                 105                 110

Gly Thr Leu Val Thr Val Ser Ser
        115                 120
```

<210> SEQ ID NO 26
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
gaggtgcagc tggtgcagtc tggcgctgag gtgaagaagc ctggctcctc cgtcaaggtg    60
tcctgcaagg cctccggcgg caccttcaac tcctacgcta tctcttgggt gcgccaggct   120
cccggacagg gcctggagtg gatgggctgg atcaaccctt tctacatcgg cgagacattc   180
tacgcccaga gttccaggg cagagtcacc atcaccgccg acgagtccac ctccaccgcc   240
tacatggagc tgtcctccct gcggtcagag gacaccgccg tgtactactg cgccagggcc   300
gcctaccacc ctctggtgtt cgacaactgg ggccagggca ccctggtgac cgtgtcctcc   360
```

<210> SEQ ID NO 27
<211> LENGTH: 330
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 27

```
gatatcgtgc tgacccagcc tccttctgtg tctggcgccc ctggccagag agtgaccatc    60
tcctgctctg gctcctcctc caatatcggc aaccactacg tgaactggta tcagcagctg   120
cccggaaccg cccctaagct gctgatctac cggaacaacc accggccttc cggcgtgccc   180
gaccggttct ccggctccaa gtctggcacc tctgcctccc tggccatcac cggcctgcag   240
tccgaggacg aggccgacta ctactgccag tcctgggact actccggctt ctcaaccgtg   300
ttcggcggag gcaccaagct gaccgtgctg                                    330
```

<210> SEQ ID NO 28
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser
        115
```

<210> SEQ ID NO 29
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gaggtgcagc tggtgcagtc tggcgctgag gtgaagaagc ctggctcctc cgtcaaggtg    60
tcctgcaagg cctccggcgg caccttcaac tcctacgcta tctcttgggt cgccaggct   120 cccggacagg gcctggagtg gatgggcaac atcatcccta tgaccggcca gacctactac   180
gcccagaagt tccagggcag agtcaccatc accgccgacg agtccacctc caccgcctac   240
atggagctgt cctccctgcg gtcagaggac accgccgtgt actactgcgc cagggccgcc   300
taccaccctc tggtgttcga caactggggc cagggcaccc tggtgaccgt gtcctcc     357
```

<210> SEQ ID NO 30
<211> LENGTH: 330
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 30
gacatcgtgc tgacacagcc tccctctgtg tctggcgccc ctggccagag agtgaccatc    60
tcctgctctg gctcctcctc caatatcggc aaccactacg tgaactggta tcagcagctg   120
cccggaaccg cccctaagct gctgatctac cggaacaacc accggccttc cggcgtgccc   180
gaccggttct ccggctccaa gtctggcacc tctgcctccc tggccatcac cggcctgcag   240
tcagaggacg aggccgacta ctactgccag tcctgggact actccggctt ctccaccgtg   300
ttcggcggag gcaccaagct gaccgtgctg                                    330

<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro His Tyr Gly Phe Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser
        115

<210> SEQ ID NO 32
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggtgcaat tggttcagtc tggcgcggaa gtgaaaaaac cgggcagcag cgtgaaagtg    60
agctgcaaag cctccggagg cacttttaat tcttatgcta tttcttgggt gcgccaagcc   120
cctgggcagg gtctcgagtg gatgggcaat attattcctc attatggttt tgcttattat   180
gctcagaagt ttcagggtcg ggtgaccatt accgcggatg aaagcaccag caccgcgtat   240
atggaactga gcagcctgcg tagcgaagat acggccgtgt attattgcgc gcgtgctgct   300
tatcatcctc ttgtttttga taattggggc caaggcaccc tggtgacggt tagctca      357

<210> SEQ ID NO 33
<211> LENGTH: 330
```

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33

```
gatatcgtgc tgacccagcc gccttcagtg agtggcgcac caggtcagcg tgtgaccatc      60
tcgtgtagcg gcagcagcag caacattggt aatcattatg tgaattggta ccagcagttg     120
cccgggacgg cgccgaaact tctgatttat cgtaataatc atcgtccctc aggcgtgccg     180
gatcgtttta gcggatccaa aagcggcacc agcgcgagcc ttgcgattac gggcctgcaa     240
agcgaagacg aagcggatta ttattgccag tcttgggatt attctggttt ttctactgtg     300
tttggcggcg gcacgaagtt aaccgtccta                                       330
```

<210> SEQ ID NO 34
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 34

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro Tyr Ser Gly Phe Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser
        115
```

<210> SEQ ID NO 35
<211> LENGTH: 357
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 35

```
gaggtgcaat tggttcagtc tggcgcggaa gtgaaaaaac cgggcagcag cgtgaaagtg      60
agctgcaaag cctccggagg cactttaat tcttatgcta tttcttgggt gcgccaagcc     120
cctgggcagg gtctcgagtg gatgggcaat attattcctt attctggttt tgcttattat     180
gctcagaagt tcagggtcg ggtgaccatt accgcggatg aaagcaccag caccgcgtat     240
atggaactga gcagcctgcg tagcgaagat acggccgtgt attattgcgc gcgtgctgct     300
tatcatcctc ttgttttga taattggggc caaggcaccc tggtgacggt tagctca        357
```

<210> SEQ ID NO 36
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gatatcgtgc tgacccagcc gccttcagtg agtggcgcac caggtcagcg tgtgaccatc      60
tcgtgtagcg gcagcagcag caacattggt aatcattatg tgaattggta ccagcagttg     120
cccgggacgg cgccgaaact tctgatttat cgtaataatc atcgtccctc aggcgtgccg     180
gatcgtttta gcggatccaa aagcggcacc agcgcgagcc ttgcgattac gggcctgcaa     240
agcgaagacg aagcggatta ttattgccag tcttgggatt attctggttt ttctactgtg     300
tttggcggcg gcacgaagtt aaccgtccta                                      330
```

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Trp Ile Asn Pro Phe Tyr Ile Gly Glu Thr Phe Tyr Ala Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Ala Tyr His Pro Leu Val Phe Asp Asn Trp Gly Gln
            100                 105                 110

Gly Thr Leu Val Thr Val Ser Ser
        115                 120
```

<210> SEQ ID NO 38
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
gaggtgcagc tggtgcagtc tggcgctgag gtgaagaagc ctggctcctc cgtcaaggtg      60
tcctgcaagg cctccggcgg caccttcaac tcctacgcta tctcttgggt cgcacaggct     120
cccggacagg gcctggagtg gatgggctgg atcaaccctt tctacatcgg cgagacattc     180
tacgcccaga gttccagggg cagagtcacc atcaccgccg acgagtccac ctccaccgcc     240
tacatggagc tgtcctccct gcggtcagag gacaccgccg tgtactactg cgccagggcc     300
gcctaccacc ctctggtgtt cgacaactgg ggccagggca ccctggtgac cgtgtcctcc     360
```

<210> SEQ ID NO 39
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
cagtccgtgc tgacccagcc tccttctgcc tctggcaccc ctggccagag agtgaccatc    60
tcctgctctg gctcctcctc caatatcggc aaccactacg tgaactggta tcagcagctg   120
cccggaaccg cccctaagct gctgatctac cggaacaacc accggccttc cggcgtgccc   180
gaccggttct ccggctccaa gtctggcacc tccgcctccc tggccatctc tggcctgcag   240
tcagaggacg aggccgacta ctactgccag tcctgggact actccggctt ctccaccgtg   300
ttcggcggag gcaccaagct gaccgtgctg                                    330
```

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser
        115
```

<210> SEQ ID NO 41
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gaggtgcagc tggtgcagtc tggcgccgag gtgaagaagc ctggctcctc cgtcaaggtg    60
tcctgcaagg cctccggcgg caccttcaac tcctacgcca tctcttgggt cgcccaggct   120
cctggacagg gcctggagtg gatgggcaac atcatcccta tgaccggcca gacctactac   180
gcccagaagt tccagggcag agtcaccatc accgccgacg agtccacctc caccgcctac   240
atggagctgt cctccctgcg gtcagaggac accgccgtgt actactgcgc cagggccgcc   300
```

```
taccaccctc tggtgttcga caactggggc cagggcaccc tggtgaccgt gtcctcc        357
```

<210> SEQ ID NO 42
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
cagtccgtgc tgacccagcc tccttctgcc tctggcaccc ctggccagag agtgaccatc        60
tcctgctctg gctcctcctc caatatcggc aaccactacg tgaactggta tcagcagctg       120
cccggaaccg cccctaagct gctgatctac cggaacaacc accggccttc cggcgtgccc       180
gaccggttct ccggctccaa gtctggcacc tccgcctccc tggccatctc tggcctgcag       240
tcagaggacg aggccgacta ctactgccag tcctgggact actccggctt ctccaccgtg       300
ttcggcggag gcaccaagct gaccgtgctg                                        330
```

<210> SEQ ID NO 43
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

```
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 44
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gaggtgcagc tggtgcagtc aggcgccgaa gtgaagaaac ccggctctag cgtgaaagtc     60
agctgtaaag ctagtggcgg caccttcaag tcctacgcta ttagctgggt cagacaggcc    120
ccaggtcagg gcctggagtg gatgggcaat attatcccta tgaccggtca gacctactac    180
gctcagaaat tcagggtaga gtgactatc accgccacg agtctactag caccgcctat     240
atggaactgt ctagcctgag atcagaggac accgccgtct actactgcgc tagagccgcc    300
tatcaccccc tggtgttcga taactggggt cagggcaccc tggtcaccgt gtctagcgct    360
agcactaagg gcccctccgt gttccctctg gcccctccca gcaagtctac ctccggcggc    420
acagctgctc tgggctgcct ggtcaaggac tacttccctg agcctgtgac agtgtcctgg    480
aactctggcg ccctgaccct ctggcgtgcac accttccctg ccgtgctgca gtcctccggc    540
ctgtactccc tgtcctccgt ggtcacagtg ccttcaagca gcctgggcac ccagacctat    600
atctgcaacg tgaaccacaa gccttccaac accaaggtgg acaagcgggt ggagcctaag    660
tcctgcgaca gacccacac ctgtcctccc tgccctgctc ctgaagctgc tggcggccct    720
```

```
tctgtgttcc tgttccctcc aaagcccaag gacaccctga tgatctcccg gaccectgaa    780 gtgacctgcg tggtggtgga cgtgtcccac gaggatcctg aagtgaagtt caattggtac    840
gtggacggcg tggaggtgca caacgccaag accaagcctc gggaggaaca gtacaactcc    900
acctaccggg tggtgtccgt gctgaccgtg ctgcaccagg actggctgaa cggcaaagag    960
tacaagtgca aagtctccaa caaggccctg cctgccccta tcgaaaagac aatctccaag   1020
gccaagggcc agcctaggga accccaggtg tacaccctgc cacccagccg ggaggaaatg   1080
accaagaacc aggtgtccct gacctgtctg gtcaagggct tctacccttc cgatatcgcc   1140
gtggagtggg agtctaacgg ccagcctgag aacaactaca agaccacccc tcctgtgctg   1200
gactccgacg gctccttctt cctgtactcc aaactgaccg tggacaagtc ccggtggcag   1260
cagggcaacg tgttctcctg ctccgtgatg cacgaggccc tgcacaacca ctacacccag   1320
aagtccctgt ccctgtctcc cggcaag                                       1347
```

<210> SEQ ID NO 45
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 46
<211> LENGTH: 648
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 46

```
gatatcgtcc tgactcagcc ccctagcgtc agcggcgctc ccggtcagag agtgactatt      60
agctgtagcg gctctagctc taatatcggt aatcactacg tgaactggta tcagcagctg     120
cccggcaccg cccctaagct gctgatctat agaaacaatc accggcctag cggcgtgccc     180
gataggttta gcggatctaa gtcaggcact agcgctagtc tggctatcac cggactgcag     240
tcagaggacg aggccgacta ctactgtcag tcctgggact atagcggctt tagcaccgtg     300
ttcggcggag gcactaagct gaccgtgctg ggtcagccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca caagtacgc cgccagcagc      540
tacctgagcc tgaccccga gcagtggaag agccacaggt cctacagctg ccaggtgacc      600
cacgagggca gcaccgtgga aaagaccgtg gccccaaccg agtgcagc                   648
```

<210> SEQ ID NO 47
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 48
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gaggtgcagc tggtgcagtc tggcgctgag gtgaagaagc ctggctcctc cgtcaaggtg      60
tcctgcaagg cctccggcgg caccttcaac tcctacgcta tctcttgggt gcgccaggct     120
cccggacagg gcctggagtg gatgggcaac atcatcccta tgaccggcca gacctactac     180
gcccagaagt tccagggcag agtcaccatc accgccgacg agtccacctc caccgcctac     240
atggagctgt cctccctgcg gtcagaggac accgccgtgt actactgcgc cagggccgcc     300
taccaccctc tggtgttcga caactggggc cagggcaccc tggtgaccgt gtcctccgct     360
agcaccaagg gcccctccgt gttccctctg gccccttcca gcaagtctac ctccggcggc     420
acagctgctc tgggctgcct ggtcaaggac tacttccctg agcctgtgac agtgtcctgg     480
aactctggcg ccctgacctc tggcgtgcac accttccctg ccgtgctgca gtcctccggc     540
ctgtactccc tgtcctccgt ggtcacagtg ccttcaagca gctgggcac ccagacctat     600 atctgcaacg tgaaccacaa gccttccaac accaaggtgg acaagcgggt ggagcctaag     660
```

```
tcctgcgaca agacccacac ctgtcctccc tgccctgctc ctgaagctgc tggcggccct    720
tctgtgttcc tgttccctcc aaagcccaag gacaccctga tgatctcccg gaccccctgaa    780 gtgacctgcg tggtggtgga cgtgtcccac gaggatcctg aagtgaagtt caattggtac    840
gtggacggcg tggaggtgca caacgccaag accaagcctc gggaggaaca gtacaactcc    900
acctaccggg tggtgtccgt gctgaccgtg ctgcaccagg actggctgaa cggcaaagag    960
tacaagtgca aagtctccaa caaggccctg cctgccccta tcgaaaagac aatctcccaag   1020 gccaagggcc agcctaggga accccaggtg tacaccctgc acccagccg ggaggaaatg    1080 accaagaacc aggtgtccct gacctgtctg gtcaagggct tctacccttc cgatatcgcc    1140
gtggagtggg agtctaacgg ccagcctgag aacaactaca agaccacccc tcctgtgctg    1200
gactccgacg gctccttctt cctgtactcc aaactgaccg tggacaagtc ccggtggcag    1260
cagggcaacg tgttctcctg ctccgtgatg cacgaggccc tgcacaacca ctacacccag    1320
aagtccctgt ccctgtctcc cggcaag                                         1347
```

<210> SEQ ID NO 49
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
gacatcgtgc tgacacagcc tccctctgtg tctggcgccc ctggccagag agtgaccatc     60
tcctgctctg gctcctcctc caatatcggc aaccactacg tgaactggta tcagcagctg    120
cccggaaccg cccctaagct gctgatctac cggaacaacc accggccttc cggcgtgccc    180
gaccggttct ccggctccaa gtctggcacc tctgcctccc tggccatcac cggcctgcag    240
tcagaggacg aggccgacta ctactgccag tcctgggact actccggctt ctccaccgtg    300
ttcggcggag gcaccaagct gaccgtgctg ggacagccta aggctgcccc cagcgtgacc    360 ctgttcccc ccagcagcga ggagctgcag gccaacaagg ccaccctggt gtgcctgatc    420
agcgacttct acccaggcgc cgtgaccgtg gcctggaagg ccgacagcag ccccgtgaag    480
gccggcgtgg agaccaccac ccccagcaag cagagcaaca acaagtacgc cgccagcagc    540
tacctgagcc tgaccccga gcagtggaag agccacaggt cctacagctg ccaggtgacc    600
cacgagggca gcaccgtgga aaagaccgtg gccccaaccg agtgcagc                 648
```

<210> SEQ ID NO 50
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Glu Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Trp Ile Asn Pro Phe Tyr Ile Gly Glu Thr Phe Tyr Ala Gln Lys
```

```
            50                  55                  60
Phe Gln Gly Arg Val Thr Ile Thr Ala Asp Glu Ser Thr Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Ala Ala Tyr His Pro Leu Val Phe Asp Asn Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 51
```

<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
gaggtgcagc tggtgcagtc tggcgctgag gtgaagaagc ctggctcctc cgtcaaggtg      60
tcctgcaagg cctccggcgg caccttcaac tcctacgcta tctcttgggt gcgccaggct     120
cccggacagg gcctggagtg gatgggctgg atcaacccct tctacatcgg cgagacattc     180
tacgcccaga agttccaggg cagagtcacc atcaccgccg acgagtccac ctccaccgcc     240
tacatggagc tgtcctccct gcggtcagag gacaccgccg tgtactactg cgccagggcc     300
gcctaccacc ctctggtgtt cgacaactgg ggccagggca ccctggtgac cgtgtcctcc     360
gctagcacca agggcccctc cgtgttccct ctggcccctt ccagcaagtc tacctccggc     420
ggcacagctg ctctgggctg cctggtcaag gactacttcc ctgagcctgt gacagtgtcc     480
tggaactctg gcgccctgac ctctggcgtg cacaccttcc ctgccgtgct gcagtcctcc     540
ggcctgtact ccctgtcctc cgtggtcaca gtgccttcaa gcagcctggg cacccagacc     600
tatatctgca acgtgaacca caagccttcc aacaccaagg tggacaagcg ggtggagcct     660
aagtcctgcg acaagaccca cacctgtcct ccctgccctg ctcctgaagc tgctggcggc     720
ccttctgtgt tcctgttccc tccaaagccc aaggacaccc tgatgatctc ccggacccct     780
gaagtgacct gcgtggtggt ggacgtgtcc cacgaggatc ctgaagtgaa gttcaattgg     840
tacgtggacg gcgtggaggt gcacaacgcc aagaccaagc ctcgggagga acagtacaac     900
tccacctacc gggtggtgtc cgtgctgacc gtgctgcacc aggactggct gaacggcaaa     960
gagtacaagt gcaaagtctc caacaaggcc ctgcctgccc ctatcgaaaa gacaatctcc    1020
aaggccaagg gccagcctag ggaaccccag gtgtacaccc tgccacccag ccgggaggaa    1080
atgaccaaga accaggtgtc cctgacctgt ctggtcaagg gcttctaccc ttccgatatc    1140
gccgtggagt gggagtctaa cggccagcct gagaacaact acaagaccac ccctcctgtg    1200
ctggactccg acggctcctt cttcctgtac tccaaactga ccgtggacaa gtcccggtgg    1260
cagcagggca acgtgttctc ctgctccgtg atgcacgagg ccctgcacaa ccactacacc    1320
cagaagtccc tgtccctgtc tcccggcaag                                     1350
```

<210> SEQ ID NO 52
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gatatcgtgc tgacccagcc tccttctgtg tctggcgccc ctggcagag agtgaccatc       60
tcctgctctg gctcctcctc caatatcggc aaccactacg tgaactggta tcagcagctg     120
cccggaaccg cccctaagct gctgatctac cggaacaacc accggccttc cggcgtgccc     180
gaccggttct ccggctccaa gtctggcacc tctgcctccc tggccatcac cggcctgcag     240
tccgaggacg aggccgacta ctactgccag tcctgggact actccggctt ctcaaccgtg     300
ttcggcggag gcaccaagct gaccgtgctg ggacagccta aggctgcccc cagcgtgacc     360
ctgttccccc ccagcagcga ggagctgcag gccaacaagg ccaccctggt gtgcctgatc     420
```

```
agcgacttct acccaggcgc cgtgaccgtg gcctggaagg ccgacagcag ccccgtgaag    480
gccggcgtgg agaccaccac ccccagcaag cagagcaaca acaagtacgc cgccagcagc    540
tacctgagcc tgacccccga gcagtggaag agccacaggt cctacagctg ccaggtgacc    600
cacgagggca gcaccgtgga aaagaccgtg gccccaaccg agtgcagc                 648
```

<210> SEQ ID NO 53
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro Met Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
              325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 54
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gaggtgcagc tggtgcagtc tggcgccgag gtgaagaagc ctggctcctc cgtcaaggtg     60
tcctgcaagg cctccggcgg caccttcaac tcctacgcca tctcttgggt gcgccaggct    120
cctggacagg gcctggagtg gatgggcaac atcatcccta tgaccggcca gacctactac    180
gcccagaagt tccagggcag agtcaccatc accgccgacg agtccacctc caccgcctac    240
atggagctgt cctccctgcg gtcagaggac accgccgtgt actactgcgc cagggccgcc    300
taccaccctc tggtgttcga caactggggc cagggcaccc tggtgaccgt gtcctccgct    360
agcaccaagg gcccctccgt gttccctctg gccccttcca gcaagtctac ctccggcggc    420
acagctgctc tgggctgcct ggtcaaggac tacttccctg agcctgtgac agtgtcctgg    480
aactctggcg ccctgacctc tggcgtgcac accttccctg ccgtgctgca gtcctccggc    540
ctgtactccc tgtcctccgt ggtcacagtg ccttcaagca gcctgggcac ccagacctat    600
atctgcaacg tgaaccacaa gccttccaac accaaggtgg acaagcgggt ggagcctaag    660
tcctgcgaca gacccacac ctgtcctccc tgccctgctc ctgaagctgc tggcggccct    720
tctgtgttcc tgttccctcc aaagcccaag gacaccctga tgatctcccg gacccctgaa    780
gtgacctgcg tggtggtgga cgtgtcccac gaggatcctg aagtgaagtt caattggtac    840
gtggacggcg tggaggtgca caacgccaag accaagcctc gggaggaaca gtacaactcc    900
acctaccggg tggtgtccgt gctgaccgtg ctgcaccagg actggctgaa cggcaaagag    960
tacaagtgca agtctccaa caaggccctg cctgccccta tcgaaaagac aatctccaag   1020
gccaagggcc agcctaggga accccaggtg tacaccctgc acccagccg ggaggaaatg   1080 accaagaacc aggtgtccct gacctgtctg gtcaagggct tctaccttc cgatatcgcc   1140 gtggagtggg agtctaacgg ccagcctgag aacaactaca agaccacccc tcctgtgctg   1200
gactccgacg gctccttctt cctgtactcc aaactgaccg tggacaagtc ccggtggcag   1260

```
cagggcaacg tgttctcctg ctccgtgatg cacgaggccc tgcacaacca ctacacccag    1320
aagtccctgt ccctgtctcc cggcaag                                        1347

<210> SEQ ID NO 55
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
cagtccgtgc tgacccagcc tccttctgcc tctggcaccc tggccagag agtgaccatc      60 tcctgctctg gctcctcctc caatatcggc aaccactacg tgaactggta tcagcagctg    120
cccggaaccg cccctaagct gctgatctac cggaacaacc accggccttc cggcgtgccc    180
gaccggttct ccggctccaa gtctggcacc tccgcctccc tggccatctc tggcctgcag    240
tcagaggacg aggccgacta ctactgccag tcctgggact actccggctt ctccaccgtg    300
ttcggcggag gcaccaagct gaccgtgctg ggacagccta aggctgcccc cagcgtgacc    360
ctgttccccc ccagcagcga ggagctgcag gccaacaagg ccaccctggt gtgcctgatc    420
agcgacttct acccaggcgc cgtgaccgtg gcctggaagg ccgacagcag ccccgtgaag    480
gccggcgtgg agaccaccac ccccagcaag cagagcaaca caagtacgc cgccagcagc    540 tacctgagcc tgacccccga gcagtggaag agccacaggt cctacagctg ccaggtgacc    600
cacgagggca gcaccgtgga aaagaccgtg gccccaaccg agtgcagc                 648

<210> SEQ ID NO 56
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Tyr Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
        435                 440                 445
Lys

<210> SEQ ID NO 57
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcaat tggttcagtc tggcgcggaa gtgaaaaaac cgggcagcag cgtgaaagtg      60
agctgcaaag cctccggagg cacttttaat tcttatgcta tttcttgggt gcgccaagcc    120
cctgggcagg gtctcgagtg gatgggcggt atcattccga tttatggcac tgcgaattac    180
gcgcagaagt tcagggccg gtgaccatt accgcggatg aaagcaccag caccgcgtat    240
atggaactga gcagcctgcg tagcgaagat acggccgtgt attattgcgc gcgtgctgct    300
tatcatcctc ttgttttga taattggggc caaggcaccc tggtgacggt tagctcagcc    360
```

```
tccaccaagg gtccatcggt cttccccctg cacccctcct ccaagagcac ctctgggggc      420
acagcggccc tgggctgcct ggtcaaggac tacttcccc aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagagagt tgagcccaaa      660
tcttgtgaca aaactcacac atgcccaccg tgcccagcac ctgaactcct ggggggaccg      720
tcagtcttcc tcttccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccggg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggaggagatg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaa                                         1347
```

<210> SEQ ID NO 58
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
gatatcgtgc tgacccagcc gccttcagtg agtggcgcac caggtcagcg tgtgaccatc       60
tcgtgtagcg gcagcagcag caacattggt aatcattatg tgaattggta ccagcagttg      120
cccgggacgg cgccgaaact tctgatttat cgtaataatc atcgtccctc aggcgtgccg      180
gatcgtttta gcggatccaa aagcggcacc agcgcgagcc ttgcgattac gggcctgcaa      240
agcgaagaca agcggatta ttattgccag tcttgggatt attctggttt ttctactgtg      300
tttggcggcg gcacgaagtt aaccgtccta ggtcagccca aggctgcccc ctcggtcact      360 ctgttccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgc ggccagcagc      540 tatctgagcc tgacgcctga gcagtggaag tcccacagaa gctacagctg ccaggtcacg      600
catgaaggga gcaccgtgga agacagtg gcccctacag aatgttca                     648
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Thr Phe Asn Ser Tyr

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Pro Met Thr Gly Gln
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Tyr His Pro Leu Val Phe Asp Asn
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ser Ser Asn Ile Gly Asn His Tyr
1               5

<210> SEQ ID NO 63
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Asn Asn
1

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Asp Tyr Ser Gly Phe Ser Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Gly Gly Thr Phe Lys Ser Tyr
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Thr Phe Ser Ser Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Pro Ile Thr Gly Gln
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Thr Phe Ser Ser Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Gly Glu Gly Ser Asn
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Met Ile Gly Tyr Gly Phe Asp Tyr
1               5

<210> SEQ ID NO 71

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Gln Ser Ile Phe Asn Tyr
1               5

<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Ser Ser
1

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Ser Gly Phe Leu Phe
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Gly Ser Tyr Tyr Trp Asn
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Ile Asn His Met Gly Ile Thr Tyr Tyr Asn Pro Ser Leu Lys Gly
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76
```

```
Glu Ile Trp His Ser Gly Pro Thr Phe Tyr Asn Pro Ser Leu Lys Ser
1               5                   10                  15
```

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Glu Ile His Gly His Gly Phe Thr Phe Tyr Asn Pro Ser Leu Lys Ser
1               5                   10                  15
```

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Glu Ile Gln Ser Pro Gly Tyr Thr Phe Tyr Asn Pro Ser Leu Lys Ser
1               5                   10                  15
```

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Thr Thr Arg Tyr Trp Met Ser His Ile Leu Ala Tyr Gly Met Asp Tyr
1               5                   10                  15
```

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ser Gly Ser Ser Ser Asn Ile Gly Asn His Tyr Val Ser
1               5                   10
```

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Ala Asn Thr Lys Arg Pro Ser
1               5
```

<210> SEQ ID NO 82
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 82

Ser Ser Tyr Asp Gly Ser Gln Ser Ile Val
1               5                   10

<210> SEQ ID NO 83
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
                20                  25                  30

Ser Tyr Tyr Trp Asn Trp Ile Arg Gln Ala Pro Gly Lys Gly Leu Glu
            35                  40                  45

Trp Ile Gly Glu Ile Asn His Met Gly Ile Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser
        115                 120                 125

<210> SEQ ID NO 84
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caggtgcaat tgcaagaaag tggtccgggc ctggtgaaac cgggcgaaac cctgagcctg      60
acctgcaccg tttccggagg tagcatttct actggttctt attattggaa ttggattcgc     120
caggcccctg ggaagggtct cgagtggatt ggcgagatca atcatatggg cattacctat     180
tataatccga gcctgaaagg ccgggtgacc attagcgttg atacttcgaa aaaccagttt     240
agcctgaaac tgagcagcgt gacggcggaa gatacggccg tgtattattg cgcgcgtact     300
actcgttatt ggatgtctca tattcttgct tatggtatgg attattgggg ccaaggcacc     360
ctggtgacgg ttagctca                                                   378

<210> SEQ ID NO 85
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn His
            20                  25                  30

Tyr Val Ser Trp Tyr Gln Gln Leu Pro Gly Thr Ala Pro Lys Leu Leu
        35                  40                  45

Ile Tyr Ala Asn Thr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ser Tyr Asp Gly Ser Gln
                85                  90                  95

Ser Ile Val Phe Gly Gly Gly Thr Lys Leu Thr Val Leu
            100                 105

<210> SEQ ID NO 86
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gatatcgtgc tgacccagcc gccttcagtg agtggcgcac caggtcagcg tgtgaccatc      60
tcgtgtagcg gcagcagcag caacattggt aatcattatg tgtcttggta ccagcagttg     120
cccgggacgg cgccgaaact tctgatttat gctaatacta agcgtccctc aggcgtgccg     180 gatcgttttta gcggatccaa aagcggcacc agcgcgagcc ttgcgattac gggcctgcaa    240
agcgaagacg aagcggatta ttattgctct tcttatgatg gttctcagtc tattgtgttt    300
ggcggcggca cgaagttaac cgtccta                                        327

<210> SEQ ID NO 87
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile Gln Ser Pro Gly Tyr Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser
        115                 120                 125
```

<210> SEQ ID NO 88
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
gaggtgcaat tgcaagaaag tggtccgggc ctggtgaaac cgggcgaaac cctgagcctg      60
acctgcaccg tttccggagg tagcatttct actggttctt attattggaa ttggattcgc     120
caggcccctg gaagggtct cgagtggatt ggcgagattc agtctcctgg ttatactttt     180
tataatcctt ctcttaagtc tcgggtgacc attagcgttg atacttcgaa aaaccagttt     240
agcctgaaac tgagcagcgt gacggcggcg gatacggccg tgtattattg cgcgcgtact     300
actcgttatt ggatgtctca tattcttgct tatggtatgg attattgggg ccaaggcacc     360
ctggtgacgg ttagctca                                                   378
```

<210> SEQ ID NO 89
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
gatatcgtgc tgacccagcc gccttcagtg agtggcgcac aggtcagcg tgtgaccatc      60
tcgtgtagcg gcagcagcag caacattggt aatcattatg tgtcttggta ccagcagttg     120
cccgggacgg cgccgaaact tctgatttat gctaatacta gcgtccctc aggcgtgccg     180
gatcgtttta gcggatccaa aagcggcacc agcgcgagcc ttgcgattac gggcctgcaa     240
agcgaagacg aagcggatta ttattgctct tcttatgatg gttctcagtc tattgtgttt     300
ggcggcggca cgaagttaac cgtccta                                         327
```

<210> SEQ ID NO 90
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile Trp His Ser Gly Pro Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Thr Arg Tyr Trp Met Ser His Ile Leu Ala Tyr Gly
            100                 105                 110
```

Met Asp Tyr Trp Gly Gln Gly Thr Leu Val Thr Val Ser Ser
            115                 120                 125

<210> SEQ ID NO 91
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gaggtgcaat tgcaagaaag tggtccgggc ctggtgaaac cgggcgaaac cctgagcctg        60
acctgcaccg tttccggagg tagcatttct actggttctt attattggaa ttggattcgc       120
caggcccctg gaagggtct cgagtggatt ggcgagattt ggcattctgg tcctactttt       180
tataatcctt ctcttaagtc tcgggtgacc attagcgttg atacttcgaa aaaccagttt       240
agcctgaaac tgagcagcgt gacggcggcg gatacggccg tgtattattg cgcgcgtact       300
actcgttatt ggatgtctca tattcttgct tatggtatgg attattgggg ccaaggcacc       360
ctggtgacgg ttagctca                                                    378

<210> SEQ ID NO 92
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gatatcgtgc tgacccagcc gccttcagtg agtggcgcac aggtcagcg tgtgaccatc        60 tcgtgtagcg gcagcagcag caacattggt aatcattatg tgtcttggta ccagcagttg       120
cccgggacgg cgccgaaact tctgatttat gctaatacta gcgtccctc aggcgtgccg       180 gatcgtttta gcggatccaa aagcggcacc agcgcgagcc ttgcgattac gggcctgcaa       240
agcgaagacg aagcggatta ttattgctct tcttatgatg gttctcagtc tattgtgttt       300
ggcggcggca cgaagttaac cgtccta                                          327

<210> SEQ ID NO 93
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile His Gly His Gly Phe Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr

```
                85                  90                  95
Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser
            115                 120                 125

<210> SEQ ID NO 94
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gaggtgcaat tgcaagaaag tggtccgggc ctggtgaaac cgggcgaaac cctgagcctg      60
acctgcaccg tttccggagg tagcatttct actggttctt attattggaa ttggattcgc     120 caggccoctg gaagggtct cgagtggatt ggcgagattc atggtcatgg tttactttt      180 tataatcctt ctcttaagtc tcgggtgacc attagcgttg atacttcgaa aaaccagttt     240
agcctgaaac tgagcagcgt gacggcggcg gatacggccg tgtattattg cgcgcgtact     300
actcgttatt ggatgtctca tattcttgct tatggtatgg attattgggg ccaaggcacc     360
ctggtgacgg ttagctca                                                   378

<210> SEQ ID NO 95
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gatatcgtgc tgacccagcc gccttcagtg agtggcgcac aggtcagcg tgtgaccatc      60 tcgtgtagcg gcagcagcag caacattggt aatcattatg tgtcttggta ccagcagttg     120
cccgggacgg cgccgaaact tctgatttat gctaatacta gcgtccctc aggcgtgccg      180 gatcgtttta gcggatccaa aagcggcacc agcgcgagcc ttgcgattac gggcctgcaa     240
agcgaagacg aagcggatta ttattgctct tcttatgatg gttctcagtc tattgtgttt     300
ggcggcggca cgaagttaac cgtccta                                         327

<210> SEQ ID NO 96
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile Asn His Met Gly Ile Thr Tyr Tyr Asn Pro Ser
    50                  55                  60
```

```
Leu Lys Gly Arg Val Thr Ile Ser Val Asp Thr Ser Lys Asn Gln Phe
 65                  70                  75                  80

Ser Leu Lys Leu Ser Ser Val Thr Ala Glu Asp Thr Ala Val Tyr Tyr
             85                   90                  95

Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 97
<211> LENGTH: 1368
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 97

```
caggtgcaat tgcaagaaag tggtccgggc ctggtgaaac cgggcgaaac cctgagcctg        60
acctgcaccg tttccggagg tagcatttct actggttctt attattggaa ttggattcgc       120
caggcccctg ggaagggtct cgagtggatt ggcgagatca atcatatggg cattaccctat      180
tataatccga gcctgaaagg ccgggtgacc attagcgttg atacttcgaa aaaccagttt       240
agcctgaaac tgagcagcgt gacggcggaa gatacggccg tgtattattg cgcgcgtact       300
actcgttatt ggatgtctca tattcttgct tatggtatgg attattgggg ccaaggcacc       360
ctggtgacgg ttagctcagc ctccaccaag ggtccatcgg tcttccccct ggcaccctcc       420
tccaagagca cctctggggg cacagcggcc ctgggctgcc tggtcaagga ctacttcccc       480
gaaccggtga cggtgtcgtg aactcaggc gccctgacca cgggcgtgca caccttcccg        540
gctgtcctac agtcctcagg actctactcc ctcagcagcg tggtgaccgt gccctccagc       600
agcttgggca cccagaccta catctgcaac gtgaatcaca agcccagcaa caccaaggtg       660
gacaagagag ttgagcccaa atcttgtgac aaaactcaca catgcccacc gtgcccagca       720
cctgaactcc tggggggacc gtcagtcttc ctcttccccc caaaacccaa ggacaccctc       780
atgatctccc ggacccctga ggtcacatgc gtggtggtgg acgtgagcca cgaagaccct       840
gaggtcaagt tcaactggta cgtggacggc gtggaggtgc ataatgccaa gacaaagccg       900
cgggaggagc agtacaacag cacgtaccgg gtggtcagcg tcctcaccgt cctgcaccag       960
gactggctga atggcaagga gtacaagtgc aaggtctcca acaaagccct cccagccccc      1020
atcgagaaaa ccatctccaa agccaaaggg cagccccgag aaccacaggt gtacaccctg      1080
cccccatccc gggaggagat gaccaagaac caggtcagcc tgacctgcct ggtcaaaggc      1140
ttctatccca gcgacatcgc cgtggagtgg gagagcaatg ggcagccgga gaacaactac      1200
aagaccacgc ctcccgtgct ggactccgac ggctccttct tcctctacag caagctcacc      1260
gtggacaaga gcaggtggca gcaggggaac gtcttctcat gctccgtgat gcatgaggct      1320
ctgcacaacc actacacgca gaagagcctc tccctgtctc cgggtaaa                   1368
```

<210> SEQ ID NO 98
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn His
            20                  25                  30

Tyr Val Ser Trp Tyr Gln Gln Leu Pro Gly Thr Ala Pro Lys Leu Leu
        35                  40                  45

Ile Tyr Ala Asn Thr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

```
Ser Glu Asp Glu Ala Asp Tyr Tyr Cys Ser Ser Tyr Asp Gly Ser Gln
                85                  90                  95

Ser Ile Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 99
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gatatcgtgc tgacccagcc gccttcagtg agtggcgcac caggtcagcg tgtgaccatc      60
tcgtgtagcg gcagcagcag caacattggt aatcattatg tgtcttggta ccagcagttg     120
cccgggacgg cgccgaaact tctgatttat gctaatacta gcgtccctc aggcgtgccg      180 gatcgtttta gcggatccaa aagcggcacc agcgcgagcc ttgcgattac gggcctgcaa     240
agcgaagacg aagcggatta ttattgctct tcttatgatg gttctcagtc tattgtgttt     300
ggcggcggca cgaagttaac cgtcctaggt cagcccaagg ctgccccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttca                    645

<210> SEQ ID NO 100
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45
```

-continued

```
Gly Trp Ile Asn Pro Phe Tyr Ile Gly Glu Thr Phe Tyr Ala Gln Lys
 50                  55                  60

Phe Gln Gly Arg Val Thr Ile Thr Ala Asp Glu Ser Thr Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Ala Ala Tyr His Pro Leu Val Phe Asp Asn Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450
```

<210> SEQ ID NO 101
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gaggtgcagc tggtgcagtc tggcgctgag gtgaagaagc tggctcctc cgtcaaggtg     60 tcctgcaagg cctccggcgg caccttcaac tcctacgcta tctcttgggt gcgccaggct    120
cccggacagg gcctggagtg gatgggctgg atcaaccctt ctacatcgg cgagacattc    180 tacgcccaga agttccaggg cagagtcacc atcaccgccg acgagtccac ctccaccgcc    240
tacatggagc tgtcctccct gcggtcagag gacaccgccg tgtactactg cgccagggcc    300
gcctaccacc ctctggtgtt cgacaactgg ggccagggca ccctggtgac cgtgtcctcc    360
gctagcacca agggcccctc cgtgttccct ctggcccctt ccagcaagtc tacctccggc    420
ggcacagctg ctctgggctg cctggtcaag gactacttcc ctgagcctgt gacagtgtcc    480
tggaactctg gcgccctgac ctctggcgtg cacaccttcc ctgccgtgct gcagtcctcc    540
ggcctgtact ccctgtcctc cgtggtcaca gtgccttcaa gcagcctggg cacccagacc    600
tatatctgca acgtgaacca caagccttcc aacaccaagg tggacaagcg ggtggagcct    660
aagtcctgcg acaagaccca cacctgtcct cctgccctg ctcctgaagc tgctggcggc    720
ccttctgtgt tcctgttccc tccaaagccc aaggacaccc tgatgatctc ccggaccct    780 gaagtgacct gcgtggtggt ggacgtgtcc cacgaggatc ctgaagtgaa gttcaattgg    840
tacgtggacg gcgtggaggt gcacaacgcc aagaccaagc ctcgggagga acagtacaac    900
tccacctacc gggtggtgtc cgtgctgacc gtgctgcacc aggactggct gaacggcaaa    960
gagtacaagt gcaaagtctc caacaaggcc ctgcctgccc ctatcgaaaa gacaatctcc    1020
aaggccaagg ccagcctag gaaccccag gtgtacaccc tgccacccag ccgggaggaa    1080
atgaccaaga accaggtgtc cctgacctgt ctggtcaagg gcttctaccc ttccgatatc    1140
gccgtggagt gggagtctaa cggccagcct gagaacaact acaagaccac ccctcctgtg    1200
ctggactccg acggctcctt cttcctgtac tccaaactga ccgtggacaa gtcccggtgg    1260
cagcagggca acgtgttctc ctgctccgtg atgcacgagg ccctgcacaa ccactacacc    1320
cagaagtccc tgtccctgtc tcccggcaag                                     1350

<210> SEQ ID NO 102
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
cagtccgtgc tgacccagcc tccttctgcc tctggcaccc ctggccagag agtgaccatc     60
tcctgctctg gctcctcctc caatatcggc aaccactacg tgaactggta tcagcagctg    120
cccggaaccg cccctaagct gctgatctac cggaacaacc accggccttc cggcgtgccc    180
gaccggttct ccggctccaa gtctggcacc tccgcctccc tggccatctc tggcctgcag    240
tcagaggacg aggccgacta ctactgccag tcctgggact actccggctt ctccaccgtg    300
ttcggcggag gcaccaagct gaccgtgctg ggacagccta aggctgcccc cagcgtgacc    360

-continued

```
ctgttccccc ccagcagcga ggagctgcag gccaacaagg ccaccctggt gtgcctgatc      420
agcgacttct acccaggcgc cgtgaccgtg gcctggaagg ccgacagcag ccccgtgaag      480
gccggcgtgg agaccaccac ccccagcaag cagagcaaca acaagtacgc cgccagcagc      540
tacctgagcc tgaccccga gcagtggaag agccacaggt cctacagctg ccaggtgacc      600
cacgagggca gcaccgtgga aaagaccgtg gccccaaccg agtgcagc                  648
```

```
<210> SEQ ID NO 103
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile Gln Ser Pro Gly Tyr Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300
```

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Glu Glu Met Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
    450                 455

<210> SEQ ID NO 104
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gaggtgcaat tgcaagaaag tggtccgggc ctggtgaaac cgggcgaaac cctgagcctg      60
acctgcaccg tttccggagg tagcatttct actggttctt attattggaa ttggattcgc     120
caggcccctg gaagggtctc gagtggatt ggcgagattc agtctcctgg ttatactttt      180
tataatcctt ctcttaagtc tcgggtgacc attagcgttg atacttcgaa aaaccagttt     240
agcctgaaac tgagcagcgt gacggcggcg atacggccg tgtattattg cgcgcgtact      300
actcgttatt ggatgtctca tattcttgct tatggtatgg attattgggg ccaaggcacc     360
ctggtgacgg ttagctcagc ctccaccaag ggtccatcgg tcttccccct ggcaccctcc     420
tccaagagca cctctggggg cacagcggcc ctgggctgcc tggtcaagga ctacttcccc     480
gaaccggtga cggtgtcgtg gaactcaggc gccctgacca gcggcgtgca caccttcccg     540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagagag ttgagcccaa atcttgtgac aaaactcaca catgcccacc gtgcccagca     720
cctgaagcag cggggggacc gtcagtcttc ctcttccccc caaaacccaa ggacaccctc     780
atgatctccc ggaccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgg gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggaggagat gaccaagaac caggtcagcc tgacctgcct ggtcaaaggc    1140

```
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcatgaggct    1320
ctgcacaacc actacacgca gaagagcctc tccctgtctc cgggtaaa                 1368

<210> SEQ ID NO 105
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gatatcgtgc tgacccagcc gccttcagtg agtggcgcac caggtcagcg tgtgaccatc      60
tcgtgtagcg gcagcagcag caacattggt aatcattatg tgtcttggta ccagcagttg     120
cccgggacgg cgccgaaact tctgatttat gctaatacta gcgtccctc aggcgtgccg      180 gatcgtttta gcggatccaa aagcggcacc agcgcgagcc ttgcgattac gggcctgcaa     240
agcgaagacg aagcggatta ttattgctct tcttatgatg gttctcagtc tattgtgttt     300
ggcggcggca cgaagttaac cgtcctaggt cagcccaagg ctgcccctc ggtcactctg      360 ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttca                    645

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Tyr Ala Ile His
1               5

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Ile Ser Gly Glu Gly Ser Asn Thr Tyr Tyr Ala Asp Ser Val Lys
1               5                   10                  15

Gly

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 108

Val Met Ile Gly Tyr Gly Phe Asp Tyr
1               5

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ala Ser Gln Ser Ile Phe Asn Tyr Leu Asn
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Ser Ser Thr Leu Gln Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Gln Tyr Ser Gly Phe Leu Phe Thr
1               5

<210> SEQ ID NO 112
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ser Val Ile Ser Gly Glu Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Met Ile Gly Tyr Gly Phe Asp Tyr Trp Gly Gln Gly Thr
            100                 105                 110
```

-continued

Leu Val Thr Val Ser Ser
        115

<210> SEQ ID NO 113
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
caggtgcagc tgctggaatc aggcggcgga ctggtgcagc ctggcggtag cctgagactg     60
agctgcgctg ctagtggctt caccttctct agctacgcta ttcactgggt cagacaggcc    120
cctggtaaag gcctggagtg ggtgtcagtg attagcggcg agggctctaa cacctactac    180
gccgatagcg tgaagggccg gttcactatc tctagggata actctaagaa caccctgtac    240
ctgcagatga atagcctgag agccgaggac accgccgtct actactgcgc tagagtgatg    300
atcggctacg gcttcgacta ctggggtcag ggcaccctgg tcaccgtgtc tagc          354

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Asn Tyr
            20                  25                  30

Leu Asn Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Gly Phe Leu Phe
                85                  90                  95

Thr Phe Gly Gln Gly Thr Lys Val Glu Ile Lys
            100                 105

<210> SEQ ID NO 115
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
gatattcaga tgactcagtc acctagtagc ctgagcgcta gtgtgggcga tagagtgact     60
atcacctgta gagcctctca gtctatcttt aactacctga ctggtatca gcagaagccc    120 ggtaaagccc ctaagctgct gatctacgac tctagcaccc tgcagtcagg cgtgccctct    180
aggtttagcg gtagcggtag tggcaccgac ttcaccctga ctatctctag cctgcagccc    240
gaggacttcg ctacctacta ctgcctgcag tatagcggct tcctgttcac cttcggtcag    300
ggcactaagg tcgagattaa g                                              321

<210> SEQ ID NO 116
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ser Val Ile Ser Gly Glu Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Met Ile Gly Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 117
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
caggtgcagc tgctggaatc aggcggcgga ctggtgcagc ctggcggtag cctgagactg      60
agctgcgctg ctagtggctt caccttctct agctacgcta ttcactgggt cagacaggcc     120
cctggtaaag gcctggagtg ggtgtcagtg attagcggcg agggctctaa cacctactac     180
gccgatagcg tgaagggccg gttcactatc tctaggata actctaagaa cacccctgtac     240 ctgcagatga atagcctgag agccgaggac accgccgtct actactgcgc tagagtgatg     300
atcggctacg gcttcgacta ctggggtcag ggcaccctgg tcaccgtgtc tagcgctagc     360
actaagggcc cctccgtgtt ccctctggcc ccttccagca gtctacctc cggcggcaca      420 gctgctctgg gtgcctggt caaggactac ttccctgagc ctgtgacagt gtcctggaac      480
tctggcgccc tgacctctgg cgtgcacacc ttccctgccg tgctgcagtc ctccggcctg     540
tactccctgt cctccgtggt cacagtgcct caagcagcc tgggcaccca gacctatatc      600
tgcaacgtga accacaagcc ttccaacacc aaggtggaca gcgggtgga gcctaagtcc      660 tgcgacaaga cccacacctg tcctcccgc cctgctcctg aagctgctgg cggcccttct      720
gtgttcctgt tccctccaaa gcccaaggac accctgatga tctcccggac ccctgaagtg     780
acctgcgtgg tggtggacgt gtcccacgag gatcctgaag tgaagttcaa ttggtacgtg     840
gacggcgtgg aggtgcacaa cgccaagacc aagcctcggg aggaacagta caactccacc     900
taccgggtgg tgtccgtgct gaccgtgctg caccaggact ggctgaacgg caaagagtac     960
aagtgcaaag tctccaacaa ggccctgcct gcccctatcg aaaagacaat ctccaaggcc    1020
aagggccagc ctagggaacc ccaggtgtac accctgccac ccagccggga ggaaatgacc    1080
aagaaccagg tgtccctgac ctgtctggtc aagggcttct acccttccga tatcgccgtg    1140
gagtgggagt ctaacggcca gcctgagaac aactacaaga ccaccccctcc tgtgctggac   1200 tccgacggct ccttcttcct gtactccaaa ctgaccgtgg acaagtcccg gtggcagcag    1260
ggcaacgtgt tctcctgctc cgtgatgcac gaggccctgc acaaccacta cacccagaag    1320
tccctgtccc tgtctcccgg caag                                            1344

<210> SEQ ID NO 118
<211> LENGTH: 214
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Asn Tyr
            20                  25                  30

Leu Asn Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Gly Phe Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 119
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119
gatattcaga tgactcagtc acctagtagc ctgagcgcta gtgtgggcga tagagtgact      60
atcacctgta gagcctctca gtctatcttt aactacctga actggtatca gcagaagccc     120
ggtaaagccc ctaagctgct gatctacgac tctagcaccc tgcagtcagg cgtgccctct     180
aggtttagcg gtagcggtag tggcaccgac ttcaccctga ctatctctag cctgcagccc     240
gaggacttcg ctacctacta ctgcctgcag tatagcggct tcctgttcac cttcggtcag     300
ggcactaagg tcgagattaa gcgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540

```
ctgagcaagg ccgactacga gaagcataag gtgtacgcct gcgaggtgac ccaccagggc    600
ctgtccagcc ccgtgaccaa gagcttcaac aggggcgagt gc                       642
```

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Thr Phe Ser Ile Ser
1               5
```

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Gly Ile Ile Pro Ile Phe Gly Thr Ala Asn Tyr Ala Gln Lys Phe Gln
1               5                   10                  15

Gly
```

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Thr Ile Gln Ser Ser Gly Glu Asn Lys Phe Tyr Ala Asp Ser Val Lys
1               5                   10                  15

Gly
```

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Gly Gly Tyr Gly Gly Tyr Tyr Tyr Phe Asp Tyr
1               5                   10
```

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Arg Ala Ser Gln Ser Ile Ser Asn Arg Leu Asn
1               5                   10
```

```
<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Gly Ser Thr Leu Gln Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

His Gln Tyr Ser Gly Leu Leu Phe Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Gln His Lys Val Trp Leu Thr Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Gln His Tyr Val Trp Ser Thr Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln His Tyr Gln Trp Leu Thr Thr
1               5

<210> SEQ ID NO 130
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Phe
            20                  25                  30

Ser Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Gly Tyr Tyr Tyr Phe Asp Tyr Trp Gly Gln
            100                 105                 110

Gly Thr Leu Val Thr Val Ser Ser
            115                 120

<210> SEQ ID NO 131
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
caggtgcagc tggtgcagtc aggcgccgaa gtgaagaaac ccggctctag cgtgaaagtc      60
agctgtaaag ctagtggcgg caccttcagc accttctcta ttagctgggt cagacaggcc     120
ccaggtcagg gcctggagtg gatgggcgga attatcccta tcttcggcac cgctaactac     180
gctcagaaat ttcagggtag agtgactatc accgccgacg agtctactag caccgcctat     240
atggaactgt ctagcctgag atcagaggac accgccgtct actactgcgc tagggggcggc     300 tacggcggct attactactt cgactactgg ggtcagggca ccctggtcac cgtgtctagc     360

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Arg
            20                  25                  30

Leu Asn Trp Tyr Gln Gln Lys Pro Gly Lys Ala Pro Lys Leu Leu Ile
            35                  40                  45

Tyr Lys Gly Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Lys Val Trp Leu Thr
                85                  90                  95

Thr Phe Gly Gln Gly Thr Lys Val Glu Ile Lys
            100                 105

<210> SEQ ID NO 133
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
gatattcaga tgactcagtc acctagtagc ctgagcgcta gtgtgggcga tagagtgact      60
atcacctgta gagcctctca gtctatctct aataggctga actggtatca gcagaagccc     120
ggtaaagccc ctaagctgct gatctataag ggctctaccc tgcagtcagg cgtgccctct     180
aggtttagcg gtagcggtag tggcaccgac ttcaccctga ctatctctag cctgcagccc     240
gaggacttcg ctacctacta ctgtcagcag cacaaagtgt ggctgactac cttcggtcag     300
ggcactaagg tcgagattaa g                                                321
```

<210> SEQ ID NO 134
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Phe
            20                  25                  30

Ser Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Gly Tyr Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240
```

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 135
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
caggtgcagc tggtgcagtc aggcgccgaa gtgaagaaac ccggctctag cgtgaaagtc     60
agctgtaaag ctagtggcgg caccttcagc accttctcta ttagctgggt cagacaggcc    120
ccaggtcagg gcctggagtg gatgggcgga attatcccta tcttcggcac cgctaactac    180
gctcagaaat ttcagggtag agtgactatc accgccacg agtctactag caccgcctat    240
atggaactgt ctagcctgag atcagaggac accgccgtct actactgcgc taggggcggc    300
tacggcggct attactactt cgactactgg ggtcagggca ccctggtcac cgtgtctagc    360
gctagcacta agggcccctc cgtgttccct ctggcccctt ccagcaagtc tacctccggc    420
ggcacagctg ctctgggctg cctggtcaag gactacttcc ctgagcctgt gacagtgtcc    480
tggaactctg gcgccctgac ctctggcgtg cacaccttcc ctgccgtgct gcagtcctcc    540
ggcctgtact ccctgtcctc cgtggtcaca gtgccttcaa gcagcctggg cacccagacc    600
tatatctgca acgtgaacca caagccttcc aacaccaagg tggacaagcg ggtggagcct    660
aagtcctgcg acaagaccca cacctgtcct cctgccctg ctcctgaagc tgctggcggc    720
ccttctgtgt tcctgttccc tccaaagccc aaggacaccc tgatgatctc ccggacccct    780

```
gaagtgacct gcgtggtggt ggacgtgtcc cacgaggatc ctgaagtgaa gttcaattgg     840
tacgtggacg gcgtggaggt gcacaacgcc aagaccaagc ctcgggagga acagtacaac     900
tccacctacc gggtggtgtc cgtgctgacc gtgctgcacc aggactggct gaacggcaaa     960
gagtacaagt gcaaagtctc caacaaggcc ctgcctgccc ctatcgaaaa gacaatctcc    1020
aaggccaagg gccagcctag ggaaccccag gtgtacaccc tgccacccag ccgggaggaa    1080
atgaccaaga accaggtgtc cctgacctgt ctggtcaagg gcttctaccc ttccgatatc    1140
gccgtggagt gggagtctaa cggccagcct gagaacaact acaagaccac ccctcctgtg    1200
ctggactccg acggctcctt cttcctgtac tccaaactga ccgtggacaa gtcccggtgg    1260
cagcagggca acgtgttctc ctgctccgtg atgcacgagg ccctgcacaa ccactacacc    1320
cagaagtccc tgtccctgtc tcccggcaag                                     1350
```

<210> SEQ ID NO 136
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Arg
            20                  25                  30

Leu Asn Trp Tyr Gln Gln Lys Pro Gly Lys Ala Pro Lys Leu Leu Ile
        35                  40                  45

Tyr Lys Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Lys Val Trp Leu Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 137
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gatattcaga tgactcagtc acctagtagc ctgagcgcta gtgtgggcga tagagtgact      60
atcacctgta gagcctctca gtctatctct aataggctga actggtatca gcagaagccc     120
ggtaaagccc ctaagctgct gatctataag ggctctaccc tgcagtcagg cgtgccctct     180
aggtttagcg gtagcggtag tggcaccgac ttcaccctga ctatctctag cctgcagccc     240
gaggacttcg ctacctacta ctgtcagcag cacaaagtgt ggctgactac cttcggtcag     300
ggcactaagg tcgagattaa cgtacggtg ccgctccca gcgtgttcat cttccccccc       360
agcgacgagc agctgaagag cggcaccgcc agcgtggtgt gcctgctgaa caacttctac     420
ccccgggagg ccaaggtgca gtggaaggtg acaacgccc tgcagagcgg caacagccag      480
gagagcgtca ccgagcagga cagcaaggac tccacctaca gcctgagcag caccctgacc     540
ctgagcaagg ccgactacga aagcataag gtgtacgcct gcgaggtgac ccaccagggc      600
ctgtccagcc ccgtgaccaa gagcttcaac aggggcgagt gc                        642

<210> SEQ ID NO 138
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ser Thr Ile Gln Ser Ser Gly Glu Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Met Ile Gly Tyr Gly Phe Asp Tyr Trp Gly Gln Gly Thr
            100                 105                 110

Leu Val Thr Val Ser Ser
        115

<210> SEQ ID NO 139
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
caggtgcagc tgctggaatc aggcggcgga ctggtgcagc ctggcggtag cctgagactg      60
agctgcgctg ctagtggctt caccttctct agctacgcta ttcactgggt cagacaggcc     120
cctggtaaag gcctggagtg ggtcagcact attcagtcta gcggcgagaa caagttctac     180

```
gccgatagcg tgaagggccg gttcactatc tctagggata actctaagaa caccctgtac    240
ctgcagatga atagcctgag agccgaggac accgccgtct actactgcgc tagagtgatg    300
atcggctacg gcttcgacta ctggggtcag ggcaccctgg tcaccgtgtc tagc          354
```

```
<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Asn Tyr
            20                  25                  30

Leu Asn Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ser Gly Leu Leu Phe
                85                  90                  95

Thr Phe Gly Gln Gly Thr Lys Val Glu Ile Lys
            100                 105
```

```
<210> SEQ ID NO 141
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gatattcaga tgactcagtc acctagtagc ctgagcgcta gtgtgggcga tagagtgact    60
atcacctgta gagcctctca gtctatcttt aactacctga actggtatca gcagaagccc    120
ggtaaagccc ctaagctgct gatctacgac tctagcaccc tgcagtcagg cgtgccctct    180
aggtttagcg gtagcggtag tggcaccgac ttcaccctga ctatctctag cctgcagccc    240
gaggacttcg ctacctacta ctgtcaccag tatagcggcc tgctgttcac cttcggtcag    300
ggcactaagg tcgagattaa g                                              321
```

```
<210> SEQ ID NO 142
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142
```

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

| | | | | | | | | | | | | |
|---|---|---|---|---|---|---|---|---|---|---|---|---|
|Ala|Ile|His|Trp|Val|Arg|Gln|Ala|Pro|Gly|Lys|Gly|Leu|Glu|Trp|Val|
| | |35| | | |40| | | |45| | | | | |

Ser Thr Ile Gln Ser Ser Gly Glu Asn Lys Phe Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Met Ile Gly Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 143
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 143

```
caggtgcagc tgctggaatc aggcggcgga ctggtgcagc ctggcggtag cctgagactg      60
agctgcgctg ctagtggctt caccttctct agctacgcta ttcactgggt cagacaggcc     120
cctggtaaag gcctggagtg ggtcagcact attcagtcta gcggcgagaa caagttctac     180
gccgatagcg tgaagggccg gttcactatc tctagggata actctaagaa caccctgtac     240
ctgcagatga atagcctgag agccgaggac accgccgtct actactgcgc tagagtgatg     300
atcggctacg gcttcgacta ctggggtcag ggcaccctgg tcaccgtgtc tagcgctagc     360
actaagggcc cctccgtgtt ccctctggcc cttccagca agtctacctc cggcggcaca     420
gctgctctgg gctgcctggt caaggactac ttccctgagc ctgtgacagt gtcctggaac     480
tctggcgccc tgacctctgg cgtgcacacc ttccctgccg tgctgcagtc ctccggcctg     540
tactccctgt cctccgtggt cacagtgcct tcaagcagcc tgggcaccca gacctatatc     600
tgcaacgtga accacaagcc ttccaacacc aaggtggaca gcgggtgga gcctaagtcc     660
tgcgacaaga cccacacctg tcctccctgc cctgctcctg aagctgctgg cggcccttct     720
gtgttcctgt ccctccaaa gcccaaggac accctgatga tctcccggac ccctgaagtg     780
acctgcgtgg tggtggacgt gtcccacgag gatcctgaag tgaagttcaa ttggtacgtg     840
gacggcgtgg aggtgcacaa cgccaagacc aagcctcggg aggaacagta caactccacc     900
taccgggtgg tgtccgtgct gaccgtgctg caccaggact ggctgaacgg caagagtac     960
aagtgcaaag tctccaacaa ggccctgcct gcccctatcg aaaagacaat ctccaaggcc    1020
aagggccagc ctagggaacc ccaggtgtac accctgccac ccagccggga ggaaatgacc    1080
aagaaccagg tgtccctgac ctgtctggtc aagggcttct acccttccga tatcgccgtg    1140
gagtgggagt ctaacggcca gcctgagaac aactacaaga ccaccctcc tgtgctggac    1200
tccgacggct ccttcttcct gtactccaaa ctgaccgtgg acaagtcccg gtggcagcag    1260
ggcaacgtgt tctcctgctc cgtgatgcac gaggccctgc acaaccacta cacccagaag    1320
tccctgtccc tgtctcccgg caag                                         1344
```

<210> SEQ ID NO 144
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Asn Tyr
            20                  25                  30

Leu Asn Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ser Gly Leu Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 145
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gatattcaga tgactcagtc acctagtagc ctgagcgcta gtgtgggcga tagagtgact    60
atcacctgta gagcctctca gtctatcttt aactacctga actggtatca gcagaagccc   120
ggtaaagccc ctaagctgct gatctacgac tctagcaccc tgcagtcagg cgtgccctct   180
aggtttagcg gtagcggtag tggcaccgac ttcaccctga ctatctctag cctgcagccc   240
gaggacttcg ctacctacta ctgtcaccag tatagcggcc tgctgttcac cttcggtcag   300
ggcactaagg tcgagattaa gcgtacggtg gccgctccca gcgtgttcat cttcccccc    360 agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag cacccctgacc  540 ctgagcaagg ccgactacga gaagcataag gtgtacgcct gcgaggtgac ccaccagggc   600
ctgtccagcc ccgtgaccaa gagcttcaac agggcgagt gc                       642

<210> SEQ ID NO 146
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
caggtgcagc tggtgcagtc aggcgccgaa gtgaagaaac ccggctctag cgtgaaagtc    60
agctgtaaag ctagtggcgg caccttcagc accttctcta ttagctgggt cagacaggcc   120
ccaggtcagg gcctggagtg gatgggcgga attatcccta tcttcggcac cgctaactac   180

```
gctcagaaat tcagggtag agtgactatc accgccgacg agtctactag caccgcctat    240
atggaactgt ctagcctgag atcagaggac accgccgtct actactgcgc tagggggcggc  300 tacggcggct attactactt cgactactgg ggtcagggca ccctggtcac cgtgtctagc   360
```

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Arg
            20                  25                  30

Leu Asn Trp Tyr Gln Gln Lys Pro Gly Lys Ala Pro Lys Leu Leu Ile
        35                  40                  45

Tyr Lys Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Val Trp Ser Thr
                85                  90                  95

Thr Phe Gly Gln Gly Thr Lys Val Glu Ile Lys
            100                 105

<210> SEQ ID NO 148
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 148

```
gatattcaga tgactcagtc acctagtagc ctgagcgcta gtgtgggcga tagagtgact    60
atcacctgta gagcctctca gtctatctct aataggctga actggtatca gcagaagccc   120
ggtaaagccc ctaagctgct gatctataag ggctctaccc tgcagtcagg cgtgccctct   180
aggtttagcg gtagcggtag tggcaccgac ttcaccctga ctatctctag cctgcagccc   240
gaggacttcg ctacctacta ctgtcagcag cactacgtgt ggtctactac cttcggtcag   300
ggcactaagg tcgagattaa g                                              321
```

<210> SEQ ID NO 149
<211> LENGTH: 1350
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 149

```
caggtgcagc tggtgcagtc aggcgccgaa gtgaagaaac ccggctctag cgtgaaagtc    60
agctgtaaag ctagtggcgg caccttcagc accttctcta ttagctgggt cagacaggcc   120
ccaggtcagg gcctggagtg gatgggcgga attatcccta tcttcggcac cgctaactac   180
```

```
gctcagaaat tcagggtag agtgactatc accgccgacg agtctactag caccgcctat    240
atggaactgt ctagcctgag atcagaggac accgccgtct actactgcgc taggggcggc    300
tacggcggct attactactt cgactactgg ggtcagggca ccctggtcac cgtgtctagc    360
gctagcacta agggcccctc cgtgttccct ctggccccct tccagcaagtc tacctccggc    420 ggcacagctg ctctgggctg cctggtcaag gactacttcc ctgagcctgt gacagtgtcc    480
tggaactctg gcgccctgac ctctggcgtg cacaccttcc ctgccgtgct gcagtcctcc    540
ggcctgtact ccctgtcctc cgtggtcaca gtgccttcaa gcagcctggg cacccagacc    600
tatatctgca acgtgaacca caagccttcc aacaccaagg tggacaagcg ggtggagcct    660
aagtcctgcg acaagaccca cacctgtcct ccctgccctg ctcctgaagc tgctggcggc    720
ccttctgtgt tcctgttccc tccaaagccc aaggacaccc tgatgatctc ccggacccct    780
gaagtgacct gcgtggtggt ggacgtgtcc cacgaggatc ctgaagtgaa gttcaattgg    840
tacgtggacg gcgtggaggt gcacaacgcc aagaccaagc ctcgggagga acagtacaac    900
tccacctacc gggtggtgtc cgtgctgacc gtgctgcacc aggactggct gaacggcaaa    960
gagtacaagt gcaaagtctc caacaaggcc ctgcctgccc ctatcgaaaa gacaatctcc    1020
aaggccaagg gccagcctag ggaaccccag gtgtacaccc tgccacccag ccgggaggaa    1080
atgaccaaga accaggtgtc cctgacctgt ctggtcaagg gcttctaccc ttccgatatc    1140
gccgtggagt gggagtctaa cggccagcct gagaacaact acaagaccac ccctcctgtg    1200
ctggactccg acggctcctt cttcctgtac tccaaactga ccgtggacaa gtcccggtgg    1260
cagcagggca acgtgttctc ctgctccgtg atgcacgagg ccctgcacaa ccactacacc    1320
cagaagtccc tgtccctgtc tcccggcaag                                    1350
```

<210> SEQ ID NO 150
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Arg
            20                  25                  30

Leu Asn Trp Tyr Gln Gln Lys Pro Gly Lys Ala Pro Lys Leu Leu Ile
        35                  40                  45

Tyr Lys Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Val Trp Ser Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 151
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gatattcaga tgactcagtc acctagtagc ctgagcgcta gtgtgggcga tagagtgact      60
atcacctgta gagcctctca gtctatctct aataggctga actggtatca gcagaagccc     120
ggtaaagccc ctaagctgct gatctataag ggctctaccc tgcagtcagg cgtgccctct     180
aggtttagcg gtagcggtag tggcaccgac ttcaccctga ctatctctag cctgcagccc     240
gaggacttcg ctacctacta ctgtcagcag cactacgtgt ggtctactac cttcggtcag     300
ggcactaagg tcgagattaa gcgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac aggggcgagt gc                       642

<210> SEQ ID NO 152
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
caggtgcaat tggtgcagag cggtgccgaa gtgaaaaaac cgggcagcag cgtgaaagtt      60
agctgcaaag catccggagg gacgttttct actttctcta tctcttgggt gcgccaggcc     120
ccgggccagg gcctcgagtg gatgggcggt atcatcccga tcttcggcac tgcgaactac     180
gcccagaaat ttcagggccg ggtgaccatt accgccgatg aaagcaccag caccgcctat     240
atggaactga gcagcctgcg cagcgaagat acggccgtgt attattgcgc gcgtggtggt     300
tacggtggtt actactactt cgattactgg ggccaaggca ccctggtgac tgttagctca     360

<210> SEQ ID NO 153
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Arg
            20                  25                  30

Leu Asn Trp Tyr Gln Gln Lys Pro Gly Lys Ala Pro Lys Leu Leu Ile
        35                  40                  45

Tyr Lys Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gln Trp Leu Thr
                85                  90                  95

Thr Phe Gly Gln Gly Thr Lys Val Glu Ile Lys
            100                 105
```

<210> SEQ ID NO 154
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154

```
gatatccaga tgacccagag cccgagcagc ctgagcgcca gcgtgggcga tcgcgtgacc    60
attacctgca gagccagcca gtctatttct aaccgtctga actggtacca gcagaaaccg   120
ggcaaagcgc cgaaactatt aatctacaaa ggttctactc tgcaaagcgg cgtgccgagc   180
cgctttagcg gcagcggatc cggcaccgat ttcacccctga ccattagctc tctgcaaccg   240
gaagactttg cgacctatta ttgccagcag cattaccagt ggctgactac ctttggccag   300
ggcacgaaag ttgaaattaa a                                            321
```

<210> SEQ ID NO 155
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155

```
caggtgcaat tggtgcagag cggtgccgaa gtgaaaaaac cgggcagcag cgtgaaagtt    60
agctgcaaag catccggagg gacgttttct actttctcta tctcttgggt gcgccaggcc   120
ccgggccagg gctcgagtg gatgggcggt atcatcccga tcttcggcac tgcgaactac   180
gcccagaaat tcagggccgg ggtgaccatt accgccgatg aaagcaccag caccgcctat   240
atggaactga gcagcctgcg cagcgaagat acggccgtgt attattgcgc gcgtggtggt   300
tacggtggtt actactactt cgattactgg ggccaaggca ccctggtgac tgttagctca   360
gcctccacca agggtccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagag agttgagccc   660
```

-continued

```
aaatcttgtg acaaaactca cacatgccca ccgtgcccag cacctgaagc agcgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gggtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 156
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Asn Arg
            20                  25                  30

Leu Asn Trp Tyr Gln Gln Lys Pro Gly Lys Ala Pro Lys Leu Leu Ile
        35                  40                  45

Tyr Lys Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gln Trp Leu Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 157

<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157

```
gatatccaga tgacccagag cccgagcagc ctgagcgcca gcgtgggcga tcgcgtgacc      60
attacctgca gagccagcca gtctatttct aaccgtctga actggtacca gcagaaaccg     120
ggcaaagcgc cgaaactatt aatctacaaa ggttctactc tgcaaagcgg cgtgccgagc     180
cgctttagcg gcagcggatc cggcaccgat ttcaccctga ccattagctc tctgcaaccg     240
gaagactttg cgacctatta ttgccagcag cattaccagt ggctgactac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg acaacgccc tgcagagcgg caacagccag     480
gaaagcgtca ccgagcagga cagcaaggac tccacctaca gcctgagcag caccctgacc     540
ctgagcaagg ccgactacga aagcacaag gtgtacgcct gcgaggtgac ccaccagggc     600
ctgtccagcc ccgtgaccaa gagcttcaac cggggcgagt gt                       642
```

<210> SEQ ID NO 158
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Asn Ile Ile Pro Ile Thr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
              195                 200                 205
Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 159
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
caggtgcagc tggtgcagtc aggcgccgaa gtgaagaaac ccggctctag cgtgaaagtc      60
agctgtaaag ctagtggcgg caccttctct agctacgcta ttagctgggt cagacaggcc     120
ccaggtcagg gcctggagtg gatgggcaat attatcccta tcaccggtca gacctactac     180
gctcagaaat ttcagggtag agtgactatc accgccgacg agtctactag caccgcctat     240
atggaactgt ctagcctgag atcagaggac accgccgtct actactgcgc tagagccgcc     300
tatcaccccc tggtgttcga taactggggt cagggcaccc tggtcaccgt gtctagcgct     360
agcactaagg gcccctccgt gttccctctg gcccctcca gcaagtctac ctccggcggc     420
acagctgctc tgggctgcct ggtcaaggac tacttccctg agcctgtgac agtgtcctgg     480
aactctggcg ccctgacctc tggcgtgcac accttccctg ccgtgctgca gtcctccggc     540
ctgtactccc tgtcctccgt ggtcacagtg ccttcaagca gcctgggcac ccagacctat     600
```

```
atctgcaacg tgaaccacaa gccttccaac accaaggtgg acaagcgggt ggagcctaag      660
tcctgcgaca gacccacac ctgtcctccc tgccctgctc ctgaagctgc tggcggccct       720
tctgtgttcc tgttccctcc aaagcccaag acaccctga tgatctcccg acccctgaa        780 gtgacctgcg tggtggtgga cgtgtcccac gaggatcctg aagtgaagtt caattggtac      840
gtggacggcg tggaggtgca acgccaag accaagcctc gggaggaaca gtacaactcc        900
acctaccggg tggtgtccgt gctgaccgtg ctgcaccagg actggctgaa cggcaaagag      960
tacaagtgca aagtctccaa caaggccctg cctgcccta tcgaaaagac aatctccaag      1020
gccaagggcc agcctaggga accccaggtg tacaccctgc cacccagccg ggaggaaatg     1080
accaagaacc aggtgtccct gacctgtctg gtcaagggct tctaccttc cgatatcgcc      1140 gtggagtggg agtctaacgg ccagcctgag aacaactaca agaccacccc tcctgtgctg     1200
gactccgacg gctccttctt cctgtactcc aaactgaccg tggacaagtc ccggtggcag     1260
cagggcaacg tgttcctg ctccgtgatg cacgaggccc tgcacaacca ctacacccag       1320
aagtccctgt ccctgtctcc cggcaag                                         1347
```

<210> SEQ ID NO 160
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 161
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

```
cagtcagtcc tgactcagcc ccctagcgct agtggcaccc ctggtcagag agtgactatt      60
agctgtagcg gctctagctc taatatcggt aatcactacg tgaactggta tcagcagctg     120
cccggcaccg cccctaagct gctgatctat agaaacaatc accggcctag cggcgtgccc     180
gataggttta gcggatctaa gtcagggact agcgctagtc tggctattag cggcctgcag     240
tcagaggacg aggccgacta ctactgtcag tcctgggact atagcggctt tagcaccgtg     300
ttcggcggag gcactaagct gaccgtgctg ggtcagccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca caagtacgc cgccagcagc      540 tacctgagcc tgacccccga gcagtggaag agccacaggt cctacagctg ccaggtgacc     600
cacgagggca gcaccgtgga aaagaccgtg gccccaaccg agtgcagc                  648
```

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Gly Ser Ile Ser Thr Gly Ser Tyr
1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Ser Pro Gly Tyr
1               5

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Thr Arg Tyr Trp Met Ser His Ile Leu Ala Tyr Gly Met Asp Tyr
1               5                   10                  15

<210> SEQ ID NO 165
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Ser Ser Asn Ile Gly Asn His Tyr
1               5

<210> SEQ ID NO 166
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Asn Thr
1

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Tyr Asp Gly Ser Gln Ser Ile
1               5

<210> SEQ ID NO 168
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile Trp His Ser Gly Pro Thr Phe Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160
```

```
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Leu Gly Thr Gln Thr Tyr Ile
        195                 200                 205
Cys Asn Val Asn His Lys Pro Ser Asn Thr Lys Val Asp Lys Arg Val
    210                 215                 220
Glu Pro Lys Ser Cys Asp Lys Thr His Thr Cys Pro Pro Cys Pro Ala
225                 230                 235                 240
Pro Glu Ala Ala Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Glu Glu Met Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Lys
    450                 455

<210> SEQ ID NO 169
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gaggtgcaat tgcaagaaag tggtccgggc ctggtgaaac cgggcgaaac cctgagcctg     60
acctgcaccg tttccggagg tagcatttct actggttctt attattggaa ttggattcgc    120
caggcccctg gaagggtctc gagtggatt ggcgagattt ggcattctgg tcctactttt     180
tataatcctt ctcttaagtc tcgggtgacc attagcgttg atacttcgaa aaaccagttt    240
agcctgaaac tgagcagcgt gacggcggcg gatacggccg tgtattattg cgcgcgtact    300
```

```
actcgttatt ggatgtctca tattcttgct tatggtatgg attattgggg ccaaggcacc    360
ctggtgacgg ttagctcagc ctccaccaag ggtccatcgg tcttcccct ggcaccctcc    420 tccaagagca cctctggggg cacagcggcc ctgggctgcc tggtcaagga ctacttcccc    480
gaaccggtga cggtgtcgtg gaactcaggc gccctgacca gcggcgtgca ccctcccg    540 gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagcag cggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgg gtggtcagcg tcctcaccgt cctgcaccag    960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggaggagat gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcatgaggct    1320
ctgcacaacc actacacgca gaagagcctc tccctgtctc cgggtaaa              1368
```

<210> SEQ ID NO 170
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn His
            20                  25                  30

Tyr Val Ser Trp Tyr Gln Gln Leu Pro Gly Thr Ala Pro Lys Leu Leu
        35                  40                  45

Ile Tyr Ala Asn Thr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ser Tyr Asp Gly Ser Gln
                85                  90                  95

Ser Ile Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 171
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

```
gatatcgtgc tgacccagcc gccttcagtg agtggcgcac caggtcagcg tgtgaccatc      60
tcgtgtagcg gcagcagcag caacattggt aatcattatg tgtcttggta ccagcagttg     120
cccgggacgg cgccgaaact tctgatttat gctaatacta agcgtccctc aggcgtgccg     180
gatcgtttta gcggatccaa aagcggcacc agcgcgagcc ttgcgattac gggcctgcaa     240
agcgaagacg aagcggatta ttattgctct tcttatgatg gttctcagtc tattgtgttt     300
ggcggcggca cgaagttaac cgtcctaggt cagcccaagg ctgccccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttca                     645
```

<210> SEQ ID NO 172
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Thr Gly
            20                  25                  30

Ser Tyr Tyr Trp Asn Trp Ile Arg Gln Ala Pro Gly Lys Gly Leu Glu
        35                  40                  45

Trp Ile Gly Glu Ile His Gly His Gly Phe Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Thr Arg Tyr Trp Met Ser His Ile Leu Ala Tyr Gly
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
```

```
        130                 135                 140
Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 173
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
gaggtgcaat tgcaagaaag tggtccgggc ctggtgaaac cgggcgaaac cctgagcctg      60
acctgcaccg tttccggagg tagcattttct actggttctt attattggaa ttggattcgc     120
caggcccctg ggaagggtct cgagtggatt ggcgagattc atggtcatgg ttttactttt      180
```

-continued

```
tataatcctt ctcttaagtc tcgggtgacc attagcgttg atacttcgaa aaaccagttt    240
agcctgaaac tgagcagcgt gacggcggcg gatacggccg tgtattattg cgcgcgtact    300
actcgttatt ggatgtctca tattcttgct tatggtatgg attattgggg ccaaggcacc    360
ctggtgacgg ttagctcagc ctccaccaag ggtccatcgg tcttcccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagcag cgggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgg gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggaggagat gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctacag caagctcacc   1260
gtggacaaga gcaggtggca gcaggggaac gtcttctcat gctccgtgat gcatgaggct   1320
ctgcacaacc actacacgca gaagagcctc tccctgtctc cgggtaaa              1368
```

<210> SEQ ID NO 174
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Ser Trp Tyr Gln Gln Leu Pro Gly Thr Ala Pro Lys Leu Leu
        35                  40                  45

Ile Tyr Ala Asn Thr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ser Tyr Asp Gly Ser Gln
                85                  90                  95

Ser Ile Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
```

```
                  145                 150                 155                 160
Gly Val Glu Thr Thr Thr Pro Ser Lys Gln Ser Asn Asn Lys Tyr Ala
                    165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
        210                 215

<210> SEQ ID NO 175
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
gatatcgtgc tgacccagcc gccttcagtg agtggcgcac caggtcagcg tgtgaccatc      60
tcgtgtagcg gcagcagcag caacattggt aatcattatg tgtcttggta ccagcagttg     120
cccgggacgg cgccgaaact tctgatttat gctaatacta gcgtccctc aggcgtgccg     180 gatcgtttta gcggatccaa aagcggcacc agcgcgagcc ttgcgattac gggcctgcaa     240
agcgaagacg aagcggatta ttattgctct tcttatgatg gttctcagtc tattgtgttt     300
ggcggcggca cgaagttaac cgtcctaggt cagcccaagg ctgccccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc tccaaacaa agcaacaaca gtacgcggc cagcagctat     540 ctgagcctga cgcctgagca gtggaagtcc cacagaagct acagctgcca ggtcacgcat     600
gaagggagca ccgtggagaa gacagtggcc cctacagaat gttca                    645

<210> SEQ ID NO 176
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro His Tyr Gly Phe Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110
```

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 177
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
gaggtgcaat tggttcagtc tggcgcggaa gtgaaaaaac cgggcagcag cgtgaaagtg    60
agctgcaaag cctccggagg cacttttaat tcttatgcta tttcttgggt gcgccaagcc   120

```
cctgggcagg gtctcgagtg gatgggcaat attattcctc attatggttt tgcttattat    180
gctcagaagt ttcagggtcg ggtgaccatt accgcggatg aaagcaccag caccgcgtat    240
atggaactga gcagcctgcg tagcgaagat acggccgtgt attattgcgc gcgtgctgct    300
tatcatcctc ttgttttttga taattggggc caaggcaccc tggtgacggt tagctcagcc    360
tccaccaagg gtccatcggt cttccccctg gcacctcct ccaagagcac ctctgggggc    420
acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagcagc ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccggg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 178
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
```

Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 179
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
gatatcgtgc tgacccagcc gccttcagtg agtggcgcac caggtcagcg tgtgaccatc      60
tcgtgtagcg gcagcagcag caacattggt aatcattatg tgaattggta ccagcagttg     120
cccgggacgg cgccgaaact tctgatttat cgtaataatc atcgtccctc aggcgtgccg     180
gatcgtttta gcggatccaa aagcggcacc agcgcgagcc ttgcgattac gggcctgcaa     240
agcgaagaca agcggattta ttattgccag tcttgggatt attctggttt ttctactgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga cagtggaag tcccacagaa gctacagctg ccaggtcacg     600
catgaaggga gcaccgtgga agagacagtg gcccctacag aatgttca                  648

<210> SEQ ID NO 180
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Asn Ile Ile Pro Tyr Ser Gly Phe Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Tyr His Pro Leu Val Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 181
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181

```
gaggtgcaat tggttcagtc tggcgcggaa gtgaaaaaac cgggcagcag cgtgaaagtg      60
agctgcaaag cctccggagg cacttttaat tcttatgcta tttcttgggt gcgccaagcc     120
cctgggcagg gtctcgagtg gatgggcaat attattcctt attctggttt tgcttattat     180
gctcagaagt tcagggtcg ggtgaccatt accgcggatg aaagcaccag caccgcgtat     240
atggaactga gcagcctgcg tagcgaagat acggccgtgt attattgcgc gcgtgctgct     300
tatcatcctc ttgttttga taattggggc caaggcaccc tggtgacggt tagctcagcc     360
tccaccaagg gtccatcggt cttccccctg gcaccctcct ccaagagcac ctctggggc     420 acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagcagc ggggggaccg     720
tcagtcttcc tcttccccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccggg tggtcagcgt cctcaccgtc ctgcaccagg actggctgaa tggcaaggag     960
tacaagtgca aggtctccaa caaagccctc ccagcccca tcgagaaaac catctccaaa    1020 gccaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 182
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn His
            20                  25                  30

Tyr Val Asn Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Tyr Ser Gly
                85                  90                  95

Phe Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
```

```
                115                 120                 125
Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 183
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

```
gatatcgtgc tgacccagcc gccttcagtg agtggcgcac caggtcagcg tgtgaccatc    60
tcgtgtagcg gcagcagcag caacattggt aatcattatg tgaattggta ccagcagttg   120
cccgggacgg cgccgaaact tctgatttat cgtaataatc atcgtccctc aggcgtgccg   180
gatcgtttta gcggatccaa aagcggcacc agcgcgagcc ttgcgattac gggcctgcaa   240
agcgaagacg aagcggatta ttattgccag tcttgggatt attctggttt ttctactgtg   300
tttggcggcg gcacgaagtt aaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca acaagtacgc ggccagcagc   540
tatctgagcc tgacgcctga gcagtggaag tcccacagaa gctacagctg ccaggtcacg   600
catgaaggga gcaccgtgga agacagtgc ccctacag aatgttca                   648
```

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Gly Gly Ser Ile Ser Thr Gly Ser Tyr
1               5
```

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn His Met Gly Ile

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Thr Thr Arg Tyr Trp Met Ser His Ile Leu Ala Tyr Gly Met Asp Tyr
1               5                   10                  15

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Ser Ser Asn Ile Gly Asn His Tyr
1               5

<210> SEQ ID NO 188
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Asn Thr
1

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Tyr Asp Gly Ser Gln Ser Ile
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Gly Ser Ile Ser Thr Gly Ser Tyr
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Trp His Ser Gly Pro
1               5

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Thr Thr Arg Tyr Trp Met Ser His Ile Leu Ala Tyr Gly Met Asp Tyr
1               5                   10                  15

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Ser Ser Asn Ile Gly Asn His Tyr
1               5

<210> SEQ ID NO 194
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Asn Thr
1

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Tyr Asp Gly Ser Gln Ser Ile
1               5

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Ile His Gly His Gly Phe Thr Phe Tyr Asn Pro Ser Leu Lys Ser
1               5                   10                  15

<210> SEQ ID NO 197

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Gly Ser Ile Ser Thr Gly Ser Tyr
1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

His Gly His Gly Phe
1               5

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Thr Thr Arg Tyr Trp Met Ser His Ile Leu Ala Tyr Gly Met Asp Tyr
1               5                   10                  15

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Ser Ser Asn Ile Gly Asn His Tyr
1               5

<210> SEQ ID NO 201
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Asn Thr
1

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202
```

```
Tyr Asp Gly Ser Gln Ser Ile
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Thr Phe Asn Ser Tyr
1               5

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Pro Ile Tyr Gly Thr
1               5

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Ala Tyr His Pro Leu Val Phe Asp Asn
1               5                   10

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Ser Ser Asn Ile Gly Asn His Tyr
1               5

<210> SEQ ID NO 207
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Asn Asn
1

<210> SEQ ID NO 208
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 208

Trp Asp Tyr Ser Gly Phe Ser Thr
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Thr Phe Asn Ser Tyr
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asn Pro Phe Tyr Ile Gly Glu
1               5

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Ala Tyr His Pro Leu Val Phe Asp Asn
1               5                   10

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Ser Ser Asn Ile Gly Asn His Tyr
1               5

<210> SEQ ID NO 213
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Arg Asn Asn
1
```

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Trp Asp Tyr Ser Gly Phe Ser Thr
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Gly Thr Phe Asn Ser Tyr
1               5

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ile Pro His Tyr Gly Phe
1               5

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Ala Tyr His Pro Leu Val Phe Asp Asn
1               5                   10

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Ser Ser Asn Ile Gly Asn His Tyr
1               5

<210> SEQ ID NO 219
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Arg Asn Asn
1

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Asp Tyr Ser Gly Phe Ser Thr
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Thr Phe Asn Ser Tyr
1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Pro Tyr Ser Gly Phe
1               5

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Ala Tyr His Pro Leu Val Phe Asp Asn
1               5                   10

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Ser Ser Asn Ile Gly Asn His Tyr
1               5

<210> SEQ ID NO 225
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 225

Arg Asn Asn
1

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Trp Asp Tyr Ser Gly Phe Ser Thr
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Gly Thr Phe Asn Ser Tyr
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Asn Pro Phe Tyr Ile Gly Glu
1               5

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Ala Tyr His Pro Leu Val Phe Asp Asn
1               5                   10

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Ser Ser Asn Ile Gly Asn His Tyr
1               5
```

```
<210> SEQ ID NO 231
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Arg Asn Asn
1

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Asp Tyr Ser Gly Phe Ser Thr
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Gly Thr Phe Asn Ser Tyr
1               5

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Pro Met Thr Gly Gln
1               5

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Ala Tyr His Pro Leu Val Phe Asp Asn
1               5                   10

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 236

Ser Ser Ser Asn Ile Gly Asn His Tyr
1               5

<210> SEQ ID NO 237
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Asn Asn
1

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Asp Tyr Ser Gly Phe Ser Thr
1               5

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asn Ile Ile Pro Ile Thr Gly Gln Thr Tyr Tyr Ala Gln Lys Phe Gln
1               5                   10                  15

Gly

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Thr Phe Ser Thr Phe
1               5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ile Pro Ile Phe Gly Thr
1               5

<210> SEQ ID NO 242
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Gly Tyr Gly Gly Tyr Tyr Tyr Phe Asp Tyr
1               5                   10

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Gln Ser Ile Ser Asn Arg
1               5

<210> SEQ ID NO 244
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Lys Gly Ser
1

<210> SEQ ID NO 245
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

His Lys Val Trp Leu Thr
1               5

<210> SEQ ID NO 246
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Thr Phe Ser Thr Phe
1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247
```

```
Ile Pro Ile Phe Gly Thr
1               5

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Gly Tyr Gly Gly Tyr Tyr Tyr Phe Asp Tyr
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ser Gln Ser Ile Ser Asn Arg
1               5

<210> SEQ ID NO 250
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Lys Gly Ser
1

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

His Tyr Val Trp Ser Thr
1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Gly Thr Phe Ser Thr Phe
1               5

<210> SEQ ID NO 253
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 253

Ile Pro Ile Phe Gly Thr
1               5

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Gly Tyr Gly Gly Tyr Tyr Tyr Phe Asp Tyr
1               5                   10

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Gln Ser Ile Ser Asn Arg
1               5

<210> SEQ ID NO 256
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Lys Gly Ser
1

<210> SEQ ID NO 257
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

His Tyr Gln Trp Leu Thr
1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Phe Thr Phe Ser Ser Tyr
1               5

```
<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Ser Ser Gly Glu Asn
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Met Ile Gly Tyr Gly Phe Asp Tyr
1               5

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ser Gln Ser Ile Phe Asn Tyr
1               5

<210> SEQ ID NO 262
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Asp Ser Ser
1

<210> SEQ ID NO 263
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Tyr Ser Gly Leu Leu Phe
1               5

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264
```

-continued

```
Gly Gly Gly Gly Ser Gly Gly Gly Gly Ser Gly Gly Gly Gly Ser
1               5                   10                  15
```

IL-18 BINDING MOLECULES

SEQUENCE LISTING

The instant application contains a Sequence Listing which has been submitted electronically in ASCII format and is hereby incorporated by reference in its entirety. Said ASCII copy, created on Dec. 11, 2013, is named PAT055256-US—NP_SL.txt and is 226,528 bytes in size.

FIELD OF THE INVENTION

The present invention concerns binding molecules, more particularly immunoglobulins such as antibodies or fragments thereof, which bind with the cytokine Interleukin 18 (IL-18) but do not bind IL-18 in complex with the Interleukin 18 binding protein (IL-18BP) endogenous inhibitor. The present invention also concerns polynucleotide encoding said binding molecules, pharmaceutical compositions comprising said binding molecules, methods of treating and/or preventing diseases using said binding molecules and method for detecting and/or measuring the presence and/or amount of IL-18 not bound to IL-18BP. Other aspects, objects and advantages of the present invention will be apparent from the description below.

BACKGROUND OF THE INVENTION

Interleukin-18 (IL-18) was originally described in 1989 as interferon-gamma inducing factor (IGIF). IL-18 is related to the IL-1 family and is structurally related to IL-1β (Okamura H et al. (1995) Nature; 378:88-91). IL-18 is primarily produced by macrophages and T cells as a precursor protein (pro-IL-18) and secreted as an active protein following cleavage by caspase-1 (Dinarello C A et al (1999) J Allergy Clin Immunol; 103:11-24). In normal physiology IL-18, in synergy with IL-12, is associated with induction of cell-mediated immunity following infection with microbial products such as lipopolysaccharide (LPS) (Sareneva T et al (2000) J Immunol; 165(4):1933-8). After stimulation with IL-18, natural killer (NK) cells and T cells release the cytokine interferon gamma (INF-γ) which plays an important role in activating macrophages and other cells. IL-18 has also various functions in addition to an ability to induce interferon gamma. These biological properties include activation of NF-κB, Fas ligand expression, the induction of both CC and CXC chemokines, and increased production of competent human immunodeficiency virus. Due to the ability of IL-18 to induce INF-γ production in T cells and macrophages, it plays an important role in Th1-type immune responses and participates in both innate and acquired immunity.

IL-18 binds with high affinity and signals through the IL-18 receptor (IL-18R), a heteromeric complex of alpha and beta chains encoded by the genes IL18R1 and IL18RAP, respectively (Torigoe K et al (1997) J Biol Chem; 272(41): 25737-42). The bioactivity of IL-18 is negatively regulated by the IL-18 binding protein (IL18BP), a naturally occurring and highly specific inhibitor. This soluble protein forms a complex with free IL-18 preventing its interaction with the IL-18 receptor, thus neutralizing and inhibiting its biological activity (Dinarello C A (2000) Ann Rheum Dis; 59 Suppl 1:i17-20). IL-18BP is a constitutively secreted protein with high affinity binding to IL-18. Alternate mRNA splicing variants of IL-18BP result in four isoforms. The prominent 'a' isoform is present in the serum of healthy humans at 20-fold molar excess compared with IL-18 (Dinarello and Kaplanski (2005) Expert Rev Clin Immunol, 1(4), 619-632).

Apart from its physiological role, IL-18 has been shown to mediate a variety of autoimmune and inflammatory diseases. It has been demonstrated that IL-18 expression is up-regulated in several autoimmune diseases, such as Crohn's disease, psoriasis, rheumatoid arthritis, multiple sclerosis and cardiovascular diseases (Braddock et al. (2004) Expert Opin Biol Ther; 4(6):847-860). IL-18 is also up-regulated in certain inflammatory diseases such as chronic obstructive pulmonary disease (COPD) (Imaoka et al. (2008) Eur Respir; J31:287-297), idiopathic pulmonary fibrosis (IPF) (Kitasato et al. (2004) Am J Resp Cell Mol Biol; 31:619-625), macrophage activation syndrome (MAS) (Dinarello and Kaplanski (2005) Expert Rev Clin Immunol; 1(4): 619-632), adult onset Still's disease (AOSD) (Arlet J B et al. (2006) Ann Rheum Dis 65(12):1596-601) and systemic juvenile idiopathic arthritis (SJIA) (Akashi et al. (1994) Br J Haematol; 87(2):243-50).

Recent studies have shown that high amounts of IL-18 and INF-γ in both inherited and acquired forms of hemophagocytic lymphohistiocytosis (HLH). HLH is characterized by activated lymphocytes and histiocytes secreting high amounts of inflammatory cytokines (Janka G E et al (2007) Eur J Paediatr; 166:95-109) and by impaired function of NK cells and cytotoxic T-cells. Most important, it has been shown that both forms are characterized by dis-regulation of IL-18 (Mazodier et al (2005) Immunobiology 106(10):3483-89).

Developing therapeutic molecules for targets such as IL-18 which are regulated by natural inhibitors can be very challenging. The presence of an increased amount of systemic or local total IL-18 does not always reflect the level of biologically active protein (IL-18 free of IL-18BP). A therapeutic compound binding both free IL-18 and IL-18 in complex to IL-18BP, although potentially capable of neutralizing the activity of IL-18, would be required in higher dose than one which can selectively bind only biologically active free IL-18. Therapeutic compounds which need to be administered in high dose may lead to more pronounced side effects or become immunogenic. High dosages also translate into high production costs.

Therapeutic compounds competing for IL-18 when bound to IL18BP may disturb the delicate balances of free/active IL-18 and IL-18BP bound/inactive IL-18 existing in patients stricken with diseases/disorders characterized by IL-18 dis-regulation.

Finally, investigating diseases characterized by dis-regulation of IL-18 free, in the absence of a diagnostic tool capable of detecting and/or measuring IL-18 free from IL-18BP as component of the total IL-18 would be very difficult.

SUMMARY OF THE INVENTION

In one aspect the present invention therefore provides for a binding molecule that specifically binds IL-18, wherein the binding molecule does not bind the IL-18/IL-18 binding protein (IL-18 BP) complex and wherein the binding molecule is not IL-18BP.

In one embodiment of this aspect, the binding molecule binds to an IL-18 epitope on IL-18 as defined with reference to SEQ ID NO:1, wherein the epitope comprises amino acids Arg140 and Glu152.

In another embodiment of this aspect, the epitope may further comprise any one or more of amino acids Gln92, Pro93, Gly95, Pro143, Glu157 or Glu177.

In yet another embodiment of this aspect, the epitope may further comprise any one or more of amino acids Lys89, Arg94, Met96, Phe138, Ser141, Gly144, His145, Asp146, Gln150 or Leu180.

In another embodiment of this aspect, the binding molecule does not compete with IL-18BP for binding IL-18 when IL-18BP is bound to IL-18.

In another embodiment of this aspect the binding molecule is selected from: an isolated antibody, a fragment of an isolated antibody, a single variable domain antibody, a bi- or multi-specific antibody, a multivalent antibody, a dual variable domain antibody, an immuno-conjugate, a fibronectin molecule, an adnectin, an DARPin, an avimer, an affibody, an anticalin, an affilin, a protein epitope mimetic or combinations thereof.

In another embodiment of this aspect, the binding molecule binds IL-18, wherein IL-18 comprises from amino acid 37 to amino acid 193 of SEQ ID NO:1 or SEQ ID NO:2.

In another embodiment of this aspect, the binding molecule inhibits IL-18-dependent interferon gamma (INF-γ) production.

In another embodiment of this aspect, the binding molecule binds IL-18 with a $K_D$ of 100 pM or less.

In another embodiment of this aspect, the binding molecule according to the invention is an isolated fully human, humanized or chimeric antibody or a fragment thereof, preferably, an isolated fully human antibody.

In another embodiment of this aspect, the binding molecule is an antibody fragment or a single variable domain antibody, preferably a Fab, a Fab', a F(ab')$_2$, a scFv, a dAb or a VHH.

In another embodiment of this aspect, the binding molecule is an isolated bispecific antibody or fragment thereof comprising a first specificity to IL-18 and a second specificity to another polypeptide, e.g. IL-12 or IL-1β.

In yet another embodiment of this aspect, the binding molecule is an isolated antibody comprising a mutated or chemically modified amino acid Fc region, wherein the mutated or chemically modified amino acid Fc region prevents or decreases ADCC activity and/or increase half life when compared with a wild type Fc region. Preferably, the mutated or chemically modified amino acid Fc region is a silent IgG1 Fc region.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable region H-CDR1 comprising SEQ ID NO: 3 or conservative variants thereof and
  ii. a heavy chain variable region H-CDR2 comprising SEQ ID NO: 4 or SEQ ID NO: 9 or SEQ ID NO: 10 or SEQ ID NO: 11 or SEQ ID NO: 12 or SEQ ID NO: 13 or conservative variants thereof and
  iii. a heavy chain variable region H-CDR3 comprising SEQ ID NO: 5 or conservative variants thereof and
  iv. a light chain variable region L-CDR1 comprising SEQ ID NO: 6 or conservative variants thereof and
  v. a light chain variable region L-CDR2 comprising SEQ ID NO: 7 or conservative variants thereof and
  vi. a light chain variable region L-CDR3 comprising SEQ ID NO: 8 or conservative variants thereof.

Preferably, the antibody or fragment thereof comprises a heavy chain variable region H-CDR 2 comprising SEQ ID NO: 9 or SEQ ID NO: 13.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises a light chain variable domain comprising SEQ ID NO: 16 or SEQ ID NO: 20 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable domain comprising SEQ ID NO: 14 or SEQ ID NO: 22 or SEQ ID NO: 25 or SEQ ID NO: 28 or SEQ ID NO: 31 or SEQ ID NO: 34 or conservative variants thereof and a light chain variable domain comprising SEQ ID NO: 16 or conservative variants thereof or
  ii. a heavy chain variable domain comprising SEQ ID NO: 18 or SEQ ID NO: 37 or SEQ ID NO: 40 or conservative variants thereof and a light chain variable domain comprising SEQ ID NO: 20 or conservative variants thereof.

Preferably, the heavy chain variable domain comprises SEQ ID NO: 14 or conservative variants thereof and a light chain variable domain comprises SEQ ID NO: 16 or conservative variants thereof and, optionally, amino acid lysine (Lys; K) in position 30 with reference to SEQ ID NO:14 is replaced by an amino acid selected from asparagine (Asn; N) or serine (Ser; S) or threonine (Thr; T) or alanine (Ala; A) or glutamate (Glu; E) or histidine (His; H) or leucine (Leu; L) or glutamine (Gln; Q) or arginine (Arg; R) or valine (Val; V) or tyrosine (Tyr; Y) or isoleucine (Ile; I).

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises a heavy chain variable domain comprising SEQ ID NO: 18 or conservative variants thereof and a light chain variable domain comprising SEQ ID NO: 20 or conservative variants thereof.

In another embodiment, when the binding molecule of the invention is an isolated antibody which binds IL-18 and does not bind the IL-18/IL-18 binding protein (IL-18 BP) complex, the isolated antibody or a fragment thereof comprises:
  i. a heavy chain comprising SEQ ID NO: 43 or SEQ ID NO: 47 or SEQ ID NO: 50 or SEQ ID NO: 56 or conservative variants thereof and a light chain comprising SEQ ID NO: 45 or conservative variants thereof or
  ii. a heavy chain comprising SEQ ID NO: 53 or SEQ ID NO: 100 or SEQ ID NO: 158 or conservative variants thereof and a light chain comprising SEQ ID NO: 160 or conservative variants thereof.

In another embodiment, when the binding molecule of the invention is an isolated antibody which binds IL-18 and does not bind the IL-18/IL-18 binding protein (IL-18 BP) complex, the isolated antibody or a fragment thereof comprises:
  i. a heavy chain comprising SEQ ID NO: 43 or conservative variants thereof and a light chain comprising SEQ ID NO: 45 or conservative variants thereof or
  ii. a heavy chain comprising SEQ ID NO: 158 or conservative variants thereof and a light chain comprising SEQ ID NO: 160 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable region H-CDR1 comprising SEQ ID NO: 74 or conservative variants thereof and
  ii. a heavy chain variable region H-CDR2 comprising SEQ ID NO: 75 or SEQ ID NO: 76 or SEQ ID NO: 77 or SEQ ID NO: 78 or conservative variants thereof and
  iii. a heavy chain variable region H-CDR3 comprising SEQ ID NO: 79 or conservative variants thereof and iv. a light chain variable region L-CDR1 comprising SEQ ID NO: 80 or conservative variants thereof and
v. a light chain variable region L-CDR2 comprising SEQ ID NO: 81 or conservative variants thereof and
vi. a light chain variable region L-CDR3 comprising SEQ ID NO: 82 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises a light chain variable domain comprising SEQ ID NO: 85 or conservative variants thereof and a heavy chain variable domain comprising SEQ ID NO: 83 or SEQ ID NO: 87 or SEQ ID NO: 90 or SEQ ID NO: 93 or conservative variants thereof.

In another embodiment, when the binding molecule of the invention is an isolated antibody which binds IL-18 and does not bind the IL-18/IL-18 binding protein (IL-18 BP) complex, the isolated antibody comprises a heavy chain comprising SEQ ID NO: 96 or SEQ ID NO: 103 or conservative variants thereof and a light chain comprising SEQ ID NO: 98 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable region H-CDR1 comprising SEQ ID NO: 106 or conservative variants thereof and
  ii. a heavy chain variable region H-CDR2 comprising SEQ ID NO: 107 or SEQ ID NO: 122 or conservative variants thereof and
  iii. a heavy chain variable region H-CDR3 comprising SEQ ID NO: 108 or conservative variants thereof and
  iv. a light chain variable region L-CDR1 comprising SEQ ID NO: 109 or conservative variants thereof and
  v. a light chain variable region L-CDR2 comprising SEQ ID NO: 110 or conservative variants thereof and
  vi. a light chain variable region L-CDR3 comprising SEQ ID NO: 111 or SEQ ID NO: 126 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable region H-CDR1 comprising SEQ ID NO: 106 conservative variants thereof and
  ii. a heavy chain variable region H-CDR2 comprising SEQ ID NO: 107 or conservative variants thereof and
  iii. a heavy chain variable region H-CDR3 comprising SEQ ID NO: 108 or conservative variants thereof and
  iv. a light chain variable region L-CDR1 comprising SEQ ID NO: 109 or conservative variants thereof and
  v. a light chain variable region L-CDR2 comprising SEQ ID NO: 110 or conservative variants thereof and
  vi. a light chain variable region L-CDR3 comprising SEQ ID NO: 111 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable domain comprising SEQ ID NO: 112 or conservative variants thereof and a light chain variable domain comprising SEQ ID NO: 114 or conservative variants thereof or
  ii. a heavy chain variable domain comprising SEQ ID NO: 138 or conservative variants thereof and a light chain variable domain comprising SEQ ID NO: 140 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain comprising SEQ ID NO: 116 or conservative variants thereof and a light chain comprising SEQ ID NO: 118 or conservative variants thereof or
  ii. a heavy chain comprising SEQ ID NO: 142 or conservative variants thereof and a light chain comprising SEQ ID NO: 144 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises:
  i. a heavy chain variable region H-CDR1 comprising SEQ ID NO: 120 or conservative variants thereof and
  ii. a heavy chain variable region H-CDR2 comprising SEQ ID NO: 121 or conservative variants thereof and
  iii. a heavy chain variable region H-CDR3 comprising SEQ ID NO: 123 or conservative variants thereof and
  iv. a light chain variable region L-CDR1 comprising SEQ ID NO: 124 or conservative variants thereof and
  v. a light chain variable region L-CDR2 comprising SEQ ID NO: 125 or conservative variants thereof and
  vi. a light chain variable region L-CDR3 comprising SEQ ID NO: 127 or SEQ ID NO: 128 or SEQ ID NO: 129 or conservative variants thereof.

In another embodiment, when the binding molecule of the invention is an isolated antibody or a fragment thereof which binds IL-18 and does not bind the IL-18/IL-18 binding protein (IL-18 BP) complex, the isolated antibody or a fragment thereof comprises a heavy chain variable domain comprising SEQ ID NO: 130 or conservative variants thereof and a light chain variable domain comprising SEQ ID NO: 132 or SEQ ID NO: 147 or SEQ ID NO: 153 or conservative variants thereof.

In another embodiment, when the binding molecule of the invention is an isolated antibody which binds IL-18 and does not bind the IL-18/IL-18 binding protein (IL-18 BP) complex, the isolated antibody comprises a heavy chain comprising SEQ ID NO: 134 or conservative variants thereof and a light chain comprising SEQ ID NO: 136 or SEQ ID NO: 150 or SEQ ID NO: 156 or conservative variants thereof.

In another aspect, there is provided an isolated polynucleotide encoding the binding molecule according to the invention.

In one embodiment of this later aspect, the isolated polynucleotide according to the invention encodes a heavy chain variable domain, wherein the polynucleotide:
  i. is at least 90% identical to SEQ ID NO: 15 or SEQ ID NO: 19 or SEQ ID NO: 23 or SEQ ID NO: 26 or SEQ ID NO: 29 or SEQ ID NO: 32 or SEQ ID NO: 35 or SEQ ID NO: 38 or SEQ ID NO: 41 or SEQ ID NO: 84 or SEQ ID NO: 88 or SEQ ID NO: 91 or SEQ ID NO: 94 or SEQ ID NO: 113 or SEQ ID NO: 131 or SEQ ID NO: 139 or SEQ ID NO: 146 or SEQ ID NO: 152; or
  ii. comprises SEQ ID NO: 15 or SEQ ID NO: 19 or SEQ ID NO: 23 or SEQ ID NO: 26 or SEQ ID NO: 29 or SEQ ID NO: 32 or SEQ ID NO: 35 or SEQ ID NO: 38 or SEQ ID NO: 41 or SEQ ID NO: 84 or SEQ ID NO: 88 or SEQ ID NO: 91 or SEQ ID NO: 94 or SEQ ID NO: 113 or SEQ ID NO: 131 or SEQ ID NO: 139 or SEQ ID NO: 146 or SEQ ID NO: 152; or iii. consists essentially of SEQ ID NO: 15 or SEQ ID NO: 19 or SEQ ID NO: 23 or SEQ ID NO: 26 or SEQ ID NO: 29 or SEQ ID NO: 32 or SEQ ID NO: 35 or SEQ ID NO: 38 or SEQ ID NO: 41 or SEQ ID NO: 84 or SEQ ID NO: 88 or SEQ ID NO: 91 or SEQ ID NO: 94 or SEQ ID NO: 113 or SEQ ID NO: 131 or SEQ ID NO: 139 or SEQ ID NO: 146 or SEQ ID NO: 152.

In another embodiment of this aspect, the isolated polynucleotide according to the invention encodes a light chain variable domain, wherein the polynucleotide:
i. is at least 90% identical to SEQ ID NO: 17 or SEQ ID NO: 21 or SEQ ID NO: 24 or SEQ ID NO: 27 or SEQ ID NO: 30 or SEQ ID NO: 33 or SEQ ID NO: 36 or SEQ ID NO: 39 or SEQ ID NO: 42 or SEQ ID NO: 86 or SEQ ID NO: 89 or SEQ ID NO: 92 or SEQ ID NO: 95 or SEQ ID NO: 115 or SEQ ID NO: 133 or SEQ ID NO: 141 or SEQ ID NO: 148 or SEQ ID NO: 154; or
ii. comprises SEQ ID NO: 17 or SEQ ID NO: 21 or SEQ ID NO: 24 or SEQ ID NO: 27 or SEQ ID NO: 30 or SEQ ID NO: 33 or SEQ ID NO: 36 or SEQ ID NO: 39 or SEQ ID NO: 42 or SEQ ID NO: 86 or SEQ ID NO: 89 or SEQ ID NO: 92 or SEQ ID NO: 95 or SEQ ID NO: 115 or SEQ ID NO: 133 or SEQ ID NO: 141 or SEQ ID NO: 148 or SEQ ID NO: 154; or
iii. consists essentially of SEQ ID NO: 17 or SEQ ID NO: 21 or SEQ ID NO: 24 or SEQ ID NO: 27 or SEQ ID NO: 30 or SEQ ID NO: 33 or SEQ ID NO: 36 or SEQ ID NO: 39 or SEQ ID NO: 42 or SEQ ID NO: 86 or SEQ ID NO: 89 or SEQ ID NO: 92 or SEQ ID NO: 95 or SEQ ID NO: 115 or SEQ ID NO: 133 or SEQ ID NO: 141 or SEQ ID NO: 148 or SEQ ID NO: 154.

In another embodiment of this aspect, the isolated polynucleotide according to the invention encodes a heavy chain, wherein the polynucleotide:
i. is at least 90% identical to SEQ ID NO: 44 or SEQ ID NO: 48 or SEQ ID NO: 51 or SEQ ID NO: 54 or SEQ ID NO: 57 or SEQ ID NO: 97 or SEQ ID NO: 101 or SEQ ID NO: 104 or SEQ ID NO: 117 or SEQ ID NO: 135 or SEQ ID NO: 143 or SEQ ID NO: 149 or SEQ ID NO: 155 or SEQ ID NO: 159; or
ii. comprises SEQ ID NO: 44 or SEQ ID NO: 48 or SEQ ID NO: 51 or SEQ ID NO: 54 or SEQ ID NO: 57 or SEQ ID NO: 97 or SEQ ID NO: 101 or SEQ ID NO: 104 or SEQ ID NO: 117 or SEQ ID NO: 135 or SEQ ID NO: 143 or SEQ ID NO: 149 or SEQ ID NO: 155 or SEQ ID NO: 159; or
iii. consists essentially of SEQ ID NO: 44 or SEQ ID NO: 48 or SEQ ID NO: 51 or SEQ ID NO: 54 or SEQ ID NO: 57 or SEQ ID NO: 97 or SEQ ID NO: 101 or SEQ ID NO: 104 or SEQ ID NO: 117 or SEQ ID NO: 135 or SEQ ID NO: 143 or SEQ ID NO: 149 or SEQ ID NO: 155 or SEQ ID NO: 159.

In another embodiment of this aspect, the isolated polynucleotide according to the invention encodes a light chain, wherein the polynucleotide:
i. is at least 90% identical to SEQ ID NO: 46 or SEQ ID NO: 49 or SEQ ID NO: 52 or SEQ ID NO: 55 or SEQ ID NO: 58 or SEQ ID NO: 99 or SEQ ID NO: 102 or SEQ ID NO: 105 or SEQ ID NO: 119 or SEQ ID NO: 137 or SEQ ID NO: 145 or SEQ ID NO: 151 or SEQ ID NO: 157 or SEQ ID NO: 161; or
ii. comprises SEQ ID NO: 46 or SEQ ID NO: 49 or SEQ ID NO: 52 or SEQ ID NO: 55 or SEQ ID NO: 58 or SEQ ID NO: 99 or SEQ ID NO: 102 or SEQ ID NO: 105 or SEQ ID NO: 119 or SEQ ID NO: 137 or SEQ ID NO: 145 or SEQ ID NO: 151 or SEQ ID NO: 157 or SEQ ID NO: 161; or
iii. consists essentially of SEQ ID NO: 46 or SEQ ID NO: 49 or SEQ ID NO: 52 or SEQ ID NO: 55 or SEQ ID NO: 58 or SEQ ID NO: 99 or SEQ ID NO: 102 or SEQ ID NO: 105 or SEQ ID NO: 119 or SEQ ID NO: 137 or SEQ ID NO: 145 or SEQ ID NO: 151 or SEQ ID NO: 157 or SEQ ID NO: 161.

In another aspect of this aspect, it is provided a cloning or expression vector comprising one or more polynucleotides as claimed herein.

In one embodiment, the cloning or expression vector according to the invention comprises at least one polynucleotide selected from the group of SEQ ID NO: 44 or SEQ ID NO: 48 or SEQ ID NO: 51 or SEQ ID NO: 54 or SEQ ID NO: 57 or SEQ ID NO: 101 or SEQ ID NO: 159 or SEQ ID NO: 97 or SEQ ID NO: 104 or SEQ ID NO: 117 or SEQ ID NO: 143 or SEQ ID NO: 135 or SEQ ID NO: 149 or SEQ ID NO: 155 or SEQ ID NO: 46 or SEQ ID NO: 49 or SEQ ID NO: 52 or SEQ ID NO: 55 or SEQ ID NO: 58 or SEQ ID NO: 102 or SEQ ID NO: 161 or SEQ ID NO: 99 or SEQ ID NO: 105 or SEQ ID NO: 119 or SEQ ID NO: 145 or SEQ ID NO: 137 or SEQ ID NO: 151 or SEQ ID NO: 157.

The present invention further provides for a host cell comprising one or more cloning or expression vectors as claimed herein.

In another aspect of the present invention there is provided a stably transformed or transfected host cell comprising one or more polynucleotides as claimed herein.

The present invention further provides for a method of producing a binding molecule, which method comprises culturing a host cell as claimed herein under conditions suitable for producing the binding molecule.

In another aspect the present invention further provides for a pharmaceutical composition comprising a pharmaceutical carrier and the binding molecule or the isolated antibody or a fragment thereof which binds IL-18 and does not bind the IL-18/IL-18 binding protein (IL-18 BP) complex and wherein the binding molecule is not IL-18BP.

Preferably, the pharmaceutical composition according to the invention is in intravenously, inhalable or sub-cutaneously administrable form.

The present invention further provide for a binding molecule which binds IL-18 and does not bind the IL-18/IL-18 binding protein (IL-18 BP) complex and wherein the binding molecule is not IL-18BP or the pharmaceutical composition comprising that binding molecule for use in therapy.

In another aspect of the present invention there is provided a binding molecule which binds IL-18 and does not bind the IL-18/IL-18 binding protein (IL-18 BP) complex and wherein the binding molecule is not IL-18BP or the pharmaceutical composition comprising that binding molecule for use in treating and/or preventing sarcoidosis, in particular pulmonary sarcoidosis, hemophagocytic lymphohistiocytosis (HLH), familial hemophagocytic lymphohistiocytosis (FHL) and other immunodeficiency syndromes, Giant Cell Arthritis (GCA), chronic obstructive pulmonary disease (COPD), adult onset Still's Disease (AOSD), systemic juvenile idiopathic arthritis (SJIA), severe asthma, Uveitis, Geographic Atrophy, diabetes type 1, diabetes type 2 or atherosclerosis and any combination thereof in a mammalian patient.

In another aspect of the present invention there is provided a method of treating and/or preventing sarcoidosis, in particular pulmonary sarcoidosis, hemophagocytic lymphohistiocytosis (HLH), familial hemophagocytic lymphohistiocytosis (FHL) and other immunodeficiency syndromes, Giant Cell Arthritis (GCA), chronic obstructive pulmonary disease (COPD), adult onset Still's Disease (AOSD), systemic juvenile idiopathic arthritis (SJIA), severe asthma, Uveitis, Geographic Atrophy, diabetes type 1, diabetes type 2 or atherosclerosis and any combination thereof in a mammalian patient which method comprises administrating to the mammalian patient a therapeutically effective amount of a binding molecule which binds IL-18 and does not bind the IL-18/IL-18 binding protein (IL-18 BP) complex and wherein the binding molecule is not IL-18BP or the pharmaceutical composition comprising that binding molecule.

In yet another aspect of the present invention there is provided the use of the binding molecule which binds IL-18 and does not bind the IL-18/IL-18 binding protein (IL-18 BP) complex and wherein the binding molecule is not IL-18BP or the pharmaceutical composition comprising that binding molecule in the manufacture of a medicament for treating and/or preventing sarcoidosis, in particular pulmonary sarcoidosis, hemophagocytic lymphohistiocytosis (HLH), familial hemophagocytic lymphohistiocytosis (FHL) and other immunodeficiency syndromes, Giant Cell Arthritis (GCA), chronic obstructive pulmonary disease (COPD), adult onset Still's Disease (AOSD), systemic juvenile idiopathic arthritis (SJIA), severe asthma, Uveitis, Geographic Atrophy, diabetes type 1, diabetes type 2 or atherosclerosis and any combination thereof in a mammalian patient.

In one embodiment according to the use of the present invention, the mammalian patient is a human patient.

In another aspect, there is provided for a complex comprising IL-18 and a binding molecule which binds IL-18 and does not bind the IL-18/IL-18 binding protein (IL-18 BP) complex and wherein the binding molecule is not IL-18BP according to the invention.

In another aspect, the invention provides for a binding molecule or isolated antibody or a fragment thereof which binds IL-18 and does not bind the IL-18/IL-18 binding protein (IL-18 BP) complex and wherein the binding molecule is not IL-18BP for use in diagnosis or for use in a diagnostic kit.

In yet another aspect, the present invention provides for a binding molecule or isolated antibody or a fragment thereof which binds IL-18 and does not bind the IL-18/IL-18 binding protein (IL-18 BP) complex and wherein the binding molecule is not IL-18BP for use in diagnosis or for use in detecting and/or measuring the presence and/or the amount of free IL-18 (i.e. IL-18 not bound to IL-18BP) in a sample.

In yet a further aspect of the present invention, there is provided a method for detecting and/or measuring the presence and/or amount of free IL-18 (i.e. IL-18 not bound to IL-18BP) in a sample, wherein the sample is optionally a human sample, wherein the method comprises contacting the sample with the binding molecule or the isolated antibody or a fragment thereof which binds IL-18 and does not bind the IL-18/IL-18 binding protein (IL-18 BP) complex and wherein the binding molecule is not IL-18BP.

In one embodiment of this aspect, the sample is human blood.

In another aspect, the present invention further provides for a diagnostic kit comprising the binding molecule or isolated antibody or a fragment thereof which binds IL-18 and does not bind the IL-18/IL-18 binding protein (IL-18 BP) complex and wherein the binding molecule is not IL-18BP and/or the complex comprising IL-18 and that binding molecule wherein the kit optionally comprises a first control compound.

In one embodiment of this aspect, the first control compound is free IL-18 and the kit optionally comprises a second control compound which is murine antibody 125-2H.

In another aspect of the present invention, there is provided a medical or diagnostic device comprising the binding molecule or the isolated antibody or a fragment thereof which binds IL-18 and does not bind the IL-18/IL-18 binding protein (IL-18 BP) complex and wherein the binding molecule is not IL-18BP and/or the complex comprising IL-18 and that binding molecule.

BRIEF DESCRIPTION OF THE DRAWINGS

FIG. 1: CDRs of the heavy chains variable regions of the antibodies exemplified herein.

FIG. 2: CDRs of the light chains variable regions of the antibodies exemplified herein.

FIG. 10: Epitope binning for anti-IL-18 antibodies MOR8775, MOR8776 (A)) and for antibodies MOR9464, MOR9464_N30K, MOR10222_N30S_M54I and MOR14431 (B) Black cell fillings indicate antibodies competing for a similar epitope, whilst no cell filling indicates no competition.

FIG. 12: Comparisons of the relevant amino acids bound on IL-18. 1) Sequence of IL-18 with reference to SEQ ID NO:1 from amino acids 37 to 193. 2) from Kim et al., (2000) Proc Natl Acad Sci; 97(3):1190-1195 (modelling of IL-18BP and its complex with human IL-18) (reference discloses residues 146-149 of SEQ ID NO: 1). 3) from Krumm et al., (2008) Proc Natl Acad Sci; 2008 105(52): 20711-2071552, Table 1 (reference discloses residues 87-91 and 93-98 of SEQ ID NO: 1). 4) from Kato et al., (-2003) Nature Struct. Biol. 2003; 10(11): 966-971; residues involved in IL-18Rα binding. 5) H/DxMS results for MOR9464 bound to IL-18 (reference discloses residues 87-99 and 119-160 of SEQ ID NO: 1).

FIG. 14: (A) sequence alignment of the sequences of mature human and cynomolgus IL-18 (from amino acid 37 to 193 of SEQ ID NOs: 1 and 2, respectively); (B) Space-filling representation of the 6 amino acids which differ across the two species. E177 is the only one present in the antibody complex interface. IL-18 is shown in Cα trace and solvent accessible surface and MOR9464_N30K is shown in cartoon representation.

FIG. 15: Ribbon representation of the IL18/MOR9464_N30K complex superposed onto the model of the IL-18/IL-18Rα complex created on the structure of the IL-1β/IL-1R complex. IL-18Rα structure is shown with a surface representation and the MOR9464_N30K heavy and light chains are in dark and light grey respectively.

DETAILED DESCRIPTION OF THE INVENTION

1. Definitions

Figure 3B:
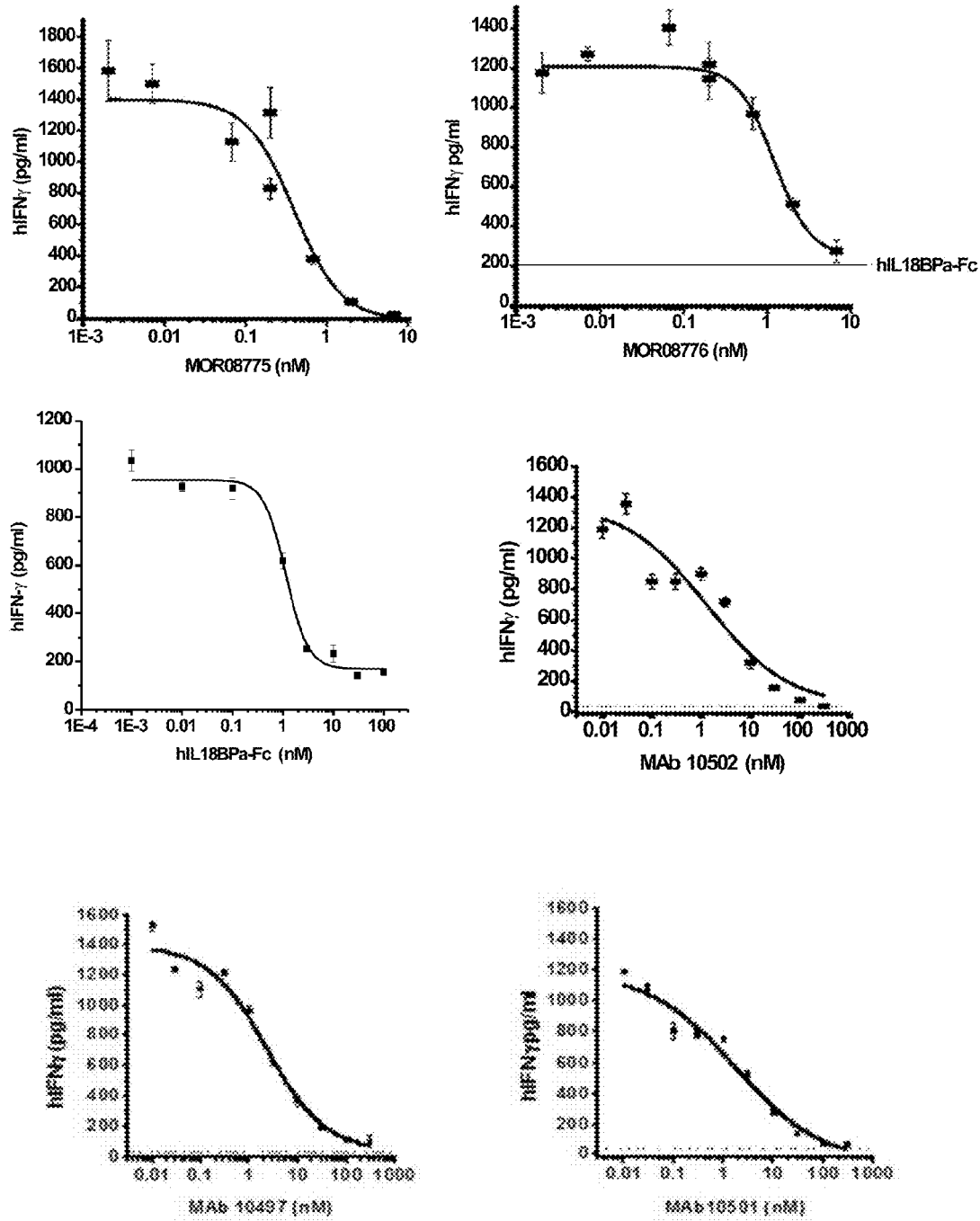
FIG. 3 (A-D): Effect of the anti-IL-18 antibodies and fragments thereof of the present invention on IFN-γ release from PBMCs induced by LPS/IL-12 (stimulation by native IL-18). Data shows concentration-dependent inhibition of native IL-18-induced IFN-γ release from freshly isolated human PBMCs from individual donors, where each data point represents mean±SEM from n=4 wells. Native IL-18 was stimulated by LPS/IL-12 treatment and the dotted line represents the extent of IL-18-dependency, as determined by maximal efficacy of human IL-18BPa-Fc.

For purposes of interpreting this specification, the following definitions will apply and whenever appropriate, terms used in the singular will also include the plural and vice versa. Additional definitions are set forth throughout the detailed description.

The term "IL-18" is synonym to IL-18 polypeptide, Interleukin-18 polypeptide, IFN-gamma-inducing factor or Interferon-gamma-inducing-factor or INF-γ inducing factor. The term "IL-18" refers to human IL-18 comprising amino acids 37 to 193 of SEQ ID NO: 1. Throughout this specification, the term IL-18 encompasses both pro-IL-18 (precursor of mature IL-18 prior protease cleavage) and mature IL-18 (post protease cleavage) interchangeably unless it is specified that the pro- or mature form is meant.

The term cm IL-18 refers to cynomolgus monkey IL-18 comprising amino acids 37 to 193 of SEQ ID NO:2.

The term "antibody" refers to an intact immunoglobulin or a functional fragment thereof. Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 ad CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chain includes kappa chains and lambda chains. The heavy and light chain variable region is typically responsible for antigen recognition, whilst the heavy and light chain constant region may mediate the binding of the immunoglobulin to host tissues or factors, including various cells of the immune system (e.g., effector cells) and the first component (Clq) of the classical complement system. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "antigen-binding portion" of an antibody (or simply "antigen portion"), as used herein, refers to full length or one or more fragments of an antibody that retain the ability to specifically bind to IL-18. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989)

Nature; 341:544-546), which consists of a VH domain; and an isolated complementarity determining region (CDR).

Furthermore, although the two domains of the Fv fragment, VL and VH, are coded for by separate genes, they can be joined, using recombinant methods, by a flexible linker that enables them to be made as a single protein chain in which the VL and VH regions pair to form monovalent molecules (known as single chain Fv (scFv); see e.g., Bird et al., (1988) Science 242:423-426; and Huston et al., (1988) Proc Natl Acad Sc; 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

The term "isolated" means throughout this specification, that the immunoglobulin, antibody or polynucleotide, as the case may be, exists in a physical milieu distinct from that in which it may occur in nature.

An isolated antibody that specifically binds the IL18 polypeptide may, however, have cross-reactivity to other antigens, such as IL18 from other species (e.g. cynomolgus monkey (cm) IL-18). Moreover, an isolated antibody may be substantially free of other cellular material and/or chemicals.

Throughout this specification, complementarity determining regions ("CDR") are defined according to the Kabat definition unless specified that the CDR are defined according to the Chothia definition or by both definitions together. The Kabat definition is a standard for numbering the residues in an antibody and it is typically used to identify CDR regions (Kabat et al., (1991), 5th edition, NIH publication No. 91-3242). The Chothia definition is similar to the Kabat definition but it takes into account positions of certain structural loops (Chothia et al., (1987) J. Mol. Biol., 196:901-17; Al-Lazikani et al., (1997) J. Mol. Biol. 273:927-948).

By convention, the CDR regions in the heavy chain are typically referred to as H-CDR1, H-CDR2 and H-CDR3 and in the light chain as L-CDR1, LCDR2 and L-CDR3. They are numbered sequentially in the direction from the amino terminus to the carboxy terminus.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al., (2000) Mol Biol; 296:57-86).

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The phrases "an antibody recognizing an antigen" and "an antibody specific for an antigen" are used interchangeably herein with the term "an antibody which binds specifically to an antigen".

As used herein, a binding molecule that "specifically binds to IL-18" is intended to refer to a binding molecule that binds to human IL-18 with a $K_D$ of a 100 nM or less, 10 nM or less, 1 nM or less.

A binding molecule that "cross-reacts with an antigen other than IL-18 is intended to refer to a binding molecule that binds that antigen with a $K_D$ of a 100 nM or less, 10 nM or less, 1 nM or less. A binding molecule that "does not cross-react with a particular antigen" is intended to refer to a binding molecule that exhibits essentially undetectable binding against these proteins in standard binding assays.

As used herein, the term "antagonist" is intended to refer to a binding molecule that inhibits IL-18 dependent signalling activity in the presence of IL-18 in a human cell assay such as IL-18 dependent Interferon-gamma (IFN-γ) production assay in human blood cells. Examples of an IL-18 dependent IFN-γ production assay in human blood cells are described in more details in the examples below.

As used herein, an antibody with "no agonistic activity" is intended to refer to a binding molecule that does not significantly increase IL-18 dependent signalling activity in the absence and/or presence of IL-18 in a cell-based assay, such as human blood cells IFN-γ production assay. Such assays are described in more details in the examples below.

The term "$K_{assoc}$" or "$K_a$", as used herein, is intended to refer to the association rate of a particular binding molecule-antigen interaction, whereas the term "$K_{dis}$" or "$K_d$," as used herein, is intended to refer to the dissociation rate of a particular binding molecule-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, such as a Biacore® system.

As used herein, the term "affinity" refers to the strength of interaction between binding molecule and antigen at single antigenic sites.

As used herein, the term "high affinity" for an antibody refers to an antibody having a $K_D$ of 1 nM or less for a target antigen.

As used herein, the term "subject" includes any human or non-human animal.

The term "non-human animal" includes all vertebrates, e.g., mammals and non-mammals, such as non-human primates, sheep, dogs, cats, horses, cows, chickens, amphibians, reptiles, etc.

As used herein, the term, "optimized nucleotide sequence" means that the nucleotide sequence has been altered to encode an amino acid sequence using codons that are preferred in the production cell or organism, generally a eukaryotic cell, for example, a cell of *Pichia pastoris*, a Chinese Hamster Ovary cell (CHO) or a human cell. The optimized nucleotide sequence is engineered to retain completely the amino acid sequence originally encoded by the starting nucleotide sequence, which is also known as the "parental" sequence. The optimized sequences herein have been engineered to have codons that are preferred in CHO mammalian cells; however optimized expression of these sequences in other eukaryotic cells is also envisioned herein.

The term "identity" refers to the similarity between at least two different sequences. This identity can be expressed as a percent identity and determined by standard alignment algorithms, for example, the Basic Local Alignment Tool (BLAST) (Altshul et al., (1990) J Mol Biol; 215:403-410); the algorithm of Needleman et al., (1970) J Mol Biol; 48:444-453 or the algorithm of Meyers et al., (1988) Comput Appl Biosci; 4:11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller, (1989) CABIOS; 4(1):1-17 which has been incorporated into the ALIGN program (version 2.0), using a PAM 120 weight residue table, a gap length penalty of 12 and a gap penalty of 4. The percent identity is usually calculated by comparing sequences of similar length.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term "neutralises" and grammatical variations thereof means throughout this specification, that the biological activity of the target is reduced either totally or partially in the presence of the binding protein or antibody, as the case may be.

The term "nucleic acid" or "polynucleotide" refers to deoxyribonucleic acid (DNA) or ribonucleic acid (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994))

The nucleotide in the "polynucleotide" or "nucleic acid" may comprise modifications including base modifications such as bromouridine and inosine derivatives, ribose modification such as phosphorothioate, phosphorodithioate, phosphoroselenoate, phosphorodiselenoate, phosphoroanilothioate, phosphoraniladate and phosphoroamidate.

The term "vector" means any molecule or entity (e.g. nucleic acid, plasmid, bacteriophage or virus) that is suitable for transformation or transfection of a host cell and contains nucleic acid sequences that direct and/or control (in conjunction with the host cell) expression of one or more heterologous coding regions operatively linked thereto.

A "conservative variant" of a sequence encoding a binding molecule, an antibody or a fragment thereof refers to a sequence comprising conservative amino acid modifications. "Conservative amino acid modifications" are intended to refer to amino acid modifications that do not significantly affect or alter the binding characteristics of the antibody containing the amino acid sequence. Such conservative modifications include amino acid substitutions, additions and deletions. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Modifications can be introduced into a binding protein of the invention by standard techniques known in the art, such as site-directed mutagenesis and PCR-mediated mutagenesis. Conservative amino acid substitution can also encompass non-naturally occurring amino acid residues which are typically incorporated by chemical peptide synthesis rather than by synthesis in biological systems. Non-naturally occurring amino acids include, but are not limited to, peptidomimetic, reversed or inverted forms of amino acid moieties.

The term "epitope" is the part of an antigen that is recognized by the immune system, such as an antibody or a fragment thereof. Within the present specification, the term "epitope" is used interchangeably for both conformational epitopes and linear epitopes. A conformational epitope is composed of discontinuous sections of the antigen's amino acid sequence, whilst a linear epitope is formed by a continuous sequence of amino acids from the antigen.

The term "treat", "treating", "treatment", "prevent", "preventing" or "prevention" includes therapeutic treatments, prophylactic treatments and applications in which one reduces the risk that a subject will develop a disorder or other risk factor. Treatment does not require the complete curing of a disorder and encompasses the reduction of the symptoms or underlying risk factors.

2. Binding Molecules

The term "binding molecule" as used herein means any protein or peptide that binds specifically to the IL-18 polypeptide. "Binding molecule" includes, but it is not limited to, antibodies and fragments thereof, such as immunologically functional fragments. The term "immunologically functional fragment" of an antibody or immunoglobulin chain as used herein is a species of binding protein comprising a portion (regardless of how that portion is obtained or synthesized) of an antibody that lacks at least some of the amino acids present in a full-length chain but which is still capable of specifically binding the IL-18 polypeptide. Such fragments are biologically active in that they bind the IL-18 polypeptide. "Binding molecule" refers to proteins which specifically bind the IL-18 polypeptide and which might additionally neutralize the interaction of the IL-18 polypeptide with the IL-18 receptor.

The term "binding molecule" as used herein also excludes the naturally occurring IL-18 binding protein and the isolated IL-18BP, for instance as described in WO2001/085201.

The binding molecule of the present invention specifically binds IL-18, wherein the binding molecule does not bind the IL-18/IL-18 binding protein (IL-18 BP) complex and wherein the binding molecule is not IL-18BP.

As used herein, the term "does not bind the IL-18/IL-18 binding protein (IL-18 BP) complex" is intended to refer to a binding molecule that binds to the IL-18/IL-18 binding protein (IL-18 BP) complex with a $K_D$ of $1 \times 10^{-5}$M or greater.

One way to assess whether a binding molecule binds IL-18 but does not bind the IL-18/IL-18 binding protein (IL-18 BP) complex is described herein in the Exemplification, section 9.

In another aspect of the present invention, the binding molecule specifically binds IL-18, wherein the binding molecule does not compete with IL-18 binding protein (IL-18 BP) for binding to IL-18 when IL-18BP is bound to IL-18.

The terms "compete", "competing" and "cross-compete" and grammatical variations thereof are used interchangeably herein to mean the ability of a binding molecule to compete with the IL-18BP for binding IL-18 when the IL-18BP is already bound to IL-18. The binding molecules of the invention, such as an antibody or a fragment thereof do not compete in this sense. Competition between binding molecules is determined by an assay in which the binding molecule is tested for specific binding to IL-18 when IL-18 is bound to IL-18BP. For the avoidance of any doubt, if a binding molecule can displace IL18 from an IL-18/IL-18BP complex, then that binding molecule competes with the IL-18 BP for binding IL-18.

The binding molecule according to the invention is not IL-18BP, either isolated or naturally occurring IL-18BP.

The binding molecule may be selected from the following scaffolds: an antibody, a fragment of an antibody, a single variable domain antibody, a bi- or multi-specific antibody, a multivalent antibody, a dual variable domain antibody, an immuno-conjugate, a fibronectin molecule, an adnectin, a DARPin, an avimer, an affibody, an anticalin, an affilin, a protein epitope mimetic or combinations thereof and as described herein below.

Preferably the IL-18 comprises from amino acid 37 to amino acid 193 of SEQ ID NO:1 (human IL-18) or SEQ ID NO:2 (cynomolgus monkey IL-18).

IL-18BP structure is characterized by a single Ig-like domain and resembles the extracellular segment of cytokine receptors with Ig-like structures. Human IL-18BP has been identified in four different isoforms. IL-18BP isoform a (IL-18BPa) exhibited the greatest affinity for IL-18 with a rapid on-rate, a slow off-rate, and a dissociation constant ($K_D$) of 399 pM. IL-18BP isoform c (IL-18BPc) shares the Ig domain of IL-18BPa except for the last 29 amino acids at the C-terminus. The $K_D$ of IL-18BPc is 10-fold less (2.94 nM) than IL-18BPa. Nevertheless, IL-18BPa and IL-18BPc neutralize IL-18>95% at a molar excess of two. IL-18BP isoforms b and d lack a complete Ig domain and lack the ability to bind or neutralize IL-18. Murine IL-18BP is known in two isoforms, c and d isoforms, possessing identical Ig domains and also neutralizing >95% murine IL-18 at a molar excess of two. However, murine IL-18BPd, which shares a common C-terminal motif with human IL-18BPa, also neutralizes human IL-18 (Kim et al. (2000) Proc Natl Acad Sci, 97(3):1190-1195).

Throughout this specification, the term "IL-18BP" refers to human, murine or viral IL-18 binding proteins in every isoform, whether naturally occurring, isolated or engineered such as the IL-18BP disclosed in WO2001/085201 which describes analogues of IL-18BP ("muteins") wherein one or more amino acids are inserted, replaced by different conservative substitutions or deleted, IL-18BP fused protein (e.g. fused protein of an IL-18BP and an immunoglobulin heavy chain region or Fc) and functional derivatives such as PEGylated IL-18BP.

In one embodiment, the binding molecule according to the invention, which binds IL-18 and does not bind the IL-18/IL-18 binding protein (IL-18 BP) complex and wherein the binding molecule is not IL-18BP, wherein the binding molecule binds with an IL-18 epitope on IL-18 as defined with reference to SEQ ID NO:1, wherein the epitope:
  a. is comprised within the following amino acids of IL-18 as defined with reference to SEQ ID NO:1:
    i. amino acids 41 and 42 and amino acids 87 to 97; or
    ii. amino acids 138 to 160; or
    iii. amino acids 177 to 181; or
    iv. amino acids 41 and 42, amino acids 87 to 97, amino acids 138 to 160 and amino acids 177 to 181; or
    v. amino acids 41, 42, 87; 89; 90; or
    vi. amino acids 93, 94; 95, 96; or
    vii. amino acids 140; 141; 150; 177; or
    viii. amino acids 92; 93; 94; 138; 140; 152; 157; or
    ix. amino acids 142; 143; 150; 152; or
    x. amino acids 143; 144; 145; 177; 180; or
    xi. amino acids 41, 42, 87; 89; 90; 93, 94; 95, 96; 140; 141; 150; 177; or
    xii. amino acids 92; 93; 94; 138; 140; 142; 143; 144; 145; 150; 152; 157; 177; 180; or
    xiii. amino acids 41; 42, 87; 89; 90; 92; 93, 94; 95, 96; 138; 140; 141; 142; 143; 144; 145; 150; 152; 157; 177; 180; or
  b. comprises of at least one, two, three, four of the amino acids as defined in any one of the groups (i) to (xiii) listed in a); or
  c. comprises the amino acids as defined in any one of the groups (iv) to (xii) listed in a).

In another embodiment, the binding molecule according to the invention, which binds IL-18 and does not bind the IL-18/IL-18 binding protein (IL-18 BP) complex and wherein the binding molecule is not IL-18BP, wherein the binding molecule binds with an IL-18 epitope on IL-18 as defined with reference to SEQ ID NO:1, wherein the epitope comprises amino acids Arg140 and Glu152. In one embodiment the epitope further comprises any one or more of amino acids Gln92, Pro93, Gly95, Pro143, Glu157 or Glu177. In another embodiment the epitope further comprises any one or more of amino acids Lys89, Arg94, Met96, Phe138, Ser141, Gly144, His145, Asp146, Gln150 or Leu180.

In one embodiment of the present invention, the binding molecule specifically binds IL-18, wherein the binding molecule does not bind the IL-18/IL-18 binding protein isoform a or isoform c (IL-18 BPa or IL-18BPc) complex, wherein the binding molecule is selected from: an antibody, a fragment of an antibody, a single variable domain antibody, a bi- or multi-specific antibody, a multivalent antibody, a dual variable domain antibody, an immuno-conjugate, a fibronectin molecule, an adnectin, a DARPin, an avimer, an affibody, an anticalin, an affilin, a protein epitope mimetic or combinations thereof. Preferably the IL-18 comprises from amino acid 37 to amino acid 193 of SEQ ID NO:1 (human IL-18) or SEQ ID NO:2 (cynomolgus monkey IL-18). More preferably the binding molecule is an antibody or a fragment thereof.

In another embodiment, the binding molecule according to the invention, which binds IL-18 and does not bind the IL-18/IL-18 binding protein isoform a or isoform c (IL-18 BPa or IL-18BPc) complex and wherein the binding molecule is not IL-18BP, wherein the binding molecule binds with an IL-18 epitope on IL-18 as defined with reference to SEQ ID NO:1, wherein the epitope comprises amino acids Arg140 and Glu152. In one embodiment the epitope further comprises any one or more of amino acids Gln92, Pro93, Gly95, Pro143, Glu157 or Glu177 and wherein the binding molecule is selected from: an antibody, a fragment of an antibody, a single variable domain antibody, a bi- or multi-specific antibody, a multivalent antibody, a dual variable domain antibody, an immuno-conjugate, a fibronectin molecule, an adnectin, a DARPin, an avimer, an affibody, an anticalin, an affilin, a protein epitope mimetic or combinations thereof.

In another embodiment, the binding molecule according to the invention, which binds IL-18 and does not bind the IL-18/IL-18 binding protein isoform a or isoform c (IL-18 BPa or IL-18BPc) complex and wherein the binding molecule is not IL-18BP, wherein the binding molecule binds with an IL-18 epitope on IL-18 as defined with reference to SEQ ID NO:1, wherein the epitope comprises amino acids Arg140 and Glu152 and wherein the binding molecule is an antibody or a fragment thereof. In this embodiment the epitope may further comprises any one or more of amino acids Gln92, Pro93, Gly95, Pro143, Glu157 or Glu177.

The binding molecule of the invention is capable of inhibiting one or more of IL-18 biological activities such as Th1 modulation; Th2 modulation, NK-modulation, neutrophil modulation, monocyte-macrophage lineage modulation, eosinophil modulation, B-cell modulation, cytokine modulation, chemokine modulation; adhesion molecule modulation, and cell recruitment modulation. In one embodiment the binding molecule of the invention inhibits IL-18-dependent interferon gamma (INF-γ) production, preferably in KG-1 cells. In another embodiment of the invention, the binding molecule inhibits IL-18-dependent interferon gamma (INF-γ) production in KG-1 cells with an $IC_{50}$ of 10 nM or less or of 1 nM or less or of 100 pM or less in an assay as defined herein below in the examples.

The binding molecule of the invention that specifically binds IL-18 has a dissociation constant ($K_D$) of 10 nM or less in an assay as defined herein below in the examples. In one embodiment the $K_D$ is of 1 nM or less. In another embodiment the binding molecule has a $K_D$ of 100 pM or less and the binding molecule is an antibody or a fragment thereof.

The binding molecule according to the invention can be a crystallized binding molecule, preferably a controlled release crystallized binding molecule and/or carrier-free. In one embodiment, the crystallized binding molecule is an antibody or a fragment thereof. In another embodiment the crystallized binding molecule has a greater half-life in vivo than the soluble counterpart and retains its biological function after crystallization.

The binding molecule according to the invention can also be a part of a complex which comprises the binding molecule and IL-18. Preferably the binding molecule is an antibody or a fragment thereof in complex with IL-18.

Finally, the binding molecule according to the invention may also compete with murine antibody 125-2H for binding human IL-18.

2) Antibodies

Binding molecules according to the present invention include antibodies or fragments thereof, isolated and structurally characterized as described hereinafter and as shown in FIGS. 1 and 2.

2.1) Human Antibodies

As used herein, a human antibody or a fragment thereof comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertoires (Winter G; (1994) Annu Rev Immunol 12:433-455, Green L L, (1999) J Immunol Methods 231:11-23).

Several strains of transgenic mice are now available wherein their mouse immunoglobulin loci has been replaced with human immunoglobulin gene segments (Tomizuka K, (2000) Proc Natl Acad Sci, 97:722-727; Fishwild D M (1996) Nature Biotechnol 14:845-851; Mendez M J, (1997) Nature Genetics 15:146-156). Upon antigen challenge such mice are capable of producing a repertoire of human antibodies from which antibodies of interest can be selected. Of particular note is the Trimera™ system (Eren R et al, (1988) Immunology 93:154-161) where human lymphocytes are transplanted into irradiated mice, the Selected Lymphocyte Isolated antibody System (SLAM, Babcook et al, Proc Natl Acad Sci (1996) 93:7843-7848) where human (or other species) lymphocytes are effectively put through a massive pooled in vitro isolated antibody generation procedure followed by deconvoluted, limiting dilution and selection procedure and the Xenomouse™ (Abgenix Inc). An alternative approach is available from Morphotek Inc using the Morphodoma™ technology.

Phage display technology can be used to produce human antibodies and fragments thereof, (McCafferty; (1990) Nature, 348:552-553 and Griffiths A D et al (1994) EMBO 13:3245-3260). According to this technique, isolated antibody variable domain genes are cloned in frame into either a major or minor coat of protein gene of a filamentous bacteriophage such as M13 or fd and displayed (usually with the aid of a helper phage) as function isolated antibody fragments on the surface of the phage particle. Selections based on the function properties of the isolated antibody result in selection of the gene encoding the isolated antibody exhibiting these properties. The phage display technique can be used to select antigen specific antibodies from libraries made from human B cells taken from individuals afflicted with a disease or disorder or alternatively from unimmunized human donors (Marks; J Mol Bio (1991) 222:581-591). Where an intact human isolated antibody is desired comprising an Fc domain it is necessary reclone the phage displayed derived fragment into a mammalian expression vectors comprising the desired constant regions and establishing stable expressing cell lines.

The technique of affinity maturation (Marks; Biotechnol (1992) 10:779-783) may be used to provide binding affinity wherein the affinity of the primary human isolated antibody is improved by sequentially replacing the H and L chain variable regions with naturally occurring variants and selecting on the basis of improved binding affinities. Variants of this technique such as 'epitope imprinting' are now also available (WO 93/06213; Waterhouse; Nucl Acids Res (1993) 21:2265-2266).

Various (enumerated) embodiments of the invention are described herein. It will be recognised that features specified in each embodiment may be combined with other specified features to provide further embodiments of the present invention.

Embodiment 1

The binding molecule which binds IL-18 and does not bind the IL-18/IL-18 binding protein (IL-18 BP) complex wherein the binding molecule is an isolated human antibody or a fragment thereof; preferably, an isolated human monoclonal antibody or a fragment thereof.

Embodiment 2

The isolated human antibody or a fragment thereof according to embodiment 1 wherein the isolated human antibody or a fragment thereof binds with an IL-18 epitope on IL-18 as defined with reference to SEQ ID NO:1, wherein the epitope:
  a. is comprised within the following amino acids of IL-18 as defined with reference to SEQ ID NO:1:
    i. amino acids 41 and 42 and amino acids 87 to 97; or
    ii. amino acids 138 to 160; or
    iii. amino acids 177 to 181; or
    iv. amino acids 41 and 42, amino acids 87 to 97, amino acids 138 to 160 and amino acids 177 to 181; or
    v. amino acids 41, 42, 87; 89; 90; or
    vi. amino acids 93, 94; 95, 96; or
    vii. amino acids 140; 141; 150; 177; or
    viii. amino acids 92; 93; 94; 138; 140; 152; 157; or
    ix. amino acids 142; 143; 150; 152; or
    x. amino acids 143; 144; 145; 177; 180; or
    xi. amino acids 41, 42, 87; 89; 90; 93, 94; 95, 96; 140; 141; 150; 177; or
    xii. amino acids 92; 93; 94; 138; 140; 142; 143; 144; 145; 150; 152; 157; 177; 180; or
    xiii. amino acids 41; 42, 87; 89; 90; 92; 93, 94; 95, 96; 138; 140; 141; 142; 143; 144; 145; 150; 152; 157; 177; 180; or
  b. comprises of at least one, two, three, four of the amino acids as defined in any one of the groups (i) to (xiii) listed in a); or
  c. comprises the amino acids as defined in any one of the groups (iv) to (xii) listed in a).

Embodiment 3

The isolated human antibody or fragment thereof according to embodiment 1, which binds to an IL-18 epitope on IL-18 as defined with reference to SEQ ID NO:1, wherein the epitope comprises amino acids Arg140 and Glu152.

Embodiment 4

The isolated human antibody or fragment thereof according to embodiment 3, wherein the epitope further comprises any one or more of amino acids Gln92, Pro93, Gly95, Pro143, Glu157 or Glu177.

Embodiment 5

The isolated human antibody or fragment thereof according to embodiments 3 and 4, wherein the epitope further comprises any one or more of amino acids Lys89, Arg94, Met96, Phe138, Ser141, Gly144, His145, Asp146, Gln150 or Leu180.

Embodiment 6

The isolated human antibody or fragment thereof according to anyone of the preceding embodiments, wherein IL-18 comprises from amino acid 37 to amino acid 193 of SEQ ID NO:1 or SEQ ID NO:2.

Embodiment 7

The isolated human antibody or fragment thereof according to anyone of the preceding embodiments, wherein the isolated human antibody or fragment thereof inhibits IL-18-dependent interferon gamma (INF-γ) production.

Embodiment 8

The isolated human antibody or fragment thereof according to anyone of the preceding embodiments, wherein the isolated human antibody or fragment thereof binds IL-18 with a KD of 100 pM or less.

Embodiment 9

The isolated human antibody or fragment thereof according to anyone of the preceding embodiments, wherein the isolated human antibody or fragment thereof further compete with murine antibody 125-2H for binding IL-18.

Embodiment 10

The isolated human antibody or fragment thereof according to anyone of the preceding embodiments, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 4 or SEQ ID NO: 9 or SEQ ID NO: 10 or SEQ ID NO: 11 or SEQ ID NO: 12 or SEQ ID NO: 13 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 11

The isolated human antibody or fragment thereof according to embodiment 10, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 4 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 12

The isolated human antibody or fragment thereof according to embodiment 11, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 4 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof and wherein the isolated human antibody or fragment thereof competes with murine antibody 125-2H for binding IL-18.

Embodiment 13

The isolated human antibody or fragment thereof according to embodiment 10, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 9 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 14

The isolated human antibody or fragment thereof according to embodiment 13, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 9 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof and wherein the isolated human antibody or fragment thereof competes with murine antibody 125-2H for binding IL-18.

Embodiment 15

The isolated human antibody or fragment thereof according to embodiments 13 or 14, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, wherein the isolated antibody or fragment thereof comprises:
  i. a heavy chain variable region H-CDR1 comprising SEQ ID NO: 3 or conservative variants thereof and
  ii. a heavy chain variable region H-CDR2 comprising SEQ ID NO: 9 or conservative variants thereof and
  iii. a heavy chain variable region H-CDR3 comprising SEQ ID NO: 5 or conservative variants thereof and
  iv. a light chain variable region L-CDR1 comprising SEQ ID NO: 6 or conservative variants thereof and
  v. a light chain variable region L-CDR2 comprising SEQ ID NO: 7 or conservative variants thereof and vi. a light chain variable region L-CDR3 comprising SEQ ID NO: 8 or conservative variants thereof.

Preferably this isolated human antibody is an isolated fully human antibody or fragment thereof, more preferably an isolated fully human monoclonal antibody or fragment thereof.

Embodiment 16

The isolated human antibody or fragment thereof according to embodiment 10, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 10 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 17

The isolated human antibody or fragment thereof according to embodiment 10, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 11 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 18

The isolated human antibody or fragment thereof according to embodiment 10, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 12 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 19

The isolated human antibody or fragment thereof according to embodiment 10, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 13 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof.

Embodiment 20

The isolated human antibody or fragment thereof according to embodiment 19, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 3 or conservative variants thereof and a heavy chain variable region H-CDR2 comprising SEQ ID NO: 13 or conservative variants thereof and a heavy chain variable region H-CDR3 comprising SEQ ID NO: 5 or conservative variants thereof and a light chain variable region L-CDR1 comprising SEQ ID NO: 6 or conservative variants thereof and a light chain variable region L-CDR2 comprising SEQ ID NO: 7 or conservative variants thereof and a light chain variable region L-CDR3 comprising SEQ ID NO: 8 or conservative variants thereof and wherein the isolated human antibody or fragment thereof competes with murine antibody 125-2H for binding IL-18.

Embodiment 21

The isolated human antibody or fragment thereof according to embodiments 19 or 20, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1 wherein the isolated antibody or fragment thereof comprises:
  i. a heavy chain variable region H-CDR1 comprising SEQ ID NO: 3 or conservative variants thereof and
  ii. a heavy chain variable region H-CDR2 comprising SEQ ID NO: 13 or conservative variants thereof and
  iii. a heavy chain variable region H-CDR3 comprising SEQ ID NO: 5 or conservative variants thereof and
  iv. a light chain variable region L-CDR1 comprising SEQ ID NO: 6 or conservative variants thereof and
  v. a light chain variable region L-CDR2 comprising SEQ ID NO: 7 or conservative variants thereof and
  vi. a light chain variable region L-CDR3 comprising SEQ ID NO: 8 or conservative variants thereof.

Preferably this isolated human antibody is an isolated fully human antibody or fragment thereof, more preferably an isolated fully human monoclonal antibody or fragment thereof.

Embodiment 22

The isolated human antibody or fragment thereof according to anyone of the embodiments 1 to 9, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 74 or conservative variants thereof and a heavy chain variable region H-CDR2 comprising SEQ ID NO: 75 or SEQ ID NO: 76 or SEQ ID NO: 77 or SEQ ID NO: 78 or conservative variants thereof and a heavy chain variable region H-CDR3 comprising SEQ ID NO: 79 or conservative variants thereof and a light chain variable region L-CDR1 comprising SEQ ID NO: 80 or conservative variants thereof and a light chain variable region L-CDR2 comprising SEQ ID NO: 81 or conservative variants thereof and a light chain variable region L-CDR3 comprising SEQ ID NO: 82 or conservative variants thereof.

Embodiment 23

The isolated human antibody or fragment thereof according to embodiment 22, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 74 or conservative variants thereof and a heavy chain variable region H-CDR2 comprising SEQ ID NO: 75 or conservative variants thereof and a heavy chain variable region H-CDR3 comprising SEQ ID NO: 79 or conservative variants thereof and a light chain variable region L-CDR1 comprising SEQ ID NO: 80 or conservative variants thereof and a light chain variable region L-CDR2 comprising SEQ ID NO: 81 or conservative variants thereof and a light chain variable region L-CDR3 comprising SEQ ID NO: 82 or conservative variants thereof.

Embodiment 24

The isolated human antibody or fragment thereof according to embodiment 22, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 74 or conservative variants thereof and a heavy chain variable region H-CDR2 comprising SEQ ID NO: 76 or conservative variants thereof and a heavy chain variable region H-CDR3 comprising SEQ ID NO: 79 or conservative variants thereof and a light chain variable region L-CDR1 comprising SEQ ID NO: 80 or conservative variants thereof and a light chain variable region L-CDR2 comprising SEQ ID NO: 81 or conservative variants thereof and a light chain variable region L-CDR3 comprising SEQ ID NO: 82 or conservative variants thereof.

Embodiment 25

The isolated human antibody or fragment thereof according to embodiment 22, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 74 or conservative variants thereof and a heavy chain variable region H-CDR2 comprising SEQ ID NO: 77 or conservative variants thereof and a heavy chain variable region H-CDR3 comprising SEQ ID NO: 79 or conservative variants thereof and a light chain variable region L-CDR1 comprising SEQ ID NO: 80 or conservative variants thereof and a light chain variable region L-CDR2 comprising SEQ ID NO: 81 or conservative variants thereof and a light chain variable region L-CDR3 comprising SEQ ID NO: 82 or conservative variants thereof.

Embodiment 26

The isolated human antibody or fragment thereof according to embodiment 22, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 74 or conservative variants thereof and a heavy chain variable region H-CDR2 comprising SEQ ID NO: 78 or conservative variants thereof and a heavy chain variable region H-CDR3 comprising SEQ ID NO: 79 or conservative variants thereof and a light chain variable region L-CDR1 comprising SEQ ID NO: 80 or conservative variants thereof and a light chain variable region L-CDR2 comprising SEQ ID NO: 81 or conservative variants thereof and a light chain variable region L-CDR3 comprising SEQ ID NO: 82 or conservative variants thereof.

Embodiment 27

The isolated human antibody or fragment thereof according to anyone of the embodiments 1 to 9, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 106 or conservative variants thereof and a heavy chain variable region H-CDR2 comprising SEQ ID NO: 107 or SEQ ID NO: 122 or conservative variants thereof and a heavy chain variable region H-CDR3 comprising SEQ ID NO: 108 or conservative variants thereof and a light chain variable region L-CDR1 comprising SEQ ID NO: 109 or conservative variants thereof and a light chain variable region L-CDR2 comprising SEQ ID NO: 110 or conservative variants thereof and a light chain variable region L-CDR3 comprising SEQ ID NO: 111 or SEQ ID NO: 126 or conservative variants thereof.

Embodiment 28

The isolated human antibody or fragment thereof according to embodiment 27, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 106 or conservative variants thereof and a heavy chain variable region H-CDR2 comprising SEQ ID NO: 107 or conservative variants thereof and a heavy chain variable region H-CDR3 comprising SEQ ID NO: 108 or conservative variants thereof and a light chain variable region L-CDR1 comprising SEQ ID NO: 109 or conservative variants thereof and a light chain variable region L-CDR2 comprising SEQ ID NO: 110 or conservative variants thereof and a light chain variable region L-CDR3 comprising SEQ ID NO: 111 or conservative variants thereof.

Preferably this isolated human antibody or fragment thereof is an isolated fully human antibody or fragment thereof, more preferably an isolated fully human monoclonal antibody or fragment thereof.

Embodiment 29

The isolated human antibody or fragment thereof according to anyone of the embodiments 1 to 9, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 106 or conservative variants thereof and a heavy chain variable region H-CDR2 comprising SEQ ID NO: 122 or conservative variants thereof and a heavy chain variable region H-CDR3 comprising SEQ ID NO: 108 or conservative variants thereof and a light chain variable region L-CDR1 comprising SEQ ID NO: 109 or conservative variants thereof and a light chain variable region L-CDR2 comprising SEQ ID NO: 110 or conservative variants thereof and a light chain variable region L-CDR3 comprising SEQ ID NO: 126 or conservative variants thereof.

Embodiment 30

The isolated human antibody or fragment thereof according to anyone of the embodiments 1 to 9, wherein the isolated human antibody or fragment thereof binds IL-18 and does not bind the IL-18/IL-18 binding protein (IL-18 BP) complex and comprise a heavy chain variable region H-CDR1 comprising SEQ ID NO: 120 or conservative variants thereof and a heavy chain variable region H-CDR2 comprising SEQ ID NO: 121 or conservative variants thereof and a heavy chain variable region H-CDR3 comprising SEQ ID NO: 123 or conservative variants thereof and a light chain variable region L-CDR1 comprising SEQ ID NO: 124 or conservative variants thereof and a light chain variable region L-CDR2 comprising SEQ ID NO: 125 or conservative variants thereof and a light chain variable region L-CDR3 comprising SEQ ID NO: 127 or SEQ ID NO: 128 or SEQ ID NO: 129 or conservative variants thereof.

Embodiment 31

The isolated human antibody or fragment thereof according to embodiment 30, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 120 or conservative variants thereof and a heavy chain variable region H-CDR2 comprising SEQ ID NO: 121 or conservative variants thereof and a heavy chain variable region H-CDR3 comprising SEQ ID NO: 123 or conservative variants thereof and a light chain variable region L-CDR1 comprising SEQ ID NO: 124 or conservative variants thereof and a light chain variable region L-CDR2 comprising SEQ ID NO: 125 or conservative variants thereof and a light chain variable region L-CDR3 comprising SEQ ID NO: 127 or conservative variants thereof.

Embodiment 32

The isolated human antibody or fragment thereof according to embodiment 30, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 120 or conservative variants thereof and a heavy chain variable region H-CDR2 comprising SEQ ID NO: 121 or conservative variants thereof and a heavy chain variable region H-CDR3 comprising SEQ ID NO: 123 or conservative variants thereof and a light chain variable region L-CDR1 comprising SEQ ID NO: 124 or conservative variants thereof and a light chain variable region L-CDR2 comprising SEQ ID NO: 125 or conservative variants thereof and a light chain variable region L-CDR3 comprising SEQ ID NO: 128 or conservative variants thereof.

Embodiment 33

The isolated human antibody or fragment thereof according to embodiment 30, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 120 or conservative variants thereof and a heavy chain variable region H-CDR2 comprising SEQ ID NO: 121 or conservative variants thereof and a heavy chain variable region H-CDR3 comprising SEQ ID NO: 123 or conservative variants thereof and a light chain variable region L-CDR1 comprising SEQ ID NO: 124 or conservative variants thereof and a light chain variable region L-CDR2 comprising SEQ ID NO: 125 or conservative variants thereof and a light chain variable region L-CDR3 comprising SEQ ID NO: 129 or conservative variants thereof.

The CDR regions outlined above are delineated using the Kabat system (Kabat, E. A., et al., 1991 Sequences of Proteins of Immunological Interest, Fifth Edition, U.S. Department of Health and Human Services, NIH Publication No. 91-3242).

In some other embodiments of the invention, the human antibody or fragment thereof comprises the CDR regions delineated using the Chothia definition (Chothia et al., (1987) J Mol Biol 196: 901-17).

Embodiment 34

The isolated human antibody or fragment thereof according to anyone of the embodiments 1 to 9, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 59 or SEQ ID NO: 65 or SEQ ID NO: 66 or conservative variants thereof and a heavy chain variable region H-CDR2 comprising SEQ ID NO: 60 or SEQ ID NO: 67 or conservative variants thereof and a heavy chain variable region H-CDR3 comprising SEQ ID NO: 61 or conservative variants thereof and a light chain variable region L-CDR1 comprising SEQ ID NO: 62 or conservative variants thereof and a light chain variable region L-CDR2 comprising SEQ ID NO: 63 or conservative variants thereof and a light chain variable region L-CDR3 comprising SEQ ID NO: 64 or conservative variants thereof.

Embodiment 35

The isolated human antibody or fragment thereof according to embodiment 34, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 59 or conservative variants thereof and a heavy chain variable region H-CDR2 comprising SEQ ID NO: 60 or conservative variants thereof and a heavy chain variable region H-CDR3 comprising SEQ ID NO: 61 or conservative variants thereof and a light chain variable region L-CDR1 comprising SEQ ID NO: 62 or conservative variants thereof and a light chain variable region L-CDR2 comprising SEQ ID NO: 63 or conservative variants thereof and a light chain variable region L-CDR3 comprising SEQ ID NO: 64 or conservative variants thereof.

Embodiment 36

The isolated human antibody or fragment thereof according to embodiment 35, wherein the isolated human antibody or fragment thereof competes with murine antibody 125-2H for binding IL-18.

Embodiment 37

The isolated human antibody or fragment thereof according to embodiment 34, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 65 or conservative variants thereof and a heavy chain variable region H-CDR2 comprising SEQ ID NO: 60 or conservative variants thereof and a heavy chain variable region H-CDR3 comprising SEQ ID NO: 61 or conservative variants thereof and a light chain variable region L-CDR1 comprising SEQ ID NO: 62 or conservative variants thereof and a light chain variable region L-CDR2 comprising SEQ ID NO: 63 or conservative variants thereof and a light chain variable region L-CDR3 comprising SEQ ID NO: 64 or conservative variants thereof.

Embodiment 38

The isolated human antibody or fragment thereof according to embodiment 37, wherein the isolated human antibody or fragment thereof competes with murine antibody 125-2H for binding IL-18.

Embodiment 39

The isolated human antibody or fragment thereof according to embodiment 34, wherein the isolated human antibody or fragment thereof binds IL-18 and does not bind the IL-18/IL-18 binding protein (IL-18 BP) complex and comprises a heavy chain variable region H-CDR1 comprising SEQ ID NO: 66 or conservative variants thereof and a heavy chain variable region H-CDR2 comprising SEQ ID NO: 67 or conservative variants thereof and a heavy chain variable region H-CDR3 comprising SEQ ID NO: 61 or conservative variants thereof and a light chain variable region L-CDR1 comprising SEQ ID NO: 62 or conservative variants thereof and a light chain variable region L-CDR2 comprising SEQ ID NO: 63 or conservative variants thereof and a light chain variable region L-CDR3 comprising SEQ ID NO: 64 or conservative variants thereof.

Embodiment 40

The isolated human antibody or fragment thereof according to embodiment 39, wherein the isolated human antibody or fragment thereof competes with murine antibody 125-2H for binding IL-18.

Embodiment 41

The isolated human antibody or fragment thereof according to embodiment 34, wherein the isolated human antibody or fragment thereof binds IL-18 and does not bind the IL-18/IL-18 binding protein (IL-18 BP) complex and comprise a heavy chain variable region H-CDR1 comprising SEQ ID NO: 68 or conservative variants thereof and a heavy chain variable region H-CDR2 comprising SEQ ID NO: 69 or conservative variants thereof and a heavy chain variable region H-CDR3 comprising SEQ ID NO: 70 or conservative variants thereof and a light chain variable region L-CDR1 comprising SEQ ID NO: 71 or conservative variants thereof and a light chain variable region L-CDR2 comprising SEQ ID NO: 72 or conservative variants thereof and a light chain variable region L-CDR3 comprising SEQ ID NO: 73 or conservative variants thereof.

Embodiment 42

The isolated human antibody or fragment thereof according to anyone of the embodiments 1 to 9, wherein the isolated human antibody or fragment thereof binds IL-18 and does not bind the IL-18/IL-18 binding protein (IL-18 BP) complex and comprise a heavy chain variable region H-CDR1 comprising SEQ ID NO: 162 or conservative variants thereof and a heavy chain variable region H-CDR2 comprising SEQ ID NO: 163 or conservative variants thereof and a heavy chain variable region H-CDR3 comprising SEQ ID NO: 164 or conservative variants thereof and a light chain variable region L-CDR1 comprising SEQ ID NO: 165 or conservative variants thereof and a light chain variable region L-CDR2 comprising SEQ ID NO: 166 or conservative variants thereof and a light chain variable region L-CDR3 comprising SEQ ID NO: 167 or conservative variants thereof.

Under Kabat definition, as discussed above, the CDR amino acid residues in the heavy chain variable domain (VH) are numbered 31-35 (H-CDR1), 50-65 (H-CDR2), and 95-102 (H-CDR3); and the CDR amino acid residues in the light chain variable domain (VL) are numbered 24-34 (L-CDR1), 50-56 (L-CDR2), and 89-97 (L-CDR3). Under Chothia the CDR amino acids in the VH are numbered 26-32 (H-CDR1), 52-56 (H-CDR2), and 95-102 (H-CDR3); and the amino acid residues in VL are numbered 26-32 (L-CDR1), 50-52 (L-CDR2), and 91-96 (L-CDR3). By combining the CDR definitions of both Kabat and Chothia and taking into consideration insertion for longer loops, the CDRs consist of amino acid residues 26-35 (H-CDR1), 50-65 (H-CDR2), and 95-102 (H-CDR3) in human VH and amino acid residues 24-34 (L-CDR1), 50-56 (L-CDR2), and 89-97 (L-CDR3) in human VL.

Embodiment 43

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) comprising SEQ ID NO: 14 or conservative variants thereof and a light chain variable region (VL) comprising SEQ ID NO: 16 or conservative variants thereof and wherein the heavy chain variable region (VH) comprises:
  i. a heavy chain variable region H-CDR1 corresponding to amino acids 26 to 35 SEQ ID NO: 14; and
  ii. a heavy chain variable region H-CDR2 corresponding to amino acids 50 to 66 SEQ ID NO: 14; and
  iii. a heavy chain variable region H-CDR3 corresponding to amino acids 99 to 108 SEQ ID NO: 14;
and wherein the light chain variable region (VL) comprises:
  iv. a light chain variable region L-CDR1 corresponding to amino acids 23 to 35 SEQ ID NO: 16; and
  v. a light chain variable region L-CDR2 corresponding to amino acids 51 to 57 SEQ ID NO: 16; and
  vi. a light chain variable region L-CDR3 corresponding to amino acids 90 to 100 SEQ ID NO: 16.

Embodiment 44

The isolated human antibody or fragment thereof according to embodiment 43, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 45

The isolated human antibody or fragment thereof according to embodiments 43 or 44, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 46

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) comprising SEQ ID NO: 18 or conservative variants thereof and a light chain variable region (VL) comprising SEQ ID NO: 20 or conservative variants thereof and wherein the heavy chain variable region (VH) comprises:
  i. a heavy chain variable region H-CDR1 corresponding to amino acids 26 to 35 SEQ ID NO: 18; and
  ii. a heavy chain variable region H-CDR2 corresponding to amino acids 50 to 66 SEQ ID NO: 18; and
  iii. a heavy chain variable region H-CDR3 corresponding to amino acids 99 to 108 SEQ ID NO: 18;
and wherein the light chain variable region (VL) comprises:
  iv. a light chain variable region L-CDR1 corresponding to amino acids 23 to 35 SEQ ID NO: 20; and
  v. a light chain variable region L-CDR2 corresponding to amino acids 51 to 57 SEQ ID NO: 20; and
  vi. a light chain variable region L-CDR3 corresponding to amino acids 90 to 100 SEQ ID NO: 20.

Embodiment 47

The isolated human antibody or fragment thereof according to embodiment 46, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 48

The isolated human antibody or fragment thereof according to embodiments 46 or 47, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1.

Given that each of these human antibodies can bind to IL18 and that antigen-binding specificity is provided primarily by the CDR1, 2 and 3 regions, the H-CDR1, 2 and 3 sequences and L-CDR1, 2 and 3 sequences can be "mixed and matched" (i.e., CDRs from different human antibodies can be mixed and matched, each antibody containing a H-CDR1, 2 and 3 set and a L-CDR1, 2 and 3 set create other anti-IL18 binding molecules of the invention. IL18 binding of such "mixed and matched" antibodies can be tested using the binding assays in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for human antibodies of the present invention (FIGS. 1 and 2).

In another aspect, the invention provides an isolated human antibody binding IL-18 and not binding the IL-18/IL-18 binding protein (IL-18 BP) complex and comprising VH amino acid sequences selected from the sequences shown in SEQ ID NOs: 14, 18, 22, 25, 28, 31, 34, 37, 40, 83, 87, 90, 93, 112, 130 and 138 and VL amino acid sequences selected from the sequences shown in SEQ ID NOs: 16, 20, 85, 114, 132, 140, 147 and 153. Other antibodies of the invention include amino acids that have been mutated by amino acid deletion, insertion or substitution, yet have at least 60, 70, 80, 90 or 95 percent identity in the CDR regions with the CDR regions depicted in the sequences described above. In some embodiments, it include mutant amino acid sequences wherein no more than 1, 2, 3, 4 or 5 amino acids have been mutated by amino acid deletion, insertion or substitution in the CDR regions when compared with the CDR regions depicted in the sequences described above.

Embodiment 49

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 28 or conservative variants thereof and a light chain variable region (VL) amino acid sequence selected from the sequence shown in SEQ ID NO: 16 or conservative variants thereof.

Embodiment 50

The isolated human antibody or fragment thereof according to embodiment 49, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 28 or conservative variants thereof and a light chain variable region (VL) amino acid sequence selected from the sequence shown in SEQ ID NO: 16 or conservative variants thereof, wherein amino acid asparagine (Asn; N) in position 30 with reference to SEQ ID NO: 28 is replaced by an amino acid selected from lysine (Lys; K) or serine (Ser; S) or threonine (Thr; T) or alanine (Ala; A) or glutamate (Glu; E) or histidine (His; H) or leucine (Leu; L) or glutamine (Gln; Q) or arginine (Arg; R) or valine (Val; V) or tyrosine (Tyr; Y) or isoleucine (Ile; I) or glycine (Gly; G).

Embodiment 51

The isolated human antibody or fragment thereof according to embodiments 49 or 50, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 52

The isolated human antibody or fragment thereof according to any one of embodiments 49 to 51, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 53

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 14 or conservative variants thereof and a light chain variable region (VL) amino acid sequence selected from the sequence shown in SEQ ID NO: 16 or conservative variants thereof.

Embodiment 54

The isolated human antibody or fragment thereof according to embodiment 53, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 55

The isolated human antibody or fragment thereof according to any one of embodiments 53 to 55, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 56

The isolated human antibody or fragment thereof according to embodiment 53, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 14 or conservative variants thereof and a light chain variable region (VL) amino acid sequence selected from the sequence shown in SEQ ID NO: 16 or conservative variants thereof, wherein amino acid lysine (Lys; K) in position 30 with reference to SEQ ID NO: 14 is replaced by an amino acid selected from asparagine (Asn; N) or serine (Ser; S) or threonine (Thr; T) or alanine (Ala; A) or glutamate (Glu; E) or histidine (His; H) or leucine (Leu; L) or glutamine (Gln; Q) or arginine (Arg; R) or valine (Val; V) or tyrosine (Tyr; Y) or isoleucine (Ile; I) or glycine (Gly; G).

Embodiment 57

The isolated human antibody or fragment thereof according to embodiment 56, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 58

The isolated human antibody or fragment thereof according to any one of embodiments 55 or 57, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 59

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) amino acid sequence selected from the sequences shown in SEQ ID NO: 18 or conservative variants thereof and a light chain variable region (VL) amino acid sequence selected from the sequence shown in SEQ ID NO: 20 or conservative variants thereof.

Embodiment 60

The isolated human antibody or fragment thereof according to embodiment 59, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 61

The isolated human antibody or fragment thereof according to any one of embodiments 59 or 60, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 62

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) amino acid sequence selected from the sequences shown in SEQ ID NO: 40 or conservative variants thereof and a light chain variable region (VL) amino acid sequence selected from the sequence shown in SEQ ID NO: 20 or conservative variants thereof.

Embodiment 63

The isolated human antibody or fragment thereof according to embodiment 62, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 40 or conservative variants thereof and a light chain variable region (VL) amino acid sequence selected from the sequence shown in SEQ ID NO: 20 or conservative variants thereof, wherein
  i. amino acid glutamate (Glu; E) in position 1 with reference to SEQ ID NO: 40 is replaced by amino acid glutamine (Gln; Q) and
  ii. wherein amino acid asparagine (Asn; N) in position 30 with reference to SEQ ID NO: 40 is replaced by an amino acid selected from serine (Ser; S) or threonine (Thr; T) or aspartate (Asp; D).

Embodiment 64

The isolated human antibody or fragment thereof according to embodiment 63, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 40 or conservative variants thereof and a light chain variable region (VL) amino acid sequence selected from the sequence shown in SEQ ID NO: 20 or conservative variants thereof, wherein
  i. amino acid glutamate (Glu; E) in position 1 with reference to SEQ ID NO: 40 is replaced by amino acid glutamine (Gln; Q); and
  ii. wherein amino acid asparagine (Asn; N) in position 30 with reference to SEQ ID NO: 40 is replaced by an amino acid selected from serine (Ser; S) or threonine (Thr; T) or aspartate (Asp; D); and
  iii. wherein amino acid methionine (Met; M) in position 54 with reference to SEQ ID NO: 40 is replaced by an amino acid selected from tyrosine (Tyr; Y) or asparagine (Asn; N) or isoleucine (Ile; I).

Embodiment 65

The isolated human antibody or fragment thereof according to embodiments 62 to 64, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 66

The isolated human antibody or fragment thereof according to any one of embodiments 65 to 66, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 67

The isolated human antibody or fragment thereof according to embodiment 62, wherein the isolated human antibody or fragment thereof binds IL-18 and does not bind the IL-18/IL-18 binding protein (IL-18 BP) complex and comprises a heavy chain variable region (VH) amino acid sequence selected from the sequence shown in SEQ ID NO: 40 or conservative variants thereof and a light chain variable region (VL) amino acid sequence selected from the sequence shown in SEQ ID NO: 20 or conservative variants thereof, wherein
  i. amino acid glutamate (Glu; E) in position 1 with reference to SEQ ID NO: 40 is replaced by amino acid glutamine (Gln; Q) and
  ii. wherein amino acid serine (Ser; S) in position 31 with reference to SEQ ID NO: 40 is replaced by an amino acid selected from threonine (Thr; T) or asparagine (Asn; N) or alanine (Ala; A).

Embodiment 68

The isolated human antibody or fragment thereof according to embodiment 67, wherein the isolated human antibody or fragment thereof binds IL-18 and does not bind the IL-binding protein (IL-18 BP) complex and comprises a heavy chain variable region (VH) amino acid sequence selected from the sequence shown in SEQ ID NO: 40 or conservative variants thereof and a light chain variable region (VL) amino acid sequence selected from the sequence shown in SEQ ID NO: 20 or conservative variants thereof, wherein
  i. amino acid glutamate (Glu; E) in position 1 with reference to SEQ ID NO: 40 is replaced by amino acid glutamine (Gln; Q); and
  ii. wherein amino acid serine (Ser; S) in position 31 with reference to SEQ ID NO: 40 is replaced by an amino acid selected from threonine (Thr; T) or asparagine (Asn; N) or alanine (Ala; A).
  iii. wherein amino acid methionine (Met; M) in position 54 with reference to SEQ ID NO: 40 is replaced by an amino acid selected from tyrosine (Tyr; Y) or asparagine (Asn; N) or isoleucine (Ile; I).

Embodiment 69

The isolated human antibody or fragment thereof according to embodiments 67 or 68, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 70

The isolated human antibody or fragment thereof according to any one of embodiments 67 to 69, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 72

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) amino acid sequence selected from the sequences shown in SEQ ID NO: 22 or SEQ ID NO: 25 SEQ ID NO: 28 or SEQ ID NO: 31 or SEQ ID NO: 34 or conservative variants thereof and a light chain variable region (VL) amino acid sequence selected from the sequence shown in SEQ ID NO: 16 or conservative variants thereof.

Embodiment 73

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a heavy chain variable region (VH) amino acid sequence selected from the sequences shown in SEQ ID NO: 37 and a light chain variable region (VL) amino acid sequence selected from the sequence shown in SEQ ID NO: 20 or conservative variants thereof.

Embodiment 74

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequences shown in SEQ ID NOs: 43, 47, 50, 53, 56, 96, 100, 103, 116, 134, 142 and 158 or conservative variants thereof; and a VL amino acid sequence selected from the sequences shown in SEQ ID NOs: 45, 98, 118, 136, 144, 150, 156 and 160 or conservative variants thereof.

Embodiment 75

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequence shown in SEQ ID NO: 43 or conservative variants thereof and a VL amino acid sequence selected from the sequence shown in SEQ ID NO: 45 or conservative variants thereof.

Embodiment 76

The isolated human antibody or fragment thereof according to embodiment 75, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 77

The isolated human antibody or fragment thereof according to any one of embodiments 75 or 76, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 78

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequence shown in SEQ ID NO: 158 or conservative variants thereof and a VL amino acid sequence selected from the sequence shown in SEQ ID NO: 160 or conservative variants thereof.

Embodiment 79

The isolated human antibody or fragment thereof according to embodiment 78, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 80

The isolated human antibody or fragment thereof according to any one of embodiments 78 or 79, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 81

The isolated human antibody or fragment thereof according to any one of embodiments 1 to 9, wherein the isolated human antibody or fragment thereof binds IL-18 and does not

Embodiment 82

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequences shown in SEQ ID NO: 53 or SEQ ID NO: 100 or conservative variants thereof and a VL amino acid sequence selected from the sequences shown in SEQ ID NO: 160 or conservative variants thereof.

Embodiment 83

The isolated human antibody or fragment thereof according to embodiments 81 or 82, wherein the isolated human antibody or fragment thereof binds IL-18 and does not bind the IL-18/IL-18 binding protein (IL-18 BP) complex and wherein the isolated human antibody or fragment thereof competes with murine antibody 125-2H for binding IL-18.

Embodiment 84

The isolated human antibody or fragment thereof according to any one of embodiments 81 to 83, wherein the isolated human antibody or fragment thereof binds IL-18 and does not bind the IL-18/IL-18 binding protein (IL-18 BP) complex and that antibody or fragment thereof binds to an epitope comprising Arg140 and Glu152 on IL-18 as defined with reference to SEQ ID NO:1, optionally the epitope further comprises any one or more of amino acids Lys89, Gln92, Pro93, Arg94, Gly95, Met96, Phe138, Ser141, Pro143, Gly144, Glu157, Glu177 or Leu180, preferably the epitope further comprises amino acids Lys89, Gln92, Pro93, Arg94, Gly95, Met96, Phe138, Ser141, Pro143, Gly144, Glu157, Glu177 and Leu180.

Embodiment 85

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequences shown in SEQ ID NO: 96 or SEQ ID NO: 103 or conservative variants thereof and a VL amino acid sequence selected from the sequences shown in SEQ ID NO: 98 or conservative variants thereof.

Embodiment 86

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequence shown in SEQ ID NO: 116 or conservative variants thereof and a VL amino acid sequence selected from the sequence shown in SEQ ID NO: 118 or conservative variants thereof.

Embodiment 87

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequence shown in SEQ ID NO: 142 or conservative variants thereof and a VL amino acid sequence selected from the sequence shown in SEQ ID NO: 144 or conservative variants thereof.

Embodiment 88

The isolated human antibody or fragment thereof according to any one of embodiments 1 to 9, wherein the isolated human antibody or fragment thereof binds IL-18 and does not bind the IL-18/IL-18 binding protein (IL-18 BP) complex and comprises a VH amino acid sequence selected from the sequence shown in SEQ ID NO: 134 or conservative variants thereof and a VL amino acid sequence selected from the sequences shown in SEQ ID NO: 136 or SEQ ID NO: 150 or SEQ ID NO: 156 or conservative variants thereof.

2.2) Humanized or Chimeric Antibodies

An obvious alternative to the invention disclosed herein is the use of humanized or chimeric antibodies in place of human antibodies.

The use of intact non-human antibodies in the treatment of human diseases or disorders carries with it the potential for the now well established problems of immunogenicity. That is, the immune system of the patient may recognise the non-human intact isolated antibody as non-self and mount an antibody response. This is particularly evident upon multiple administration of the non-human isolated antibody to a human patient. Various techniques have been developed over the years to overcome these problems and generally involve reducing the non-human immunogenicity signature in the intact isolated antibody whilst retaining the relative ease in obtaining non-human antibodies from an immunised animal, e.g. mouse, rat or rabbit. Broadly two approaches have been used to achieve this. The first are chimeric (sometimes "chimaeric") antibodies, which generally comprise a non-human (e.g. rodent such as mouse) variable domain fused to a human constant region. Because the antigen-binding site of an isolated antibody is localised within the variable regions the chimeric isolated antibody retains its binding affinity for the antigen but acquires the effector functions of the human constant region and are therefore able to perform effector functions such as described supra. Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the heavy and light chains of the isolated antibody of the invention. Hybridoma cells serve as a typical source of such DNA. Once isolated, the DNA is placed into expression vectors which are then transfected into host cells such as *E. coli*, COS cells, CHO cells or myeloma cells that do not otherwise produce immunoglobulin protein to obtain synthesis of the isolated antibody. The DNA may be modified by substituting the coding sequence for human L and H chains for the corresponding non-human (e.g. murine) H and L constant regions (Morrison; PNAS 81, 6851 (1984)).

The second approach involves the generation of humanized antibodies wherein the non-human content of the isolated antibody is reduced by humanizing the variable regions. Two techniques for humanization have gained popularity.

The first is humanization by CDR grafting. CDRs build loops close to the isolated antibody's N-terminus where they form a surface mounted in a scaffold provided by the framework region. Antigen-binding specificity of the isolated antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ('donor' antibodies) onto human framework ('acceptor framework') and constant regions (Jones et al (1986) Nature 321:522-525 and Verhoeyen M et al (1988) Science 239:1534-1536). However, CDR grafting per se may not result in the complete retention of antigen-binding properties and it is frequency found that some framework residues (sometimes referred to as 'backmutations') of the donor isolated antibody need to be preserved in the humanised compound if significant antigen-binding affinity is to be recovered (Queen C et al., (1989) Proc Natl Acad Sci 86:10029-10033, Co, M et al (1991) Nature 351, 501-502). In this case, human variable regions showing the greatest sequence homology to the non-human donor isolated antibody are chosen from a database in order to provide the human framework (FR). The selection of human FRs can be made either from human consensus or individual human antibodies. Where necessary, key residues from the donor isolated antibody are substituted into the human acceptor framework to preserve CDR conformations. Computer modelling of the isolated antibody may be used to help identify such structurally important residues.

Alternatively, humanisation may be achieved by a process of 'veneering'. A statistical analysis of unique human and murine immunoglobulin heavy and light chain variable regions revealed that the precise patterns of exposed residues are different in human and murine antibodies, and most individual surface positions have a strong preference for a small number of different residues (Padlan E A, et al; (1991) Mol Immunol 28:489-498 and Pedersen J T et al (1994) J Mol Biol 235:959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region 'invisible' to the human immune system (also Mark G E et al (1994) in Handbook of Experimental Pharmacology vol 113: The pharmacology of monoclonal Antibodies, Springer-Verlag, pp 105-134). This procedure of humanisation is referred to as 'veneering' because only the surface of the isolated antibody is altered, the supporting residues remain undisturbed.

2.3) Isolated Antibody Fragments and Single Variable Domain Antibodies

In another embodiment of the invention, the binding molecule is a fragment of an antibody or a single variable domain antibody which binds IL-18 and does not bind the IL-18/IL-18 binding protein (IL-18 BP) complex. Preferably, the binding molecule is a Fab, a Fab', a F(ab')$_2$, a Fv, a scFv, a dAb or a V$_{HH}$.

Traditionally, such fragments are produced by the proteolytic digestion of intact antibodies by e.g. papain digestion (see for example WO 94/29348) but may be produced directly from recombinantly transformed host cells. In addition, isolated antibody fragments may be produced using a variety of engineering techniques as described below.

Fv fragments appear to have lower interaction energy of their two chains than Fab fragments. To stabilise the association of the VH and VL domains, they have been linked with peptides (Bird et al, (1988) Science, 242:423-426, Huston et al, (1998) PNAS, 85:5879-5883), disulphide bridges (Glockshuber et al, (1990) Biochemistry, 29:1362-1367) and 'knob in hole' mutations (Zhu et al (1997), Protein Sci, 6:781-788). ScFv fragments can be produced by methods well known to those skilled in the art (Whitlow et al (1991), Methods companion Methods Enzymol, 2:97-105 and Huston et al (1993) Int Rev Immunol 10:195-217). ScFv may be produced in bacterial cells such as E. coli but are more preferably produced in eukaryotic cells. One disadvantage of scFv is the monovalency of the product, which precludes an increased avidity due to polyvalent binding, and their short half-life. Attempts to overcome these problems include bivalent (scFv')$_2$ produced from scFv containing an additional C terminal cysteine by chemical coupling (Adams et al (1993) Can Res 53:4026-4034 and McCartney et al (1995) Protein Eng, 8:301-314) or by spontaneous site-specific dimerization of scFv containing an unpaired C terminal cysteine residue (Kipriyanov et al (1995) Cell. Biophys 26:187-204). Alternatively, scFv can be forced to form multimers by shortening the peptide linker to 3 and 12 residues to form 'diabodies' (Holliger et al PNAS (1993), 90:6444-6448). Reducing the linker still further can result in scFv trimers ('triabodies' see Kortt et al (1997) Protein Eng, 10:423-433) and tetramers ('tetrabodies', Le Gall et al (1999) FEBS Lett, 453:164-168). Construction of bivalent scFv compounds can also be achieved by genetic fusion with protein dimerzing motifs to form 'miniantibodies' (Pack et al (1992) Biochemistry 31:1579-1584) and 'minibodies' (Hu et al (1996), Cancer Res. 56:3055-3061). ScFv-sc-Fv tandems ((scFv)2) may also be produced by linking two scFv units by a third peptide linker, (see Kurucz et al (1995) J Immunol, 154:4576-4582). Bispecific diabodies can be produced through the noncovalent association of two single chain fusion products consisting of VH domain from one isolated antibody connected by a short linker to the VL domain of another isolated antibody, (see Kipriyanov et al (1998), Int J Can 77:763-772). The stability of such bispecific diabodies can be enhanced by the introduction of disulphide bridges or 'knob in hole' mutations as described supra or by the formation of single chain diabodies (ScDb) wherein two hydrid scFv fragments are connected through a peptide linker (see Kontermann et al (1999) J Immunol Methods 226:179-188). Tetravalent bispecific compounds are available by e.g. fusing a scFv fragment to the CH3 domain of an IgG compound or to a Fab fragment through the hinge region (see Coloma et al (1997) Nature Biotechnol, 15:159-163). Alternatively, tetravalent bispecific compounds have been created by the fusion of bispecific single chain diabodies (see Alt et al (1999) FEBS Lett 454:90-94). Smaller tetravalent bispecific compounds can also be formed by the dimerization of either scFv-scFv tandems with a linker containing a helix-loop-helix motif (DiBi miniantibodies, see Muller et al (1998) FEBS Lett 432:45-49) or a single chain compound comprising four isolated antibody variable domains (VH and VL) in an orientation preventing intramolecular pairing (tandem diabody, see Kipriyanov et al, (1999) J Mol Biol 293:41-56). Bispecific F(ab')$_2$ fragments can be created by chemical coupling of Fab' fragments or by heterodimerization through leucine zippers (see Shalaby et al (1992) J Exp Med 175:217-225 and Kostelny et al (1992), J Immunol 148:1547-1553).

The term "single variable domain antibody" refers to an antibody variable domain (VH, V$_{HH}$, VL) that specifically binds an antigen or epitope independently of a different V region or domain. A single variable domain antibody can be present in a format (e.g., homo- or hetero-multimer) with other, different variable regions or variable domains where the other regions or domains are not required for antigen binding by the single variable domain (i.e., where the single domain antibody binds antigen independently of the additional variable domains). A "domain antibody" or "dAb" is the same as a "single variable domain antibody" which is capable of binding to an antigen as the term is used herein. A single variable domain antibody may be a human antibody variable domain, but also includes single antibody variable domains from other species such as rodent (for example, as disclosed in WO 00/29004), nurse shark and camelid $V_{HH}$ dAbs. Camelid $V_{HH}$ are single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are still considered to be "domain antibodies" according to the invention. As used herein "VH" includes camelid $V_{HH}$ domains.

2.4) Homologous Antibodies or Fragments Thereof and Conservative Variants

In another embodiment of the present invention, the binding molecule is an antibody or a fragment thereof which has variable region heavy and light chain amino acid sequences or heavy and light chain amino acid sequences that are homologous to the amino acid sequences of the antibodies described herein, and wherein the homologous antibodies or fragment thereof retain the desired functional properties of the binding molecule according to the invention.

For example, the invention provides an isolated antibody or fragment thereof comprising a VH and a VL, wherein: the VH is at least 80%, or at least 90% identical to an amino acid sequence selected from the group consisting of SEQ ID NOs: 14; 18; 22; 25; 28; 31; 34; 37; 40; 83; 87; 90; 93; 112; 130 or 138; the VL is at least 80%, or at least 90% identical to an amino acid sequence selected from the group consisting of SEQ ID NOs:16; 20; 85; 114; 132; 140; 147 or 153, wherein the homologous antibody specifically binds to IL18 and does not bind the IL-18/IL-18 binding protein (IL-18 BP) complex. The homologous antibody may exhibit at least one additional functional properties such as inhibiting IL18 binding to IL18R or inhibiting IL18 dependent IFN-γ production.

In other embodiments, the VH and/or VL amino acid sequences may be 50%, 60%, 70%, 80%, 90%, 95%, 96%, 97%, 98% or 99% identical to the sequences set forth above. In other embodiments, the VH and/or VL amino acid sequences may be identical except an amino acid substitution in no more than 1, 2, 3, 4 or 5 amino acid positions. An antibody having VH and VL regions having high (i.e., 80% or greater) identity to the VH and VL regions of SEQ ID NOs 14; 18; 22; 25; 28; 31; 34; 37; 40; 83; 87; 90; 93; 112; 130 or 138 and SEQ ID NOs 16; 20; 85; 114; 132; 140; 147 or 153 respectively, can be obtained by mutagenesis (e.g., site-directed or PCR-mediated mutagenesis) of nucleic acid molecules encoding SEQ ID NOs: 15; 19; 23; 26; 29; 32; 35; 38; 41; 84; 88; 91; 94; 113; 131; 139; 146 or 152 and 17; 21; 24; 27; 30; 33; 36; 39; 42; 86; 89; 92; 95; 115; 133; 141; 148 or 154, respectively, followed by testing of the encoded altered antibody for retained function (i.e., the functions set forth above) using the functional assays described herein.

The homologous antibody can be, for example, a human antibody, a humanized antibody or a chimeric antibody. Preferably the antibody is a fully human silent IgG1 antibody.

As used herein, the percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller, (1988) Comput. Appl. Biosci 4:11-17 which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch (1970) J Mol Biol 48:444-453, algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

2.5) Dual Variable Domain Antibodies

Dual variable domain (DVD) antibodies comprise two or more antigen binding sites and are tetravalent or multivalent antibodies, as for example divalent and tetravalent. The multivalent antibody is particularly engineered to have two or more antigen binding sites, and is generally not a naturally occurring antibody. The DVD antibodies may be capable of binding two or more related or unrelated targets. Such DVD antibodies may be monospecific, i.e. capable of binding one antigen or multispecific, i.e. capable of binding two or more antigens. In some embodiments the DVD antibody comprises two heavy chains and two light chains. Each heavy chain and light chain comprises two antigen binding sites. Each binding site comprises a heavy chain variable domain and a light chain variable domain with a total of 6 CDRs involved in antigen binding per antigen binding site.

In one embodiment, the binding molecule of the present invention is a dual variable domain (DVD) antibody which binds IL-18 and does not bind the IL-18/IL-18 binding protein (IL-18 BP) complex.

Particularly the dual variable domain antibody according to the invention is capable of binding IL-18 and a second target. The second target can be selected from IL-1, IL-6, IL-8, IL-11, IL-12, IL-17, IL-25, IL-33, IL-1β, TNF alpha/beta and IFN-γ.

2.6) Bispecific and Multispecific Molecules and Antibodies

In one embodiment, the binding molecule of the present invention is an isolated bispecific antibody or fragment thereof comprising a first specificity to IL-18 and a second specificity to another polypeptide, e.g. IL-12; wherein the bispecific antibody does not bind the IL-18/IL-18 binding protein (IL-18 BP) complex.

Particularly the bispecific antibody according to the invention is capable of binding IL-18 and a second target. The second target can be selected from IL-1, IL-6, IL-8, IL-11, IL-12, IL-17, IL-25, IL-33, IL-1β, TNF alpha/beta and IFN-γ.

In yet another aspect, the present invention provides for a binding molecule which is an isolated multispecific antibody or fragment thereof comprising a first specificity to IL-18, a second specificity to another polypeptide, e.g. IL-12 and at least a third specificity to an another polypeptide, wherein the multispecific antibody does not bind the IL-18/IL-18 binding protein (IL-18 BP) complex.

Particularly the multispecific antibody according to the invention is capable of binding IL-18, a second and a third target. The second and third targets can be selected from IL-1, IL-6, IL-8, IL-11, IL-12, IL-17, IL-25, IL-33, IL-1β, TNF alpha/beta and IFN-γ.

A bispecific isolated antibody is an isolated antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities, (see Millstein et al, (1983) Nature 305: 537-539, WO93/08829 and Traunecker et al, (1991) EMBO 10:3655-3659). Because of the random assortment of H and L chains, a potential mixture of ten different isolated antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions and, if desired, the L chain, are inserted into separate expression vectors and are then co-transfected into a suitable host organism. It is possible though to insert the coding sequences for two or all three chains into one expression vector. In one preferred approach, the bispecific isolated antibody is composed of an H chain with a first binding specificity in one arm and an H-L chain pair, providing a second binding specificity in the other arm, see WO94/04690. Also see Suresh et al, Methods in Enzymology 121, 210, 1986.

Bispecific and multispecific antibodies of the invention can be derivatized or linked to another functional molecule, e.g., another peptide or protein (e.g., another antibody or ligand for a receptor) to generate a bispecific molecule that binds to at least two different binding sites or target molecules. An antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules of the invention are murine, chimeric and humanized monoclonal antibodies.

The bispecific and multispecific molecules of the present invention can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohexane-1-carboxylate (sulfo-SMCC) (see e.g., Karpovsky et al (1984) J Exp Med; 160:1686; Liu, M A et al (1985) Proc Natl Acad Sci USA; 82:8648). Other methods include those described in Paulus (1985) Behring Inst Mitt; 78:118-132; Brennan et al (1985) Science; 229:81-83), and Glennie et al (1987) J Immunol; 139:2367-2375. Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013, 653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

2.7) Multivalent Antibodies

In another aspect, the present invention provides multivalent antibodies comprising at least two identical or different antigen-binding portions of the antibodies of the invention binding to IL-18 and not binding the IL-18/IL-18 binding protein (IL-18 BP) complex.

In one embodiment, the multivalent antibody provides at least two, three or four antigen-binding portions of the antibodies described herein. The antigen-binding portions can be linked together via protein fusion or covalent or non covalent linkage. Alternatively, methods of linkage have been described for the bispecific molecules. Tetravalent compounds can be obtained for example by cross-linking antibodies of the invention with an antibody that binds to the constant regions of the antibodies of the invention, for example the Fc or hinge region.

2.8) Immunoconjugates

In another embodiment, the binding molecule of the present invention is an antibody or a fragment thereof which binds to IL-18 but does not bind the IL-18/IL-18 binding protein (IL-18 BP) complex, wherein the antibody or fragment thereof is conjugated to a therapeutic moiety, such as a cytotoxin, a drug (e.g., an immunosuppressant) or a radiotoxin.

Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G et al (2003) Adv Drug Deliv Rev; 55:199-215; Trail, P A et al (2003) Cancer Immunol Immunother; 52:328-337; Payne, G (2003) Cancer Cell; 3:207-212; Allen, T M (2002) Nat Rev Cancer; 2:750-763; Pastan, I and Kreitman, R J (2002) Curr Opin Investig Drugs; 3:1089-1091; Senter, P D and Springer, C J (2001) Adv Drug Deliv Rev; 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine131, indium111, yttrium90, and lutetium177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; or growth factors.

Techniques for conjugating such therapeutic moiety to antibodies are well known, see, e.g., Amon et al "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al "Antibodies For Drug Delivery", in Controlled Drug Delivery (2nd Ed.), Robinson et al (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", (1982) Immunol Rev; 62:119-58.

2.9) Heteroconjugate Antibodies

Heteroconjugate antibodies also form an embodiment of the present invention. Heteroconjugate antibodies are composed of two covalently joined antibodies formed using any convenient cross-linking methods, wherein at least of the joined antibodies is an antibody according to the invention which binds IL-18 but does not bind the IL-18/IL-18 binding protein (IL-18 BP) complex. See, for example, U.S. Pat. No. 4,676,980.

2.10) Framework Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

2.11) Other Modifications

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody.

More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al, (2001) J Biol Chem 276:6591-6604).

In certain embodiments, the Fc domain of IgG1 isotype is used. In some specific embodiments, a mutant variant of IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant wherein Leucine residue is replaced by Alanine residue at amino acid positions 234 and 235 as described by Hezareh et al, J. Virol (2001); 75(24):12161-8.

In certain embodiments, the Fc domain is a mutant preventing glycosylation at position 297 of Fc domain. For example, the Fc domain contains an amino acid substitution of asparagine residue at position 297. Example of such amino acid substitution is the replacement of N297 by a glycine or an alanine.

In still another embodiment, the glycosylation of an antibody is modified. For example, an aglycosylated antibody can be made (i.e., the antibody lacks aglycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the invention are produced by recombinant expression in a cell line which exhibit hypofucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277: 26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies of the invention can be produced in a yeast or a filamentous fungi engineered for mammalian-like glycosylation pattern, and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

3. Grafting Antigen-Binding Domains into Alternative Frameworks or Scaffolds A wide variety of antibody/immunoglobulin frameworks or scaffolds can be employed so long as the resulting polypeptide includes at least one binding region which specifically binds to IL18 and does not bind the IL-18/IL-18 binding protein (IL-18 BP) complex and wherein the binding molecule is not IL-18BP. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

3.1) Non-Immunoglobulin Frameworks

Known or future non-immunoglobulin frameworks and scaffolds may be employed, as long as they comprise a binding region specific for IL-18 and not binding the IL-18/IL-18 binding protein (IL-18 BP) complex and wherein the binding molecule is not IL-18BP. Such compounds are referred herein as "polypeptides comprising a target-specific binding region". Known non-immunoglobulin frameworks or scaffolds include, but are not limited to, adnectins (Adnectins®-Compound Therapeutics, Inc., Waltham, Mass.), DARPins, avimers, Affibodys® (Affibody AG, Sweden), anticalins (Pieris Proteolab AG, Freising, Germany), Affilins® (gamma-crystallin or ubiquitin; Scil Proteins GmbH, Halle, Germany) and protein epitope mimetics (PEM; Polyphor® Ltd, Allschwil, Switzerland).

3.2) Fibronectin Molecules and Adnectins

In one aspect of the invention the binding molecule is a fibronectin molecule. The fibronectin molecule has a scaffold based preferably on fibronectin type III domain (e.g., the tenth module of the fibronectin type III (10 Fn3 domain)). In one embodiment the binding molecule is an adnectin (Adnectins®).

The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

Accordingly, in one embodiment the binding molecule is a fibronectin molecule that binds (e.g. specifically binds) to IL18 and does not bind the IL-18/IL-18 binding protein (IL-18 BP) complex.

In another embodiments the binding molecule is an adnectin that binds (e.g. specifically binds) to IL18 and does not bind the IL-18/IL-18 binding protein (IL-18 BP) complex.

3.3) DARPins

"Designed Ankyrin Repeat Protein" or "DARPin" technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn Binding of the variable regions is mostly optimized by using ribosome display.

Accordingly, in one embodiment the binding molecule is an ankyrin/DARPins that binds (e.g. specifically binds) to IL18 and does not bind the IL-18/IL-18 binding protein (IL-18 BP) complex.

3.4) Avimers

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that bind to the target antigen using the methodology described in, for example, US20040175756; US20050053973; US20050048512; and US20060008844.

Accordingly, in one embodiment the binding molecule is an avimer that binds (e.g. specifically binds) to IL18 and does not bind the IL-18/IL-18 binding protein (IL-18 BP) complex.

3.5) Affibody®

Affibody® are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies; they have a molecular weight of 6 kDa, compared to the molecular weight of antibodies, which is 150 kDa. In spite of its small size, the binding site of Affibody® molecules is similar to that of an antibody.

Accordingly, in one embodiment the binding molecule is an affibody that binds (e.g. specifically binds) to IL18 and does not bind the IL-18/IL-18 binding protein (IL-18 BP) complex.

3.6) Anticalins®

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target compounds of different shape with high affinity and specificity.

One protein of the lipocalin family, the bilin-binding protein (BBP) of *Pieris Brassicae* has been used to develop anticalins by mutagenizing the set of four loops. One example of a patent application describing "anticalins" is PCT WO 199916873.

Accordingly, in one embodiment the binding molecule is an anticalin that binds (e.g. specifically binds) to IL18 and does not bind the IL-18/IL-18 binding protein (IL-18 BP) complex.

3.7) Affilin®

Affilin® molecules are small non-immunoglobulin proteins which are designed for specific affinities towards proteins and small molecules. New Affilin® molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368

Accordingly, in one embodiment the binding molecule is an affilin that binds (e.g. specifically binds) to IL18 and does not bind the IL-18/IL-18 binding protein (IL-18 BP) complex.

3.8) Protein Epitope Mimetics

Protein Epitope Mimetics (PEM) are medium-sized, cyclic, peptide-like molecules (ca. 1-2 kDa) mimicking beta-hairpin secondary structures of proteins, the major secondary structure involved in protein-protein interactions.

Accordingly, in one embodiment the binding molecule is a protein epitope mimetic that binds (e.g. specifically binds) to IL18 and does not bind the IL-18/IL-18 binding protein (IL-18 BP) complex.

4. Polynucleotides Encoding the Binding Molecules of the Invention

Another aspect of the invention pertains to isolated polynucleotides encoding the binding molecules of the invention.

Heavy chain variable domain polynucleotides encoding the isolated human antibodies described herein are shown in SEQ ID NOs: 15, 19, 23, 26, 29, 32, 35, 38, 41, 84, 88, 91, 94, 113, 131, 139, 146 and 152. Light chain variable domain polynucleotides encoding the isolated human antibodies described herein are shown in SEQ ID NOs: 17, 21, 24, 27, 30, 33, 36, 39, 42, 86, 89, 92, 95, 115, 133, 141, 148 and 154. Other polynucleotides encoding antibodies of the invention include polynucleotides that have been mutated, yet have at least 60, 70, 80, 90 or 95 percent identity to the sequences described above such as polynucleotides which have been optimized for protein expression in mammalian cells, for example, CHO cell lines.

Embodiment 89

A variant nucleic acids wherein no more than 1, 2, 3, 4 or 5 nucleotides have been changed by nucleotide deletion, insertion or substitution in the variable regions when compared with the variable regions depicted in the sequences described above.

Embodiment 90

The isolated polynucleotide which encodes the heavy chain variable domain of an antibody or fragment thereof according to the invention, wherein the polynucleotide:
a. is at least 90% identical to SEQ ID NO: 15 or SEQ ID NO: 19 or SEQ ID NO: 23 or SEQ ID NO: 26 or SEQ ID NO: 29 or SEQ ID NO: 32 or SEQ ID NO: 35 or SEQ ID NO: 38 or SEQ ID NO: 41 or SEQ ID NO: 84 or SEQ ID NO: 88 or SEQ ID NO: 91 or SEQ ID NO: 94 or SEQ ID NO: 113 or SEQ ID NO: 131 or SEQ ID NO: 139 or SEQ ID NO: 146 or SEQ ID NO: 152 or
b. comprises SEQ ID NO: 15 or SEQ ID NO: 19 or SEQ ID NO: 23 or SEQ ID NO: 26 or SEQ ID NO: 29 or SEQ ID NO: 32 or SEQ ID NO: 35 or SEQ ID NO: 38 or SEQ ID NO: 41 or SEQ ID NO: 84 or SEQ ID NO: 88 or SEQ ID NO: 91 or SEQ ID NO: 94 or SEQ ID NO: 113 or SEQ ID NO: 131 or SEQ ID NO: 139 or SEQ ID NO: 146 or SEQ ID NO: 152 or
c. consists essentially of SEQ ID NO: 15 or SEQ ID NO: 19 or SEQ ID NO: 23 or SEQ ID NO: 26 or SEQ ID NO: 29 or SEQ ID NO: 32 or SEQ ID NO: 35 or SEQ ID NO: 38 or SEQ ID NO: 41 or SEQ ID NO: 84 or SEQ ID NO: 88 or SEQ ID NO: 91 or SEQ ID NO: 94 or SEQ ID NO: 113 or SEQ ID NO: 131 or SEQ ID NO: 139 or SEQ ID NO: 146 or SEQ ID NO: 152.

Embodiment 91

The isolated polynucleotide which encodes the light chain variable domain of an antibody or a fragment thereof according to the invention, wherein the polynucleotide:
a. is at least 90% identical to SEQ ID NO: 17 or SEQ ID NO: 21 or SEQ ID NO: 24 or SEQ ID NO: 27 or SEQ ID NO: 30 or SEQ ID NO: 33 or SEQ ID NO: 36 or SEQ ID NO: 39 or SEQ ID NO: 42 or SEQ ID NO: 86 or SEQ ID NO: 89 or SEQ ID NO: 92 or SEQ ID NO: 95 or SEQ ID NO: 115 or SEQ ID NO: 133 or SEQ ID NO: 141 or SEQ ID NO: 148 or SEQ ID NO: 154 or
b. comprises SEQ ID NO: 17 or SEQ ID NO: 21 or SEQ ID NO: 24 or SEQ ID NO: 27 or SEQ ID NO: 30 or SEQ ID NO: 33 or SEQ ID NO: 36 or SEQ ID NO: 39 or SEQ ID NO: 42 or SEQ ID NO: 86 or SEQ ID NO: 89 or SEQ ID NO: 92 or SEQ ID NO: 95 or SEQ ID NO: 115 or SEQ ID NO: 133 or SEQ ID NO: 141 or SEQ ID NO: 148 or SEQ ID NO: 154 or
c. consists essentially of SEQ ID NO: 17 or SEQ ID NO: 21 or SEQ ID NO: 24 or SEQ ID NO: 27 or SEQ ID NO: 30 or SEQ ID NO: 33 or SEQ ID NO: 36 or SEQ ID NO: 39 or SEQ ID NO: 42 or SEQ ID NO: 86 or SEQ ID NO: 89 or SEQ ID NO: 92 or SEQ ID NO: 95 or SEQ ID NO: 115 or SEQ ID NO: 133 or SEQ ID NO: 141 or SEQ ID NO: 148 or SEQ ID NO: 154.

Embodiment 92

The isolated polynucleotide which encodes the heavy chain of an antibody according to the invention, wherein the polynucleotide:
a. is at least 90% identical to SEQ ID NO: 44 or SEQ ID NO: 48 or SEQ ID NO: 51 or SEQ ID NO: 54 or SEQ ID NO: 57 or SEQ ID NO: 101 or SEQ ID NO: 159 or SEQ ID NO: 97 or SEQ ID NO: 104 or SEQ ID NO: 117 or SEQ ID NO: 143 or SEQ ID NO: 135 or SEQ ID NO: 149 or SEQ ID NO: 155; or b. comprises SEQ ID NO: 44 or SEQ ID NO: 48 or SEQ ID NO: 51 or SEQ ID NO: 54 or SEQ ID NO: 57 or SEQ ID NO: 101 or SEQ ID NO: 159 or SEQ ID NO: 97 or SEQ ID NO: 104 or SEQ ID NO: 117 or SEQ ID NO: 143 or SEQ ID NO: 135 or SEQ ID NO: 149 or SEQ ID NO: 155; or
c. consists essentially of SEQ ID NO: 44 or SEQ ID NO: 48 or SEQ ID NO: 51 or SEQ ID NO: 54 or SEQ ID NO: 57 or SEQ ID NO: 101 or SEQ ID NO: 159 or SEQ ID NO: 97 or SEQ ID NO: 104 or SEQ ID NO: 117 or SEQ ID NO: 143 or SEQ ID NO: 135 or SEQ ID NO: 149 or SEQ ID NO: 155.

Embodiment 93

The isolated polynucleotide encodes the light chain of an antibody according to the invention, wherein the polynucleotide:
a. is at least 90% identical to SEQ ID NO: 46 or SEQ ID NO: 49 or SEQ ID NO: 52 or SEQ ID NO: 55 or SEQ ID NO: 58 or SEQ ID NO: 102 or SEQ ID NO: 161 or SEQ ID NO: 99 or SEQ ID NO: 105 or SEQ ID NO: 119 or SEQ ID NO: 145 or SEQ ID NO: 137 or SEQ ID NO: 151 or SEQ ID NO: 157; or
b. comprises SEQ ID NO: 46 or SEQ ID NO: 49 or SEQ ID NO: 52 or SEQ ID NO: 55 or SEQ ID NO: 58 or SEQ ID NO: 102 or SEQ ID NO: 161 or SEQ ID NO: 99 or SEQ ID NO: 105 or SEQ ID NO: 119 or SEQ ID NO: 145 or SEQ ID NO: 137 or SEQ ID NO: 151 or SEQ ID NO: 157; or
c. consists essentially of SEQ ID NO: 46 or SEQ ID NO: 49 or SEQ ID NO: 52 or SEQ ID NO: 55 or SEQ ID NO: 58 or SEQ ID NO: 102 or SEQ ID NO: 161 or SEQ ID NO: 99 or SEQ ID NO: 105 or SEQ ID NO: 119 or SEQ ID NO: 145 or SEQ ID NO: 137 or SEQ ID NO: 151 or SEQ ID NO: 157.

The polynucleotide may be present in whole cells, in a cell lysate, or may be in a partially purified or substantially pure form. A polynucleotide is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., (1987) Current Protocols in Molecular Biology, Greene Publishing and Wiley Interscience, New York. A polynucleotide of the invention can be, for example, DNA or RNA and may or may not contain intronic sequences. In an embodiment, the polynucleotide is a cDNA molecule. The polynucleotide may be present in a vector such as a phage display vector, or in a recombinant plasmid vector.

Polynucleotides of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), polynucleotides encoding the antibody can be recovered from various phage clones that are members of the library.

Once DNA fragments encoding VH and VL segments are obtained, these DNA fragments can be further manipulated by standard recombinant DNA techniques, for example to convert the variable region genes to full-length antibody chain genes, to Fab fragment genes or to an scFv gene. In these manipulations, a VL- or VH-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as to a Fab light chain gene) by operatively linking the VL-encoding DNA to another DNA molecule encoding the light chain constant region, CL. The sequences of human light chain constant region genes are known in the art (see e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the VH- and VL-encoding DNA fragments are operatively linked to another fragment encoding a flexible linker, e.g., encoding the amino acid sequence (Gly4-Ser)3 (SEQ ID NO: 264), such that the VH and VL sequences can be expressed as a contiguous single-chain protein, with the VL and VH regions joined by the flexible linker (see e.g., Bird et al., 1988 Science 242:423-426; Huston et at., (1988) Proc. Natl. Acad. Sci. USA 85:5879-5883; McCafferty et al., (1990) Nature 348:552-554).

The polynucleotide according to any one of embodiments 89 to 93 may be in-vitro modified in such a way that when injected into a mammalian cells, it prevents digestion of the polynucleotide and allows the translation machinery of the mammalian cell to produce an antibody starting from the modified polynucleotide (such as described in U.S. Pat. No. 8,278,036 B2 to Kariko et al.). Such an in vitro-synthesized modified RNA can then be injected into a mammalian cells or into a patient as part of a gene therapy.

Hence, another aspect of the present invention encompasses a method for inducing a mammalian cell to produce an antibody as described herein, the method comprising: contacting said mammalian cell with in vitro-synthesized modified RNA derived from a polynucleotide according to any one of embodiments 89 to 93, wherein said in vitro-synthesized modified RNA comprises one or more modification as described in U.S. Pat. No. 8,278,036 B2.

5. Production of Antibodies

Monoclonal antibodies (mAbs) can be produced by a variety of techniques, including conventional monoclonal antibody methodology e.g., the standard somatic cell hybridization technique of Kohler and Milstein, (1975) Nature 256:

495. Many techniques for producing monoclonal antibody can be employed e.g., viral or oncogenic transformation of B lymphocytes.

Immunization protocols and techniques for isolation of immunized splenocytes for fusion are known in the art. Fusion partners (e.g., murine myeloma cells) and fusion procedures are also known.

Chimeric or humanized monoclonal antibodies of the present invention can be prepared based on the sequence of a murine monoclonal antibody prepared as described above. DNA encoding the heavy and light chain of immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

Human monoclonal antibodies can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy ($\mu$ and $\gamma$) and $\kappa$ light chain immunoglobulin sequences, together with targeted mutations that inactivate the endogenous $\mu$ and $\kappa$ chain loci (see e.g., Lonberg et al (1994) Nature; 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal (Lonberg, N et al (1994) supra; reviewed in Lonberg, N (1994) Handbook of Experimental Pharmacology 113:49-101; Lonberg, N and Huszar, D (1995) Intern Rev Immunol; 13: 65-93, and Harding, F and Lonberg, N (1995) Ann N Y Acad Sci; 764:536-546). The preparation and use of HuMAb mice, and the genomic modifications carried by such mice, is further described in Taylor, L et al; (1992) Nucl Acids Res; 20:6287-6295; Chen, J et al (1993) Int Immunol; 5: 647-656; Tuaillon et al (1993) Proc Natl Acad Sci USA; 94:3720-3724; Choi et al (1993) Nature Gen; 4:117-123; Chen, J et al (1993) EMBO J; 12: 821-830; Tuaillon et al (1994) J Immunol; 152:2912-2920; Taylor, L et al (1994) Int Immuno; 6:579-591; and Fishwild, D et al (1996) Nature Biotech; 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In one embodiment, human antibodies according to the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotech 20:889-894).

Human recombinant antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into cloning or expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The cloning or expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In one aspect, the invention provides a cloning or expression vector comprising one or more polynucleotides according to the invention.

Embodiment 94

The cloning or expression vector which comprises at least one polynucleotide selected from: SEQ ID NO: 44 or SEQ ID NO: 48 or SEQ ID NO: 51 or SEQ ID NO: 54 or SEQ ID NO: 57 or SEQ ID NO: 101 or SEQ ID NO: 159 or SEQ ID NO: 97 or SEQ ID NO: 104 or SEQ ID NO: 117 or SEQ ID NO: 143 or SEQ ID NO: 135 or SEQ ID NO: 149 or SEQ ID NO: 155 or SEQ ID NO: 46 or SEQ ID NO: 49 or SEQ ID NO: 52 or SEQ ID NO: 55 or SEQ ID NO: 58 or SEQ ID NO: 102 or SEQ ID NO: 161 or SEQ ID NO: 99 or SEQ ID NO: 105 or SEQ ID NO: 119 or SEQ ID NO: 145 or SEQ ID NO: 137 or SEQ ID NO: 151 or SEQ ID NO: 157.

In addition to the polynucleotides encoding the antibody chains, the cloning or expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

Furthermore, the cloning or expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Suitable host cells for cloning or expressing vectors encoding antibodies of the invention are prokaryotic, yeast or higher eukaryotic cells. Suitable prokaryotic cells include eubacteria e.g. enterobacteriaceae such as *Escherichia* e.g. *E. coli* (for example ATCC 31, 446; 31, 537; 27,325), *Enterobacter, Erwinia, Klebsiella proteus, Salmonella* e.g. *Salmonella typhimurium, Serratia* e.g. *Serratia marcescens* and *Shigella* as well as Bacilli such as *B. subtilis* and *B. licheniformis* (see DD 266 710), *Pseudomonas* such as *P. aeruginosa* and *Streptomyces*. Of the yeast or fungi host cells, *Saccharomyces cerevisiae, Schizosaccharomyces pombe, Kluyveromyces* (e.g. ATCC 16,045; 12,424; 24178; 56,500), *Yarrowia* (EP402, 226), *Pichia pastoris* (EP183070, see also Peng et al (2004) J Biotechnol; 108:185-192), *Candida, Trichoderma reesei* (EP244234), *Penicillium, Tolypocladium* and *Aspergillus* hosts such as *A. nidulans* and *A. niger* are also contemplated.

Although prokaryotic and yeast host cells are specifically contemplated by the invention, preferably however, host cells of the present invention are higher eukaryotic cells.

Accordingly, in one aspect the present invention provides for a host cell comprising one or more cloning or expression vectors comprising the polynucleotides as described herein.

In another aspect, the invention provide a stably transformed or transfected host cell comprising one or more polynucleotides as described herein.

Embodiment 95

A stably transformed host cell comprising a vector encoding a heavy chain and/or light chain of the isolated antibody or fragment thereof according to any one of embodiments 1 to 88. Preferably such host cells comprise a first vector encoding the light chain and a second vector encoding said heavy chain.

Suitable higher eukaryotic host cells include mammalian cells such as COS-1 (ATCC No. CRL 1650) COS-7 (ATCC CRL 1651), human embryonic kidney line 293, baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al, (1986) Somatic Cell Mol. Genet. 12, 555-556)), particularly those CHO cell lines adapted for suspension culture, mouse Sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NSO (see U.S. Pat. No. 5,807,715), Sp2/0, YO.

Preferably, the mammalian host cells for expressing the binding molecule of the invention include mammalian cell lines deficient for FUT8 gene expression, for example as described in U.S. Pat. No. 6,946,292.

Host cells transformed with vectors encoding the binding molecules may be cultured by any method known to those skilled in the art. Host cells may be cultured in spinner flasks, roller bottles or hollow fibre systems but it is preferred for large scale production that stirred tank reactors are used particularly for suspension cultures. Preferably the stirred tankers are adapted for aeration using e.g. spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes such as fed-batch, repeated batch processing (see Drapeau et al (1994) cytotechnology 15: 103-109), extended batch process or perfusion culture. Although recombinantly transformed mammalian host cells may be cultured in serum-containing media such as fetal calf serum (FCS), it is preferred that such host cells are cultured in synthetic serum-free media such as disclosed in Keen et al (1995) Cytotechnology 17:153-163, or commercially available media such as ProCHO-CDM or Ultra-CHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in Animal Cell technology: Developments towards the 21st century (Beuvery E. G. et al eds), pp 619-623, Kluwer Academic publishers).

Binding molecules of the invention secreted into the media may be recovered and purified using a variety of techniques to provide a degree of purification suitable for the intended use. For example the use of isolated antibodies of the invention for the treatment of human patients typically mandates at least 95% purity, more typically 98% or 99% or greater purity (compared to the crude culture medium). In the first instance, cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulfate precipitation. Typically, various virus removal steps are also employed (e.g. nanofiltration using e.g. a DV-20 filter). Following these various steps, a purified (preferably monoclonal) preparation comprising at least 75 mg/ml or greater e.g. 100 mg/ml or greater of the isolated antibody of the invention or antigen binding fragment thereof is provided and therefore forms an embodiment of the invention. Suitably such preparations are substantially free of aggregated forms of antibodies of the invention.

Bacterial systems may be used for the expression of non-immunoglobulin binding molecules described above. Bacterial systems are also particularly suited for the expression of isolated antibody fragments. Such fragments are localised intracellularly or within the periplasma. Insoluble periplasmic proteins can be extracted and refolded to form active proteins according to methods known to those skilled in the art, see Sanchez et al (1999) J. Biotechnol. 72, 13-20 and Cupit P M et al (1999) Lett Appl Microbiol, 29, 273-277.

Accordingly, in one aspect the present invention provide a method for producing a binding molecule which binds IL-18 and does not bind the IL-18/IL-18 binding protein (IL-18 BP) complex wherein the method comprises culturing a host cell under conditions suitable for producing the binding molecule, wherein the host cell comprises a vector as described herein.

Embodiment 95

The method of producing a human antibody or a fragment thereof according to any one of embodiments 1 to 88, wherein the method comprises culturing a host cell under conditions suitable for producing the binding molecule, wherein the host cell comprises a vector as described herein.

6. Pharmaceutical Compositions

The invention provides for pharmaceutical compositions comprising the binding molecule which binds IL-18 and does not bind the IL-18/IL-18 binding protein (IL-18 BP) complex and wherein the binding molecule is not IL-18BP and a pharmaceutically acceptable carrier.

Embodiment 96

The pharmaceutical compositions comprising a human antibody or a fragment thereof according to any one of embodiments 1 to 88 and a pharmaceutically acceptable carrier.

The compositions can additionally contain other therapeutic agents that are suitable for treating or preventing a human disease or disorder noted below. Pharmaceutically carriers enhance or stabilize the composition, or facilitate the preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound (particularly low molecular weight chemical entities) may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of an antibody of the invention described herein is employed in the pharmaceutical compositions of the invention. They are typically formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a fibrotic disease or disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Binding molecules of the invention, especially antibodies and fragments thereof, are usually administered on multiple occasions. Intervals between single dosages can be weekly, monthly or yearly. Intervals can also be irregular as indicated by measuring blood levels of therapeutic protein in the patient. In some methods, dosage is adjusted to achieve a plasma antibody concentration of 1-1000 µg/ml and in some methods 25-300 µg/ml. Alternatively, antibodies of the invention can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic (preventative) applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The pharmaceutical composition may comprise (e.g. as its sole therapeutically active ingredient) a binding molecule that binds with IL18 (e.g. specifically binds) and does not bind the IL-18/IL-18 binding protein (IL-18 BP) complex, wherein the binding molecule is not IL-18BP, wherein the binding molecule is selected from: an isolated antibody, a fragment of an isolated antibody, a single variable domain antibody, a bi- or multi-specific antibody, a multivalent antibody, a dual variable domain antibody, an immuno-conjugate, a fibronectin molecule, an adnectin, a DARPin, an avimer, an affibody, an anticalin, an affilin, a protein epitope mimetic or combinations thereof and wherein the composition may further comprise a pharmaceutically acceptable carrier.

Typically the composition will be in an intravenously, inhalable or subcutaneously administrable form. In other embodiments, the composition maybe in lyophilized form.

Preferably, the binding molecule is an antibody, preferably a monoclonal intact antibody (e.g. human, humanised or chimeric) or a fragment thereof as described herein.

Embodiment 97

A pharmaceutical composition comprises (e.g. as its sole therapeutically active ingredient) an antibody or a fragment thereof that binds IL18 (e.g. specifically binds) and does not bind the IL-18/IL-18 binding protein (IL-18 BP) complex wherein said antibody comprises;
(a) CDRH1 of SEQ ID NO:3;
(b) CDRH2 of SEQ ID NO:9;
(c) CDRH3 of SEQ ID NO:5;
(d) CDRL1 of SEQ ID NO:6;
(e) CDRL2 of SEQ ID NO:7 and
(f) CDRL3 of SEQ ID NO:8.

Embodiment 98

The pharmaceutical composition according to embodiment 97 wherein the antibody competes with murine antibody 125-2H for binding IL-18.

Embodiment 99

A pharmaceutical composition comprises (e.g. as its sole therapeutically active ingredient) an antibody or a fragment thereof that binds IL18 (e.g. specifically binds) and does not bind the IL-18/IL-18 binding protein (IL-18 BP) complex wherein said antibody comprises;
(a) CDRH1 of SEQ ID NO:3;
(b) CDRH2 of SEQ ID NO:10;
(c) CDRH3 of SEQ ID NO:5;
(d) CDRL1 of SEQ ID NO:6;
(e) CDRL2 of SEQ ID NO:7 and
(f) CDRL3 of SEQ ID NO:8.

Embodiment 100

A pharmaceutical composition comprises (e.g. as its sole therapeutically active ingredient) an antibody or a fragment thereof that binds IL18 (e.g. specifically binds) and does not bind the IL-18/IL-18 binding protein (IL-18 BP) complex wherein said antibody comprises;
(a) CDRH1 of SEQ ID NO:3;
(b) CDRH2 of SEQ ID NO:13;
(c) CDRH3 of SEQ ID NO:5;
(d) CDRL1 of SEQ ID NO:6;
(e) CDRL2 of SEQ ID NO:7 and
(f) CDRL3 of SEQ ID NO:8.

Embodiment 101

The pharmaceutical composition according to embodiment 100 wherein the antibody competes with murine antibody 125-2H for binding IL-18.

Embodiment 102

A pharmaceutical composition comprises (e.g. as its sole therapeutically active ingredient) an antibody or a fragment thereof that binds IL18 (e.g. specifically binds) and does not bind the IL-18/IL-18 binding protein (IL-18 BP) complex wherein said antibody comprises;
(a) CDRH1 of SEQ ID NO:106;
(b) CDRH2 of SEQ ID NO:107;
(c) CDRH3 of SEQ ID NO:108;
(d) CDRL1 of SEQ ID NO:109;
(e) CDRL2 of SEQ ID NO:110 and
(f) CDRL3 of SEQ ID NO:111.

Embodiment 103

A pharmaceutical composition comprises (e.g. as its sole therapeutically active ingredient) an antibody that binds IL18 (e.g. specifically binds) and does not bind the IL-18/IL-18 binding protein (IL-18 BP) complex wherein said antibody comprises:
a. a heavy chain variable domain of SEQ ID NO: 14 and a light chain variable domain of SEQ ID NO: 16 or
b. a heavy chain variable domain of SEQ ID NO: 25 and a light chain variable domain of SEQ ID NO: 16 or
c. a heavy chain variable domain of SEQ ID NO: 28 and a light chain variable domain of SEQ ID NO: 16 or
d. a heavy chain variable domain of SEQ ID NO: 18 and a light chain variable domain of SEQ ID NO: 20 or
e. a heavy chain variable domain of SEQ ID NO: 37 and a light chain variable domain of SEQ ID NO: 20 or
f. a heavy chain variable domain of SEQ ID NO: 40 and a light chain variable domain of SEQ ID NO: 20 or
g. a heavy chain variable domain of SEQ ID NO: 112 and a light chain variable domain of SEQ ID NO: 114.

Embodiment 104

The pharmaceutical composition according to embodiment 103, wherein said antibody comprises a heavy chain variable domain of SEQ ID NO: 14 and a light chain variable domain of SEQ ID NO: 16 or a heavy chain variable domain of SEQ ID NO: 18 and a light chain variable domain of SEQ ID NO: 20.

Embodiment 105

The pharmaceutical composition according to embodiment 104 wherein the antibody competes with murine antibody 125-2H for binding IL-18.

Embodiment 106

A pharmaceutical composition comprises (e.g. as its sole therapeutically active ingredient) an antibody that binds IL18 (e.g. specifically binds) and does not bind the IL-18/IL-18 binding protein (IL-18 BP) complex wherein said antibody comprises:
a. a heavy chain variable domain capable of being encoded by an isolated polynucleotide having at least 90% identity (e.g. 95% or greater such as 96%, 97%, 98% or 99%) to an isolated polynucleotide encoding SEQ ID NO: 14 or 18 or 25 or 28 or 37 or 40 or 112 and
b. a light chain variable domain capable of being encoded by an isolated polynucleotide having at least 90% identity (e.g. 95% or greater such as 96%, 97%, 98% or 99%) to an isolated polynucleotide encoding SEQ ID NO: 16 or 20 or 114.

Embodiment 107

A pharmaceutical composition comprises (e.g. as its sole therapeutically active ingredient) an antibody that binds IL18 (e.g. specifically binds) and does not bind the IL-18/IL-18 binding protein (IL-18 BP) complex wherein said antibody comprises:
a. a heavy chain of SEQ ID NO: 43 and a light chain variable domain of SEQ ID NO: 45 or
b. a heavy chain of SEQ ID NO: 47 and a light chain variable domain of SEQ ID NO: 45 or
c. a heavy chain of SEQ ID NO: 50 and a light chain variable domain of SEQ ID NO: 45 or
d. a heavy chain variable domain of SEQ ID NO: 53 and a light chain variable domain of SEQ ID NO: 160 or
e. a heavy chain variable domain of SEQ ID NO: 100 and a light chain variable domain of SEQ ID NO: 160 or
f. a heavy chain variable domain of SEQ ID NO: 158 and a light chain variable domain of SEQ ID NO: 160 or
g. a heavy chain variable domain of SEQ ID NO: 116 and a light chain variable domain of SEQ ID NO: 118.

Embodiment 108

The pharmaceutical composition according to embodiment 107, wherein the antibody comprises a heavy chain of SEQ ID NO: 43 and a light chain variable domain of SEQ ID NO: 45 or a heavy chain variable domain of SEQ ID NO: 158 and a light chain variable domain of SEQ ID NO: 160.

Embodiment 109

The pharmaceutical composition according to embodiment 108, wherein the antibody competes with murine antibody 125-2H for binding IL-18.

Embodiment 110

A pharmaceutical composition comprises (e.g. as its sole therapeutically active ingredient) an antibody that binds IL18 (e.g. specifically binds) and does not bind the IL-18/IL-18 binding protein (IL-18 BP) complex wherein said antibody comprises:
a. a heavy chain capable of being encoded by an isolated polynucleotide having at least 90% identity (e.g. 95% or greater such as 96%, 97%, 98% or 99%) to an isolated polynucleotide encoding SEQ ID NO: 43 or 47 or 50 or 53 or 100 or 116 or 158 and
b. a light chain capable of being encoded by an isolated polynucleotide having at least 90% identity (e.g. 95% or greater such as 96%, 97%, 98% or 99%) to an isolated polynucleotide encoding SEQ ID NO: 45 or 160 or 118.

7. Clinical Uses

It has been demonstrated that IL-18 expression is up-regulated in several autoimmune, cardiovascular and inflammatory diseases.

Accordingly, the binding molecules of the invention, which bind IL-18 and do not bind the IL-18/IL-18 binding protein (IL-18 BP) complex and wherein the binding molecules are not IL-18BP, may be used in therapy.

Embodiment 110(a)

The antibody according to any one of embodiments 1 to 88 for use in therapy.

In one aspect of the present invention there is provided a method of treating and/or preventing autoimmune diseases, including Rheumatoid Arthritis (RA), Systemic Onset Juvenile Arthritis (SOJA), Systemic Juvenile Idiopathic Arthritis (SJIA), Ankylosing Spondylitis, Autoimmune Inner Ear Disease (AIED), Autoimmune Lymphoproliferative Syndrome (ALPS), Behcet's Disease, Berger's Disease (IgA Nephropathy), Bullous Pemphigoid, Churg Strauss Syndrome, Colitis, Crohn's Disease (CD), Diabetes Type 1, Diabetes Type 2, Sjögren's Syndrome (SS), Graft-Versus-Host Disease (GVHD), Glomerulonephritis, Lupus, Multiple Sclerosis (MS), Psoriasis, Rheumatic Fever, Sarcoidosis, Scleroderma, Adult Onset Still's Disease (AOSD), Systemic Lupus Erythematosus (SLE), Ulcerative Colitis, Hemophagocytic lymphohistiocytosis (HLH, also known as hemophagocytic syndrome, macrophage activation syndrome), Familial hemophagocytic lymphohistiocytosis (FHL) and other immunodeficiency syndromes, Giant Cell Arteritis (GCA), coronary artery disease (CAD), Coronary Vasculopathy (CV), Acute Coronary Syndromes (ACS), Congestive Heart Failure (CHF), atherosclerosis, arteriosclerosis, myocardial infarction (MI), Cardiorenal Syndrome (CRS), Acute Kidney Injury (AKI), Diabetic Nephropathy, insulin resistance, obesity and the metabolic syndrome (MetS), lung diseases including pulmonary sarcoidosis, in particular pulmonary sarcoidosis pulmonary fibrosis, asthma, especially severe asthma, Uveitis, Geographic Atrophy Chronic Obstructive Pulmonary Disease (COPD), cystic fibrosis, Adult Respiratory Distress Syndrome (ARDS), Acute Lung Injury (ALI), Ventilator Induced Lung Injury (VILI), Pulmonary Arterial Hypertension (PAH), Alzheimer's Disease (AD) and sepsis and any combinations thereof which method comprises administrating to a mammalian patient a therapeutically effective amount of a binding molecule (e.g. an antibody) or pharmaceutical composition as described herein which binds IL-18 and does not bind the IL-18/IL-18 binding protein (IL-18 BP) complex.

Embodiment 111

A method of treating and/or preventing sarcoidosis, in particular pulmonary sarcoidosis, hemophagocytic lymphohistiocytosis (HLH), familial hemophagocytic lymphohistiocytosis (FHL), chronic obstructive pulmonary disease (COPD), Adult Onset Still's Disease (AOSD), atherosclerosis, systemic juvenile idiopathic arthritis (SJIA), severe asthma, Uveitis, Geographic Atrophy, Giant Cell Arthritis (GCA), diabetes type 1, diabetes type 2 and any combination thereof in a mammalian patient which method comprises administrating to the mammalian patient a therapeutically effective amount of a binding molecule (e.g. an antibody) or pharmaceutical composition as described herein which binds IL-18 and does not bind the IL-18/IL-18 binding protein (IL-18 BP) complex and wherein the binding molecule is not IL-18BP.

Embodiment 112

The binding molecules or the pharmaceutical compositions of the invention which bind IL-18 and do not bind the IL-18/IL-18 binding protein (IL-18 BP) complex and wherein the binding molecule is not IL-18BP, for use in treating and/or preventing sarcoidosis, in particular pulmonary sarcoidosis, hemophagocytic lymphohistiocytosis (HLH), familial hemophagocytic lymphohistiocytosis (FHL), chronic obstructive pulmonary disease (COPD), Adult Onset Still's Disease (AOSD), atherosclerosis, systemic juvenile idiopathic arthritis (SJIA), severe asthma, Uveitis, Geographic Atrophy, Giant Cell Arthritis (GCA), diabetes type 1, diabetes type 2 and any combination thereof in a mammalian patient.

Embodiment 113

A method of treating and/or preventing autoimmune diseases, including Rheumatoid Arthritis (RA), Systemic Onset Juvenile Arthritis (SOJA), Systemic Juvenile Idiopathic Arthritis (SJIA), Ankylosing Spondylitis, Autoimmune Inner Ear Disease (AIED), Autoimmune Lymphoproliferative Syndrome (ALPS), Behcet's Disease, Berger's Disease (IgA Nephropathy), Bullous Pemphigoid, Churg Strauss Syndrome, Colitis, Crohn's Disease (CD), Diabetes Type 1, Diabetes Type 2, Sjögren's Syndrome (SS), Graft-Versus-Host Disease (GVHD), Glomerulonephritis, Lupus, Multiple Sclerosis (MS), Psoriasis, Rheumatic Fever, Sarcoidosis, Scleroderma, Adult Onset Still's Disease (AOSD), Systemic Lupus Erythematosus (SLE), Ulcerative Colitis, Hemophagocytic lymphohistiocytosis (HLH, also known as hemophagocytic syndrome, macrophage activation syndrome), Familial hemophagocytic lymphohistiocytosis (FHL) and other immunodeficiency syndromes, Giant Cell Arteritis (GCA), coronary artery disease (CAD), Coronary Vasculopathy (CV), Acute Coronary Syndromes (ACS), Congestive Heart Failure (CHF), atherosclerosis, arteriosclerosis, myocardial infarction (MI), Cardiorenal Syndrome (CRS), Acute Kidney Injury (AKI), Diabetic Nephropathy, insulin resistance, obesity and the metabolic syndrome (MetS), lung diseases including pulmonary sarcoidosis, pulmonary fibrosis, asthma, especially severe asthma, Uveitis, Geographic Atrophy, Chronic Obstructive Pulmonary Disease (COPD), cystic fibrosis, Adult Respiratory Distress Syndrome (ARDS)), Acute Lung Injury (ALI), Ventilator Induced Lung Injury (VILI), Pulmonary Arterial Hypertension (PAH), Alzheimer's Disease (AD) and sepsis and any combinations thereof which method comprises administrating to a mammalian patient a therapeutically effective amount of an antibody or pharmaceutical composition as described in any one of embodiments 1 to 88 or 96 to 110 which binds IL-18 and does not bind the IL-18/IL-18 binding protein (IL-18 BP) complex.

Embodiment 114

A method of treating and/or preventing sarcoidosis, in particular pulmonary sarcoidosis, hemophagocytic lymphohistiocytosis (HLH), familial hemophagocytic lymphohistiocytosis (FHL), chronic obstructive pulmonary disease (COPD), Adult Onset Still's Disease (AOSD), atherosclerosis, systemic juvenile idiopathic arthritis (SJIA), severe asthma, Uveitis, Geographic Atrophy, Giant Cell Arthritis (GCA), diabetes type 1, diabetes type 2 and any combination thereof in a mammalian patient which method comprises administrating to the mammalian patient a therapeutically effective amount of an antibody or pharmaceutical composition as described in any one of embodiments 1 to 88 or 96 to 110 which binds IL-18 and does not bind the IL-18/IL-18 binding protein (IL-18 BP) complex.

Embodiment 115

The antibody or pharmaceutical composition as described in any one of embodiments 1 to 88 or 96 to 110 which binds IL-18 and does not bind the IL-18/IL-18 binding protein (IL-18 BP) complex and wherein the binding molecule is not IL-18BP, for use in treating and/or preventing sarcoidosis, in particular pulmonary sarcoidosis, hemophagocytic lymphohistiocytosis (HLH), familial hemophagocytic lymphohistiocytosis (FHL), chronic obstructive pulmonary disease (COPD), Adult Onset Still's Disease (AOSD), atherosclerosis, systemic juvenile idiopathic arthritis (SJIA), severe asthma, Uveitis, Geographic Atrophy, Giant Cell Arthritis (GCA), diabetes type 1, diabetes type 2 and any combination thereof in a mammalian patient.

8. Diagnostic Uses and Kits

One of the advantages of the binding molecule or isolated antibody or fragment thereof as described herein is that they bind IL-18 but do not bind the IL-18/IL-18 binding protein (IL-18 BP) complex and that they are not IL-18BP. Hence, the binding molecule or isolated antibody or fragment thereof as described herein are capable of only detecting free IL-18, not bound to IL-18BP. As free IL-18 is the biologically active molecule, it becomes immediately apparent that a binding molecule capable of recognizing only such entity may allow differentiation of free IL-18 from IL-18 bound to IL-18BP, which is inactive. Moreover, as the binding molecules of the invention do not encompass the IL-18BP, either isolated or naturally occurring, they lend themselves not only as therapeutic agents but also as tools in many other applications such as in diagnosis or in a diagnostic kit.

Hence, in another aspect, the present invention provides for binding molecules or isolated antibodies or fragments thereof as described herein which bind IL-18 and do not bind the IL-18/IL-18 binding protein (IL-18 BP) complex wherein the binding molecule is not IL-18BP for use in diagnosis or for use in a diagnostic kit.

The binding molecules or the isolated antibody or a fragment thereof as described herein can be used in combination with detecting antibodies in ELISA assays, western blots etc. and can be used only to detect the presence of free IL-18 but also to measure the amount of free IL-18.

Therefore, in another aspect, the present invention provides for binding molecules or isolated antibodies or fragments thereof which bind IL-18 and do not bind the IL-18/IL-18 binding protein (IL-18 BP) complex wherein the binding molecule is not IL-18BP for use in diagnosis or for use in detecting and/or measuring the presence and/or the amount of free IL-18 (i.e. IL-18 not bound to IL-18BP) in a sample.

In yet a further aspect of the present invention, there is provided a method for detecting and/or measuring the presence and/or amount of free IL-18 (i.e. IL-18 not bound to IL-18BP) in a sample, wherein the sample is optionally a human sample, wherein the method comprises contacting the sample with a binding molecule or an isolated antibody or a fragment thereof which binds IL-18 and does not bind the IL-18/IL-18 binding protein (IL-18 BP) complex wherein the binding molecule is not IL-18BP.

In yet a further aspect of the present invention, there is provided a method which comprises the steps of:
a. contacting a sample obtained from a subject (e.g. a subject afflicted with an inflammatory disease or disorder) with the binding molecule or the isolated antibody or a fragment thereof as described herein which binds IL-18 and does not bind the IL-18/IL-18 binding protein (IL-18 BP) complex wherein the binding molecule is not IL-18BP;
b. measuring the level of free IL-18;
c. optionally, measuring the level of total IL-18 and IL-18 BP;
d. wherein the steps b) and c) may be carried out simultaneously or consecutively or in inverted order (e.g. step b) before step c) or step c) before step b).

The sample may be a sample isolated from a mammalian body, preferably from a human body. The isolated sample may be:
i. from an accessible body site, for example a mucous membrane of the nose, skin, conjunctiva, mouth or throat, anus, vagina, urethra, cervix; and or
ii. comprises a fluid or semi-solid (for example a bodily fluid or semi-solid e.g. discharge, vomit, secretion, excreta, gastric and/or intestinal juices, sputum, blood, blood serum, plasma, urine, tears, synovial fluid, semen, prostate fluid, saliva, tissue homogenate or mucus); and or
iii. comprises a solid (e.g. stool, tissue, or biopsy sample); and/or
iv. comprises a culture (e.g. macrophage culture);
The sample may be human blood or a part of human blood such as plasma.

The isolated sample may be preferably selected from human whole blood, human blood monocyte-derived macrophages and human lung macrophages.

In another aspect, the present invention further provides for a diagnostic kit comprising the binding molecule or isolated antibody or a fragment thereof (which binds IL-18 and does not bind the IL-18/IL-18 binding protein (IL-18 BP) complex wherein the binding molecule is not IL-18BP) and/or the complex comprising IL-18 and that binding molecule wherein the kit optionally comprises a first control compound.

A control compound is a compound that will indicate the diagnostic kit is working. A control compound may be positive or negative and it will verify that any result is valid.

The first control compound may be free IL-18 and the kit optionally may comprise a second control compound which is murine antibody 125-2H.

In another aspect of the present invention, there is provided a medical or diagnostic device comprising the binding molecule or the isolated antibody or a fragment thereof (which binds IL-18 and does not bind the IL-18/IL-18 binding protein (IL-18 BP) complex) and/or the complex wherein the binding molecule is not IL-18BP comprising IL-18 and that binding molecule.

9. Exemplification

Sequences of the antibodies of the present invention exemplified herein, together with a sequence correlation table are described towards the end of this specification.

9.1) Materials

Recombinant human IL-18 (generated in *E. coli* using the method described by Liu et al (2000) Cytokine 12(10):1519-25).

Recombinant cynomogus IL18 (generated in *E. coli* using the method described in U.S. Pat. No. 6,432,678)

Recombinant human TNFα (R&D #210-TA)

Recombinant human IL-18 Binding Protein-IgG$_1$ Fc (hIL-18BPa-Fc, R&D Systems #119-BP-100)

Mouse anti-human IL-18 IgG$_1$ (125-2H; R&D Systems # D044-3)

Human anti-lysozyme antibody (MOR03207 Morphosys)

KG-1 cell line (ATCC #CCL-246)

Cell media: RPMI 1640 (Invitrogen #31870) supplemented with 10% Foetal Bovine Serum (Invitrogen #10108-157), 1% L-Glutamine (Invitrogen #25030-03), 1% penicillin/streptomycin (Invitrogen #15140-148).

Flat bottomed, tissue-culture treated 96-well plates (Costar #3596)

Human IFN-γ DuoSet ELISA assay (R&D #DY285)

Maxisorb microtitre plates (Sigma #M9410)

Heparin (Sigma #H3393)

Recombinant human IL-12 (R&D Systems #219-IL-CF)

LPS (Sigma #L4516)

Falcon tubes (Corning #430829)

Ficoll-Paque™ Plus (GE Healthcare Life Sciences #17-1440-02)

KG-1 cells were maintained in RPMI 1640 supplemented with 10% FBS, 1% L-Glutamine and 1% penicillin/streptomycin at a density of $2\times10^5$ to $1\times10^6$ viable cells/ml.

9.2) Antibodies and Fragments Thereof Selected for Functional Analysis

The antibodies and fragments thereof were generated by phage display. The phagemid library used is based on the HuCAL® concept (Knappik, A. at al. (2000) J Mol Biol 296, 57-86) and employs the CysDisplay™ technology for displaying the Fab on the phage surface (WO 01/05950). To increase affinity and biological activity of selected antibody fragments, L-CDR3 and H-CDR2 regions were optimized in parallel by cassette mutagenesis using trinucleotide directed mutagenesis (Virnekas, B et al. (1994) Nucleic Acids Res 22, 5600-5607), while the framework regions were kept constant. Antibodies from different parental frameworks were selected for IgG conversion and functional characterization. These antibodies and fragment thereof are shown in Table 1A below.

TABLE 1A

IgGs and Fabs selected for functional analysis

|  | Framework |
| --- | --- |
| MOR08776 | VL1/VH4 |
| MOR10497 | VL1/VH4 |
| MOR10501 | VL1/VH4 |
| MOR10502 | VL1/VH4 |
| MOR8775 | VL1/VH1 |
| MOR9441 | VL1/VH1 |
| MOR9464 | VL1/VH1 |
| MOR9465 | VL1/VH1 |
| MOR9466 | VL1/VH1 |
| MOR10579 | VL1/VH1 |
| MOR10222 | VL1/VH1 |
| MOR13363 | VK1/VH3 |
| MOR13361 | VK1/VH3 |
| MOR13341 | VK1/VH1 |
| MOR13342 | VK1/VH1 |
| MOR13347 | VK1/VH1 |

Antibody MOR9464 when formulated in a liquid formulation appeared to lose potency over time. It was hypothesized that the molecule may undergo some modifications which affected its potency. MOR9464 was incubated at a temperature higher than physiological temperature to accelerate the appearing of the loss of potency. By combining complex biophysical techniques, including mass spectrometry and reverse phase HPLC, two distinct, yet unknown, forms of MOR9464 were isolated.

A number of modifications may occur to protein when they are in the extracellular media, during in vitro manipulation and in vivo circulation. Whatever the modification is, it can widely impact the properties relevant to protein-based pharmaceutical. Hence, it becomes paramount to understand the structure-functional relationship of these modifications. Exocellular modifications are modifications which occur soon after therapeutic proteins complete the trafficking pathway, reach cell surface and they are released in the extracellular medium environment and incubated there during the production period. They also encompass modification occurring during in vitro manipulation, such as purification and formulation in suitable buffers, or even in vivo circulation (Zhong X. and Wright J. F., Int J of Cell Biol., 2013, 1-19). Proteolytic processing is the most common and well-known exocellular modifications as its products are easily identified. Oxidation of single amino acid residues may be more difficult to characterize and may involve methionine residues as well as tryptophan, cysteine, histidine and tyrosine residues. N-terminal pyroglutamate formation is also a well-known exocellular modification whereby the N-terminal Glutamine or Glutamate residues can readily cyclize with its own terminal group to form pyrrolidone carboxylic acid. Deamidation of asparagine and aspartate residues or aspartate isomerization are also known, yet not well characterized modifications.

If the exocellular modifications occur in specific regions of the antibody, they may have a deep effect on the functional characteristics of an antibody, such as loss of potency. If the modification occurs in the CDR or in a very near location, it may impact of the ability of the antibody to recognize and/or specifically bind its antigen.

Analyses of the MOR9464 sequence were carried out to identify potential site of exocellular modifications. The mutants shown in Table 1B were generated.

TABLE 2B

MOR9464/MOR10222 mutants

MOR9464_N30T
MOR9464_N30A
MOR9464_N30E
MOR9464_N30H
MOR9464_N30K
MOR9464_N30Q
MOR9464_N30G
MOR9464_N30V
MOR9464_N30Y
MOR9464_N30R
MOR9464_N30I
MOR9464_N30L
MOR9464_N30S
MOR10222_E1Q
MOR10222_E1Q_N30S
MOR10222_E1Q_N30D
MOR10222_E1Q_N30T
MOR10222_E1Q_N30S_M54Y
MOR10222_E1Q_N30S_M54N
MOR10222_E1Q_N30S_M54I
(indicated hereafter as
MOR10222_N30S_M54I)
MOR10222_E1Q_S31T
MOR10222_E1Q_S31N
MOR10222_E1Q_S31A
MOR10222_E1Q_S31T_M54Y
MOR10222_E1Q_S31T_M54N
MOR10222_E1Q_S31T_M54I
MOR10222_E1Q_S31N_M54Y
MOR10222_E1Q_S31N_M54N
MOR10222_E1Q_S31N_M54I Asparagine 30 just flanking the H-CDR1 of MOR9464 was considered to be a possible site of modification, together with serine 31 in the H-CDR1 and methionine 54 in the H-CDR2. Non-enzymatic deamidation of asparagine and glutamine residues to aspartate and glutamate occurs through hydrolytic reaction and is pH, temperature and ionic strength-dependent. It also depends on the amino acid residues preceding the asparagine and glutamine residues, with serine and threonine increasing the deamidation rates.

Most of the MOR10222_S31X mutants, with or without methionine mutation, heavily aggregated after production. Hence these mutants were not characterized any further.

9.3) Determination of Affinities Using Solution Equilibrium Titration (SET)

For $K_D$ determination by solution equilibrium titration (SET), monomer fractions of antibodies were used (analyzed by analytical SEC).

Affinity determination in solution was basically performed as described in the literature (Friguet B at al. (1985) J Immunol Methods; 77(2):305-19). In order to improve the sensitivity and accuracy of the SET method, it was transferred from classical ELISA to electro-chemiluminescent (ECL)-based technology (Haenel C et al. (2005) Anal Biochem; 339(1):182-4).

Goat-anti-human (Fab)$_2$ fragment specific antibodies (Dianova) were labeled with MSD SULFO-TAG™ NHS-Ester (Meso Scale Discovery, Gaithersburg, Md., USA) according to the manufacturer's instructions. Experiments were carried out in polypropylene microtiter plates and phosphate-based assay buffer. Unlabeled human IL-18 was serially diluted, starting with a concentration at least 10 times higher than the expected $K_D$. Wells without antigen were used to determine $B_{max}$ values; wells with assay buffer were used to determine background. After addition of a constant amount of antibodies or fragment thereof (e.g. 10 pM final concentration in 60 µl final volume), the mixture was incubated over night at RT. The applied antibodies or fragments thereof concentration was similar to or below the expected $K_D$.

Streptavidin MSD plates were blocked with BSA-containing phosphate buffer over night. After blocking of the plate, biotinylated human IL-18 was added and incubated for 1 h at RT. Subsequently the equilibrated samples were transferred to those plates and incubated for a short time at RT. After washing, MSD SULFO-TAG labeled detection antibody (goat anti-human (Fab)$_2$) was added to the MSD plate and incubated for a short time at RT.

After washing the plate and adding MSD Read Buffer T with surfactant, electrochemi-luminescence signals were detected using a Sector Imager 6000 (Meso Scale Discovery, Gaithersburg, Md., USA).

Data was evaluated with XLfit (IDBS) software applying customized fitting models. For $K_D$ determination of Fab molecules the following fit model was used (according to Haenel et al., 2005), modified according to Abraham et al, 1996):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

$[Fab]_t$: applied total Fab concentration
x: applied total soluble antigen concentration (binding sites)
$B_{max}$: maximal signal of Fab without antigen
$K_D$: affinity In principle the same protocol was applied to determine $K_D$ values for antibodies and fragments with the following differences: whole antibodies were added to the dilution series of antigen, and equilibrated over night at RT. Subsequently, the samples were treated as described above.

For data evaluation i.e. $K_D$ determination of IgG molecules the following fit model for IgG was used (modified according to Piehler et al., 1997):

$$y = \frac{2B_{max}}{[IgG]} \left( \frac{[IgG]}{2} - \frac{\left( \frac{x + [IgG] + K_D}{2} - \sqrt{\frac{(x + [IgG] + K_D)^2}{4} - x[IgG]} \right)^2}{2[IgG]} \right)$$

[IgG]: applied total IgG concentration
x: applied total soluble antigen concentration (binding sites)
$B_{max}$: maximal signal of IgG without antigen
$K_D$: affinity Affinities of the anti-IL-18 antibodies or fragments thereof were determined in solution using the assay conditions described above and are indicated in Table 2A (column 2). Where IL-18 from cynomolgus monkey (cm IL-18) was also tested, the resulting $K_D$ are indicated in brackets.

9.4) Inhibition of IFN-γ Release from IL-18 Stimulated Human PBMCs

Peripheral blood mononuclear cells (PBMCs) were freshly isolated from heparinized human whole blood using standard techniques. Briefly, diluted blood containing Heparin (15 U/ml) as an anti-coagulant was layered onto Ficoll-Paque™ Plus and centrifuged (800×g, 20 minutes, 18° C.). The PBMCs were collected from the plasma:Ficoll interface and washed twice (600×g, 10 minutes, 4° C.), before re-suspending in medium.

PBMCs were re-suspended in media and applied to a 96 well cell culture plate to give a final cell density of 1.5×10$^6$/ml (in a final assay volume of 200 µl). To ensure the antibodies and fragment thereof according to the invention recognised native IL-18, which may be glycosylated, PBMCs were stimulated with LPS and IL-12 which induces IFN-γ via IL-18-dependent autocrine feedback.

Cells were stimulated with 3 nM human recombinant IL-18 plus IL-12 (1 ng/ml) or LPS (3 μg/ml) plus IL-12 (10 ng/ml) to induce secretion of native IL-18 protein (all final concentrations). In the case of recombinant human IL-18, the concentration selected was pre-determined as an approximate $EC_{80}$ in this assay. In the case of native IL-18, LPS stimulates production of IL-18, whilst IL-12 increases IL-18 receptor expression (Yoshimoto T et al. (1998) J Immunol; 161(7): 3400-7). The extent of IL-18-dependency in this assay was determined via inclusion of the highly specific protein, IL-18 Binding Protein-IgG$_1$ Fc (hIL-18BPa-Fc) as a positive control (dotted line in FIGS. 3 (A-D).

To assess their potency and efficacy, the antibodies and fragments thereof were pre-equilibrated for 30 min with either IL-12 and LPS (native conditions) or IL-12 and IL-18 (recombinant conditions) prior to applying to cells with a final concentration between 0.1 and 300 nM. Anti-lysozyme control antibody MOR03207 was used as a negative control.

From each treatment group, a mean±SEM value (where n=3 or more) was determined from n=2-5 wells.

Cells were incubated at 37° C., 5% $CO_2$ for 24 hours after treatment, after which time the supernatant was collected by centrifugation (1200 rpm for 5 min) and stored at −20° C. for subsequent analysis. IFN-γ protein levels were assessed using ELISA as per the manufacturer's instructions.

Figure 3C:
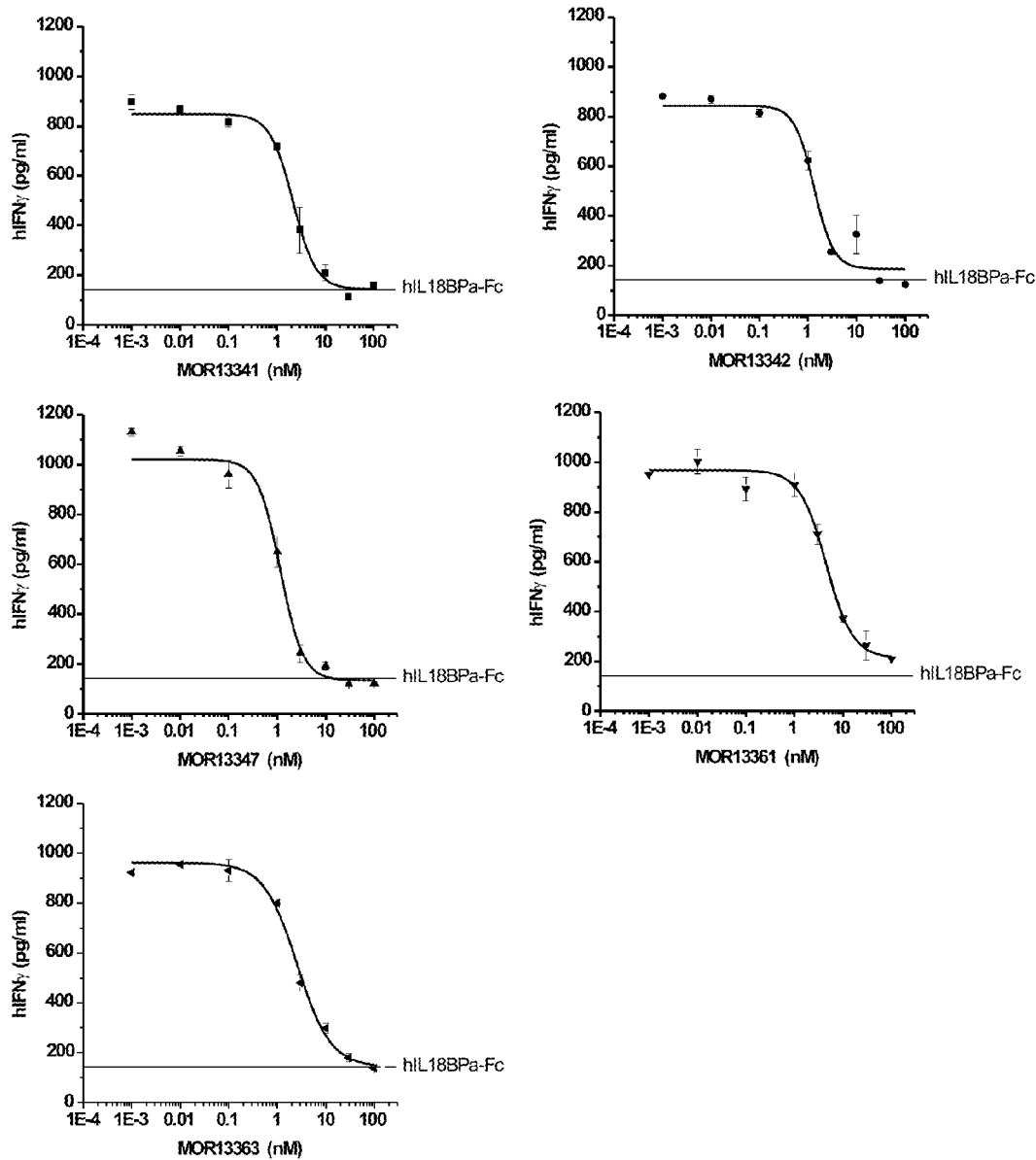
Figure 4A:
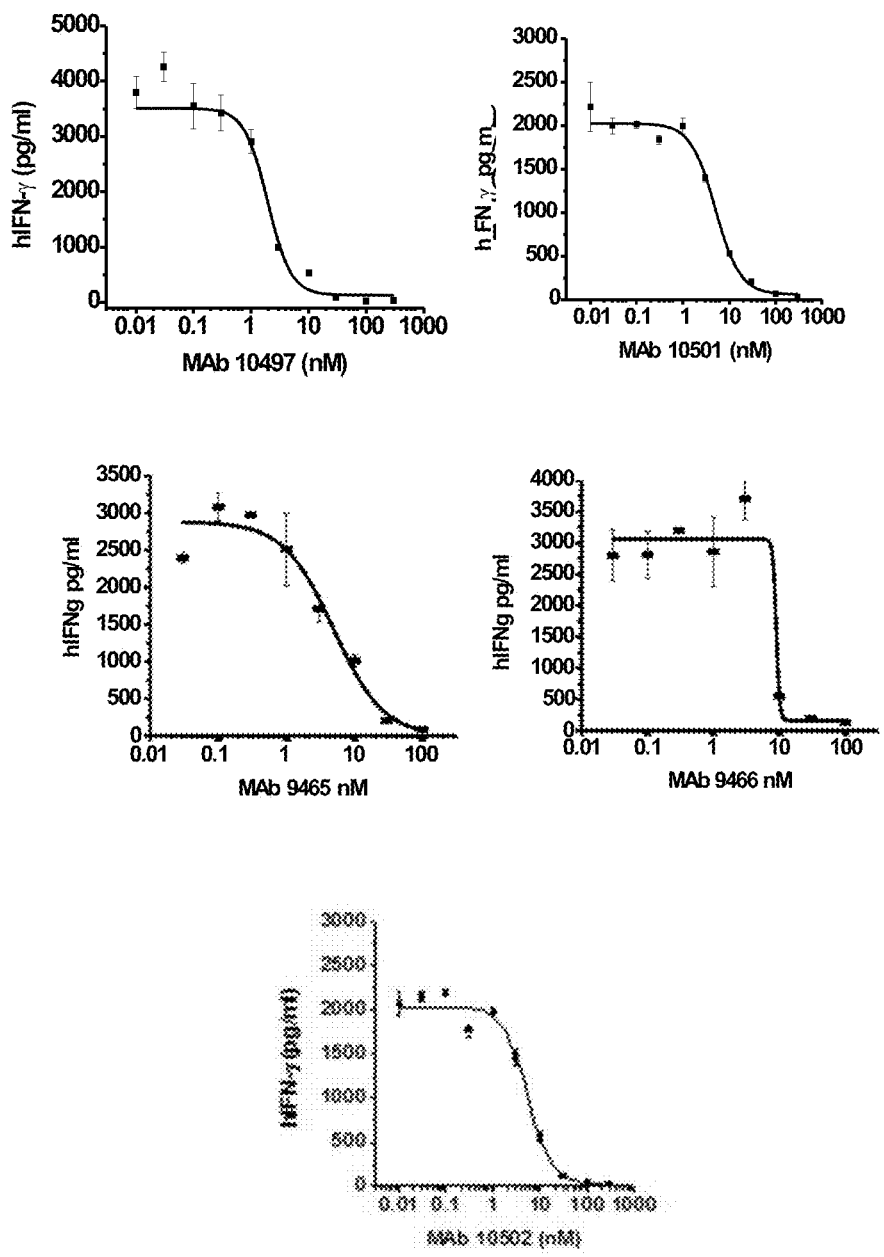
FIG. 4 (A-B): Effect of anti-IL-18 antibodies and fragments thereof of the present invention on IFN-γ release from PBMCs induced by recombinant IL-18. Data shows concentration-dependent inhibition of recombinant human IL-18 (1 nM)-induced IFN-γ release from freshly isolated human PBMCs from representative individual donors, where each data point represents mean±SEM from n=4 wells.
Figure 4B:
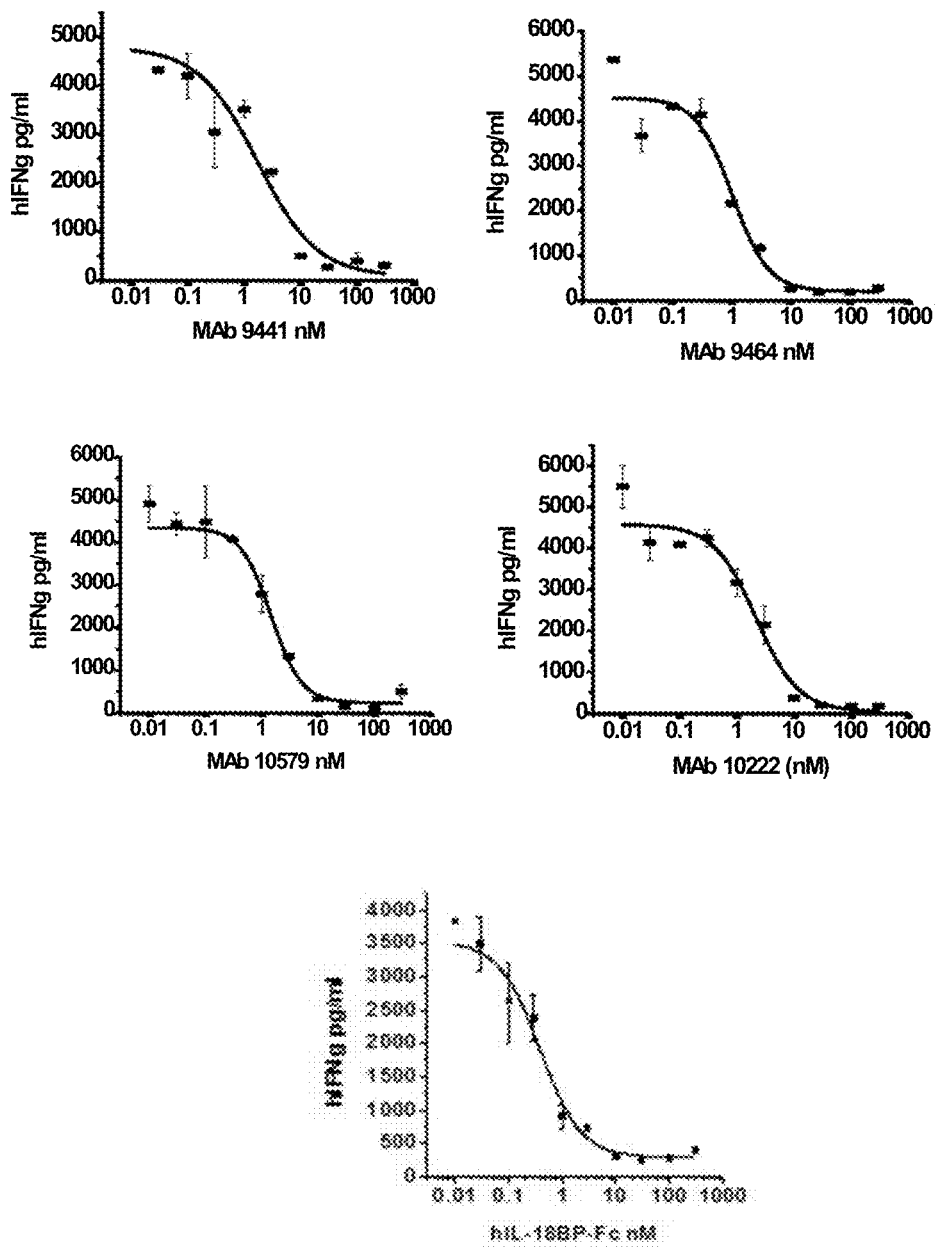
Figure 5A:
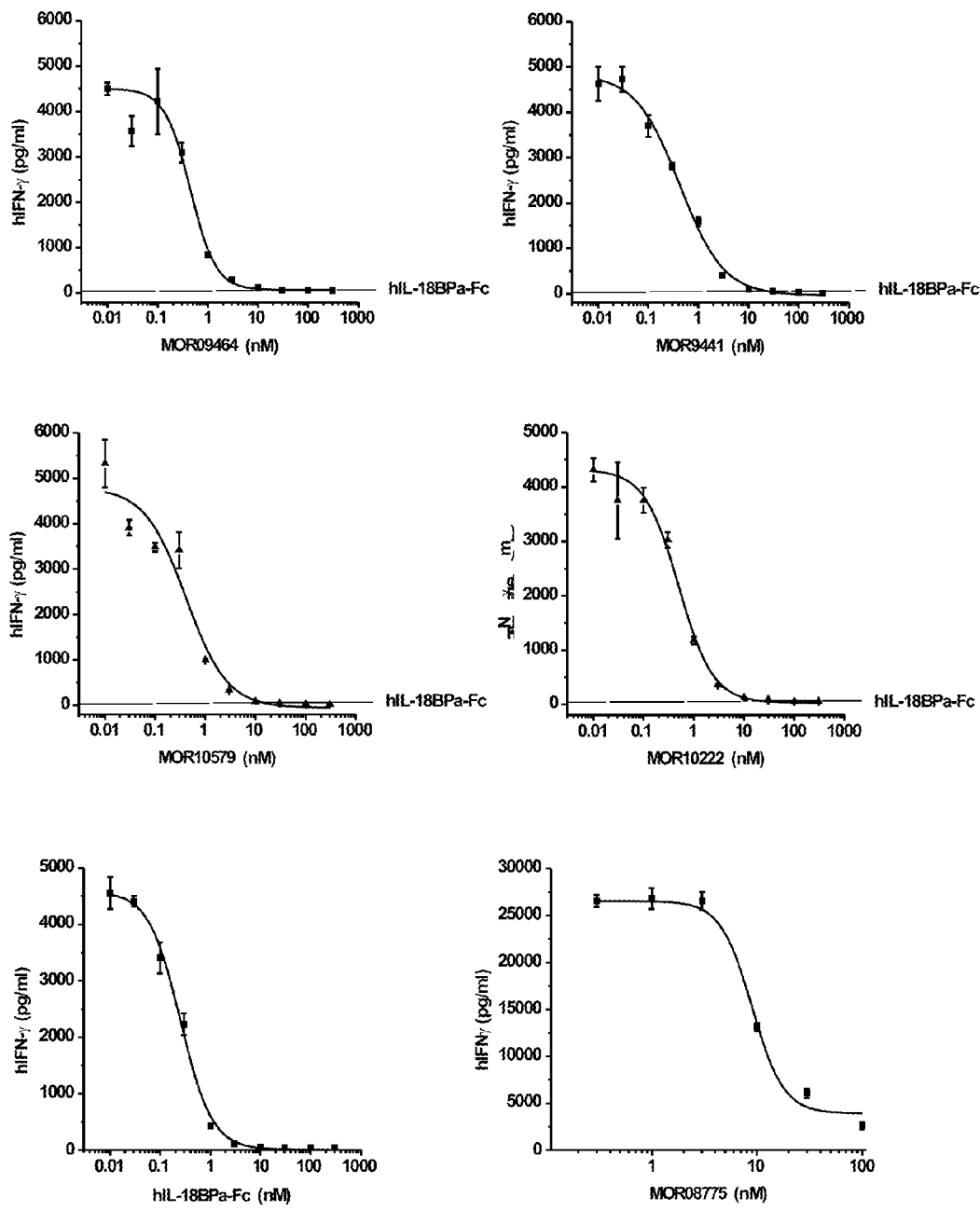
FIG. 5 (A-C): Effect of anti-IL-18 antibodies and fragments thereof of the present invention on IFN-γ release from KG-1 cells induced by human IL-18. Data shows concentration-dependent inhibition of recombinant human IL-18 (1 nM)-induced IFN-γ release from KG-1 cells, where each data point represents mean±SEM from n=4 wells.
Figure 5B:
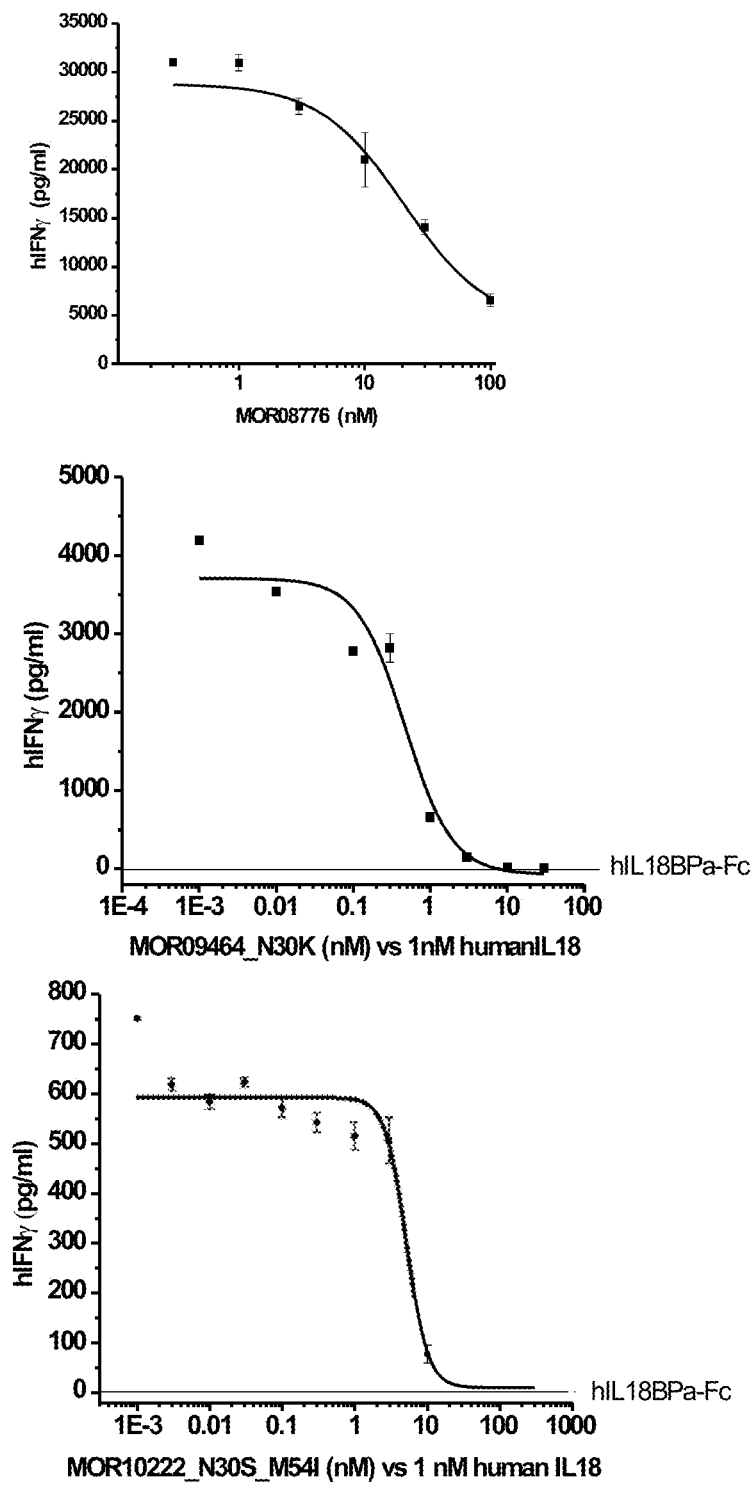
Figure 6A:
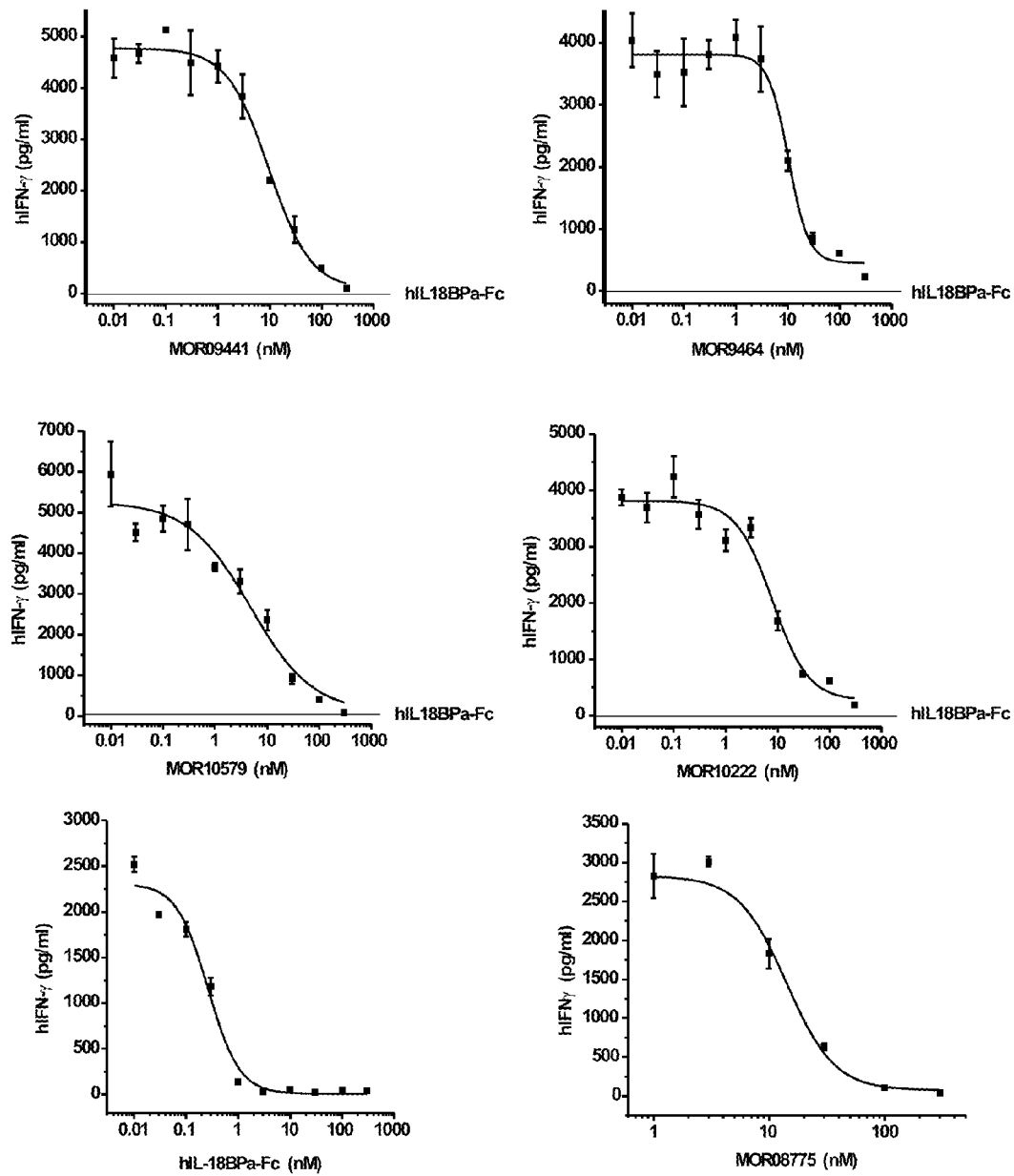
FIG. 6 (A-C): Effect of anti-IL-18 antibodies and fragments thereof of the present invention on IFN-γ release from KG-1 cells induced by cynomolgus IL-18. Data shows concentration-dependent inhibition of recombinant cynomolgus IL-18 (0.2 nM)-induced IFN-γ release from KG-1 cells, where each data point represents mean±SEM from n=4 wells.

All antibodies and fragments thereof dose-dependently inhibited IFN-γ production with a similar level of efficacy achieved at the highest concentrations as that seen for recombinant IL-18BPa-Fc (Table 2A columns 5-6, Table 2B column 2 and FIGS. 3 (A-D) where efficacy of the IL-18BPa is denoted by dotted line). The control antibody, MOR03207 (anti-lysozyme control antibody) did not inhibit the IL-18 response. Germlining antibodies, (e.g. MOR10579 from MOR09441 and MOR10222) from MOR09464 did not significantly alter their neutralizing capacity. Mutants of MOR9464 and MOR10222, in particular MOR9464_N30K and MOR10222_N30S_M54I did have comparable neutralizing capacity to the wild type antibodies.

TABLE 2B $IC_{50}$ values (nM) for inhibition of human recombinant (hr) IL-18 (1 nM), native IL-18-induced IFNγ release

| Identification | KG-1 Hu IL-18 | PBMC Native IL-18 |
|---|---|---|
| MOR1022_N30S | 3.3 ± 2.1 | 0.05 ± 0.00 |
| MOR1022_N30S_M54Y | 4.8 ± 0.3 | 0.09 ± 0.01 |
| MOR1022_N30S_M54N | 5.2 ± 4.4 | 0.03 ± 0.02 |
| MOR1022_N30S_M54I | 4.2 ± 1.4 | 0.05 ± 0.03* |
| MOR09464_N30T | 0.31 ± 0.02 | 0.19 ± 0.09 |
| MOR09464_N30E | 0.49 ± 0.05 | 0.13 ± 0.05 |
| MOR09464_N30H | 0.23 ± 0.11 | 0.10 ± 0.05 |
| MOR09464_N30K | 0.36 ± 0.15 | 0.20 ± 0.14 |
| MOR09464_N30Q | 0.22 ± 0.03 | 0.07 ± 0.14 |
| MOR09464_N30G | 0.54 ± 0.06 | 0.11 ± 0.07 |
| MOR09464_N30V | 0.29 ± 0.03 | 0.11 ± 0.02 |
| MOR09464_N30Y | 0.23 ± 0.01 | 0.03 ± 0.01 |
| MOR09464_N30R | 0.47 ± 0.49 | 0.04 ± 0.01 |
| MOR09464_N30I | 0.32 ± 0.09 | 0.11 ± 0.06 |
| MOR09464_N30L | 0.23 ± 0.03 | 0.05 ± 0.04 |
| | (n = 2; Mean +/− SD) | n = 3 Mean +/− SEM *n = 2, Mean +/− SD |

9.5) Inhibition of IFN-γ Release from IL-18 Stimulated KG-1 Cells

Anti-IL-18 antibodies and fragments thereof were analyzed for their ability to inhibit IFN-γ release from IL-18-stimulated KG-1 cells. In the absence of an antagonist, IL-18 promotes maximal stimulation of IFN-γ (release in the presence of a co-stimulus such as TNFα and IL-12 through upregulation of IL-18 receptors (Nakamura S et al. (2000) Leukemia; 14(6):1052-9). Inhibitory activity of the antibodies and fragments was assessed against 1 nM of either human or cynomolgus IL-18 (unless otherwise specified), predetermined as an $EC_{80}$ in this cell-based system.

KG-1 cells were re-suspended in culture media and applied to a 96 well cell culture plate to give a final cell density of $0.3 \times 10^6$/ml (in a final assay volume of 200 μl). Cells were stimulated with 1 nM human or cynomolgus recombinant

TABLE 2A $K_D$ values of IL-18 affinity and $IC_{50}$ values (nM) for inhibition of human recombinant (hr) IL-18 (1 nM) and native IL-18-induced IFNγ release

| | $K_D$ (SET, pM) Hu IL-18 | KG-1 Hu IL-18 | KG-1 Cyno IL-18 | PBMC Hu IL-18 | PBMC Native IL-18 |
|---|---|---|---|---|---|
| MOR08776 | 38 | 18 | ND | 50.8 | 5.9 |
| MOR010497 | 2 | 0.3 | 0.3 | 5.8 ± 2.2 | 1.8 ± 0.6 |
| MOR010501 | 1 | 0.3 | 0.2 | 6.3 ± 1.5 | 1.3 ± 0.5 |
| MOR010502 | 4 | 0.4 | 0.2 | 6.3 ± 0.7 | 2.3 ± 1.1 |
| MOR08775 | 65 | 68 | 22 | 9.2 | 0.7 |
| MOR09465 | 6 | 0.3 | 1.8 | 0.6 | 0.89 ± 0.3 |
| MOR09466 | 5 | 0.4 | 5.6 | 1.2 | 2.1 ± 0.6 |
| MOR09441 | 1 | 0.6 ± 0.1 | 16.4 ± 7.1 | 2.5 ± 1.0 | 0.45 ± 0.1 |
| MOR09464 | 3 | 0.8 ± 0.2 | 8.3 ± 1.6 | 1.3 ± 0.5 | 0.2 ± 0.03 |
| MOR010579 | N/A | 0.8 ± 0.2 | 9.8 ± 5.3 | 1.9 ± 0.6 | 0.3 ± 0.02 |
| MOR010222 | N/A | 0.7 ± 0.1 | 6.6 ± 2.0 | 2.3 ± 0.5 | 0.22 ± 0.03 |
| IL-18BP-Fc | N/A | 0.3 ± 0.1 | 0.4 ± 0.1 | 1.0 ± 0.5 | 0.17 ± 0.02 |
| MOR09464_N30K | 2 ± 1 (20 ± 10) | 0.36 ± 0.15 | 4.7 | | 0.2 ± 0.14 |
| MOR1022_N30S_M54I | 3 ± 2 (30 ± 0) | 4.21 ± 0.14 | 8.12 | | 0.05 ± 0.03 |
| MOR13363 | 10 ± 0 (10 ± 0) | 0.49 ± 0.9* | 0.28 ± 0.16# | | 0.18 ± 0.1 |
| MOR13361 | 7 ± 3 (6 ± 1) | 0.41* | 0.13# | | 0.5 ± 0.01 |
| MOR13341 | 3 ± 2 (30 ± 0) | 0.13 ± 0.08* | 2.8 ± 0.26# | | 0.8 ± 0.7 |
| MOR13342 | N/A | 0.11 ± 0.03* | 2.9# | | 0.5 ± 0.4 |
| MOR13347 | N/A | 0.12 ± 0.07* | 2.8 ± 0.3# | | 0.5 ± 0.4 |

N/A = not available;
*human IL-18 concentration = [0.5 nM];
cyno IL-18 concentration = [0.2 nM]

IL-18 plus TNFα (final concentration 20 ng/ml). The concentration of recombinant IL-18 selected was pre-determined as an approximate $EC_{80}$ in this assay.

To assess the potency and efficacy of these antibodies, the antibodies and fragments thereof were pre-equilibrated for 30 min with TNFα and IL-18 (human or cynomolgus) prior to applying to cells with a final concentration between 0.1 and 300 nM. Anti-lysozyme control antibody MOR03207 was used as a negative control.

From each treatment group, a mean±SEM value (where available) was determined from n=2-5 wells.

Cells were incubated at 37° C., 5% $CO_2$ for 24 hours after treatment, after which time the supernatant was collected by centrifugation (885×g for 5 min) and stored at −20° C. for subsequent analysis. IFN-γ protein levels were assessed using ELISA as per the manufacturer's instructions.

All antibodies and fragments thereof dose-dependently inhibited IFN-γ production with full inhibition achieved at the highest concentrations. For affinity-matured antibodies, $IC_{50}$ values ranged from 0.3-0.8 nM against 0.8 nM human IL-18, therefore representing a 1:1 molar ratio antibody:antigen or better. VH4_3b framework antibodies (MOR08776, MOR010501, MOR010502) demonstrated similar potency against both human and cynomolgus IL-18, whilst VH1A_3 framework antibodies were slightly less potent against cynomolgus IL-18 (Table 2, columns 3 and 4). The control antibody, MOR03207 did not inhibit the IL-18 response.

9.6) IL-18 Induced INF-γ Release in Human Whole Blood

The whole blood assay incorporates both the presence and function of the endogenous IL-18BP since the IL-18BP is primarily generated by the spleen and is present systemically at levels of around 10-20 ng/ml in healthy individuals. IL-18BP binds with high affinity to IL-18 and neutralizes its activity, and therefore might represent a sink for antibodies that recognize accessible epitopes of this complex.

The activity of the anti-IL-18 antibodies was assessed in heparinized human whole blood taken from a healthy volunteer. All reagents were prepared at twenty-fold the final desired concentration using serum free medium. Cells were stimulated with either 7 nM human recombinant IL-18 plus IL-12 (1 ng/mL) or LPS (10 µg/mL) plus IL-12 (10 ng/mL) to induce secretion of native IL-18 protein (all final concentrations). In the case of recombinant human IL-18, the concentration selected was pre-determined as an approximate $EC_{80}$ in this assay. In the case of native IL-18, LPS stimulates production of IL-18, whilst IL-12 increases IL-18 receptor expression and the extent of IL-18-dependency is determined via inclusion of recombinant human IL-18 Binding Protein-$IgG_1$ Fc (hIL-18BPa-Fc) as a positive control.

To assess the potency and efficacy of these antibodies, the anti-IL-18 antibodies and fragments thereof were pre-equilibrated for 30 min with the relevant stimulus prior to applying to cells with a final concentration between 0.1 and 1000 nM. Anti-lysozyme control antibody MOR03207 was used as a negative control.

The stimulus mixture (+/− antibody or fragment) was added to each well of a 96-well tissue culture sterile microtitre plate as 30 µL and 170 µL heparinised whole blood was then added to each well, such that the final volume in each well was 200 µl. The plates were then returned to a humidified incubator (37° C.). After 24 h, the plates were centrifuged (885×g, 4° C., 5 min) and the supernatants removed and assayed for hIFN-γ production using a commercially available ELISA kit. Final data was derived as a mean±standard error of mean from 3-5 healthy human donors.

Figure 7A:
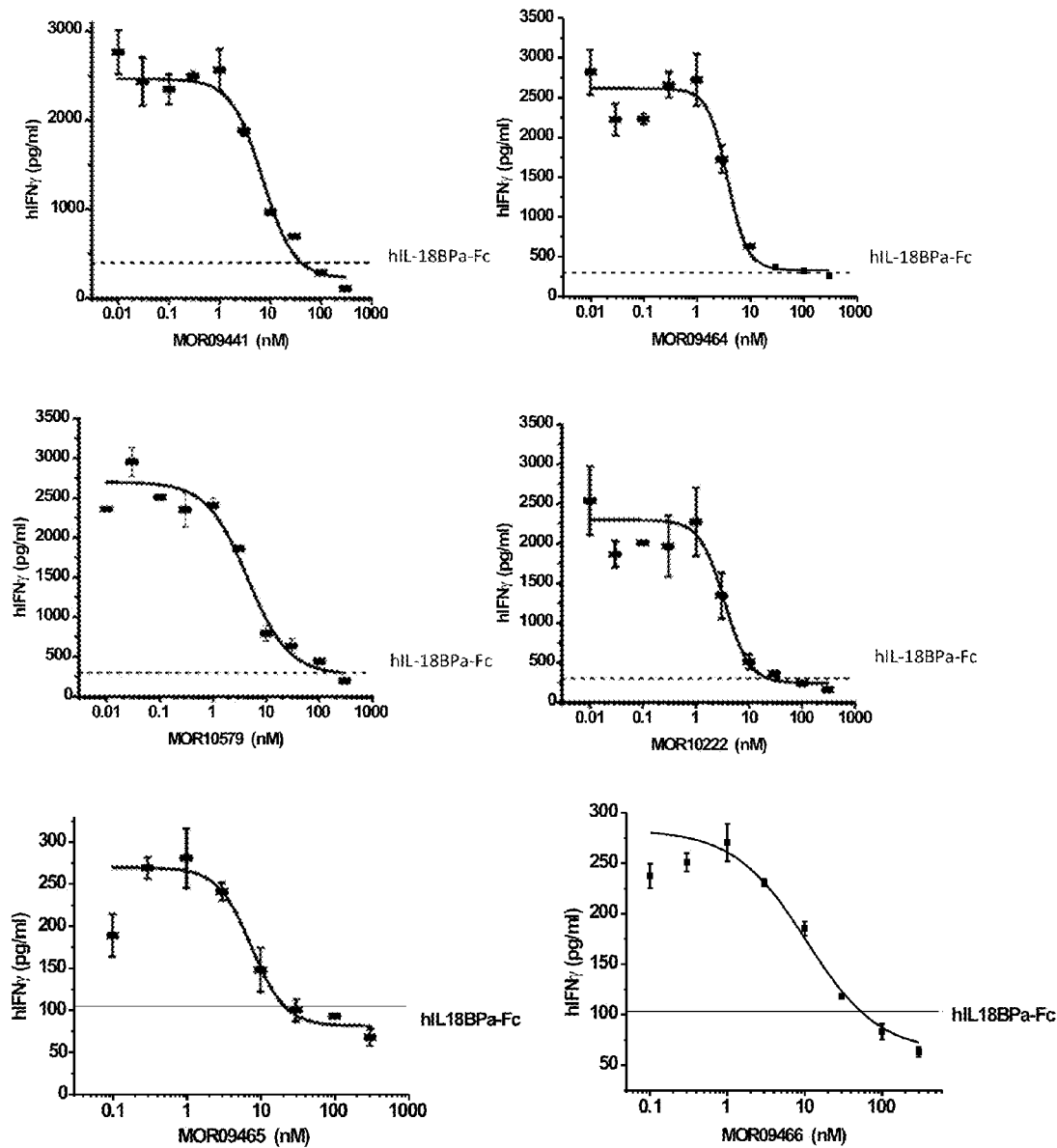
FIG. 7 (A-E): Effect of anti-IL-18 antibodies and fragments thereof of the present invention on human IL-18-induced by LPS/IL-12 (stimulation of native IL-18) and subsequent IFN-γ release in human whole blood.
Figure 7B:
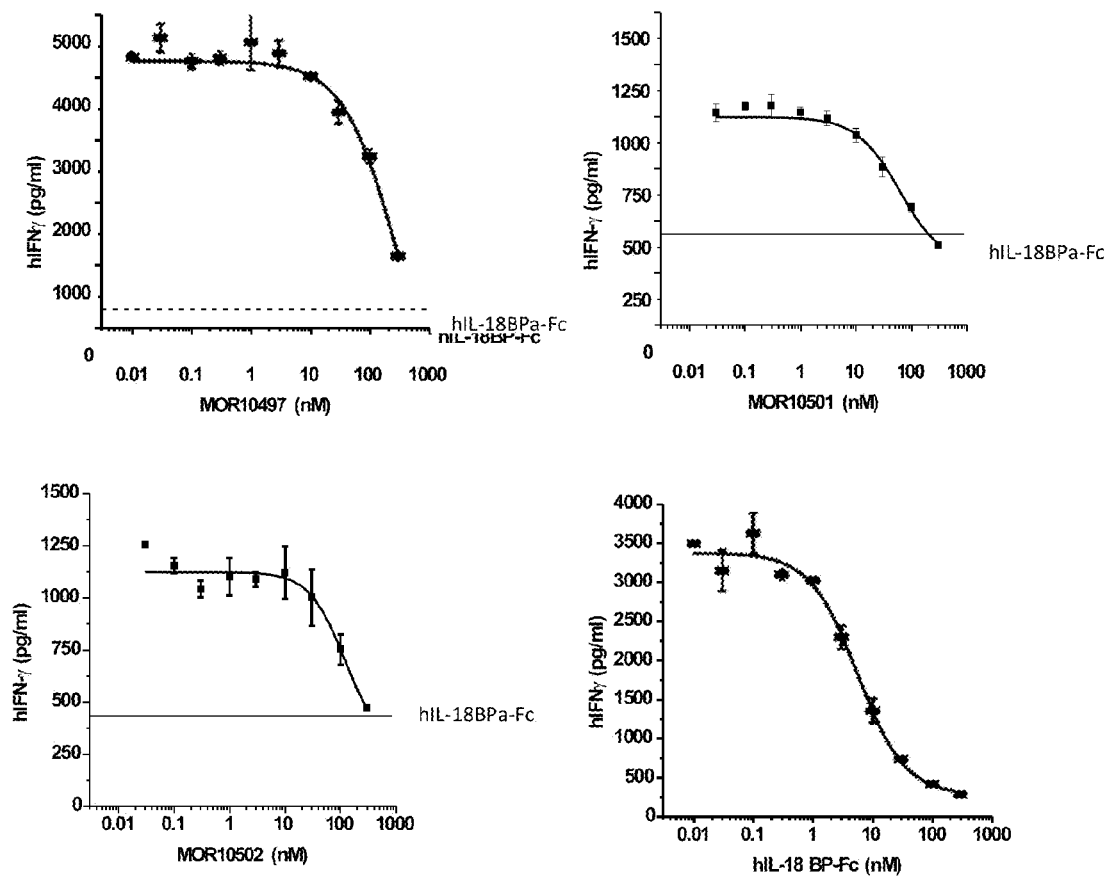
Figure 8A:
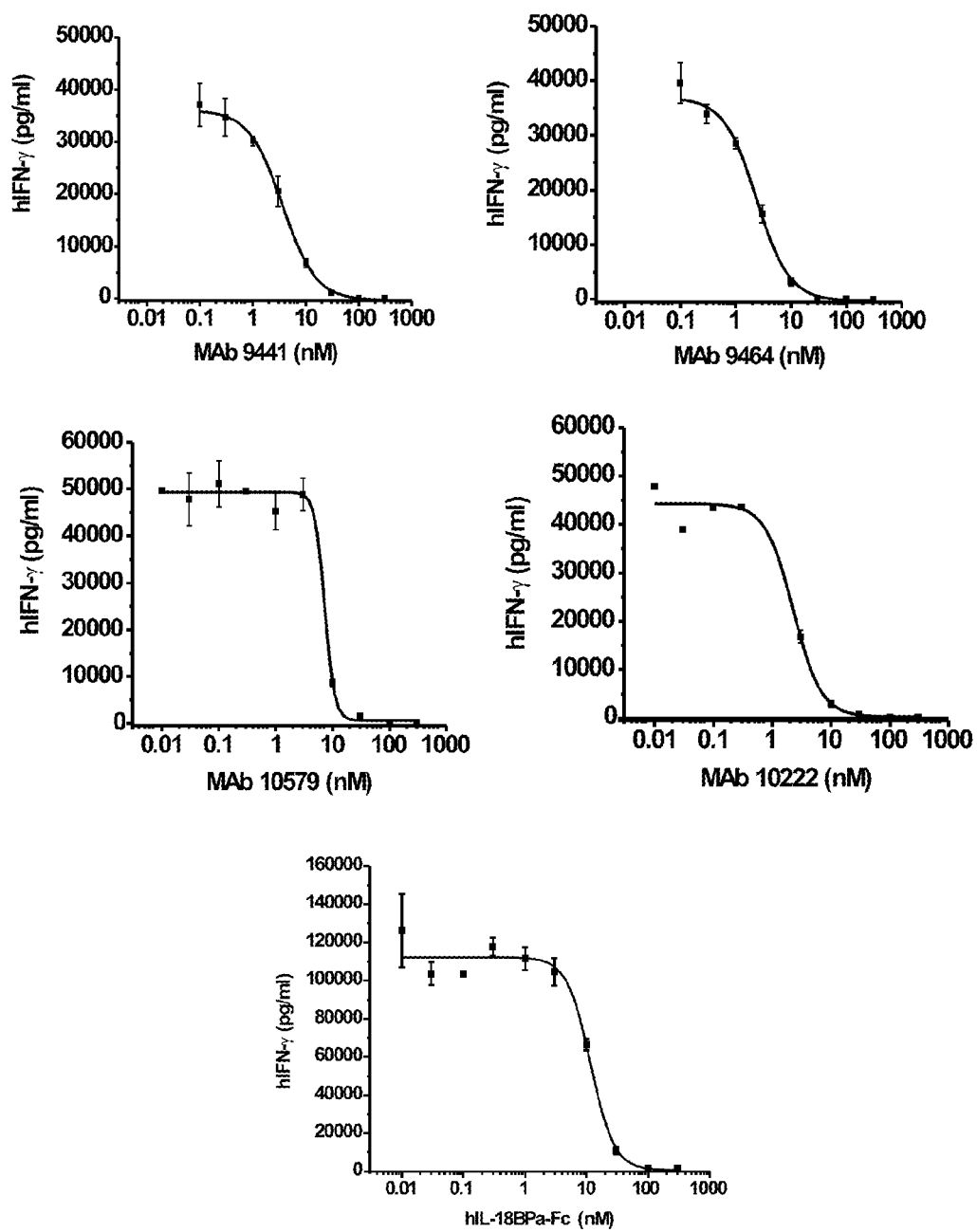
FIG. 8 (A-E): Effect of anti-IL-18 antibodies and fragments thereof of the present invention on human IL-18-induced IFN-γ release in human whole blood. Data shows concentration-dependent inhibition of recombinant human IL-18-induced IFN-γ release from whole blood taken from individual donors, where each data point represents mean±SEM from n=4 wells.
Figure 8B:
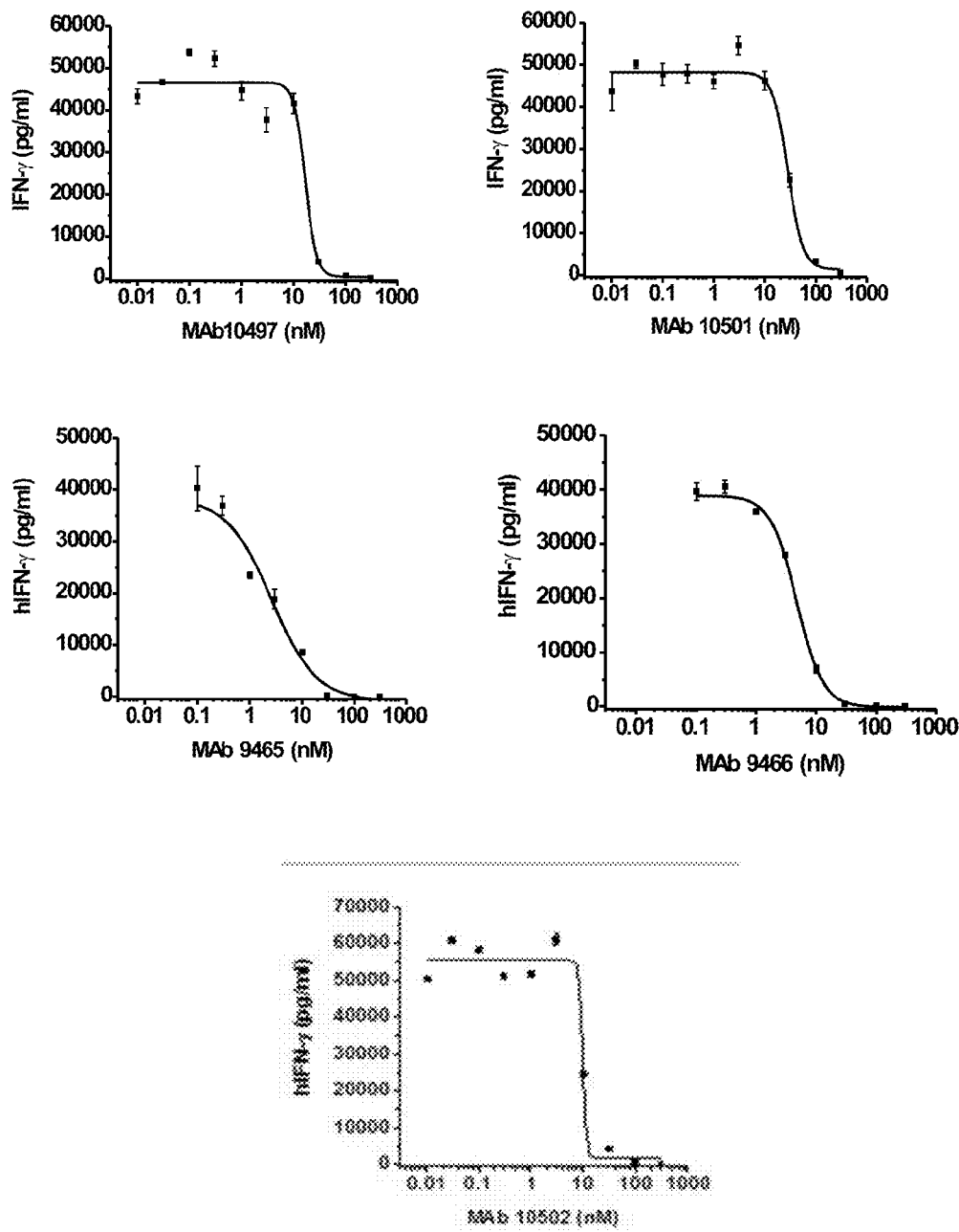

All antibodies and fragments dose-dependently inhibited IFNγ production against either stimulus. Full inhibition of the recombinant IL-18-induced response was achieved at the highest concentrations, whilst similar efficacy was observed against LPS/IL-12 stimulation as that for the IL-18BPa-Fc (Table 3; FIGS. 7(A-E) and 8(A-E)). Germlining MOR09441 and MOR09464 did not significantly alter their neutralizing capacity. The control antibody, MOR03207 did not inhibit the IL-18 response. Selected antibodies were also assessed for their ability to inhibit recombinant cynomolgus IL-18 bioactivity (7 nM) in whole blood from the cynomolgus monkey. MOR09441, MOR09464, MOR09465, MOR09466 all dose-dependently inhibited IFN-γ production with full inhibition observed at the highest concentrations. Observed $IC_{50}$ values were 110±36 nM, 51±8 nM, 55±3 nM, 179±30 nM, respectively.

TABLE 3

$IC_{50}$ values (nM) for inhibition of IL-18-induced IFN-γ release in whole blood

| Identification | Human whole blood stimulated with recombinant human IL-18 (7 nM) | Human whole blood stimulated with LPS/IL-12 |
| --- | --- | --- |
| MOR010497 | 16.1 ± 6.6 | 107.9 ± 8.3 |
| MOR010501 | 20.3 ± 5.6 | 101.3 ± 44 |
| MOR010502 | 17.9 ± 5.0 | 110.4 |
| MOR09465 | 4.2 ± 1.0 | 19.4 ± 7.8 |
| MOR09466 | 5.6 ± 0.5 | 18.5 ± 1.6 |
| MOR09441 | 8 ± 2.1 | 16.3 ± 5.4 |
| MOR09464 | 3.6 ± 0.4 | 9.8 ± 3.2 |
| MOR010579 | 5.6 ± 1.4 | 16.7 ± 7.0 |
| MOR010222 | 4.7 ± 1.5 | 21.6 ± 9.9 |
| IL-18BP-Fc | 5.7 ± 2.0 | 12.1 ± 6.2 |
| MOR13363 | 29.4 | 91.7 ± 66.9 |
| MOR13361 | 15.72 ± 5.5 | 39.4 ± 13.5 |
| MOR13341 | 5.6 ± 0.4 | 19.6 ± 5.3 |
| MOR13342 | 6.6 ± 1.0 | 21.5 ± 6.7 |
| MOR13347 | 3.5 | 8.3 |
| MOR1022_N30S | 58.4 ± 14.4 | 16.9 ± 7.4 |
| MOR1022_N30S_M54Y | 34.3 ± 16.6 | 18.8 ± 6.5 |
| MOR1022_N30S_M54N | 46.5 ± 9.9 | 16.1 ± 5.1 |
| MOR1022_N30S_M54I | 47.3 ± 15.1 | 9.3 ± 4.4 |
| MOR09464_N30T | 12.46 ± 2.67 | 20.76 ± 5.74 |
| MOR09464_N30E | 12.88 ± 2.79 | 19.16 ± 6.67 |
| MOR09464_N30H | 11.93 ± 2.14 | 22.98 ± 11.04 |
| MOR09464_N30K | 8.62 ± 2.62 | 17.09 ± 3.64 |
| MOR09464_N30Q | 8.10 ± 1.00 | 13.40 ± 2.91 |
| MOR09464_N30G | 25.14 ± 5.26 | 15.07 ± 2.80 |
| MOR09464_N30V | 12.68 ± 1.86 | 19.60 ± 4.90 |
| MOR09464_N30Y | 12.39 ± 1.59 | 17.85 ± 5.12 |
| MOR09464_N30R | 10.07 ± 1.32 | 11.03 ± 1.26 |
| MOR09464_N30I | 11.42 ± 2.37 | 13.15 ± 4.53 |
| MOR09464_N30L | 9.85 ± 1.64 | 15.46 ± 2.29 |
| | n = 3-4 Mean +/− SEM | n = 3-4 Mean +/− SEM * n = 2, Mean +/− SD |

Mutants of MOR9464 and MOR10222, in particular MOR9464_N30K and MOR10222_N30S_M54I did have comparable neutralizing capacity to the wild type antibodies.

9.7) ELISA Binding of Anti-IL-18 Antibodies to the IL-18-IL-18BP Complex

To confirm that the anti-IL18 antibodies or fragments thereof described herein do not recognise IL-18 bound to the IL-18BP (IL-18/IL-18BP complex) IL-18 was incubated with IL-18BP (rhIL-18BP/Fc, R&D Systems, Cat#119) in a molar excess. Anti-IL18 antibodies and fragments were added as described below and binding to the complex was detected. In general, signals at high concentrations of the anti-IL-18 antibodies and fragments are detected where they bind accessible epitopes on the antigen different to the IL-18BP (i.e. recognize the IL-18/IL-1BP complex). In a first setup, control antibodies and anti-IL18 antibodies and fragments were diluted using PBST/0.5% BSA and added to the biotinylated IL-18/IL18-BP complex (incubation in polypropylene plates for 30 min at RT and shaking gently). Control antibodies were MOR03207 (anti-lysozyme) as negative control, MOR08741 as well as mouse 125-2H, an anti-human IL-18 mouse IgG, as positive control antibodies (they both recognises IL-18/IL-18BP complex) (Argiriadi M A et al. (2009) J Biol Chem; 284(36):24478-89). The whole complex was captured via the biotin moieties onto NeutrAvidin plates, which were blocked o/n with 1× ChemiBlocker-PBS.

Plates were washed 5× with PBST and incubated for 1 h with 20 μl/well detection antibody anti-Fab-AP-goat anti human IgG, F(ab)2 fragment specific (Jackson Immuno Research, 109-055-097, lot: 69655) or anti-mouse IgG (whole molecule)-AP (SIGMA, #A4312) both diluted 1:5000 in 0.5% BSA/0.05% Tween20/1×PBS. Plates were washed 5× with TBST, 20 μl AttoPhos (Roche) solution (1:5 diluted in ddH2O) were added and fluorescence was measured at the Tecan Reader.

Figure 9A:
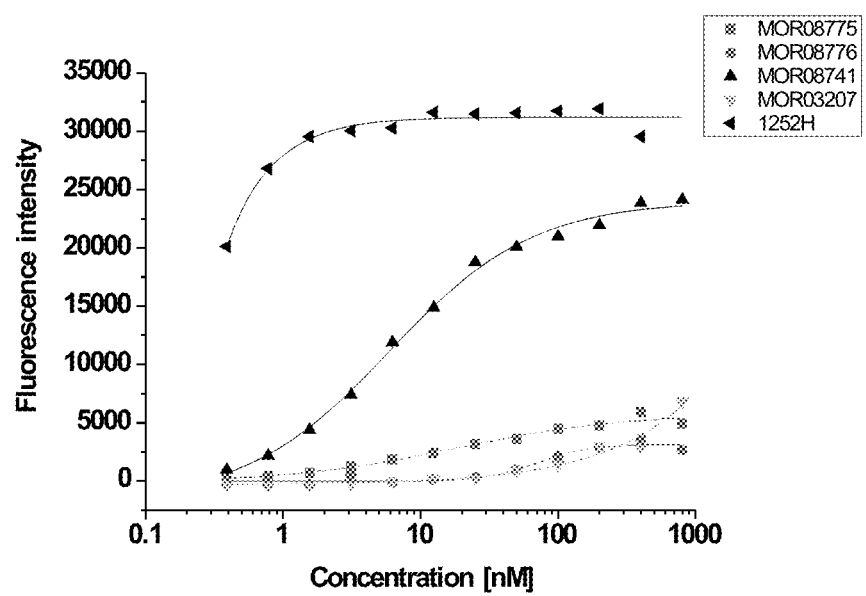
FIG. 9 (A-B): Binding of anti-IL-18 antibodies and fragments to IL-18/IL-18BP complex. (A) Parental MOR08775 and MOR08776 do not recognize the IL-18/IL-18BP complex. In this experiment, MOR08775 and MOR08776 were incubated with biotinylated IL-18/IL-18BP complex. (B) The experiment was performed in a similar way as shown in A), except for using unbiotinylated human IL-18. MOR03207 is an anti-lysozyme antibody and 125-2H is anti-IL-18 mouse IgG which binds the IL-18/IL-18BP complex.
Figure 9B:
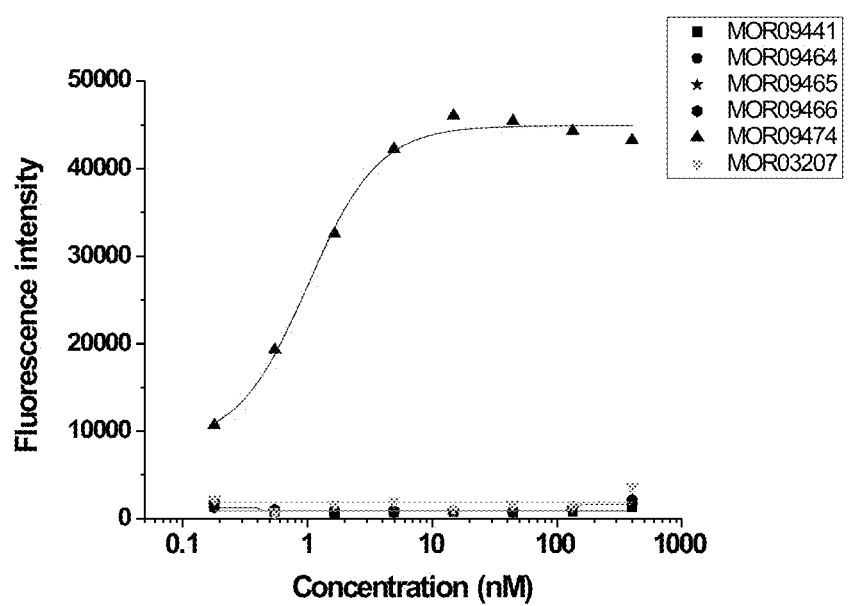

For anti-IL-18 antibodies MOR8775 and MOR8776 which do not bind the IL-18/IL-18BP complex, binding signals were significantly decreased or no signals were observed (FIG. 9(A)). In comparison, a strong signal was observed in the presence of mouse 125-2H supporting the reported ability of this control antibody to bind an epitope distinct from that of the IL-18BP. Similarly, a dose-dependent signal was observed in the presence of control antibody MOR08741.

In a second setup, the experiment was done in a similar way, except for using unbiotinylated hu IL-18. The IL-18/IL-18BP complex was captured onto a Maxisorp plate via the Fc tag of the rhIL-18BP/Fc using a goat anti-hu IgG (Fc gamma fragment specific, Jackson ImmunoResearch #109-005-098). A concentration-dependent signal was observed for controls MOR08741, again highlighting the ability of this antibody to recognise the IL-18/IL-18BP complex. In comparison, no signal was observed for MOR09441, MOR09464, MOR09465, MOR09466, confirming that they do not bind the IL-18/IL-18BP complex.

9.8) Epitope Binning of Anti-IL18 Antibodies and Fragments Via ELISA

For epitope binning two set-ups were used. For the first set-up, an antibody fragment (Fab A) was titrated and incubated with biotinylated human IL-18. Fab A was tested with a constant concentration of an antibody B (IgG B). As a positive control, Fab A was analyzed with itself in the IgG format. NeutrAvidin plates (Thermo Scientific Cat#15402) were blocked with Chemiblocker (1:1 diluted with PBS) and incubated for 2 h at RT (or over night at 4° C.). Next day plates were washed 2× with PBST and Fabs were titrated from 500 nM down to 2 nM in PBS buffer containing 10 nM final concentration biotinylated human IL-18. The complex of antibody fragments and biotinylated IL-18 was added to the NeutrAvidin plates and incubated for 1 hour. After washing 3× with PBST IgG B was added at 20 nM to the corresponding wells of the NeutrAvidin plates. After 20 minutes incubation, and 3×PBST wash, detection antibodies anti-Fc-AP-goat anti human IgG, Fc gamma-chain specific (Jackson Immuno Research, 109-055-098) and anti-mouse IgG (whole molecule)-AP (SIGMA, #A4312, Lot: 067K4863) were added diluted 1:5000 in 0.5% BSA/0.05% Tween20/1×PBS.

Plates were washed 5× with PBST, 20 μl AttoPhos solution (1:5 diluted in ddH2O) was added and plates were measured at the Tecan Reader. Fluorescence emission at 535 nm was recorded with excitation at 430 nm.

In general, signals could only be obtained when the IgG B was able to bind to accessible epitopes on the antigen which are different to the tested Fab A (i.e. antibody binding to a different epitope). In contrast, for antibodies with partially overlapping or identical epitopes, binding signals were significantly decreased in comparison to controls.

The second ELISA set-up was performed on Maxisorp plates. Fab A was coated to different concentrations in PBS and incubated o/n at 4° C. Next day plates were washed 3× with PBST and blocked for 2 hours at RT with 5% MPBST (100 μl/well). After a 3×PBST washing step, human IL-18 was added at a constant concentration for 1 h. Plates were washed 3× with PBST and biotinylated antibody fragment (biotinylated Fab B) was titrated (max. conc. 5 μg/mL, 10 μg/mL or 20 μg/mL). For complex formation of Fab A with IL-18 and biotinylated Fab B, plates were incubated for 1 h, subsequently washed 3× with PBST and detection antibody ZyMax Streptavidin-Alkaline Phosphatase (Zymed, Cat. No. 43-8322, Lot 51102099) was diluted 1:2,000 in PBST and 20 μL/well was added to the ELISA plates. Plates were washed 5× with TBST, 20 μL AttoPhos (Roche) solution (1:5 diluted in ddH2O) were added and plates were measured at the Tecan Reader.

In this case, as for the first set-up, signals could only be obtained when the biotinylated Fab B was able to bind to accessible epitopes on the antigen which are different to the tested Fab A (i.e. antibody binding a different epitope).

As shown in FIG. 10A, antibodies MOR8775 compete with murine antibody 125-2H (black cell filling) whilst MOR8776 does not compete with 125-2H for binding to IL-18 (no cell filling). Both antibodies do compete with IL-18BP-Fc for binding IL-18 (black cell fillings). Neither MOR8775 nor MOR8776 compete with ABT325 antibody (U.S. patent application Ser. No. 09/780,035 and Ser. No. 10/988,360). Depending on the experiments settings, MOR8775 and MOR8776 compete with each other (striped cell filling)

In a second set of experiments antibodies MOR9464, MOR9464_N30K, MOR10222_N30S_M54I and MOR13341 were tested for their ability to bind IL-18 in the presence of any of these antibodies, IL-18BP-Fc, ABT325 and murine antibody 125-2H using the Proteon XPR36 instrument, a surface plasmon resonance (SPR) based, real-time label-free biosensor. Prior to analysis the integrity of the proteins was confirmed-, and the concentration assessed by LC-MS.

All antibodies and IL18BP-Fc were immobilized on the interaction spots of a GLC sensor chip by standard amine coupling. In a first step IL18 was injected as analyte 1 and in a second step either an anti-IL18 antibody or IL18BPa-Fc was injected as analyte 2.

Ligands to be immobilized were prepared at a concentration of either 20 μg/mL (antibodies) or 10 μg/mL (IL18BP-Fc) in 10 mM Acetate Buffer, pH 4.0. Analytes were diluted in PBS buffer (TEKNOVA) containing 0.005% Tween 20, the same buffer solution was used as running buffer for the instrument. Analyte 1 (25 nM IL18) was injected at a flow rate of 50 μL/min for 180 seconds with a dissociation time of 60 seconds. Analyte 2 (25 nM IL18BPa-Fc or anti-IL18 antibody) was injected at a flow rate of 50 μL/min for 180 seconds with a dissociation time of 180 seconds. Regeneration was performed with 10 mM Glycine, pH 1.5 at a flow rate of 100 μL/min for 20 seconds. Two independent sets of experiments were performed. Data evaluation was based on whether the sensorgram signal increased upon injection of analyte 2 compared to the signal of analyte 1. If the signal increased it was concluded that the immobilized ligand and injected analyte 2 recognized different epitopes. If the signal did not increase it was concluded the two shared the same or overlapping epitopes.

As shown in FIG. 10B, antibodies MOR9464, MOR9464_N30K, MOR10222_N30S_M54I and MOR13341 compete with each other (black cell fillings), with IL-18BP-Fc and with murine antibody 125-2H. None of these antibodies compete with ABT325 (white cell fillings).

Antibodies such as MOR9464_N30K and MOR10222_N30S_M54I which show to dually compete with the IL-18BP-Fc and with murine antibody 125-2H appear to have the advantage of not only binding free IL-18, not bound to the natural inhibitor IL-18BP-Fc, but also appear to have the potential to prevent binding of IL-18 to the IL-18Rα/β. As described in Wu et al. (Wu C. et al., J. Immunol. 2003, 170: 5571-5577), IL-18Rβ does not appear to bind IL-18 alone, but form a functional high affinity receptor complex with IL-18Rα that is able to signal in response to IL-18. Biochemical data combined with epitope mapping of 125-2H on IL-18 have revealed that the C-terminal 17 amino acids of the human IL-18 are critical for signal transduction through the heterodimeric receptor. Hence, antibodies capable of binding within the 125-2H epitope and equally competing with the IL-18 BP for binding IL-18 appear to have the potential of preventing IL-18-dependent pathway activation not only through blocking the binding to IL-18Rα but also through blocking the binding of IL-18 to IL-18Rα/β complex. As it will be apparent in section 9.11, antibody MOR9464_N30K binds, among others, amino acids Glu177 and Leu180 which are within the 17-amino acid stretch described in Wu et al.

9.9) IL-18 Epitope Mapping by Modelling

Human IL-18 from SwissProt entry Q14116 was used to search for structural information in the PDB (Berman H. M et al (2000) Nucl Acids Res; 28:235-242). Three structures were found with the code 1J0S (Kato Z et al (2003) Nat Struct Biol; 10:966), 2VXT (Argiriadi M A et al (2009) J Biol Chem; 284:24478) and 3F62 (Krumm B et al (2008) Proc Natl Acad Sci USA; 105:20711). 1J0S is the NMR structure of human IL-18. 2VXT is the crystal structure of the engineered human IL-18 in complex with mouse 125-2H antibody fragment at 1.49 Å resolution and 3F62 is the crystal structure of the engineered human IL-18 in complex with the poxvirus IL-18 binding protein at 2.0 Å resolution.

Three binding sites on IL-18 have been identified by mutational analysis. Two of them, site 1 and 2, are important for binding IL-18Rα and the third one, site 3, for binding IL-18Rβ (Kato Z. et al. (2003) Nat. Struct. Biol, 10:966). Site 2 is also important for binding IL-18BP.

Figure 11A:
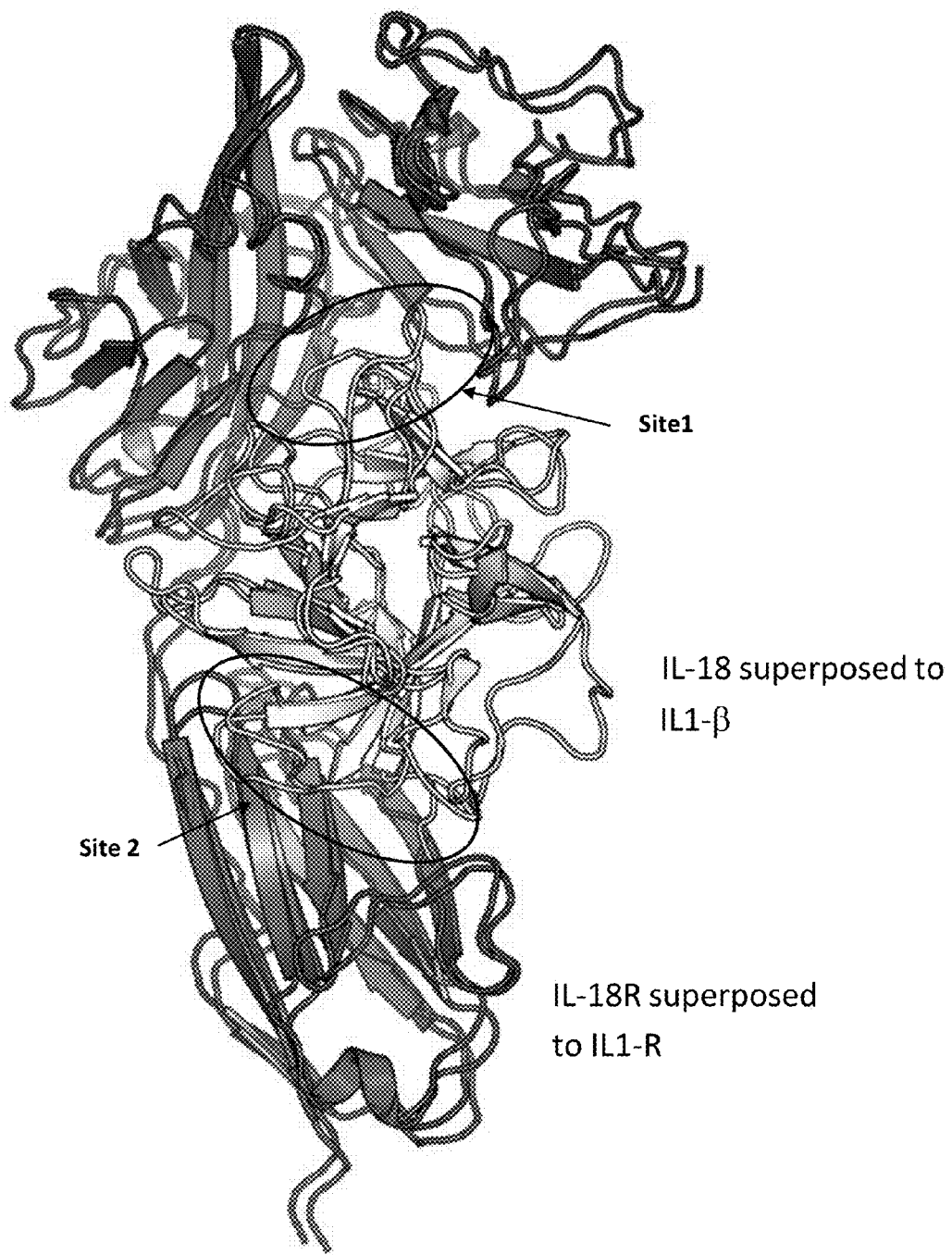
FIG. 11 (A-B): A) Structure of the IL-1β/IL-1R complex superposed onto the model of the IL-18/IL-18Rα created on the structure of the IL-1β/IL-1R complex. All the structures have been represented as ribbon. The structures of IL-18 and IL-1β have been used for the superimposition. B) Model of the IL-18/IL-18Rα complex created on the structure of the IL-1β/IL-1R complex. IL-18Rα (shown in surface representation) comprises three immunoglobulin-like domains, D1, D2 and D3. On IL-18 (shown in ribbon representation) sites 1 and 2 are the IL-18Rα binding sites. Site 3 is the IL-18Rβ binding site.

A structural complex between IL-1β and IL-1R1 is also available (1ITB, Vigers G. P et al (1997) Nature, 386:190). The structure of the complex between IL-1β and IL-1R1 shows that IL-1β has two binding sites for the receptor, site 1 and 2 (FIG. 11(A)). Since no structure is available for the complex between IL-18 and IL-18Rα, the crystal structure of IL-1β in complex with IL-1R1 was used as template for protein modelling (PDB code 1ITB). The model of IL-18Rα was built by using the structure of IL-1R1 as template. The crystal structure of IL-18 (pdb code 2VXT, Argiriadi M. A et al (2009) J. Biol. Chem. 284:24478) and the modelled structure of IL-18Rα were structurally superposed to the complex IL-1β/IL-1R1 and the IL-18/IL-18Rα model so obtained was refined to obtain the final structural model (FIG. 11(B)). MOE v2009.1 (Chemical Computing Group Inc.) is the software used for modeling the complex between IL-18 and IL-18Rα. The Homology Model panel has been used to build the model of IL-18Rα, by selecting AMBER99 forcefield and the default panel parameters. The energy minimization panel in MOE has been used for the refinement of the final IL-18/IL-18Rα complex.

Figure 11B:
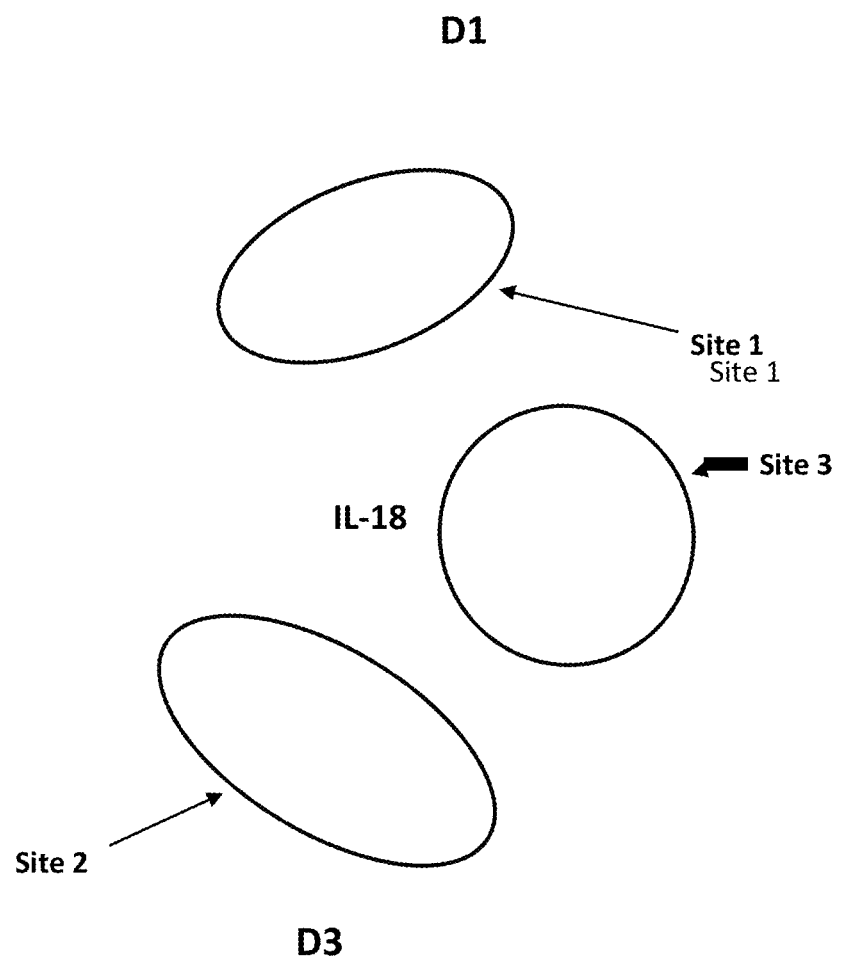

The overall structure of human IL-18 shows similarity with that of IL-1β. In particular, the RMSD (root mean square deviation) between IL-18 and IL-1β Cα atoms in secondary structure elements indicates that they are related proteins belonging to the same structure class (Kato Z. et al. (2003) Nat. Struct. Biol, 10:966). A comparison between the structures of IL-1β and IL-18 revealed that site 1 and 2 in IL-18 correspond to site 1 and 2 in IL-1β. In FIG. 11(B), sites 1 and 2 are shown in the model of the complex between IL-18 and IL-18Rα, site 3 is also shown. Site 3 is reported as the site of interaction for IL-18Rβ (Kato Z. et al. (2003) Nat. Struct. Biol, 10:966).

The IL-18 binding site for IL-18BP has been somehow identified by alanine mutations and by the X-ray crystal structure of a poxvirus IL-18BP in complex with IL-18 (Krumm et al (2008) Proc Natl Acad Sci USA; 105(52):20711-20715). This putative binding site also corresponds to the region on IL-18 that has been identified as site 2, one of the two regions of interaction of IL-18 with IL-18Rα.

9.10) IL-18 Epitope Mapping by Hydrogen/Deuterium Exchange Mass Spectrometry (H/D×MS)

Hydrogen/Deuterium exchange Mass Spectrometry was used to probe human IL-18 for information regarding the epitope for MOR9464. H/D×MS mapping relies upon the mass differences between "normal" hydrogen atoms and the "heavy" isotope deuterium which also comprises a neutron in addition to the single proton present in the normal hydrogen nucleus.

Upon transfer from water to a deuterium based solvent system (heavy water), a protein will experience an increase in mass as the amide hydrogen on the protein's backbone become gradually replaced with deuterons (heavier isotope of hydrogen). The likelihood of a hydrogen/deuterium exchange event is largely determined by protein structure and solvent accessibility. The H/D×MS technology is used to measure relative hydrogen/deuterium exchange and as a consequence protein structure and solvent accessibility.

When a protein binding partner binds to an antibody (e.g. antigen/antibody interaction) experimentally observable changes in its exchange rate may be observed. Surface regions that exclude solvent upon complex formation exchange much more slowly. Solvent excluded regions are useful for deducing the location of a binding site. In the case of an antigen-antibody interaction, changes in the rate of deuterium exchange might highlight the location of the epitope, but also any other perturbation resulting from the binding of the antibody to the antigen. For example, a decrease in the amount of deuterium uptake in the antigen at a given exchange time after antibody binding might represent either increased protection due to direct binding of the antibody to this region or indirect perturbation of the structure (allosteric changes) because of antibody binding. These two effects cannot be distinguished very easily, though the strongest effect observed is often attributed to direct protection from the antibody.

The location of decreased deuteron incorporation after antibody binding may be deduced by digestion of the target protein following hydrogen/deuterium exchange (e.g. with a suitable enzyme such as pepsin) and then mass spectrometry to determine the mass of the relevant fragments.

Triplicate control experiments were carried out on 316 pmol IL-18 antigen at deuterium exchange times of 3 and 25 minutes by diluting a stock solution of IL-18 with 95% deuterated PBS buffer to a concentration of 83.6% D. Deuterium exchange was quenched with quenching buffer (6M Urea and 1M TCEP). After quenching, the vial was analyzed by on-line pepsin digestion/LC-MS analysis. On-line pepsin digestion was performed using Life Science's Poroszyme immobilized pepsin packed into 2.0×20 mm column, and LC separation was performed on a Thermo C18 BioBasic column (1.0×50 mm) at a flow rate of 100 µL/min using a fast gradient so all peptides eluted in less than 20 minutes. Mobile phases are standard reverse-phase mobile phases: 0.1% formic acid in water and 0.1% formic acid in acetonitrile. In these experiments backbone amide hydrogens that are exposed on the surface of IL-18 will incorporate deuterons.

Next, triplicate labeling experiments were carried out. First, MOR9464 antibody was immobilized on Protein G agarose beads (Thermo 22851) using standard techniques. Antibody beads were centrifuged to remove a PBS solution. Then 200 µL of cold PBS (pH 7.4) and 6 µL (316 pmol) of IL-18 was added to the immobilized MOR9464 antibody and incubated for 15 min at 4° C. After incubation, the complex was centrifuged and washed with 200 µL PBS and centrifuged again. For deuterium exchange, 200 µL of 83.6% deuterium PBS buffer was added to the antigen-antibody complex for incubation at 4° C. for 3 or 25 min. Deuterium exchange was then removed, and immediately, 125 µL quench buffer (as above) was added. After quenching, the flow-through was transferred into pre-chilled HPLC vial and analysed using the identical on-line pepsin digestion/LC-MS analysis that was in the control experiments. The backbone amides that are present in the antigen-antibody interface will incorporate fewer deuterons at a given exchange time relative to the control experiments. By comparing the H/Dx patterns of the labeling and control experiments, the epitope is revealed as that area of the antigen that is protected from on-exchange in the labelling experiments.

The results of this analysis, when conducted with MOR9464, revealed three most significant regions of protection on IL-18. These were (with reference to SEQ ID NO:1) from amino acid 87 to 99, from amino acid 119 to 137 and from amino acid 138 to 160. These regions are shown to contain amino acids which are involved in the binding of the IL-18BP (FIG. 12).

9.11) X-Ray Structural Characterization of IL-18/Antibody Fragment

The general epitope identification provided by modelling and H/DxMS confirmed that the antibodies and fragments thereof as described herein recognise a region on IL-18 which is also recognised by the IL-18BP (FIG. 12). In order to identify the relevant amino acids on IL-18 in these regions, X-ray structure determination of an IL-18/antibody complex was carried out.

To prepare the antibody fragment, 13 mg of MOR9464_N30K at a concentration of 18 mg/mL in 10 mM Histidine pH 5.0, were cleaved with 1/300 (w/w) papain in 100 mM Tris-HCl pH 7.0, 10 mM DTT during 200 min at room temperature. The reaction was stopped with 50 µM of papain inhibitor E64. The Fab fragment was then purified over a protein A column equilibrated with 20 mM sodium phosphate buffer pH 7.0.

Purification of the Fab complex with IL-18: A 1.33-fold excess of human IL-18 (1.6 mg in PBS) was added to 3.2 mg of the MOR9464_N30K antibody fragment (recovered from the Protein A flow-through). The IL-18 complex with the MOR9464_N30K antibody fragment was concentrated by ultrafiltration, loaded on a SPX-75 size-exclusion chromatography and eluted isocratically in 10 mM Tris-HCl pH 7.4, 25 mM NaCl.

Crystallization: The IL-18/MOR9464_N30K antibody fragment complex was concentrated by ultrafiltration to 11.8 mg/mL and crystallization screening was performed by vapor diffusion in sitting drops in 96-well plates. The experiments were set up with a Phoenix robotic system and stored in a RockImager hotel at 19° C. Two crystal forms (form A and form B) were identified and characterized:
1) Crystal form A grew from 0.1M Lithium sulfate, 0.1M ADA pH 6.5, 12% PEG 4,000. (Cryo-protectant was a 1:1 mix of the reservoir solution with 20% PEG 4,000, 30% glycerol)
2) Crystal form B grew from 59.5% 2-methyl-2,4-pentanediol (MPD), 15% glycerol, 85 mM HEPES pH 7.5. (No cryo-protectant needed).

X-ray data were collected at the Swiss Light Source, beamline X10SA, with a Pilatus pixel detector. All diffraction images were processed with XDS (version Dec. 6, 2010), as implemented in APRV.

For crystal form A, 720 images of 0.25° oscillation each were recorded at a crystal-to-detector distance of 460 mm, using X-ray radiation of 0.99999 Å wavelength.

For crystal form B, 720 images of 0.25° oscillation each were recorded at a crystal-to-detector distance of 430 mm, using X-ray radiation of 0.99984 Å wavelength.

The structure of crystal form A was determined by molecular replacement with the program Phaser, using PDB entry 3 GBM.pdb and 2VXT.pdb as starting models for the MOR9464_N30K antibody fragment and IL-18 molecule, respectively. The variable and first constant domains of the antibody fragment in 3 GBM.pdb were used as independent search models. A clear solution for one IL-18/MOR9464_N30K antibody fragment complex per asymmetric unit was readily obtained. The structure of crystal form B was determined in the same way, but using the refined models derived from crystal form A instead of the PDB entries.

Structure refinement: The structure was refined by multiple cycles of electron-density map inspection and model rebuilding in Coot 0.6.2 followed by automated refinement using autoBUSTER (1.11.2/buster 2.11.2). Intermolecular contacts were identified with NCONT and the buried surface was analyzed with AREAIMOL, both from the CCP4 program suite (version 6.1.2). X-ray data collection and refinement statistics are shown in Table 4 below.

TABLE 4

X-ray data collection and refinement statistics

|  | Crystal form A | Crystal form B |
|---|---|---|
| Data collection | | |
| Space group | $P2_1$ | $C2$ |
| Cell dimensions | | |
| a, b, c (Å) | 43.46, 85.86, 85.77 | 213.72, 41.81, 71.37 |
| α, β, γ (°) | 90.00, 94.29, 90.00 | 90.00, 100.13, 90.00 |
| Resolution (Å) | 2.80 (2.87-2.80)* | 2.70 (2.77-2.70)* |
| $R_{sym}$ or $R_{merge}$ | 0.10 (0.454) | 0.074 (0.487) |
| I/σI | 13.0 (3.2) | 12.0 (2.8) |
| Completeness (%) | 98.7 (98.2) | 98.8 (98.6) |
| Redundancy | 3.4 (3.5) | 3.3 (3.4) |
| Refinement | | |
| Resolution (Å) | 85.53-2.80 | 54.19-2.70 |
| No. reflections | 15,406 | 17,335 |
| $R_{work}/R_{free}$ | 0.175/0.257 | 0.192/0.254 |
| No. atoms | | |
| Protein | 4,447 | 4,445 |
| Buffer component | 10 (2 sulfate ions) | 6 (1 glycerol) |

TABLE 4-continued

X-ray data collection and refinement statistics

|  | Crystal form A | Crystal form B |
|---|---|---|
| Water | 89 | 62 |
| B-factors ($Å^2$) | | |
| Ab light-chain (L) | 54.3 ($V_L$: 34.6; $V_C$: 76.5) | 50.3 |
| Ab heavy-chain (H) | 37.0 | 51.4 |
| hIL-18 (I) | 35.3 | 64.7 |
| Water | 30.4 | 51.6 |
| R.m.s. deviations | | |
| Bond lengths (Å)/ angles (°) | 0.010/1.31 | 0.010/1.28 |

Figure 13:
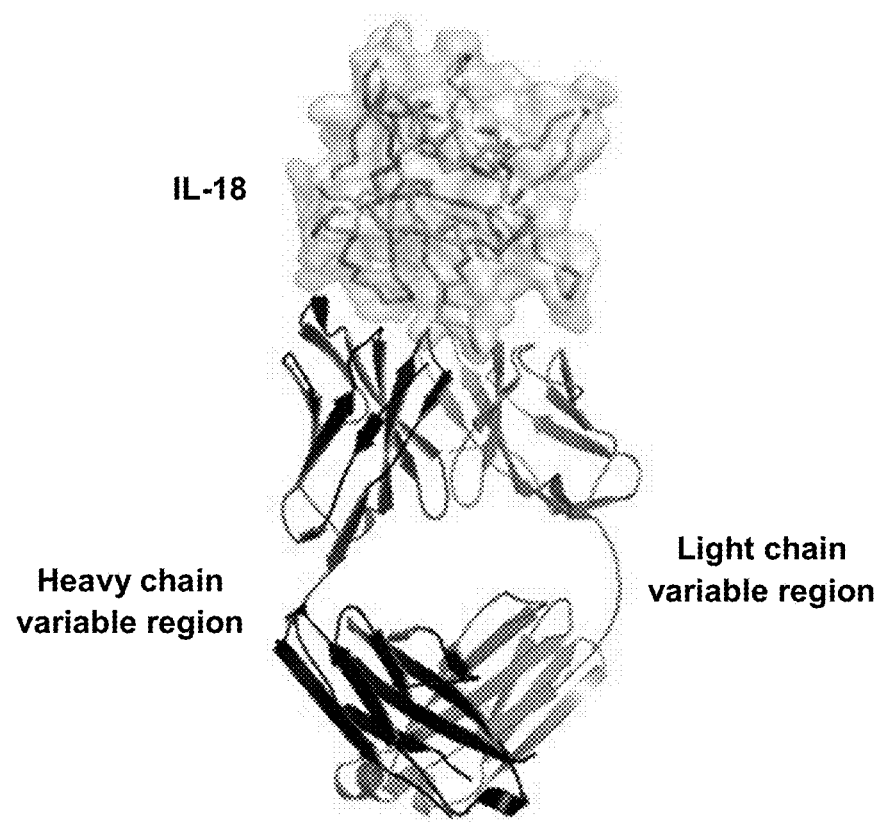
FIG. 13: Overall view of the three-dimensional structure of the complex between human IL-18 (shown in Cα trace and solvent accessible surface) and MOR9464_N30K (shown in cartoon representation).

The overall view of the structure of the complex of IL-18/MOR9464_N30K fragment is shown in FIG. 13. Upon complex formation, 36 amino acids on IL-18 with reduced solvent accessibility are identified at the binding interface of IL-18 with the antibody fragment. These residues are Leu41, Glu42, Met87, Tyr88, Lys89, Asp90, Ser91, Gln92, Pro93, Arg94, Gly95, Met96, Ala97, Phe138, Gln139, Arg140, Ser141, Val142, Pro143, Gly144, His145, Asp146, Asn147, Met149, Gln150, Glu152, Ser153, Ser154, Glu157, Gly158, Phe160, Glu177, Asp178, Glu179, Leu180 and Gly181.

Further characterization of the relevant contacts made in the complex interface identified that Arg140 and Glu152 are the amino acids which are likely to contribute the most to this particular complex formation. Both residues are located at the centre of the binding interface, and contribute to a large number of intermolecular contacts (21 and 18, respectively, using a cut-off distance of 4.0 Å). Arg140 interacts with both L-CDR3 (Tyr94L) and H-CDR3 (Tyr101H, His102H) residues. Glu152 forms a strong (buried) salt-bridge interaction with L-CDR2 Arg51L and accepts a H-bond from L-CDR3 Tyr94L. All residues in the antibody chains are numbered sequentially, the letter L or H following the residue number indicate a residue in the light chain or heavy chain, respectively.

The three dimensional structure of IL-18/MOR9464_N30K antibody fragment complex allowed some further investigations on the different cross-reactivity between the human IL-18 and the cynomolgus IL-18. MOR9464_N30K is 10-fold weaker against cynomolgus IL-18 (20 pM) compared to 2 pM against human IL-18 (Table 2). Cynomolgus IL-18 differs from human IL-18 in 6 positions (human vs cynomolgus): V47I; S86N; T99A; K115R; F170Y and E177K (FIG. 14(A). Of these positions only glutamic acid 177 (Glu177; E177) is at the IL-18/antibody fragment complex interface (FIG. 14(B)). Thus, it is arguable that K177 in the cynomolgous monkey sequence of cynomolgus IL-18 causes a 10-fold drop in affinity to MOR9464_N30K as indicated in Table 2A column 1, where the $K_D$ (SET, pM) for MOR9464_N30K for human IL-18 is 2±1 pM whereas for cynomolgus IL-18 is 20±10 pM.

In order to identify with what part of the IL-18Rα MOR9464_N30K antibody fragment competes, a superposition of the IL-18/MOR9464_N30K antibody fragment complex with the IL-18/IL-18Rα complex was performed. In brief, the structures of IL-18 in the IL-18/IL-18Rα complex and IL-18 in the IL-18/MOR9464_N30K complex were superposed by using the align command in PyMol (The PyMol Molecular Graphic system, version 1.2r3pre, Schroedinger LLC).

As shown in FIG. 15, it appears that MOR9464_N30K antibody fragment competes with the Ig-domain D3 of IL-18Rα for binding IL-18.

Similarly, the structure of the IL-18/MOR9464_N30K antibody fragment complex was superimposed onto the structure of the human IL-18 in complex with poxvirus IL-18BP (coordinate file used 3F62.pdb) using the "align" command in PyMOL (The PyMOL Molecular Graphic system, version 1.5.0., Schrödinger LLC).

Figure 16:
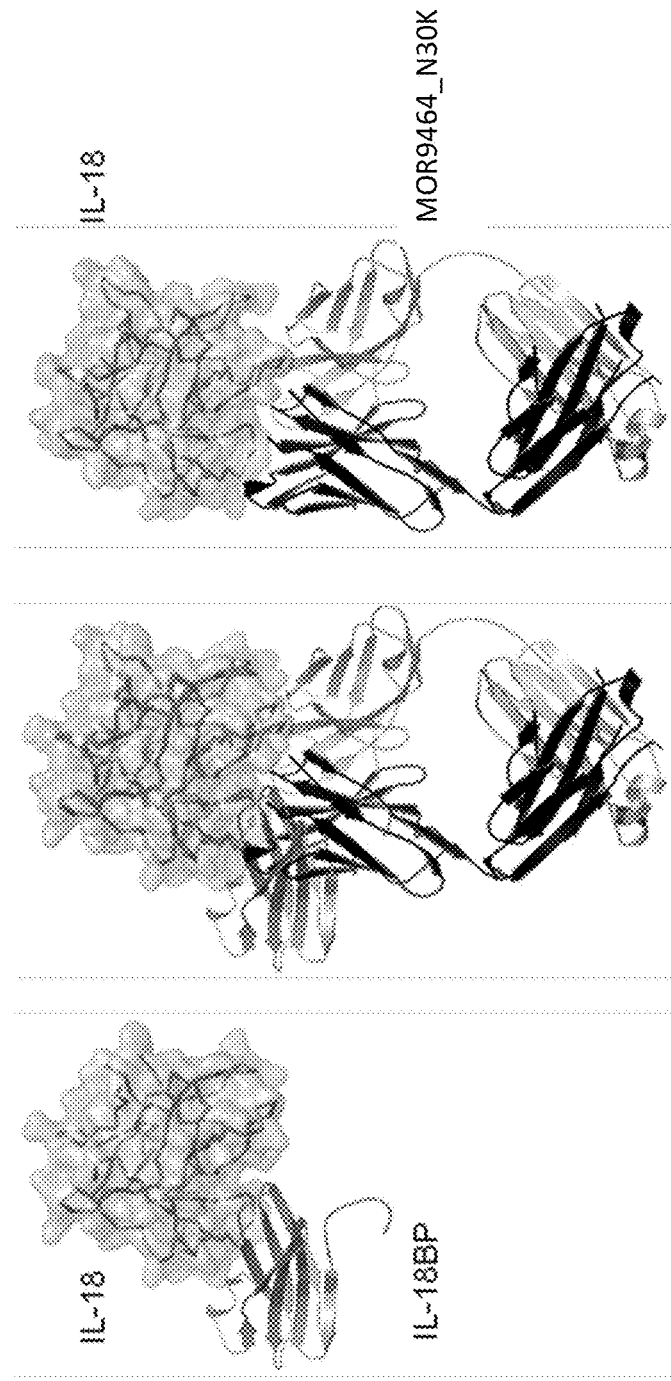
FIG. 16: Ribbon representation of human IL-18 bound to IL-18 BP from poxvirus (left) and to MOR9464_N30K antibody fragment (right) and their superposition (centre). Overlay is based on the IL-18 structure. IL-18 is shown in Cα trace and solvent accessible surface and MOR9464_N30K and IL-18 BP from poxvirus are shown in cartoon representation.

As shown in FIG. 16, the poxvirus IL-18BP clashes with the heavy chain variable domain of the MOR9464_N30K antibody fragment and competes predominantly for binding amino acids residues Met87 to Met96 on IL-18.

These findings further confirm the biochemical and epitope binning data showed herein and show that the binding molecules as described herein, in particular the antibodies and the fragments thereof, do not bind the IL-18/IL-18BP complex.

Finally, comparison with the prior art murine antibody 125-2H was performed. The analysis was carried out with the structure of 125-2H antibody fragment as found in the 2VXT-.pdb file. In brief, the structure of IL-18 in complex with MOR9464_N30K antibody fragment was superimposed onto IL-18 in complex with the 125-2H Fab using the "align" command in PyMOL (The PyMOL Molecular Graphic system, version 1.5.0., Schrödinger LLC).

Figure 17:
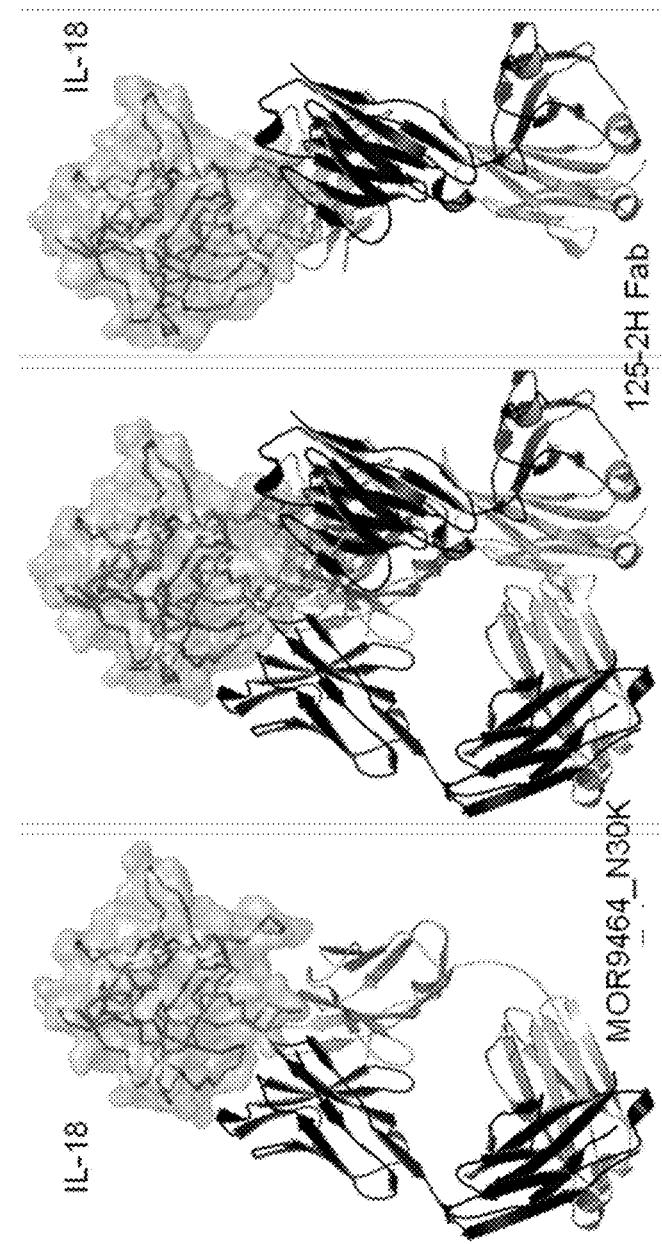
FIG. 17: Ribbon representation of human IL-18 bound to MOR9464_N30K antibody fragment (right) and to murine 125-2H antibody fragment (right) and their superposition (centre). Overlay is based on the IL-18 structure. IL-18 is shown in Cα trace and solvent accessible surface and MOR9464_N30K and 125-2H are shown in cartoon representation
Figure 18:
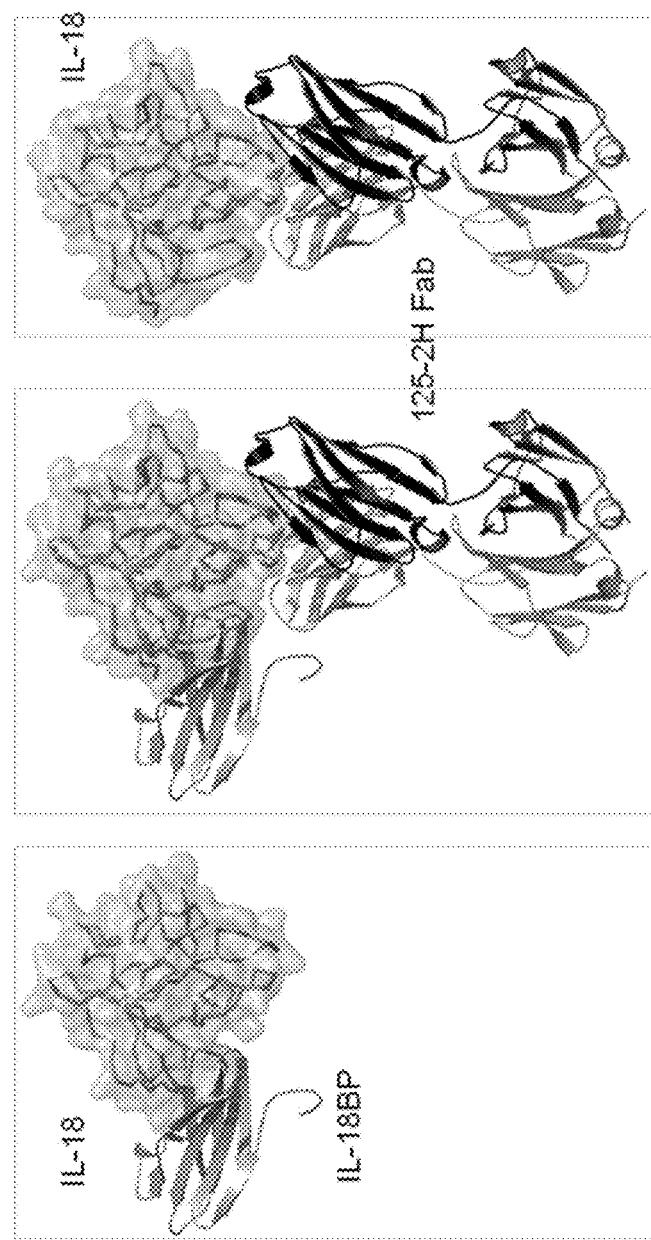
FIG. 18: Ribbon representation of human IL-18 bound to 125-2H overlaid onto IL-18 bound to IL-18BP from poxvirus. Overlay is based on the IL-18 structure. IL-18 is shown in Cα trace and solvent accessible surface and MOR9464_N30K, 125-2H and IL-18BP from poxvirus are shown in cartoon representation.

As shown in FIG. 17, MOR9464_N30K antibody fragment (left side of the superimposition) and 125-2H antibody fragment (right side of the superimposition) overlap in recognising IL-18. However, 125-2H antibody fragment does not bind the epitope recognised by the IL-18BP as shown in FIG. 18 where the 125-2H/IL-18 complex was superposed with the poxvirus IL-complex. These data further confirm, both the prior art literature with regard to 125-2H (Argiriadi M. A et al (2009) J. Biol. Chem. 284:24478) and also the biochemical and epitope binning data showed herein that murine antibody 125-2H binds the IL-18/IL-18BP complex.

Figure 19:
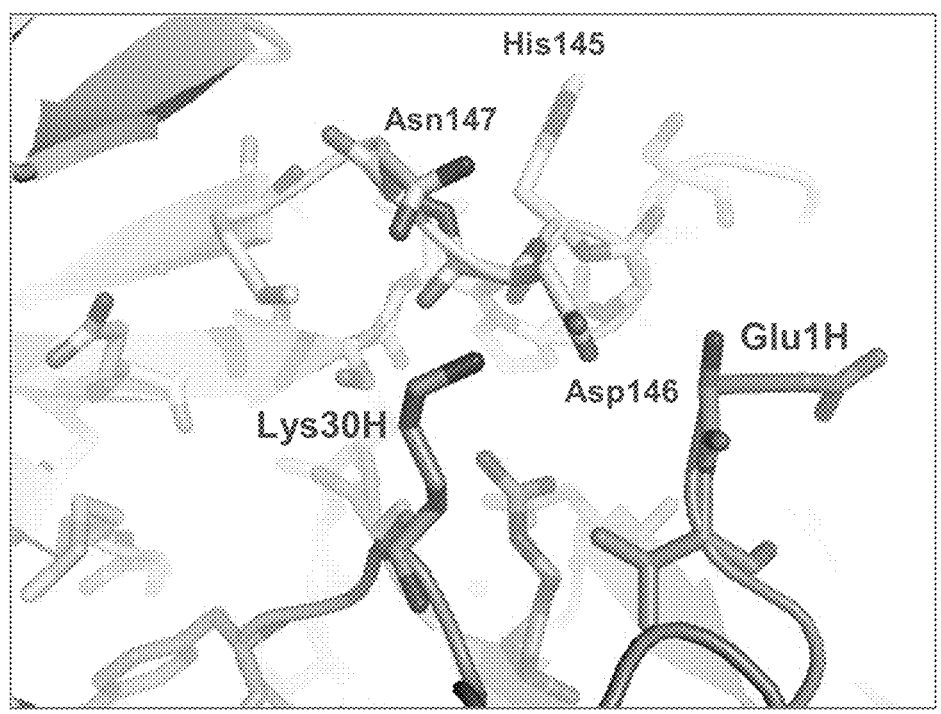
FIG. 19: Ribbon representation of human IL-18 bound to MOR9464_N30K antibody fragment, with epitope and paratope residues depicted in stick representation, showing the specific interaction with amino acid lysine at position 30 of MOR9464_N30K.

Finally, as shown in FIG. 19, Lysine in position 30 in the heavy chain of MOR9464_N30K appears to form electrostatic/polar interactions with Asp 146 and Asn 147 of human IL-18 indicating that lysine 30 is involved in the formation of the antibody-antigen complex. It is, therefore, apparent that an exocellular modification as described in section 9.2 herein such as asparagine deamidation, may have contributed to the loss of potency over time of MOR9464. Replacement of asparagine 30 with a lysine in MOR9464_N30K appears to provide MOR9464_N30K with increased stability.

Sequence Correlation Table

| SEQ ID NO: | Identity |
|---|---|
| 1 | Human IL-18 |
| 2 | Cynomolgus IL-18 |
| 3 | H-CDR1 of MOR8775; MOR9464; MOR9441; MOR10222; MOR10579; MOR9464_N30K; MOR10222_N30S_M54I; MOR9465; MOR9466; |
| 4 | H-CDR2 of MOR8775; |
| 5 | H-CDR3 of MOR8775; MOR9464; MOR9441; MOR10222; MOR10579; MOR9464_N30K; MOR10222_N30S_M54I; MOR9465; MOR9466; |

Sequence Correlation Table

| SEQ ID NO: | Identity |
|---|---|
| 6 | L-CDR1 of MOR8775; MOR9464; MOR9441; MOR10222; MOR10579; MOR9464_N30K; MOR10222_N30S_M54I; MOR9465; MOR9466; |
| 7 | L-CDR2 of MOR8775; MOR9464; MOR9441; MOR10222; MOR10579; MOR9464_N30K; MOR10222_N30S_M54I; MOR9465; MOR9466; |
| 8 | L-CDR3 of MOR8775; MOR9464; MOR9441; MOR10222; MOR10579; MOR9464_N30K; MOR10222_N30S_M54I; MOR9465; MOR9466; |
| 9 | H-CDR2 of MOR9464; MOR10222; MOR9464_N30K; |
| 10 | H-CDR2 of MOR9441; MOR10579; |
| 11 | H-CDR2 of MOR9465 |
| 12 | H-CDR2 of MOR9466 |
| 13 | H-CDR2 of MOR10222_N30S_M54I; |
| 14 | VH of MOR9464_N30K |
| 15 | Polynucleotide VH of MOR9464_N30K |
| 16 | VL of MOR9464_N30K; MOR9464; MOR8775; MOR9465; MOR9466; MOR9441 |
| 17 | Polynucleotide VL of MOR9464_N30K |
| 18 | VH of MOR10222_N30S_M54I |
| 19 | Polynucleotide VH of MOR10222_N30S_M54I |
| 20 | VL of MOR10222_N30S_M54I; MOR10579; MOR10222 |
| 21 | Polynucleotide VL of MOR10222_N30S_M54I |
| 22 | VH MOR8775; |
| 23 | Polynucleotide VH MOR8775; |
| 24 | Polynucleotide VL MOR8775; |
| 25 | VH MOR9441; |
| 26 | Polynucleotide VH MOR9441; |
| 27 | Polynucleotide VL MOR9441; |
| 28 | VH MOR9464; |
| 29 | Polynucleotide VH MOR9464; |
| 30 | Polynucleotide VL MOR9464; |
| 31 | VH MOR9465; |
| 32 | Polynucleotide VH MOR9465; |
| 33 | Polynucleotide VL MOR9465; |
| 34 | VH MOR9466; |
| 35 | Polynucleotide VH MOR9466; |
| 36 | Polynucleotide VL MOR9466; |
| 37 | VH MOR10579; |
| 38 | Polynucleotide VH MOR10579; |
| 39 | Polynucleotide VL MOR10579; |
| 40 | VH MOR10222; |
| 41 | Polynucleotide VH MOR10222; |
| 42 | Polynucleotide VL MOR10222; |
| 43 | Heavy chain of MOR9464_N30K |
| 44 | Polynucleotide Heavy chain of MOR9464_N30K |
| 45 | Light chain of MOR9464_N30K; MOR9464; MOR8775; MOR9441 |
| 46 | Polynucleotide Light chain of MOR9464_N30K |
| 47 | Heavy Chain MOR9464; |
| 48 | Polynucleotide Heavy Chain MOR9464; |
| 49 | Polynucleotide Light Chain MOR9464; |
| 50 | Heavy Chain MOR9441; |
| 51 | Polynucleotide Heavy Chain MOR9441; |
| 52 | Polynucleotide Light Chain MOR9441; |
| 53 | Heavy Chain MOR10222; |
| 54 | Polynucleotide Heavy Chain MOR10222; |
| 55 | Polynucleotide Light Chain MOR10222; |
| 56 | Heavy Chain MOR8775; |
| 57 | Polynucleotide Heavy Chain MOR8775; |
| 58 | Polynucleotide Light Chain MOR8775; |
| 59 | (Chothia) H-CDR1 MOR9464; |
| 60 | (Chothia) H-CDR2 MOR9464; MOR9464_N30K |
| 61 | (Chothia) H-CDR3 MOR9464; MOR9464_N30K; MOR10222_N30S_M54I |
| 62 | (Chothia) L-CDR1 MOR9464; MOR9464_N30K; MOR10222_N30S_M54I |
| 63 | (Chothia) L-CDR2 MOR9464; MOR9464_N30K; MOR10222_N30S_M54I |
| 64 | (Chothia) L-CDR3 MOR9464; MOR9464_N30K; MOR10222_N30S_M54I |
| 65 | (Chothia) H-CDR1 MOR9464_N30K; |
| 66 | (Chothia) H-CDR1 MOR10222_N30S_M54I |
| 67 | (Chothia) H-CDR2 MOR10222_N30K_M54I; |
| 68 | (Chothia) H-CDR1 MOR13363; |
| 69 | (Chothia) H-CDR2 MOR13363; |
| 70 | (Chothia) H-CDR3 MOR13363; |
| 71 | (Chothia) L-CDR1 MOR13363; |
| 72 | (Chothia) L-CDR2 MOR13363; |
| 73 | (Chothia) L-CDR3 MOR13363; |
| 74 | H-CDR1 of MOR8776; MOR10497; MOR10501; MOR10502; |
| 75 | H-CDR2 of MOR8776; |
| 76 | H-CDR2 of MOR10501 |
| 77 | H-CDR2 of MOR1010502; |

-continued

Sequence Correlation Table

SEQ ID NO: Identity

| | |
|---|---|
| 78 | H-CDR2 of MOR10497; |
| 79 | H-CDR3 of MOR8776; MOR10497; MOR10501; MOR10502; |
| 80 | L-CDR1 of MOR8776; MOR10497; MOR10501; MOR10502; |
| 81 | L-CDR2 of MOR8776; MOR10497; MOR10501; MOR10502; |
| 82 | L-CDR3 of MOR8776; MOR10497; MOR10501; MOR10502; |
| 83 | VH MOR8776; |
| 84 | Polynucleotide VH MOR8776; |
| 85 | VL MOR8776; MOR10497; MOR10501; MOR10502 |
| 86 | Polynucleotide VL MOR8776; |
| 87 | VH MOR10497; |
| 88 | Polynucleotide VH MOR10497; |
| 89 | Polynucleotide VL MOR10497; |
| 90 | VH MOR10501; |
| 91 | Polynucleotide VH MOR10501; |
| 92 | Polynucleotide VL MOR10501; |
| 93 | VH MOR10502; |
| 94 | Polynucleotide VH MOR10502; |
| 95 | Polynucleotide VL MOR10502; |
| 96 | Heavy Chain of MOR8776; |
| 97 | Polynucleotide Heavy Chain of MOR8776; |
| 98 | Light Chain of MOR8776; MOR10497 |
| 99 | Polynucleotide Light Chain of MOR8776; |
| 100 | Heavy Chain MOR10579; |
| 101 | Polynucleotide Heavy Chain MOR10579; |
| 102 | Polynucleotide Light Chain MOR10579; |
| 103 | Heavy Chain MOR10497; |
| 104 | Polynucleotide Heavy Chain MOR10497; |
| 105 | Polynucleotide Light Chain MOR10497; |
| 106 | H-CDR1 of MOR13363; MOR13361 |
| 107 | H-CDR2 of MOR13363 |
| 108 | H-CDR3 of MOR13363; MOR13361 |
| 109 | L-CDR1 of MOR13363; MOR13361 |
| 110 | L-CDR2 of MOR13363; MOR13361 |
| 111 | L-CDR3 of MOR13363 |
| 112 | VH of MOR13363 |
| 113 | Polynucleotide VH of MOR13363 |
| 114 | VL of MOR13363 |
| 115 | Polynucleotide VL of MOR13363 |
| 116 | Heavy Chain of MOR13363 |
| 117 | Polynucleotide Heavy Chain of MOR13363 |
| 118 | Light Chain of MOR13363 |
| 119 | Polynucleotide Light Chain of MOR13363 |
| 120 | H-CDR1 MOR13341; MOR13342; MOR13347 |
| 121 | H-CDR2 MOR13341; MOR13342; MOR13347 |
| 122 | H-CDR2 MOR13361 |
| 123 | H-CDR3 MOR13341; MOR13342; MOR13347 |
| 124 | L-CDR1 MOR13341; MOR13342; MOR13347 |
| 125 | L-CDR2 MOR13341; MOR13342; MOR13347 |
| 126 | L-CDR3 MOR13361 |
| 127 | L-CDR3 MOR13341 |
| 128 | L-CDR3 MOR13342 |
| 129 | L-CDR3 MOR13347 |
| 130 | VH MOR13341; MOR13342; MOR13347 |
| 131 | Polynucleotide VH MOR13341 |
| 132 | VL MOR13341 |
| 133 | Polynucleotide VL MOR13341 |
| 134 | Heavy chain MOR13341; MOR13342; MOR13347 |
| 135 | Polynucleotide Heavy chain MOR13341 |
| 136 | Light chain MOR13341 |
| 137 | Polynucleotide Light chain MOR13341 |
| 138 | VH MOR13361 |
| 139 | Polynucleotide VH MOR13361 |
| 140 | VL MOR13361 |
| 141 | Polynucleotide VL MOR13361 |
| 142 | Heavy chain MOR13361 |
| 143 | Polynucleotide Heavy chain MOR13361 |
| 144 | Light chain MOR13361 |
| 145 | Polynucleotide Light chain MOR13361 |
| 146 | Polynucleotide VH MOR13342 |
| 147 | VL MOR13342 |
| 148 | Polynucleotide VL MOR13342 |
| 149 | Polynucleotide Heavy chain MOR13342 |
| 150 | Light chain MOR13342 |
| 151 | Polynucleotide Light chain MOR13342 |
| 152 | Polynucleotide VH MOR13347 |

-continued

Sequence Correlation Table

| SEQ ID NO: | Identity |
|---|---|
| 153 | VL MOR13347 |
| 154 | Polynucleotide VL MOR13347 |
| 155 | Polynucleotide Heavy chain MOR13347 |
| 156 | Light chain MOR13347 |
| 157 | Polynucleotide Light chain MOR13347 |
| 158 | Heavy Chain of MOR10222_N30S_M54I |
| 159 | Polynucleotide Heavy Chain of MOR10222_N30S_M54I |
| 160 | Light Chain of MOR10222_N30S_M54I; MOR10222; MOR10579 |
| 161 | Polynucleotide Light Chain of MOR10222_N30S_M54I |
| 162 | (Chothia) H-CDR1 MOR10497 |
| 163 | (Chothia) H-CDR2 MOR10497 |
| 164 | (Chothia) H-CDR3 MOR10497 |
| 165 | (Chothia) L-CDR1 MOR10497 |
| 166 | (Chothia) L-CDR2 MOR10497 |
| 167 | (Chothia) L-CDR3 MOR10497 |
| 168 | Heavy chain MOR10501 |
| 169 | Polynucleotide Heavy chain MOR10501 |
| 170 | Light chain MOR10501 |
| 171 | Polynucleotide Light chain MOR10501 |
| 172 | Heavy chain MOR10502 |
| 173 | Polynucleotide Heavy chain MOR10502 |
| 174 | Light chain MOR10502 |
| 175 | Polynucleotide Light chain MOR10502 |
| 176 | Heavy chain MOR9465 |
| 177 | Polynucleotide Heavy chain MOR9465 |
| 178 | Light chain MOR9465 |
| 179 | Polynucleotide Light chain MOR9465 |
| 180 | Heavy chain MOR9466 |
| 181 | Polynucleotide Heavy chain MOR9466 |
| 182 | Light chain MOR9466 |
| 183 | Polynucleotide Light chain MOR9466 |
| 184 | (Chothia) H-CDR1 MOR8776 |
| 185 | (Chothia) H-CDR2 MOR8776 |
| 186 | (Chothia) H-CDR3 MOR8776 |
| 187 | (Chothia) L-CDR1 MOR8776 |
| 188 | (Chothia) L-CDR2 MOR8776 |
| 189 | (Chothia) L-CDR3 MOR8776 |
| 190 | (Chothia) H-CDR1 MOR10501 |
| 191 | (Chothia) H-CDR2 MOR10501 |
| 192 | (Chothia) H-CDR3 MOR10501 |
| 193 | (Chothia) L-CDR1 MOR10501 |
| 194 | (Chothia) L-CDR2 MOR10501 |
| 195 | (Chothia) L-CDR3 MOR10501 |
| 196 | H-CDR2 MOR10502 |
| 197 | (Chothia) H-CDR1 MOR10502 |
| 198 | (Chothia) H-CDR2 MOR10502 |
| 199 | (Chothia) H-CDR3 MOR10502 |
| 200 | (Chothia) L-CDR1 MOR10502 |
| 201 | (Chothia) L-CDR2 MOR10502 |
| 202 | (Chothia) L-CDR3 MOR10502 |
| 203 | (Chothia) H-CDR1 MOR8775 |
| 204 | (Chothia) H-CDR2 MOR8775 |
| 205 | (Chothia) H-CDR3 MOR8775 |
| 206 | (Chothia) L-CDR1 MOR8775 |
| 207 | (Chothia) L-CDR2 MOR8775 |
| 208 | (Chothia) L-CDR3 MOR8775 |
| 209 | (Chothia) H-CDR1 MOR9441 |
| 210 | (Chothia) H-CDR2 MOR9441 |
| 211 | (Chothia) H-CDR3 MOR9441 |
| 212 | (Chothia) L-CDR1 MOR9441 |
| 213 | (Chothia) L-CDR2 MOR9441 |
| 214 | (Chothia) L-CDR3 MOR9441 |
| 215 | (Chothia) H-CDR1 MOR9465 |
| 216 | (Chothia) H-CDR2 MOR9465 |
| 217 | (Chothia) H-CDR3 MOR9465 |
| 218 | (Chothia) L-CDR1 MOR9465 |
| 219 | (Chothia) L-CDR2 MOR9465 |
| 220 | (Chothia) L-CDR3 MOR9465 |
| 221 | (Chothia) H-CDR1 MOR9466 |
| 222 | (Chothia) H-CDR2 MOR9466 |
| 223 | (Chothia) H-CDR3 MOR9466 |
| 224 | (Chothia) L-CDR1 MOR9466 |
| 225 | (Chothia) L-CDR2 MOR9466 |
| 226 | (Chothia) L-CDR3 MOR9466 |
| 227 | (Chothia) H-CDR1 MOR10579 |

| Sequence Correlation Table | |
|---|---|
| SEQ ID NO: | Identity |
| 228 | (Chothia) H-CDR2 MOR10579 |
| 229 | (Chothia) H-CDR3 MOR10579 |
| 230 | (Chothia) L-CDR1 MOR10579 |
| 231 | (Chothia) L-CDR2 MOR10579 |
| 232 | (Chothia) L-CDR3 MOR10579 |
| 233 | (Chothia) H-CDR1 MOR10222 |
| 234 | (Chothia) H-CDR2 MOR10222 |
| 235 | (Chothia) H-CDR3 MOR10222 |
| 236 | (Chothia) L-CDR1 MOR10222 |
| 237 | (Chothia) L-CDR2 MOR10222 |
| 238 | (Chothia) L-CDR3 MOR10222 |
| 239 | H-CDR2 MOR10222_N30S_M54I |
| 240 | (Chothia) H-CDR1 MOR13341 |
| 241 | (Chothia) H-CDR2 MOR13341 |
| 242 | (Chothia) H-CDR3 MOR13341 |
| 243 | (Chothia) L-CDR1 MOR13341 |
| 244 | (Chothia) L-CDR2 MOR13341 |
| 245 | (Chothia) L-CDR3 MOR13341 |
| 246 | (Chothia) H-CDR1 MOR13342 |
| 247 | (Chothia) H-CDR2 MOR13342 |
| 248 | (Chothia) H-CDR3 MOR13342 |
| 249 | (Chothia) L-CDR1 MOR13342 |
| 250 | (Chothia) L-CDR2 MOR13342 |
| 251 | (Chothia) L-CDR3 MOR13342 |
| 252 | (Chothia) H-CDR1 MOR13347 |
| 253 | (Chothia) H-CDR2 MOR13347 |
| 254 | (Chothia) H-CDR3 MOR13347 |
| 255 | (Chothia) L-CDR1 MOR13347 |
| 256 | (Chothia) L-CDR2 MOR13347 |
| 257 | (Chothia) L-CDR3 MOR13347 |
| 258 | (Chothia) H-CDR1 MOR13361 |
| 259 | (Chothia) H-CDR2 MOR13361 |
| 260 | (Chothia) H-CDR3 MOR13361 |
| 261 | (Chothia) L-CDR1 MOR13361 |
| 262 | (Chothia) L-CDR2 MOR13361 |
| 263 | (Chothia) L-CDR3 MOR13361 |

```
Sequence Listing

SEQ ID NO: 1
MAAEPVEDNCINFVAMKFIDNTLYFIAEDDENLESDYFGKLESKLSVIRNLNDQVLFIDQGNRPLFEDMTDSDCRDNAP

RTIFIISMYKDSQPRGMAVTISVKCEKISTLSCENKIISFKEMNPPDNIKDTKSDIIFFQRSVPGHDNKMQFESSSYEGYFLA

CEKERDLFKLILKKEDELGDRSIMFTVQNED

SEQ ID NO: 2
MAAEPAEDNCINFVAMKPIDSTLYFIAEDDENLESDYFGKLESKLSIIRNLNDQVLFIDQGNRPLFEDMTDSDCRDNAPR

TIFIINMYKDSQPRGMAVAISVKCEKISTLSCENRIISFKEMNPPDNIKDTKSDIIFFQRSVPGHDNKMQFESSSYEGYFLA

CEKERDLYKLILKKKDELGDRSIMFTVQNED

SEQ ID NO: 3
SYAIS

SEQ ID NO: 4
GIIPIYGTANYAQKFQG

SEQ ID NO: 5
AAYHPLVFDN

SEQ ID NO: 6
SGSSSNIGNHYVN

SEQ ID NO: 7
RNNHRPS

SEQ ID NO: 8
QSWDYSGFSTV
```

Sequence Listing

SEQ ID NO: 9
NIIPMTGQTYYAQKFQG

SEQ ID NO: 10
WINPFYIGETFYAQKFQG

SEQ ID NO: 11
NIIPHYGFAYYAQKFQG

SEQ ID NO: 12
NIIPYSGFAYYAQKFQG

SEQ ID NO: 13
NIIPITGQTYYAQKFQG

SEQ ID NO: 14
EVQLVQSGAEVKKPGSSVKVSCKASGGTFKSYAISWVRQAPGQGLEWMGNIIPMTGQTYYAQKFQGRVTITADESTS

TAYMELSSLRSEDTAVYYCARAAYHPLVFDNWGQGTLVTVSS

SEQ ID NO: 15
GAGGTGCAGCTGGTGCAGTCAGGCGCCGAAGTGAAGAAACCCGGCTCTAGCGTGAAAGTCAGCTGTAAAGCTAG

TGGCGGCACCTTCAAGTCCTACGCTATTAGCTGGGTCAGACAGGCCCCAGGTCAGGGCCTGGAGTGGATGGGCA

ATATTATCCCTATGACCGGTCAGACCTACTACGCTCAGAAATTTCAGGGTAGAGTGACTATCACCGCCGACGAGTC

TACTAGCACCGCCTATATGGAACTGTCTAGCCTGAGATCAGAGGACACCGCCGTCTACTACTGCGCTAGAGCCGCC

TATCACCCCCTGGTGTTCGATAACTGGGGTCAGGGCACCCTGGTCACCGTGTCTAGC

SEQ ID NO: 16
DIVLTQPPSVSGAPGQRVTISCSGSSSNIGNHYVNWYQQLPGTAPKLLIYRNNHRPSGVPDRFSGSKSGTSASLAITGLQ

SEDEADYYCQSWDYSGFSTVFGGGTKLTVL

SEQ ID NO: 17
GATATCGTCCTGACTCAGCCCCCTAGCGTCAGCGGCGCTCCCGGTCAGAGAGTGACTATTAGCTGTAGCGGCTCTA

GCTCTAATATCGGTAATCACTACGTGAACTGGTATCAGCAGCTGCCCGGCACCGCCCCTAAGCTGCTGATCTATAG

AAACAATCACCGGCCTAGCGGCGTGCCCGATAGGTTTAGCGGATCTAAGTCAGGCACTAGCGCTAGTCTGGCTAT

CACCGGACTGCAGTCAGAGGACGAGGCCGACTACTACTGTCAGTCCTGGGACTATAGCGGCTTTAGCACCGTGTT

CGGCGGAGGCACTAAGCTGACCGTGCTG

SEQ ID NO: 18
QVQLVQSGAEVKKPGSSVKVSCKASGGTFSSYAISWVRQAPGQGLEWMGNIIPITGQTYYAQKFQGRVTITADESTST

AYMELSSLRSEDTAVYYCARAAYHPLVFDNWGQGTLVTVSS

SEQ ID NO: 19
CAGGTGCAGCTGGTGCAGTCAGGCGCCGAAGTGAAGAAACCCGGCTCTAGCGTGAAAGTCAGCTGTAAAGCTAG

TGGCGGCACCTTCTCTAGCTACGCTATTAGCTGGGTCAGACAGGCCCCAGGTCAGGGCCTGGAGTGGATGGGCAA

TATTATCCCTATCACCGGTCAGACCTACTACGCTCAGAAATTTCAGGGTAGAGTGACTATCACCGCCGACGAGTCT

ACTAGCACCGCCTATATGGAACTGTCTAGCCTGAGATCAGAGGACACCGCCGTCTACTACTGCGCTAGAGCCGCCT

ATCACCCCCTGGTGTTCGATAACTGGGGTCAGGGCACCCTGGTCACCGTGTCTAGC

SEQ ID NO: 20
QSVLTQPPSASGTPGQRVTISCSGSSSNIGNHYVNWYQQLPGTAPKLLIYRNNHRPSGVPDRFSGSKSGTSASLAISGLQ

SEDEADYYCQSWDYSGFSTVFGGGTKLTVL

SEQ ID NO: 21
CAGTCAGTCCTGACTCAGCCCCCTAGCGCTAGTGGCACCCCTGGTCAGAGAGTGACTATTAGCTGTAGCGGCTCTA

GCTCTAATATCGGTAATCACTACGTGAACTGGTATCAGCAGCTGCCCGGCACCGCCCCTAAGCTGCTGATCTATAG

AAACAATCACCGGCCTAGCGGCGTGCCCGATAGGTTTAGCGGATCTAAGTCAGGGACTAGCGCTAGTCTGGCTAT

```
TAGCGGCCTGCAGTCAGAGGACGAGGCCGACTACTACTGTCAGTCCTGGGACTATAGCGGCTTTAGCACCGTGTT

CGGCGGAGGCACTAAGCTGACCGTGCTG

SEQ ID NO: 22
QVQLVQSGAEVKKPGSSVKVSCKASGGTFNSYAISWVRQAPGQGLEWMGGIIPIYGTANYAQKFQGRVTITADESTST

AYMELSSLRSEDTAVYYCARAAYHPLVFDNWGQGTLVTVSS

SEQ ID NO: 23
CAGGTGCAATTGGTTCAGTCTGGCGCGGAAGTGAAAAAACCGGGCAGCAGCGTGAAAGTGAGCTGCAAAGCCTC

CGGAGGCACTTTTAATTCTTATGCTATTTCTTGGGTGCGCCAAGCCCCTGGGCAGGGTCTCGAGTGGATGGGCGG

TATCATTCCGATTTATGGCACTGCGAATTACGCGCAGAAGTTTCAGGGCCGGGTGACCATTACCGCGGATGAAAG

CACCAGCACCGCGTATATGGAACTGAGCAGCCTGCGTAGCGAAGATACGGCCGTGTATTATTGCGCGCGTGCTGC

TTATCATCCTCTTGTTTTTGATAATTGGGGCCAAGGCACCCTGGTGACGGTTAGCTCA

SEQ ID NO: 24
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGAATTGGTACCAGCAGTTGCCCGGGACGGCGCCGAAACTTCTGATTTATC

GTAATAATCATCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCCAGTCTTGGGATTATTCTGGTTTTTCTACTGTGTTT

GGCGGCGGCACGAAGTTAACCGTCCTA

SEQ ID NO: 25
EVQLVQSGAEVKKPGSSVKVSCKASGGTFNSYAISWVRQAPGQGLEWMGWINPFYIGETFYAQKFQGRVTITADESTS

TAYMELSSLRSEDTAVYYCARAAYHPLVFDNWGQGTLVTVSS

SEQ ID NO: 26
GAGGTGCAGCTGGTGCAGTCTGGCGCTGAGGTGAAGAAGCCTGGCTCCTCCGTCAAGGTGTCCTGCAAGGCCTCC

GGCGGCACCTTCAACTCCTACGCTATCTCTTGGGTGCGCCAGGCTCCCGGACAGGGCCTGGAGTGGATGGGCTGG

ATCAACCCTTTCTACATCGGCGAGACATTCTACGCCCAGAAGTTCCAGGGCAGAGTCACCATCACCGCCGACGAGT

CCACCTCCACCGCCTACATGGAGCTGTCCTCCCTGCGGTCAGAGGACACCGCCGTGTACTACTGCGCCAGGGCCGC

CTACCACCCTCTGGTGTTCGACAACTGGGGCCAGGGCACCCTGGTGACCGTGTCCTCC

SEQ ID NO: 27
GATATCGTGCTGACCCAGCCTCCTTCTGTGTCTGGCGCCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCTGCCTCCCTGGCCATCA

CCGGCCTGCAGTCCGAGGACGAGGCCGACTACTACTGCCAGTCCTGGGACTACTCCGGCTTCTCAACCGTGTTCGG

CGGAGGCACCAAGCTGACCGTGCTG

SEQ ID NO: 28
EVQLVQSGAEVKKPGSSVKVSCKASGGTFNSYAISWVRQAPGQGLEWMGNIIPMTGQTYYAQKFQGRVTITADESTS

TAYMELSSLRSEDTAVYYCARAAYHPLVFDNWGQGTLVTVSS

SEQ ID NO: 29
GAGGTGCAGCTGGTGCAGTCTGGCGCTGAGGTGAAGAAGCCTGGCTCCTCCGTCAAGGTGTCCTGCAAGGCCTCC

GGCGGCACCTTCAACTCCTACGCTATCTCTTGGGTGCGCCAGGCTCCCGGACAGGGCCTGGAGTGGATGGGCAAC

ATCATCCCTATGACCGGCCAGACCTACTACGCCCAGAAGTTCCAGGGCAGAGTCACCATCACCGCCGACGAGTCCA

CCTCCACCGCCTACATGGAGCTGTCCTCCCTGCGGTCAGAGGACACCGCCGTGTACTACTGCGCCAGGGCCGCCTA

CCACCCTCTGGTGTTCGACAACTGGGGCCAGGGCACCCTGGTGACCGTGTCCTCC
```

SEQ ID NO: 30
GACATCGTGCTGACACAGCCTCCCTCTGTGTCTGGCGCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCTGCCTCCCTGGCCATCA

CCGGCCTGCAGTCAGAGGACGAGGCCGACTACTACTGCCAGTCCTGGGACTACTCCGGCTTCTCCACCGTGTTCGG

CGGAGGCACCAAGCTGACCGTGCTG

SEQ ID NO: 31
EVQLVQSGAEVKKPGSSVKVSCKASGGTFNSYAISWVRQAPGQGLEWMGNIIPHYGFAYYAQKFQGRVTITADESTST

AYMELSSLRSEDTAVYYCARAAYHPLVFDNWGQGTLVTVSS

SEQ ID NO: 32
GAGGTGCAATTGGTTCAGTCTGGCGCGGAAGTGAAAAAACCGGGCAGCAGCGTGAAAGTGAGCTGCAAAGCCTC

CGGAGGCACTTTTAATTCTTATGCTATTTCTTGGGTGCGCCAAGCCCCTGGGCAGGGTCTCGAGTGGATGGGCAAT

ATTATTCCTCATTATGGTTTTGCTTATTATGCTCAGAAGTTTCAGGGTCGGGTGACCATTACCGCGGATGAAAGCAC

CAGCACCGCGTATATGGAACTGAGCAGCCTGCGTAGCGAAGATACGGCCGTGTATTATTGCGCGCGTGCTGCTTA

TCATCCTCTTGTTTTTGATAATTGGGGCCAAGGCACCCTGGTGACGGTTAGCTCA

SEQ ID NO: 33
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGAATTGGTACCAGCAGTTGCCCGGGACGGCGCCGAAACTTCTGATTTATC

GTAATAATCATCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCCAGTCTTGGGATTATTCTGGTTTTTCTACTGTGTTT

GGCGGCGGCACGAAGTTAACCGTCCTA

SEQ ID NO: 34
EVQLVQSGAEVKKPGSSVKVSCKASGGTFNSYAISWVRQAPGQGLEWMGNIIPYSGFAYYAQKFQGRVTITADESTST

AYMELSSLRSEDTAVYYCARAAYHPLVFDNWGQGTLVTVSS

SEQ ID NO: 35
GAGGTGCAATTGGTTCAGTCTGGCGCGGAAGTGAAAAAACCGGGCAGCAGCGTGAAAGTGAGCTGCAAAGCCTC

CGGAGGCACTTTTAATTCTTATGCTATTTCTTGGGTGCGCCAAGCCCCTGGGCAGGGTCTCGAGTGGATGGGCAAT

ATTATTCCTTATTCTGGTTTTGCTTATTATGCTCAGAAGTTTCAGGGTCGGGTGACCATTACCGCGGATGAAAGCAC

CAGCACCGCGTATATGGAACTGAGCAGCCTGCGTAGCGAAGATACGGCCGTGTATTATTGCGCGCGTGCTGCTTA

TCATCCTCTTGTTTTTGATAATTGGGGCCAAGGCACCCTGGTGACGGTTAGCTCA

SEQ ID NO: 36
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGAATTGGTACCAGCAGTTGCCCGGGACGGCGCCGAAACTTCTGATTTATC

GTAATAATCATCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCCAGTCTTGGGATTATTCTGGTTTTTCTACTGTGTTT

GGCGGCGGCACGAAGTTAACCGTCCTA

SEQ ID NO: 37
EVQLVQSGAEVKKPGSSVKVSCKASGGTFNSYAISWVRQAPGQGLEWMGWINPFYIGETFYAQKFQGRVTITADESTS

TAYMELSSLRSEDTAVYYCARAAYHPLVFDNWGQGTLVTVSS

SEQ ID NO: 38
GAGGTGCAGCTGGTGCAGTCTGGCGCTGAGGTGAAGAAGCCTGGCTCCTCCGTCAAGGTGTCCTGCAAGGCCTCC

GGCGGCACCTTCAACTCCTACGCTATCTCTTGGGTGCGCCAGGCTCCCGGACAGGGCCTGGAGTGGATGGGCTGG

ATCAACCCTTTCTACATCGGCGAGACATTCTACGCCCAGAAGTTCCAGGGCAGAGTCACCATCACCGCCGACGAGT

-continued

Sequence Listing

CCACCTCCACCGCCTACATGGAGCTGTCCTCCCTGCGGTCAGAGGACACCGCCGTGTACTACTGCGCCAGGGCCGC

CTACCACCCTCTGGTGTTCGACAACTGGGGCCAGGGCACCCTGGTGACCGTGTCCTCC

SEQ ID NO: 39
CAGTCCGTGCTGACCCAGCCTCCTTCTGCCTCTGGCACCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCCGCCTCCCTGGCCATCTC

TGGCCTGCAGTCAGAGGACGAGGCCGACTACTACTGCCAGTCCTGGGACTACTCCGGCTTCTCCACCGTGTTCGGC

GGAGGCACCAAGCTGACCGTGCTG

SEQ ID NO: 40
EVQLVQSGAEVKKPGSSVKVSCKASGGTFNSYAISWVRQAPGQGLEWMGNIIPMTGQTYYAQKFQGRVTITADESTS

TAYMELSSLRSEDTAVYYCARAAYHPLVFDNWGQGTLVTVSS

SEQ ID NO: 41
GAGGTGCAGCTGGTGCAGTCTGGCGCCGAGGTGAAGAAGCCTGGCTCCTCCGTCAAGGTGTCCTGCAAGGCCTCC

GGCGGCACCTTCAACTCCTACGCCATCTCTTGGGTGCGCCAGGCTCCTGGACAGGGCCTGGAGTGGATGGGCAAC

ATCATCCCTATGACCGGCCAGACCTACTACGCCCAGAAGTTCCAGGGCAGAGTCACCATCACCGCCGACGAGTCCA

CCTCCACCGCCTACATGGAGCTGTCCTCCCTGCGGTCAGAGGACACCGCCGTGTACTACTGCGCCAGGGCCGCCTA

CCACCCTCTGGTGTTCGACAACTGGGGCCAGGGCACCCTGGTGACCGTGTCCTCC

SEQ ID NO: 42
CAGTCCGTGCTGACCCAGCCTCCTTCTGCCTCTGGCACCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCCGCCTCCCTGGCCATCTC

TGGCCTGCAGTCAGAGGACGAGGCCGACTACTACTGCCAGTCCTGGGACTACTCCGGCTTCTCCACCGTGTTCGGC

GGAGGCACCAAGCTGACCGTGCTG

SEQ ID NO: 43
EVQLVQSGAEVKKPGSSVKVSCKASGGTFKSYAISWVRQAPGQGLEWMGNIIPMTGQTYYAQKFQGRVTITADESTS

TAYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 44
GAGGTGCAGCTGGTGCAGTCAGGCGCCGAAGTGAAGAAACCCGGCTCTAGCGTGAAAGTCAGCTGTAAAGCTAG

TGGCGGCACCTTCAAGTCCTACGCTATTAGCTGGGTCAGACAGGCCCCAGGTCAGGGCCTGGAGTGGATGGGCA

ATATTATCCCTATGACCGGTCAGACCTACTACGCTCAGAAATTTCAGGGTAGAGTGACTATCACCGCCGACGAGTC

TACTAGCACCGCCTATATGGAACTGTCTAGCCTGAGATCAGAGGACACCGCCGTCTACTACTGCGCTAGAGCCGCC

TATCACCCCCTGGTGTTCGATAACTGGGGTCAGGGCACCCTGGTCACCGTGTCTAGCGCTAGCACTAAGGGCCCCT

CCGTGTTCCCTCTGGCCCCTTCCAGCAAGTCTACCTCCGGCGGCACAGCTGCTCTGGGCTGCCTGGTCAAGGACTA

CTTCCCTGAGCCTGTGACAGTGTCCTGGAACTCTGGCGCCCTGACCTCTGGCGTGCACACCTTCCCTGCCGTGCTGC

AGTCCTCCGGCCTGTACTCCCTGTCCTCCGTGGTCACAGTGCCTTCAAGCAGCCTGGGCACCCAGACCTATATCTGC

AACGTGAACCACAAGCCTTCCAACACCAAGGTGGACAAGCGGGTGGAGCCTAAGTCCTGCGACAAGACCCACACC

TGTCCTCCCTGCCCTGCTCCTGAAGCTGCTGGCGGCCCTTCTGTGTTCCTGTTCCCTCCAAAGCCCAAGGACACCCT

```
GATGATCTCCCGGACCCCTGAAGTGACCTGCGTGGTGGTGGACGTGTCCCACGAGGATCCTGAAGTGAAGTTCAA

TTGGTACGTGGACGGCGTGGAGGTGCACAACGCCAAGACCAAGCCTCGGGAGGAACAGTACAACTCCACCTACC

GGGTGGTGTCCGTGCTGACCGTGCTGCACCAGGACTGGCTGAACGGCAAAGAGTACAAGTGCAAAGTCTCCAAC

AAGGCCCTGCCTGCCCCTATCGAAAAGACAATCTCCAAGGCCAAGGGCCAGCCTAGGGAACCCCAGGTGTACACC

CTGCCACCCAGCCGGGAGGAAATGACCAAGAACCAGGTGTCCCTGACCTGTCTGGTCAAGGGCTTCTACCCTTCC

GATATCGCCGTGGAGTGGGAGTCTAACGGCCAGCCTGAGAACAACTACAAGACCACCCCTCCTGTGCTGGACTCC

GACGGCTCCTTCTTCCTGTACTCCAAACTGACCGTGGACAAGTCCCGGTGGCAGCAGGGCAACGTGTTCTCCTGCT

CCGTGATGCACGAGGCCCTGCACAACCACTACACCCAGAAGTCCCTGTCCCTGTCTCCCGGCAAG

SEQ ID NO: 45
DIVLTQPPSVSGAPGQRVTISCSGSSSNIGNHYVNWYQQLPGTAPKLLIYRNNHRPSGVPDRFSGSKSGTSASLAITGLQ

SEDEADYYCQSWDYSGFSTVFGGGTKLTVLGQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEKTVAPTECS

SEQ ID NO: 46
GATATCGTCCTGACTCAGCCCCCTAGCGTCAGCGGCGCTCCCGGTCAGAGAGTGACTATTAGCTGTAGCGGCTCTA

GCTCTAATATCGGTAATCACTACGTGAACTGGTATCAGCAGCTGCCCGGCACCGCCCCTAAGCTGCTGATCTATAG

AAACAATCACCGGCCTAGCGGCGTGCCCGATAGGTTTAGCGGATCTAAGTCAGGCACTAGCGCTAGTCTGGCTAT

CACCGGACTGCAGTCAGAGGACGAGGCCGACTACTACTGTCAGTCCTGGGACTATAGCGGCTTTAGCACCGTGTT

CGGCGGAGGCACTAAGCTGACCGTGCTGGGTCAGCCTAAGGCTGCCCCCAGCGTGACCCTGTTCCCCCCCAGCAG

CGAGGAGCTGCAGGCCAACAAGGCCACCCTGGTGTGCCTGATCAGCGACTTCTACCCAGGCGCCGTGACCGTGGC

CTGGAAGGCCGACAGCAGCCCCGTGAAGGCCGGCGTGGAGACCACCACCCCCAGCAAGCAGAGCAACAACAAGT

ACGCCGCCAGCAGCTACCTGAGCCTGACCCCCGAGCAGTGGAAGAGCCACAGGTCCTACAGCTGCCAGGTGACCC

ACGAGGGCAGCACCGTGGAAAAGACCGTGGCCCCAACCGAGTGCAGC

SEQ ID NO: 47
EVQLVQSGAEVKKPGSSVKVSCKASGGTFNSYAISWVRQAPGQGLEWMGNIIPMTGQTYYAQKFQGRVTITADESTS

TAYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 48
GAGGTGCAGCTGGTGCAGTCTGGCGCTGAGGTGAAGAAGCCTGGCTCCTCCGTCAAGGTGTCCTGCAAGGCCTCC

GGCGGCACCTTCAACTCCTACGCTATCTCTTGGGTGCGCCAGGCTCCCGGACAGGGCCTGGAGTGGATGGGCAAC

ATCATCCCTATGACCGGCCAGACCTACTACGCCCAGAAGTTCCAGGGCAGAGTCACCATCACCGCCGACGAGTCCA

CCTCCACCGCCTACATGGAGCTGTCCTCCCTGCGGTCAGAGGACACCGCCGTGTACTACTGCGCCAGGGCCGCCTA

CCACCCTCTGGTGTTCGACAACTGGGGCCAGGGCACCCTGGTGACCGTGTCCTCCGCTAGCACCAAGGGCCCCTCC

GTGTTCCCTCTGGCCCCTTCCAGCAAGTCTACCTCCGGCGGCACAGCTGCTCTGGGCTGCCTGGTCAAGGACTACT

TCCCTGAGCCTGTGACAGTGTCCTGGAACTCTGGCGCCCTGACCTCTGGCGTGCACACCTTCCCTGCCGTGCTGCA

GTCCTCCGGCCTGTACTCCCTGTCCTCCGTGGTCACAGTGCCTTCAAGCAGCCTGGGCACCCAGACCTATATCTGCA

ACGTGAACCACAAGCCTTCCAACACCAAGGTGGACAAGCGGGTGGAGCCTAAGTCCTGCGACAAGACCCACACCT

GTCCTCCCTGCCCTGCTCCTGAAGCTGCTGGCGGCCCTTCTGTGTTCCTGTTCCCTCCAAAGCCCAAGGACACCCTG

ATGATCTCCCGGACCCCTGAAGTGACCTGCGTGGTGGTGGACGTGTCCCACGAGGATCCTGAAGTGAAGTTCAAT
```

```
TGGTACGTGGACGGCGTGGAGGTGCACAACGCCAAGACCAAGCCTCGGGAGGAACAGTACAACTCCACCTACCG

GGTGGTGTCCGTGCTGACCGTGCTGCACCAGGACTGGCTGAACGGCAAAGAGTACAAGTGCAAAGTCTCCAACA

AGGCCCTGCCTGCCCCTATCGAAAAGACAATCTCCAAGGCCAAGGGCCAGCCTAGGGAACCCCAGGTGTACACCC

TGCCACCCAGCCGGGAGGAAATGACCAAGAACCAGGTGTCCCTGACCTGTCTGGTCAAGGGCTTCTACCCTTCCG

ATATCGCCGTGGAGTGGGAGTCTAACGGCCAGCCTGAGAACAACTACAAGACCACCCCTCCTGTGCTGGACTCCG

ACGGCTCCTTCTTCCTGTACTCCAAACTGACCGTGGACAAGTCCCGGTGGCAGCAGGGCAACGTGTTCTCCTGCTC

CGTGATGCACGAGGCCCTGCACAACCACTACACCCAGAAGTCCCTGTCCCTGTCTCCCGGCAAG

SEQ ID NO: 49
GACATCGTGCTGACACAGCCTCCCTCTGTGTCTGGCGCCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCTGCCTCCCTGGCCATCA

CCGGCCTGCAGTCAGAGGACGAGGCCGACTACTACTGCCAGTCCTGGGACTACTCCGGCTTCTCCACCGTGTTCGG

CGGAGGCACCAAGCTGACCGTGCTGGGACAGCCTAAGGCTGCCCCCAGCGTGACCCTGTTCCCCCCCAGCAGCGA

GGAGCTGCAGGCCAACAAGGCCACCCTGGTGTGCCTGATCAGCGACTTCTACCCAGGCGCCGTGACCGTGGCCTG

GAAGGCCGACAGCAGCCCCGTGAAGGCCGGCGTGGAGACCACCACCCCCAGCAAGCAGAGCAACAACAAGTACG

CCGCCAGCAGCTACCTGAGCCTGACCCCCGAGCAGTGGAAGAGCCACAGGTCCTACAGCTGCCAGGTGACCCACG

AGGGCAGCACCGTGGAAAAGACCGTGGCCCCAACCGAGTGCAGC

SEQ ID NO: 50
EVQLVQSGAEVKKPGSSVKVSCKASGGTFNSYAISWVRQAPGQGLEWMGWINPFYIGETFYAQKFQGRVTITADESTS

TAYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 51
GAGGTGCAGCTGGTGCAGTCTGGCGCTGAGGTGAAGAAGCCTGGCTCCTCCGTCAAGGTGTCCTGCAAGGCCTCC

GGCGGCACCTTCAACTCCTACGCTATCTCTTGGGTGCGCCAGGCTCCCGGACAGGGCCTGGAGTGGATGGGCTGG

ATCAACCCTTTCTACATCGGCGAGACATTCTACGCCCAGAAGTTCCAGGGCAGAGTCACCATCACCGCCGACGAGT

CCACCTCCACCGCCTACATGGAGCTGTCCTCCCTGCGGTCAGAGGACACCGCCGTGTACTACTGCGCCAGGGCCGC

CTACCACCCTCTGGTGTTCGACAACTGGGGCCAGGGCACCCTGGTGACCGTGTCCTCCGCTAGCACCAAGGGCCCC

TCCGTGTTCCCTCTGGCCCCTTCCAGCAAGTCTACCTCCGGCGGCACAGCTGCTCTGGGCTGCCTGGTCAAGGACT

ACTTCCCTGAGCCTGTGACAGTGTCCTGGAACTCTGGCGCCCTGACCTCTGGCGTGCACACCTTCCCTGCCGTGCT

GCAGTCCTCCGGCCTGTACTCCCTGTCCTCCGTGGTCACAGTGCCTTCAAGCAGCCTGGGCACCCAGACCTATATCT

GCAACGTGAACCACAAGCCTTCCAACACCAAGGTGGACAAGCGGGTGGAGCCTAAGTCCTGCGACAAGACCCAC

ACCTGTCCTCCCTGCCCTGCTCCTGAAGCTGCTGGCGGCCCTTCTGTGTTCCTGTTCCCTCCAAAGCCCAAGGACAC

CCTGATGATCTCCCGGACCCCTGAAGTGACCTGCGTGGTGGTGGACGTGTCCCACGAGGATCCTGAAGTGAAGTT

CAATTGGTACGTGGACGGCGTGGAGGTGCACAACGCCAAGACCAAGCCTCGGGAGGAACAGTACAACTCCACCT

ACCGGGTGGTGTCCGTGCTGACCGTGCTGCACCAGGACTGGCTGAACGGCAAAGAGTACAAGTGCAAAGTCTCC

AACAAGGCCCTGCCTGCCCCTATCGAAAAGACAATCTCCAAGGCCAAGGGCCAGCCTAGGGAACCCCAGGTGTAC

ACCCTGCCACCCAGCCGGGAGGAAATGACCAAGAACCAGGTGTCCCTGACCTGTCTGGTCAAGGGCTTCTACCCTT
```

```
CCGATATCGCCGTGGAGTGGGAGTCTAACGGCCAGCCTGAGAACAACTACAAGACCACCCCTCCTGTGCTGGACT

CCGACGGCTCCTTCTTCCTGTACTCCAAACTGACCGTGGACAAGTCCCGGTGGCAGCAGGGCAACGTGTTCTCCTG

CTCCGTGATGCACGAGGCCCTGCACAACCACTACACCCAGAAGTCCCTGTCCCTGTCTCCCGGCAAG

SEQ ID NO: 52
GATATCGTGCTGACCCAGCCTCCTTCTGTGTCTGGCGCCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCTGCCTCCCTGGCCATCA

CCGGCCTGCAGTCCGAGGACGAGGCCGACTACTACTGCCAGTCCTGGGACTACTCCGGCTTCTCAACCGTGTTCGG

CGGAGGCACCAAGCTGACCGTGCTGGGACAGCCTAAGGCTGCCCCCAGCGTGACCCTGTTCCCCCCCAGCAGCGA

GGAGCTGCAGGCCAACAAGGCCACCCTGGTGTGCCTGATCAGCGACTTCTACCCAGGCGCCGTGACCGTGGCCTG

GAAGGCCGACAGCAGCCCCGTGAAGGCCGGCGTGGAGACCACCACCCCCAGCAAGCAGAGCAACAACAAGTACG

CCGCCAGCAGCTACCTGAGCCTGACCCCCGAGCAGTGGAAGAGCCACAGGTCCTACAGCTGCCAGGTGACCCACG

AGGGCAGCACCGTGGAAAAGACCGTGGCCCCAACCGAGTGCAGC

SEQ ID NO: 53
EVQLVQSGAEVKKPGSSVKVSCKASGGTFNSYAISWVRQAPGQGLEWMGNIIPMTGQTYYAQKFQGRVTITADESTS

TAYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 54
GAGGTGCAGCTGGTGCAGTCTGGCGCCGAGGTGAAGAAGCCTGGCTCCTCCGTCAAGGTGTCCTGCAAGGCCTCC

GGCGGCACCTTCAACTCCTACGCCATCTCTTGGGTGCGCCAGGCTCCTGGACAGGGCCTGGAGTGGATGGGCAAC

ATCATCCCTATGACCGGCCAGACCTACTACGCCCAGAAGTTCCAGGGCAGAGTCACCATCACCGCCGACGAGTCCA

CCTCCACCGCCTACATGGAGCTGTCCTCCCTGCGGTCAGAGGACACCGCCGTGTACTACTGCGCCAGGGCCGCCTA

CCACCCTCTGGTGTTCGACAACTGGGGCCAGGGCACCCTGGTGACCGTGTCCTCCGCTAGCACCAAGGGCCCCTCC

GTGTTCCCTCTGGCCCCTTCCAGCAAGTCTACCTCCGGCGGCACAGCTGCTCTGGGCTGCCTGGTCAAGGACTACT

TCCCTGAGCCTGTGACAGTGTCCTGGAACTCTGGCGCCCTGACCTCTGGCGTGCACACCTTCCCTGCCGTGCTGCA

GTCCTCCGGCCTGTACTCCCTGTCCTCCGTGGTCACAGTGCCTTCAAGCAGCCTGGGCACCCAGACCTATATCTGCA

ACGTGAACCACAAGCCTTCCAACACCAAGGTGGACAAGCGGGTGGAGCCTAAGTCCTGCGACAAGACCCACACCT

GTCCTCCCTGCCCTGCTCCTGAAGCTGCTGGCGGCCCTTCTGTGTTCCTGTTCCCTCCAAAGCCCAAGGACACCCTG

ATGATCTCCCGGACCCCTGAAGTGACCTGCGTGGTGGTGGACGTGTCCCACGAGGATCCTGAAGTGAAGTTCAAT

TGGTACGTGGACGGCGTGGAGGTGCACAACGCCAAGACCAAGCCTCGGGAGGAACAGTACAACTCCACCTACCG

GGTGGTGTCCGTGCTGACCGTGCTGCACCAGGACTGGCTGAACGGCAAAGAGTACAAGTGCAAAGTCTCCAACA

AGGCCCTGCCTGCCCCTATCGAAAAGACAATCTCCAAGGCCAAGGGCCAGCCTAGGGAACCCCAGGTGTACACCC

TGCCACCCAGCCGGGAGGAAATGACCAAGAACCAGGTGTCCCTGACCTGTCTGGTCAAGGGCTTCTACCCTTCCG

ATATCGCCGTGGAGTGGGAGTCTAACGGCCAGCCTGAGAACAACTACAAGACCACCCCTCCTGTGCTGGACTCCG

ACGGCTCCTTCTTCCTGTACTCCAAACTGACCGTGGACAAGTCCCGGTGGCAGCAGGGCAACGTGTTCTCCTGCTC

CGTGATGCACGAGGCCCTGCACAACCACTACACCCAGAAGTCCCTGTCCCTGTCTCCCGGCAAG
```

SEQ ID NO: 55
CAGTCCGTGCTGACCCAGCCTCCTTCTGCCTCTGGCACCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCCGCCTCCCTGGCCATCTC

TGGCCTGCAGTCAGAGGACGAGGCCGACTACTACTGCCAGTCCTGGGACTACTCCGGCTTCTCCACCGTGTTCGGC

GGAGGCACCAAGCTGACCGTGCTGGGACAGCCTAAGGCTGCCCCAGCGTGACCCTGTTCCCCCCCAGCAGCGAG

GAGCTGCAGGCCAACAAGGCCACCCTGGTGTGCCTGATCAGCGACTTCTACCCAGGCGCCGTGACCGTGGCCTGG

AAGGCCGACAGCAGCCCCGTGAAGGCCGGCGTGGAGACCACCACCCCCAGCAAGCAGAGCAACAACAAGTACGC

CGCCAGCAGCTACCTGAGCCTGACCCCCGAGCAGTGGAAGAGCCACAGGTCCTACAGCTGCCAGGTGACCCACGA

GGGCAGCACCGTGGAAAAGACCGTGGCCCCAACCGAGTGCAGC

SEQ ID NO: 56
QVQLVQSGAEVKKPGSSVKVSCKASGGTFNSYAISWVRQAPGQGLEWMGGIIPIYGTANYAQKFQGRVTITADESTST

AYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPELL

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 57
CAGGTGCAATTGGTTCAGTCTGGCGCGGAAGTGAAAAAACCGGGCAGCAGCGTGAAAGTGAGCTGCAAAGCCTC

CGGAGGCACTTTTAATTCTTATGCTATTTCTTGGGTGCGCCAAGCCCCTGGGCAGGGTCTCGAGTGGATGGGCGG

TATCATTCCGATTTATGGCACTGCGAATTACGCGCAGAAGTTTCAGGGCCGGGTGACCATTACCGCGGATGAAAG

CACCAGCACCGCGTATATGGAACTGAGCAGCCTGCGTAGCGAAGATACGGCCGTGTATTATTGCGCGCGTGCTGC

TTATCATCCTCTTGTTTTTGATAATTGGGGCCAAGGCACCCTGGTGACGGTTAGCTCAGCCTCCACCAAGGGTCCAT

CGGTCTTCCCCCTGGCACCCTCCTCCAAGAGCACCTCTGGGGGCACAGCGGCCCTGGGCTGCCTGGTCAAGGACT

ACTTCCCCGAACCGGTGACGGTGTCGTGGAACTCAGGCGCCCTGACCAGCGGCGTGCACACCTTCCCGGCTGTCCT

ACAGTCCTCAGGACTCTACTCCCTCAGCAGCGTGGTGACCGTGCCCTCCAGCAGCTTGGGCACCCAGACCTACATC

TGCAACGTGAATCACAAGCCCAGCAACACCAAGGTGGACAAGAGAGTTGAGCCCAAATCTTGTGACAAAACTCAC

ACATGCCCACCGTGCCCAGCACCTGAACTCCTGGGGGGACCGTCAGTCTTCCTCTTCCCCCCAAAACCCAAGGACA

CCCTCATGATCTCCCGGACCCCTGAGGTCACATGCGTGGTGGTGGACGTGAGCCACGAAGACCCTGAGGTCAAGT

TCAACTGGTACGTGGACGGCGTGGAGGTGCATAATGCCAAGACAAAGCCGCGGGAGGAGCAGTACAACAGCAC

GTACCGGGTGGTCAGCGTCCTCACCGTCCTGCACCAGGACTGGCTGAATGGCAAGGAGTACAAGTGCAAGGTCTC

CAACAAAGCCCTCCCAGCCCCCATCGAGAAAACCATCTCCAAAGCCAAAGGGCAGCCCCGAGAACCACAGGTGTA

CACCCTGCCCCCATCCCGGGAGGAGATGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTACAAGACCACGCCTCCCGTGCTGGA

CTCCGACGGCTCCTTCTTCCTCTACAGCAAGCTCACCGTGGACAAGAGCAGGTGGCAGCAGGGGAACGTCTTCTCA

TGCTCCGTGATGCATGAGGCTCTGCACAACCACTACACGCAGAAGAGCCTCTCCCTGTCTCCGGGTAAA

SEQ ID NO: 58
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGAATTGGTACCAGCAGTTGCCCGGGACGGCGCCGAAACTTCTGATTTATC

GTAATAATCATCGTCCCTCAGGCGTGCCGGATCGTTTTAGCGGATCCAAAAGCGGCACCAGCGCGAGCCTTGCGA

```
TTACGGGCCTGCAAAGCGAAGACGAAGCGGATTATTATTGCCAGTCTTGGGATTATTCTGGTTTTTCTACTGTGTTT
GGCGGCGGCACGAAGTTAACCGTCCTAGGTCAGCCCAAGGCTGCCCCCTCGGTCACTCTGTTCCCGCCCTCCTCTG
AGGAGCTTCAAGCCAACAAGGCCACACTGGTGTGTCTCATAAGTGACTTCTACCCGGGAGCCGTGACAGTGGCCT
GGAAGGCAGATAGCAGCCCCGTCAAGGCGGGAGTGGAGACCACCACACCCTCCAAACAAAGCAACAACAAGTAC
GCGGCCAGCAGCTATCTGAGCCTGACGCCTGAGCAGTGGAAGTCCCACAGAAGCTACAGCTGCCAGGTCACGCAT
GAAGGGAGCACCGTGGAGAAGACAGTGGCCCCTACAGAATGTTCA
```

SEQ ID NO: 59
GGTFNSY

SEQ ID NO: 60
IPMTGQ

SEQ ID NO: 61
AAYHPLVFDN

SEQ ID NO: 62
SSSNIGNHY

SEQ ID NO: 63
RNN

SEQ ID NO: 64
WDYSGFST

SEQ ID NO: 65
GGTFKSY

SEQ ID NO: 66
GGTFSSY

SEQ ID NO: 67
IPITGQ

SEQ ID NO: 68
GFTFSSY

SEQ ID NO: 69
SGEGSN

SEQ ID NO: 70
VMIGYGFDY

SEQ ID NO: 71
SQSIFNY

SEQ ID NO: 72
DSS

SEQ ID NO: 73
YSGFLF

SEQ ID NO: 74
TGSYYWN

SEQ ID NO: 75
EINHMGITYYNPSLKG

SEQ ID NO: 76
EIWHSGPTFYNPSLKS

SEQ ID NO: 77
EIHGHGFTFYNPSLKS

SEQ ID NO: 78
EIQSPGYTFYNPSLKS

SEQ ID NO: 79
TTRYWMSHILAYGMDY

SEQ ID NO: 80
SGSSSNIGNHYVS

Sequence Listing

SEQ ID NO: 81
ANTKRPS

SEQ ID NO: 82
SSYDGSQSIV

SEQ ID NO: 83
QVQLQESGPGLVKPGETLSLTCTVSGGSISTGSYYWNWIRQAPGKGLEWIGEINHMGITYYNPSLKGRVTISVDTSKNQ

FSLKLSSVTAEDTAVYYCARTTRYWMSHILAYGMDYWGQGTLVTVSS

SEQ ID NO: 84
CAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATCAATCATATGGGCATTACCTATTATAATCCGAGCCTGAAAGGCCGGGTGACCATTAGCGTTGATACTTC

GAAAAACCAGTTTAGCCTGAAACTGAGCAGCGTGACGGCGGAAGATACGGCCGTGTATTATTGCGCGCGTACTAC

TCGTTATTGGATGTCTCATATTCTTGCTTATGGTATGGATTATTGGGGCCAAGGCACCCTGGTGACGGTTAGCTCA

SEQ ID NO: 85
DIVLTQPPSVSGAPGQRVTISCSGSSSNIGNHYVSWYQQLPGTAPKLLIYANTKRPSGVPDRFSGSKSGTSASLAITGLQS

EDEADYYCSSYDGSQSIVFGGGTKLTVL

SEQ ID NO: 86
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTA

SEQ ID NO: 87
EVQLQESGPGLVKPGETLSLTCTVSGGSISTGSYYWNWIRQAPGKGLEWIGEIQSPGYTFYNPSLKSRVTISVDTSKNQF

SLKLSSVTAADTAVYYCARTTRYWMSHILAYGMDYWGQGTLVTVSS

SEQ ID NO: 88
GAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATTCAGTCTCCTGGTTATACTTTTTATAATCCTTCTCTTAAGTCTCGGGTGACCATTAGCGTTGATACTTCGA

AAACCAGTTTAGCCTGAAACTGAGCAGCGTGACGGCGGCGGATACGGCCGTGTATTATTGCGCGCGTACTACTC

GTTATTGGATGTCTCATATTCTTGCTTATGGTATGGATTATTGGGGCCAAGGCACCCTGGTGACGGTTAGCTCA

SEQ ID NO: 89
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTA

SEQ ID NO: 90
EVQLQESGPGLVKPGETLSLTCTVSGGSISTGSYYWNWIRQAPGKGLEWIGEIWHSGPTFYNPSLKSRVTISVDTSKNQF

SLKLSSVTAADTAVYYCARTTRYWMSHILAYGMDYWGQGTLVTVSS

SEQ ID NO: 91
GAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATTTGGCATTCTGGTCCTACTTTTTATAATCCTTCTCTTAAGTCTCGGGTGACCATTAGCGTTGATACTTCGA

```
AAAACCAGTTTAGCCTGAAACTGAGCAGCGTGACGGCGGCGGATACGGCCGTGTATTATTGCGCGCGTACTACTC

GTTATTGGATGTCTCATATTCTTGCTTATGGTATGGATTATTGGGGCCAAGGCACCCTGGTGACGGTTAGCTCA

SEQ ID NO: 92
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTA

SEQ ID NO: 93
EVQLQESGPGLVKPGETLSLTCTVSGGSISTGSYYWNWIRQAPGKGLEWIGEIHGHGFTFYNPSLKSRVTISVDTSKNQF

SLKLSSVTAADTAVYYCARTTRYWMSHILAYGMDYWGQGTLVTVSS

SEQ ID NO: 94
GAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATTCATGGTCATGGTTTTACTTTTTATAATCCTTCTCTTAAGTCTCGGGTGACCATTAGCGTTGATACTTCGA

AAAACCAGTTTAGCCTGAAACTGAGCAGCGTGACGGCGGCGGATACGGCCGTGTATTATTGCGCGCGTACTACTC

GTTATTGGATGTCTCATATTCTTGCTTATGGTATGGATTATTGGGGCCAAGGCACCCTGGTGACGGTTAGCTCA

SEQ ID NO: 95
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTA

SEQ ID NO: 96
QVQLQESGPGLVKPGETLSLTCTVSGGSISTGSYYWNWIRQAPGKGLEWIGEINHMGITYYNPSLKGRVTISVDTSKNQ

FSLKLSSVTAEDTAVYYCARTTRYWMSHILAYGMDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKRVEPKSCDKTHTCPPC

PAPELLGGPSVFLFPPKPKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQKSLSLSPGK

SEQ ID NO: 97
CAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATCAATCATATGGGCATTACCTATTATAATCCGAGCCTGAAAGGCCGGGTGACCATTAGCGTTGATACTTC

GAAAAACCAGTTTAGCCTGAAACTGAGCAGCGTGACGGCGGAAGATACGGCCGTGTATTATTGCGCGCGTACTAC

TCGTTATTGGATGTCTCATATTCTTGCTTATGGTATGGATTATTGGGGCCAAGGCACCCTGGTGACGGTTAGCTCA

GCCTCCACCAAGGGTCCATCGGTCTTCCCCCTGGCACCCTCCTCCAAGAGCACCTCTGGGGGCACAGCGGCCCTGG

GCTGCCTGGTCAAGGACTACTTCCCCGAACCGGTGACGGTGTCGTGGAACTCAGGCGCCCTGACCAGCGGCGTGC

ACACCTTCCCGGCTGTCCTACAGTCCTCAGGACTCTACTCCCTCAGCAGCGTGGTGACCGTGCCCTCCAGCAGCTTG

GGCACCCAGACCTACATCTGCAACGTGAATCACAAGCCCAGCAACACCAAGGTGGACAAGAGAGTTGAGCCCAAA

TCTTGTGACAAAACTCACACATGCCCACCGTGCCCAGCACCTGAACTCCTGGGGGGACCGTCAGTCTTCCTCTTCCC
```

```
CCCAAAACCCAAGGACACCCTCATGATCTCCCGGACCCCTGAGGTCACATGCGTGGTGGTGGACGTGAGCCACGA

AGACCCTGAGGTCAAGTTCAACTGGTACGTGGACGGCGTGGAGGTGCATAATGCCAAGACAAAGCCGCGGGAGG

AGCAGTACAACAGCACGTACCGGGTGGTCAGCGTCCTCACCGTCCTGCACCAGGACTGGCTGAATGGCAAGGAGT

ACAAGTGCAAGGTCTCCAACAAAGCCCTCCCAGCCCCCATCGAGAAAACCATCTCCAAAGCCAAAGGGCAGCCCC

GAGAACCACAGGTGTACACCCTGCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGCAGAAGAGCCTCTCCCTGTC

TCCGGGTAAA
```

SEQ ID NO: 98
DIVLTQPPSVSGAPGQRVTISCSGSSSNIGNHYVSWYQQLPGTAPKLLIYANTKRPSGVPDRFSGSKSGTSASLAITGLQS
EDEADYYCSSYDGSQSIVFGGGTKLTVLGQPKAAPSVTLFPPSSEELQANKATLVCLISDFYPGAVTVAWKADSSPVKAG
VETTTPSKQSNNKYAASSYLSLTPEQWKSHRSYSCQVTHEGSTVEKTVAPTECS

SEQ ID NO: 99
```
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTAGGTCAGCCCAAGGCTGCCCCCTCGGTCACTCTGTTCCCGCCCTCCTCTGAGG

AGCTTCAAGCCAACAAGGCCACACTGGTGTGTCTCATAAGTGACTTCTACCCGGGAGCCGTGACAGTGGCCTGGA

AGGCAGATAGCAGCCCCGTCAAGGCGGGAGTGGAGACCACCACACCCTCCAAACAAAGCAACAACAAGTACGCG

GCCAGCAGCTATCTGAGCCTGACGCCTGAGCAGTGGAAGTCCCACAGAAGCTACAGCTGCCAGGTCACGCATGAA

GGGAGCACCGTGGAGAAGACAGTGGCCCCTACAGAATGTTCA
```

SEQ ID NO: 100
EVQLVQSGAEVKKPGSSVKVSCKASGGTFNSYAISWVRQAPGQGLEWMGWINPFYIGETFYAQKFQGRVTITADESTS
TAYMELSSLRSEDTAVYYCARAAYHPLVFDNWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

SEQ ID NO: 101
```
GAGGTGCAGCTGGTGCAGTCTGGCGCTGAGGTGAAGAAGCCTGGCTCCTCCGTCAAGGTGTCCTGCAAGGCCTCC

GGCGGCACCTTCAACTCCTACGCTATCTCTTGGGTGCGCCAGGCTCCCGGACAGGGCCTGGAGTGGATGGGCTGG

ATCAACCCTTTCTACATCGGCGAGACATTCTACGCCCAGAAGTTCCAGGGCAGAGTCACCATCACCGCCGACGAGT

CCACCTCCACCGCCTACATGGAGCTGTCCTCCCTGCGGTCAGAGGACACCGCCGTGTACTACTGCGCCAGGGCCGC

CTACCACCCTCTGGTGTTCGACAACTGGGGCCAGGGCACCCTGGTGACCGTGTCCTCCGCTAGCACCAAGGGCCCC

TCCGTGTTCCCTCTGGCCCCTTCCAGCAAGTCTACCTCCGGCGGCACAGCTGCTCTGGGCTGCCTGGTCAAGGACT

ACTTCCCTGAGCCTGTGACAGTGTCCTGGAACTCTGGCGCCCTGACCTCTGGCGTGCACACCTTCCCTGCCGTGCT

GCAGTCCTCCGGCCTGTACTCCCTGTCCTCCGTGGTCACAGTGCCTTCAAGCAGCCTGGGCACCCAGACCTATATCT

GCAACGTGAACCACAAGCCTTCCAACACCAAGGTGGACAAGCGGGTGGAGCCTAAGTCCTGCGACAAGACCCAC

ACCTGTCCTCCCTGCCCTGCTCCTGAAGCTGCTGGCGGCCCCTTCTGTGTTCCTGTTCCCTCCAAAGCCCAAGGACAC
```

```
CCTGATGATCTCCCGGACCCCTGAAGTGACCTGCGTGGTGGTGGACGTGTCCCACGAGGATCCTGAAGTGAAGTT

CAATTGGTACGTGGACGGCGTGGAGGTGCACAACGCCAAGACCAAGCCTCGGGAGGAACAGTACAACTCCACCT

ACCGGGTGGTGTCCGTGCTGACCGTGCTGCACCAGGACTGGCTGAACGGCAAAGAGTACAAGTGCAAAGTCTCC

AACAAGGCCCTGCCTGCCCCTATCGAAAAGACAATCTCCAAGGCCAAGGGCCAGCCTAGGGAACCCCAGGTGTAC

ACCCTGCCACCCAGCCGGGAGGAAATGACCAAGAACCAGGTGTCCCTGACCTGTCTGGTCAAGGGCTTCTACCCTT

CCGATATCGCCGTGGAGTGGGAGTCTAACGGCCAGCCTGAGAACAACTACAAGACCACCCCTCCTGTGCTGGACT

CCGACGGCTCCTTCTTCCTGTACTCCAAACTGACCGTGGACAAGTCCCGGTGGCAGCAGGGCAACGTGTTCTCCTG

CTCCGTGATGCACGAGGCCCTGCACAACCACTACACCCAGAAGTCCCTGTCCCTGTCTCCCGGCAAG

SEQ ID NO: 102
CAGTCCGTGCTGACCCAGCCTCCTTCTGCCTCTGGCACCCCTGGCCAGAGAGTGACCATCTCCTGCTCTGGCTCCTC

CTCCAATATCGGCAACCACTACGTGAACTGGTATCAGCAGCTGCCCGGAACCGCCCCTAAGCTGCTGATCTACCGG

AACAACCACCGGCCTTCCGGCGTGCCCGACCGGTTCTCCGGCTCCAAGTCTGGCACCTCCGCCTCCTGGCCATCTC

TGGCCTGCAGTCAGAGGACGAGGCCGACTACTACTGCCAGTCCTGGGACTACTCCGGCTTCTCCACCGTGTTCGGC

GGAGGCACCAAGCTGACCGTGCTGGGACAGCCTAAGGCTGCCCCCAGCGTGACCCTGTTCCCCCCCAGCAGCGAG

GAGCTGCAGGCCAACAAGGCCACCCTGGTGTGCCTGATCAGCGACTTCTACCCAGGCGCCGTGACCGTGGCCTGG

AAGGCCGACAGCAGCCCCGTGAAGGCCGGCGTGGAGACCACCACCCCCAGCAAGCAGAGCAACAACAAGTACGC

CGCCAGCAGCTACCTGAGCCTGACCCCCGAGCAGTGGAAGAGCCACAGGTCCTACAGCTGCCAGGTGACCCACGA

GGGCAGCACCGTGGAAAAGACCGTGGCCCCAACCGAGTGCAGC

SEQ ID NO: 103
EVQLQESGPGLVKPGETLSLTCTVSGGSISTGSYYWNWIRQAPGKGLEWIGEIQSPGYTFYNPSLKSRVTISVDTSKNQF

SLKLSSVTAADTAVYYCARTTRYWMSHILAYGMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNTKVDKRVEPKSCDKTHTCPPCP

APEAAGGPSVFLFPPKPKDTLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 104
GAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATTCAGTCTCCTGGTTATACTTTTTATAATCCTTCTCTTAAGTCTCGGGTGACCATTAGCGTTGATACTTCGA

AAAACCAGTTTAGCCTGAAACTGAGCAGCGTGACGGCGGCGGATACGGCCGTGTATTATTGCGCGCGTACTACTC

GTTATTGGATGTCTCATATTCTTGCTTATGGTATGGATTATTGGGGCCAAGGCACCCTGGTGACGGTTAGCTCAGC

CTCCACCAAGGGTCCATCGGTCTTCCCCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACCGTGCCCTCCAGCAGCTTGG

GCACCCAGACCTACATCTGCAACGTGAATCACAAGCCCAGCAACACCAAGGTGGACAAGAGAGTTGAGCCCAAAT

CTTGTGACAAAACTCACACATGCCCACCGTGCCCAGCACCTGAAGCAGCGGGGGACCGTCAGTCTTCCTCTTCCC

CCCAAAACCCAAGGACACCCTCATGATCTCCCGGACCCCTGAGGTCACATGCGTGGTGGTGGACGTGAGCCACGA

AGACCCTGAGGTCAAGTTCAACTGGTACGTGGACGGCGTGGAGGTGCATAATGCCAAGACAAAGCCGCGGGAGG

AGCAGTACAACAGCACGTACCGGGTGGTCAGCGTCCTCACCGTCCTGCACCAGGACTGGCTGAATGGCAAGGAGT

ACAAGTGCAAGGTCTCCAACAAAGCCCTCCCAGCCCCCATCGAGAAAACCATCTCCAAAGCCAAAGGGCAGCCCC
```

GAGAACCACAGGTGTACACCCTGCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGCAGAAGAGCCTCTCCCTGTC

TCCGGGTAAA

SEQ ID NO: 105
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTAGGTCAGCCCAAGGCTGCCCCCTCGGTCACTCTGTTCCCGCCCTCCTCTGAGG

AGCTTCAAGCCAACAAGGCCACACTGGTGTGTCTCATAAGTGACTTCTACCCGGGAGCCGTGACAGTGGCCTGGA

AGGCAGATAGCAGCCCCGTCAAGGCGGGAGTGGAGACCACCACACCCTCCAAACAAAGCAACAACAAGTACGCG

GCCAGCAGCTATCTGAGCCTGACGCCTGAGCAGTGGAAGTCCCACAGAAGCTACAGCTGCCAGGTCACGCATGAA

GGGAGCACCGTGGAGAAGACAGTGGCCCCTACAGAATGTTCA

SEQ ID NO: 106
SYAIH

SEQ ID NO: 107
VISGEGSNTYYADSVKG

SEQ ID NO: 108
VMIGYGFDY

SEQ ID NO: 109
RASQSIFNYLN

SEQ ID NO: 110
DSSTLQS

SEQ ID NO: 111
LQYSGFLFT

SEQ ID NO: 112
QVQLLESGGGLVQPGGSLRLSCAASGFTFSSYAIHWVRQAPGKGLEWVSVISGEGSNTYYADSVKGRFTISRDNSKNTL

YLQMNSLRAEDTAVYYCARVMIGYGFDYWGQGTLVTVSS

SEQ ID NO: 113
CAGGTGCAGCTGCTGGAATCAGGCGGCGGACTGGTGCAGCCTGGCGGTAGCCTGAGACTGAGCTGCGCTGCTAG

TGGCTTCACCTTCTCTAGCTACGCTATTCACTGGGTCAGACAGGCCCCTGGTAAAGGCCTGGAGTGGGTGTCAGTG

ATTAGCGGCGAGGGCTCTAACACCTACTACGCCGATAGCGTGAAGGGCCGGTTCACTATCTCTAGGGATAACTCT

AAGAACACCCTGTACCTGCAGATGAATAGCCTGAGAGCCGAGGACACCGCCGTCTACTACTGCGCTAGAGTGATG

ATCGGCTACGGCTTCGACTACTGGGGTCAGGGCACCCTGGTCACCGTGTCTAGC

SEQ ID NO: 114
DIQMTQSPSSLSASVGDRVTITCRASQSIFNYLNWYQQKPGKAPKLLIYDSSTLQSGVPSRFSGSGSGTDFTLTISSLQPE

DFATYYCLQYSGFLFTFGQGTKVEIK

SEQ ID NO: 115
GATATTCAGATGACTCAGTCACCTAGTAGCCTGAGCGCTAGTGTGGGCGATAGAGTGACTATCACCTGTAGAGCC

TCTCAGTCTATCTTTAACTACCTGAACTGGTATCAGCAGAAGCCCGGTAAAGCCCCTAAGCTGCTGATCTACGACTC

TAGCACCCTGCAGTCAGGCGTGCCCTCTAGGTTTAGCGGTAGCGGTAGTGGCACCGACTTCACCCTGACTATCTCT

SEQ ID NO: 116
QVQLLESGGGLVQPGGSLRLSCAASGFTFSSYAIHWVRQAPGKGLEWVSVISGEGSNTYYADSVKGRFTISRDNSKNTL
YLQMNSLRAEDTAVYYCARVMIGYGFDYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKRVEPKSCDKTHTCPPCPAPEAAG
GPSVFLFPPKPKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

SEQ ID NO: 117
CAGGTGCAGCTGCTGGAATCAGGCGGCGGACTGGTGCAGCCTGGCGGTAGCCTGAGACTGAGCTGCGCTGCTAG
TGGCTTCACCTTCTCTAGCTACGCTATTCACTGGGTCAGACAGGCCCCTGGTAAAGGCCTGGAGTGGGTGTCAGTG
ATTAGCGGCGAGGGCTCTAACACCTACTACGCCGATAGCGTGAAGGGCCGGTTCACTATCTCTAGGGATAACTCT
AAGAACACCCTGTACCTGCAGATGAATAGCCTGAGAGCCGAGGACACCGCCGTCTACTACTGCGCTAGAGTGATG
ATCGGCTACGGCTTCGACTACTGGGGTCAGGGCACCCTGGTCACCGTGTCTAGCGCTAGCACTAAGGGCCCCTCC
GTGTTCCCTCTGGCCCCTTCCAGCAAGTCTACCTCCGGCGGCACAGCTGCTCTGGGCTGCCTGGTCAAGGACTACT
TCCCTGAGCCTGTGACAGTGTCCTGGAACTCTGGCGCCCTGACCTCTGGCGTGCACACCTTCCCTGCCGTGCTGCA
GTCCTCCGGCCTGTACTCCCTGTCCTCCGTGGTCACAGTGCCTTCAAGCAGCCTGGGCACCCAGACCTATATCTGCA
ACGTGAACCACAAGCCTTCCAACACCAAGGTGGACAAGCGGGTGGAGCCTAAGTCCTGCGACAAGACCCACACCT
GTCCTCCCTGCCCTGCTCCTGAAGCTGCTGGCGGCCCTTCTGTGTTCCTGTTCCCTCCAAAGCCCAAGGACACCCTG
ATGATCTCCCGGACCCCTGAAGTGACCTGCGTGGTGGTGGACGTGTCCCACGAGGATCCTGAAGTGAAGTTCAAT
TGGTACGTGGACGGCGTGGAGGTGCACAACGCCAAGACCAAGCCTCGGGAGGAACAGTACAACTCCACCTACCG
GGTGGTGTCCGTGCTGACCGTGCTGCACCAGGACTGGCTGAACGGCAAAGAGTACAAGTGCAAAGTCTCCAACA
AGGCCCTGCCTGCCCCTATCGAAAAGACAATCTCCAAGGCCAAGGGCCAGCCTAGGGAACCCCAGGTGTACACCC
TGCCACCCAGCCGGGAGGAAATGACCAAGAACCAGGTGTCCCTGACCTGTCTGGTCAAGGGCTTCTACCCTTCCG
ATATCGCCGTGGAGTGGGAGTCTAACGGCCAGCCTGAGAACAACTACAAGACCACCCCTCCTGTGCTGGACTCCG
ACGGCTCCTTCTTCCTGTACTCCAAACTGACCGTGGACAAGTCCCGGTGGCAGCAGGGCAACGTGTTCTCCTGCTC
CGTGATGCACGAGGCCCTGCACAACCACTACACCCAGAAGTCCCTGTCCCTGTCTCCCGGCAAG

SEQ ID NO: 118
DIQMTQSPSSLSASVGDRVTITCRASQSIFNYLNWYQQKPGKAPKLLIYDSSTLQSGVPSRFSGSGSGTDFTLTISSLQPE
DFATYYCLQYSGFLFTFGQGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC

SEQ ID NO: 119
GATATTCAGATGACTCAGTCACCTAGTAGCCTGAGCGCTAGTGTGGGCGATAGAGTGACTATCACCTGTAGAGCC
TCTCAGTCTATCTTTAACTACCTGAACTGGTATCAGCAGAAGCCCGGTAAAGCCCCTAAGCTGCTGATCTACGACTC
TAGCACCCTGCAGTCAGGCGTGCCCTCTAGGTTTAGCGGTAGCGGTAGTGGCACCGACTTCACCCTGACTATCTCT
AGCCTGCAGCCCGAGGACTTCGCTACCTACTACTGCCTGCAGTATAGCGGCTTCCTGTTCACCTTCGGTCAGGGCA
CTAAGGTCGAGATTAAGCGTACGGTGGCCGCTCCCAGCGTGTTCATCTTCCCCCCCAGCGACGAGCAGCTGAAGA
GCGGCACCGCCAGCGTGGTGTGCCTGCTGAACAACTTCTACCCCCGGGAGGCCAAGGTGCAGTGGAAGGTGGAC
AACGCCCTGCAGAGCGGCAACAGCCAGGAGAGCGTCACCGAGCAGGACAGCAAGGACTCCACCTACAGCCTGAG

```
CAGCACCCTGACCCTGAGCAAGGCCGACTACGAGAAGCATAAGGTGTACGCCTGCGAGGTGACCCACCAGGGCC

TGTCCAGCCCCGTGACCAAGAGCTTCAACAGGGGCGAGTGC
```

SEQ ID NO: 120
TFSIS

SEQ ID NO: 121
GIIPIFGTANYAQKFQG

SEQ ID NO: 122
TIQSSGENKFYADSVKG

SEQ ID NO: 123
GGYGGYYYFDY

SEQ ID NO: 124
RASQSISNRLN

SEQ ID NO: 125
KGSTLQS

SEQ ID NO: 126
HQYSGLLFT

SEQ ID NO: 127
QQHKVWLTT

SEQ ID NO: 128
QQHYVWSTT

SEQ ID NO: 129
QQHYQWLTT

SEQ ID NO: 130
QVQLVQSGAEVKKPGSSVKVSCKASGGTFSTFSISWVRQAPGQGLEWMGGIIPIFGTANYAQKFQGRVTITADESTST

AYMELSSLRSEDTAVYYCARGGYGGYYYFDYWGQGTLVTVSS

SEQ ID NO: 131
```
CAGGTGCAGCTGGTGCAGTCAGGCGCCGAAGTGAAGAAACCCGGCTCTAGCGTGAAAGTCAGCTGTAAAGCTAG

TGGCGGCACCTTCAGCACCTTCTCTATTAGCTGGGTCAGACAGGCCCCAGGTCAGGGCCTGGAGTGGATGGGCGG

AATTATCCCTATCTTCGGCACCGCTAACTACGCTCAGAAATTTCAGGGTAGAGTGACTATCACCGCCGACGAGTCT

ACTAGCACCGCCTATATGGAACTGTCTAGCCTGAGATCAGAGGACACCGCCGTCTACTACTGCGCTAGGGGCGGC

TACGGCGGCTATTACTACTTCGACTACTGGGGTCAGGGCACCCTGGTCACCGTGTCTAGC
```

SEQ ID NO: 132
DIQMTQSPSSLSASVGDRVTITCRASQSISNRLNWYQQKPGKAPKLLIYKGSTLQSGVPSRFSGSGSGTDFTLTISSLQPE

DFATYYCQQHKVWLTTFGQGTKVEIK

SEQ ID NO: 133
```
GATATTCAGATGACTCAGTCACCTAGTAGCCTGAGCGCTAGTGTGGGCGATAGAGTGACTATCACCTGTAGAGCC

TCTCAGTCTATCTCTAATAGGCTGAACTGGTATCAGCAGAAGCCCGGTAAAGCCCCTAAGCTGCTGATCTATAAGG

GCTCTACCCTGCAGTCAGGCGTGCCCTCTAGGTTTAGCGGTAGCGGTAGTGGCACCGACTTCACCCTGACTATCTC

TAGCCTGCAGCCCGAGGACTTCGCTACCTACTACTGTCAGCAGCACAAAGTGTGGCTGACTACCTTCGGTCAGGGC

ACTAAGGTCGAGATTAAG
```

SEQ ID NO: 134
QVQLVQSGAEVKKPGSSVKVSCKASGGTFSTFSISWVRQAPGQGLEWMGGIIPIFGTANYAQKFQGRVTITADESTST

AYMELSSLRSEDTAVYYCARGGYGGYYYFDYWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 135
CAGGTGCAGCTGGTGCAGTCAGGCGCCGAAGTGAAGAAACCCGGCTCTAGCGTGAAAGTCAGCTGTAAAGCTAG

TGGCGGCACCTTCAGCACCTTCTCTATTAGCTGGGTCAGACAGGCCCCAGGTCAGGGCCTGGAGTGGATGGGCGG

AATTATCCCTATCTTCGGCACCGCTAACTACGCTCAGAAATTTCAGGGTAGAGTGACTATCACCGCCGACGAGTCT

ACTAGCACCGCCTATATGGAACTGTCTAGCCTGAGATCAGAGGACACCGCCGTCTACTACTGCGCTAGGGGCGGC

TACGGCGGCTATTACTACTTCGACTACTGGGGTCAGGGCACCCTGGTCACCGTGTCTAGCGCTAGCACTAAGGGCC

CCTCCGTGTTCCCTCTGGCCCCTTCCAGCAAGTCTACCTCCGGCGGCACAGCTGCTCTGGGCTGCCTGGTCAAGGA

CTACTTCCCTGAGCCTGTGACAGTGTCCTGGAACTCTGGCGCCCTGACCTCTGGCGTGCACACCTTCCCTGCCGTGC

TGCAGTCCTCCGGCCTGTACTCCCTGTCCTCCGTGGTCACAGTGCCTTCAAGCAGCCTGGGCACCCAGACCTATATC

TGCAACGTGAACCACAAGCCTTCCAACACCAAGGTGGACAAGCGGGTGGAGCCTAAGTCCTGCGACAAGACCCAC

ACCTGTCCTCCCTGCCCTGCTCCTGAAGCTGCTGGCGGCCCTTCTGTGTTCCTGTTCCCTCCAAAGCCCAAGGACAC

CCTGATGATCTCCCGGACCCCTGAAGTGACCTGCGTGGTGGTGGACGTGTCCCACGAGGATCCTGAAGTGAAGTT

CAATTGGTACGTGGACGGCGTGGAGGTGCACAACGCCAAGACCAAGCCTCGGGAGGAACAGTACAACTCCACCT

ACCGGGTGGTGTCCGTGCTGACCGTGCTGCACCAGGACTGGCTGAACGGCAAAGAGTACAAGTGCAAAGTCTCC

AACAAGGCCCTGCCTGCCCCTATCGAAAAGACAATCTCCAAGGCCAAGGGCCAGCCTAGGGAACCCCAGGTGTAC

ACCCTGCCACCCAGCCGGGAGGAAATGACCAAGAACCAGGTGTCCCTGACCTGTCTGGTCAAGGGCTTCTACCCTT

CCGATATCGCCGTGGAGTGGGAGTCTAACGGCCAGCCTGAGAACAACTACAAGACCACCCCTCCTGTGCTGGACT

CCGACGGCTCCTTCTTCCTGTACTCCAAACTGACCGTGGACAAGTCCCGGTGGCAGCAGGGCAACGTGTTCTCCTG

CTCCGTGATGCACGAGGCCCTGCACAACCACTACACCCAGAAGTCCCTGTCCCTGTCTCCCGGCAAG

SEQ ID NO: 136
DIQMTQSPSSLSASVGDRVTITCRASQSISNRLNWYQQKPGKAPKLLIYKGSTLQSGVPSRFSGSGSGTDFTLTISSLQPE

DFATYYCQQHKVWLTTFGQGTKVEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

SEQ ID NO: 137
GATATTCAGATGACTCAGTCACCTAGTAGCCTGAGCGCTAGTGTGGGCGATAGAGTGACTATCACCTGTAGAGCC

TCTCAGTCTATCTCTAATAGGCTGAACTGGTATCAGCAGAAGCCCGGTAAAGCCCCTAAGCTGCTGATCTATAAGG

GCTCTACCCTGCAGTCAGGCGTGCCCTCTAGGTTTAGCGGTAGCGGTAGTGGCACCGACTTCACCCTGACTATCTC

TAGCCTGCAGCCCGAGGACTTCGCTACCTACTACTGTCAGCAGCACAAAGTGTGGCTGACTACCTTCGGTCAGGGC

ACTAAGGTCGAGATTAAGCGTACGGTGGCCGCTCCCAGCGTGTTCATCTTCCCCCCCAGCGACGAGCAGCTGAAG

AGCGGCACCGCCAGCGTGGTGTGCCTGCTGAACAACTTCTACCCCCGGGAGGCCAAGGTGCAGTGGAAGGTGGA

CAACGCCCTGCAGAGCGGCAACAGCCAGGAGAGCGTCACCGAGCAGGACAGCAAGGACTCCACCTACAGCCTGA

GCAGCACCCTGACCCTGAGCAAGGCCGACTACGAGAAGCATAAGGTGTACGCCTGCGAGGTGACCCACCAGGGC

CTGTCCAGCCCCGTGACCAAGAGCTTCAACAGGGGCGAGTGC

SEQ ID NO: 138
QVQLLESGGGLVQPGGSLRLSCAASGFTFSSYAIHWVRQAPGKGLEWVSTIQSSGENKFYADSVKGRFTISRDNSKNTL

YLQMNSLRAEDTAVYYCARVMIGYGFDYWGQGTLVTVSS

SEQ ID NO: 139
CAGGTGCAGCTGCTGGAATCAGGCGGCGGACTGGTGCAGCCTGGCGGTAGCCTGAGACTGAGCTGCGCTGCTAG

TGGCTTCACCTTCTCTAGCTACGCTATTCACTGGGTCAGACAGGCCCCTGGTAAAGGCCTGGAGTGGGTCAGCACT

```
ATTCAGTCTAGCGGCGAGAACAAGTTCTACGCCGATAGCGTGAAGGGCCGGTTCACTATCTCTAGGGATAACTCT

AAGAACACCCTGTACCTGCAGATGAATAGCCTGAGAGCCGAGGACACCGCCGTCTACTACTGCGCTAGAGTGATG

ATCGGCTACGGCTTCGACTACTGGGGTCAGGGCACCCTGGTCACCGTGTCTAGC

SEQ ID NO: 140
DIQMTQSPSSLSASVGDRVTITCRASQSIFNYLNWYQQKPGKAPKLLIYDSSTLQSGVPSRFSGSGSGTDFTLTISSLQPE

DFATYYCHQYSGLLFTFGQGTKVEIK

SEQ ID NO: 141
GATATTCAGATGACTCAGTCACCTAGTAGCCTGAGCGCTAGTGTGGGCGATAGAGTGACTATCACCTGTAGAGCC

TCTCAGTCTATCTTTAACTACCTGAACTGGTATCAGCAGAAGCCCGGTAAAGCCCCTAAGCTGCTGATCTACGACTC

TAGCACCCTGCAGTCAGGCGTGCCCTCTAGGTTTAGCGGTAGCGGTAGTGGCACCGACTTCACCCTGACTATCTCT

AGCCTGCAGCCCGAGGACTTCGCTACCTACTACTGTCACCAGTATAGCGGCCTGCTGTTCACCTTCGGTCAGGGCA

CTAAGGTCGAGATTAAG

SEQ ID NO: 142
QVQLLESGGGLVQPGGSLRLSCAASGFTFSSYAIHWVRQAPGKGLEWVSTIQSSGENKFYADSVKGRFTISRDNSKNTL

YLQMNSLRAEDTAVYYCARVMIGYGFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

GPSVFLFPPKPKDTLMISRTPEVTCVVVDVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLSPGK

SEQ ID NO: 143
CAGGTGCAGCTGCTGGAATCAGGCGGCGGACTGGTGCAGCCTGGCGGTAGCCTGAGACTGAGCTGCGCTGCTAG

TGGCTTCACCTTCTCTAGCTACGCTATTCACTGGGTCAGACAGGCCCCTGGTAAAGGCCTGGAGTGGGTCAGCACT

ATTCAGTCTAGCGGCGAGAACAAGTTCTACGCCGATAGCGTGAAGGGCCGGTTCACTATCTCTAGGGATAACTCT

AAGAACACCCTGTACCTGCAGATGAATAGCCTGAGAGCCGAGGACACCGCCGTCTACTACTGCGCTAGAGTGATG

ATCGGCTACGGCTTCGACTACTGGGGTCAGGGCACCCTGGTCACCGTGTCTAGCGCTAGCACTAAGGGCCCCTCC

GTGTTCCCTCTGGCCCCTTCCAGCAAGTCTACCTCCGGCGGCACAGCTGCTCTGGGCTGCCTGGTCAAGGACTACT

TCCCTGAGCCTGTGACAGTGTCCTGGAACTCTGGCGCCCTGACCTCTGGCGTGCACACCTTCCCTGCCGTGCTGCA

GTCCTCCGGCCTGTACTCCCTGTCCTCCGTGGTCACAGTGCCTTCAAGCAGCCTGGGCACCCAGACCTATATCTGCA

ACGTGAACCACAAGCCTTCCAACACCAAGGTGGACAAGCGGGTGGAGCCTAAGTCCTGCGACAAGACCCACACCT

GTCCTCCCTGCCCTGCTCCTGAAGCTGCTGGCGGCCCTTCTGTGTTCCTGTTCCCTCCAAAGCCCAAGGACACCCTG

ATGATCTCCCGGACCCCTGAAGTGACCTGCGTGGTGGTGGACGTGTCCCACGAGGATCCTGAAGTGAAGTTCAAT

TGGTACGTGGACGGCGTGGAGGTGCACAACGCCAAGACCAAGCCTCGGGAGGAACAGTACAACTCCACCTACCG

GGTGGTGTCCGTGCTGACCGTGCTGCACCAGGACTGGCTGAACGGCAAAGAGTACAAGTGCAAAGTCTCCAACA

AGGCCCTGCCTGCCCCTATCGAAAAGACAATCTCCAAGGCCAAGGGCCAGCCTAGGGAACCCCAGGTGTACACCC

TGCCACCCAGCCGGGAGGAAATGACCAAGAACCAGGTGTCCCTGACCTGTCTGGTCAAGGGCTTCTACCCTTCCG

ATATCGCCGTGGAGTGGGAGTCTAACGGCCAGCCTGAGAACAACTACAAGACCACCCCTCCTGTGCTGGACTCCG

ACGGCTCCTTCTTCCTGTACTCCAAACTGACCGTGGACAAGTCCCGGTGGCAGCAGGGCAACGTGTTCTCCTGCTC

CGTGATGCACGAGGCCCTGCACAACCACTACACCCAGAAGTCCCTGTCCCTGTCTCCCGGCAAG

SEQ ID NO: 144
DIQMTQSPSSLSASVGDRVTITCRASQSIFNYLNWYQQKPGKAPKLLIYDSSTLQSGVPSRFSGSGSGTDFTLTISSLQPE

DFATYYCHQYSGLLFTFGQGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

SEQ ID NO: 145
GATATTCAGATGACTCAGTCACCTAGTAGCCTGAGCGCTAGTGTGGGCGATAGAGTGACTATCACCTGTAGAGCC

TCTCAGTCTATCTTTAACTACCTGAACTGGTATCAGCAGAAGCCCGGTAAAGCCCCTAAGCTGCTGATCTACGACTC

TAGCACCCTGCAGTCAGGCGTGCCCTCTAGGTTTAGCGGTAGCGGTAGTGGCACCGACTTCACCCTGACTATCTCT

AGCCTGCAGCCCGAGGACTTCGCTACCTACTACTGTCACCAGTATAGCGGCCTGCTGTTCACCTTCGGTCAGGGCA

CTAAGGTCGAGATTAAGCGTACGGTGGCCGCTCCCAGCGTGTTCATCTTCCCCCCCAGCGACGAGCAGCTGAAGA

GCGGCACCGCCAGCGTGGTGTGCCTGCTGAACAACTTCTACCCCCGGGAGGCCAAGGTGCAGTGGAAGGTGGAC

AACGCCCTGCAGAGCGGCAACAGCCAGGAGAGCGTCACCGAGCAGGACAGCAAGGACTCCACCTACAGCCTGAG

CAGCACCCTGACCCTGAGCAAGGCCGACTACGAGAAGCATAAGGTGTACGCCTGCGAGGTGACCCACCAGGGCC

TGTCCAGCCCCGTGACCAAGAGCTTCAACAGGGGCGAGTGC

SEQ ID NO: 146
CAGGTGCAGCTGGTGCAGTCAGGCGCCGAAGTGAAGAAACCCGGCTCTAGCGTGAAAGTCAGCTGTAAAGCTAG

TGGCGGCACCTTCAGCACCTTCTCTATTAGCTGGGTCAGACAGGCCCCAGGTCAGGGCCTGGAGTGGATGGGCGG

AATTATCCCTATCTTCGGCACCGCTAACTACGCTCAGAAATTTCAGGGTAGAGTGACTATCACCGCCGACGAGTCT

ACTAGCACCGCCTATATGGAACTGTCTAGCCTGAGATCAGAGGACACCGCCGTCTACTACTGCGCTAGGGGCGGC

TACGGCGGCTATTACTACTTCGACTACTGGGGTCAGGGCACCCTGGTCACCGTGTCTAGC

SEQ ID NO: 147
DIQMTQSPSSLSASVGDRVTITCRASQSISNRLNWYQQKPGKAPKLLIYKGSTLQSGVPSRFSGSGSGTDFTLTISSLQPE

DFATYYCQQHYVWSTTFGQGTKVEIK

SEQ ID NO: 148
GATATTCAGATGACTCAGTCACCTAGTAGCCTGAGCGCTAGTGTGGGCGATAGAGTGACTATCACCTGTAGAGCC

TCTCAGTCTATCTCTAATAGGCTGAACTGGTATCAGCAGAAGCCCGGTAAAGCCCCTAAGCTGCTGATCTATAAGG

GCTCTACCCTGCAGTCAGGCGTGCCCTCTAGGTTTAGCGGTAGCGGTAGTGGCACCGACTTCACCCTGACTATCTC

TAGCCTGCAGCCCGAGGACTTCGCTACCTACTACTGTCAGCAGCACTACGTGTGGTCTACCTTCGGTCAGGGC

ACTAAGGTCGAGATTAAG

SEQ ID NO: 149
CAGGTGCAGCTGGTGCAGTCAGGCGCCGAAGTGAAGAAACCCGGCTCTAGCGTGAAAGTCAGCTGTAAAGCTAG

TGGCGGCACCTTCAGCACCTTCTCTATTAGCTGGGTCAGACAGGCCCCAGGTCAGGGCCTGGAGTGGATGGGCGG

AATTATCCCTATCTTCGGCACCGCTAACTACGCTCAGAAATTTCAGGGTAGAGTGACTATCACCGCCGACGAGTCT

ACTAGCACCGCCTATATGGAACTGTCTAGCCTGAGATCAGAGGACACCGCCGTCTACTACTGCGCTAGGGGCGGC

TACGGCGGCTATTACTACTTCGACTACTGGGGTCAGGGCACCCTGGTCACCGTGTCTAGCGCTAGCACTAAGGGCC

CCTCCGTGTTCCCTCTGGCCCCTTCCAGCAAGTCTACCTCCGGCGGCACAGCTGCTCTGGGCTGCCTGGTCAAGGA

CTACTTCCCTGAGCCTGTGACAGTGTCCTGGAACTCTGGCGCCCTGACCTCTGGCGTGCACACCTTCCCTGCCGTGC

TGCAGTCCTCCGGCCTGTACTCCCTGTCCTCCGTGGTCACAGTGCCTTCAAGCAGCCTGGGCACCCAGACCTATATC

TGCAACGTGAACCACAAGCCTTCCAACACCAAGGTGGACAAGCGGGTGGAGCCTAAGTCCTGCGACAAGACCCAC

ACCTGTCCTCCCTGCCCTGCTCCTGAAGCTGCTGGCGGCCCTTCTGTGTTCCTGTTCCCTCCAAAGCCCAAGGACAC

CCTGATGATCTCCCGGACCCCTGAAGTGACCTGCGTGGTGGTGGACGTGTCCCACGAGGATCCTGAAGTGAAGTT

CAATTGGTACGTGGACGGCGTGGAGGTGCACAACGCCAAGACCAAGCCTCGGGAGGAACAGTACAACTCCACCT

ACCGGGTGGTGTCCGTGCTGACCGTGCTGCACCAGGACTGGCTGAACGGCAAAGAGTACAAGTGCAAAGTCTCC

AACAAGGCCCTGCCTGCCCCTATCGAAAAGACAATCTCCAAGGCCAAGGGCCAGCCTAGGGAACCCCAGGTGTAC

ACCCTGCCACCCAGCCGGGAGGAAATGACCAAGAACCAGGTGTCCCTGACCTGTCTGGTCAAGGGCTTCTACCCTT

```
CCGATATCGCCGTGGAGTGGGAGTCTAACGGCCAGCCTGAGAACAACTACAAGACCACCCCTCCTGTGCTGGACT

CCGACGGCTCCTTCTTCCTGTACTCCAAACTGACCGTGGACAAGTCCCGGTGGCAGCAGGGCAACGTGTTCTCCTG

CTCCGTGATGCACGAGGCCCTGCACAACCACTACACCCAGAAGTCCCTGTCCCTGTCTCCCGGCAAG

SEQ ID NO: 150
DIQMTQSPSSLSASVGDRVTITCRASQSISNRLNWYQQKPGKAPKLLIYKGSTLQSGVPSRFSGSGSGTDFTLTISSLQPE

DFATYYCQQHYVWSTTFGQGTKVEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

SEQ ID NO: 151
GATATTCAGATGACTCAGTCACCTAGTAGCCTGAGCGCTAGTGTGGGCGATAGAGTGACTATCACCTGTAGAGCC

TCTCAGTCTATCTCTAATAGGCTGAACTGGTATCAGCAGAAGCCCGGTAAAGCCCCTAAGCTGCTGATCTATAAGG

GCTCTACCCTGCAGTCAGGCGTGCCCTCTAGGTTTAGCGGTAGCGGTAGTGGCACCGACTTCACCCTGACTATCTC

TAGCCTGCAGCCCGAGGACTTCGCTACCTACTACTGTCAGCAGCACTACGTGTGGTCTACTACCTTCGGTCAGGGC

ACTAAGGTCGAGATTAAGCGTACGGTGGCCGCTCCCAGCGTGTTCATCTTCCCCCCCAGCGACGAGCAGCTGAAG

AGCGGCACCGCCAGCGTGGTGTGCCTGCTGAACAACTTCTACCCCCGGGAGGCCAAGGTGCAGTGGAAGGTGGA

CAACGCCCTGCAGAGCGGCAACAGCCAGGAGAGCGTCACCGAGCAGGACAGCAAGGACTCCACCTACAGCCTGA

GCAGCACCCTGACCCTGAGCAAGGCCGACTACGAGAAGCATAAGGTGTACGCCTGCGAGGTGACCCACCAGGGC

CTGTCCAGCCCCGTGACCAAGAGCTTCAACAGGGGCGAGTGC

SEQ ID NO: 152
CAGGTGCAATTGGTGCAGAGCGGTGCCGAAGTGAAAAAACCGGGCAGCAGCGTGAAAGTTAGCTGCAAAGCATC

CGGAGGGACGTTTTCTACTTTCTCTATCTCTTGGGTGCGCCAGGCCCCGGGCCAGGGCCTCGAGTGGATGGGCGG

TATCATCCCGATCTTCGGCACTGCGAACTACGCCCAGAAATTTCAGGGCCGGGTGACCATTACCGCCGATGAAAGC

ACCAGCACCGCCTATATGGAACTGAGCAGCCTGCGCAGCGAAGATACGGCCGTGTATTATTGCGCGCGTGGTGGT

TACGGTGGTTACTACTACTTCGATTACTGGGGCCAAGGCACCCTGGTGACTGTTAGCTCA

SEQ ID NO: 153
DIQMTQSPSSLSASVGDRVTITCRASQSISNRLNWYQQKPGKAPKLLIYKGSTLQSGVPSRFSGSGSGTDFTLTISSLQPE

DFATYYCQQHYQWLTTFGQGTKVEIK

SEQ ID NO: 154
GATATCCAGATGACCCAGAGCCCGAGCAGCCTGAGCGCCAGCGTGGGCGATCGCGTGACCATTACCTGCAGAGC

CAGCCAGTCTATTTCTAACCGTCTGAACTGGTACCAGCAGAAACCGGGCAAAGCGCCGAAACTATTAATCTACAAA

GGTTCTACTCTGCAAAGCGGCGTGCCGAGCCGCTTTAGCGGCAGCGGATCCGGCACCGATTTCACCCTGACCATTA

GCTCTCTGCAACCGGAAGACTTTGCGACCTATTATTGCCAGCAGCATTACCAGTGGCTGACTACCTTTGGCCAGGG

CACGAAAGTTGAAATTAAA

SEQ ID NO: 155
CAGGTGCAATTGGTGCAGAGCGGTGCCGAAGTGAAAAAACCGGGCAGCAGCGTGAAAGTTAGCTGCAAAGCATC

CGGAGGGACGTTTTCTACTTTCTCTATCTCTTGGGTGCGCCAGGCCCCGGGCCAGGGCCTCGAGTGGATGGGCGG

TATCATCCCGATCTTCGGCACTGCGAACTACGCCCAGAAATTTCAGGGCCGGGTGACCATTACCGCCGATGAAAGC

ACCAGCACCGCCTATATGGAACTGAGCAGCCTGCGCAGCGAAGATACGGCCGTGTATTATTGCGCGCGTGGTGGT

TACGGTGGTTACTACTACTTCGATTACTGGGGCCAAGGCACCCTGGTGACTGTTAGCTCAGCCTCCACCAAGGGTC

CATCGGTCTTCCCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGCAGCTTGGGCACCCAGACCTA
```

| Sequence Listing |
|---|
| CATCTGCAACGTGAATCACAAGCCCAGCAACACCAAGGTGGACAAGAGAGTTGAGCCCAAATCTTGTGACAAAAC |
| TCACACATGCCCACCGTGCCCAGCACCTGAAGCAGCGGGGGGACCGTCAGTCTTCCTCTTCCCCCCAAAACCCAAG |
| GACACCCTCATGATCTCCCGGACCCCTGAGGTCACATGCGTGGTGGTGGACGTGAGCCACGAAGACCCTGAGGTC |
| AAGTTCAACTGGTACGTGGACGGCGTGGAGGTGCATAATGCCAAGACAAAGCCGCGGGAGGAGCAGTACAACA |
| GCACGTACCGGGTGGTCAGCGTCCTCACCGTCCTGCACCAGGACTGGCTGAATGGCAAGGAGTACAAGTGCAAG |
| GTCTCCAACAAAGCCCTCCCAGCCCCCATCGAGAAAACCATCTCCAAAGCCAAAGGGCAGCCCCGAGAACCACAG |
| GTGTACACCCTGCCCCCATCCCGGGAGGAGATGACCAAGAACCAGGTCAGCCTGACCTGCCTGGTCAAAGGCTTC |
| TATCCCAGCGACATCGCCGTGGAGTGGGAGAGCAATGGGCAGCCGGAGAACAACTACAAGACCACGCCTCCCGT |
| GCTGGACTCCGACGGCTCCTTCTTCCTCTACAGCAAGCTCACCGTGGACAAGAGCAGGTGGCAGCAGGGGAACGT |
| CTTCTCATGCTCCGTGATGCATGAGGCTCTGCACAACCACTACACGCAGAAGAGCCTCTCCCTGTCTCCGGGTAAA |
| SEQ ID NO: 156 |
| DIQMTQSPSSLSASVGDRVTITCRASQSISNRLNWYQQKPGKAPKLLIYKGSTLQSGVPSRFSGSGSGTDFTLTISSLQPE |
| DFATYYCQQHYQWLTTFGQGTKVEIKRTVAAPSVFIFPPSDEQLKSGTASVVCLLNNFYPREAKVQWKVDNALQSGNS |
| QESVTEQDSKDSTYSLSSTLTLSKADYEKHKVYACEVTHQGLSSPVTKSFNRGEC |
| SEQ ID NO: 157 |
| GATATCCAGATGACCCAGAGCCCGAGCAGCCTGAGCGCCAGCGTGGGCGATCGCGTGACCATTACCTGCAGAGC |
| CAGCCAGTCTATTTCTAACCGTCTGAACTGGTACCAGCAGAAACCGGGCAAAGCGCCGAAACTATTAATCTACAA |
| GGTTCTACTCTGCAAAGCGGCGTGCCGAGCCGCTTTAGCGGCAGCGGATCCGGCACCGATTTCACCCTGACCATTA |
| GCTCTCTGCAACCGGAAGACTTTGCGACCTATTATTGCCAGCAGCATTACCAGTGGCTGACTACCTTTGGCCAGGG |
| CACGAAAGTTGAAATTAAACGTACGGTGGCCGCTCCCAGCGTGTTCATCTTCCCCCCCAGCGACGAGCAGCTGAA |
| GAGCGGCACCGCCAGCGTGGTGTGCCTGCTGAACAACTTCTACCCCCGGGAGGCCAAGGTGCAGTGGAAGGTGG |
| ACAACGCCCTGCAGAGCGGCAACAGCCAGGAAAGCGTCACCGAGCAGGACAGCAAGGACTCCACCTACAGCCTG |
| AGCAGCACCCTGACCCTGAGCAAGGCCGACTACGAGAAGCACAAGGTGTACGCCTGCGAGGTGACCCACCAGGG |
| CCTGTCCAGCCCCGTGACCAAGAGCTTCAACCGGGGCGAGTGT |
| SEQ ID NO: 158 |
| QVQLVQSGAEVKKPGSSVKVSCKASGGTFSSYAISWVRQAPGQGLEWMGNIIPITGQTYYAQKFQGRVTITADESTST |
| AYMELSSLRSEDTAVYYCARAAYHPLVFDNWGQGTLVTVSSASTKGPSVFPLAPSSKSTSGGTAALGCLVKDYFPEPVT |
| VSWNSGALTSGVHTFPAVLQSSGLYSLSSVVTVPSSSLGTQTYICNVNHKPSNTKVDKRVEPKSCDKTHTCPPCPAPEAA |
| GGPSVFLFPPKPKDTLMISRTPEVTCVVVDVSHEDPEVKFNWYVDGVEVHNAKTKPREEQYNSTYRVVSVLTVLHQD |
| WLNGKEYKCKVSNKALPAPIEKTISKAKGQPREPQVYTLPPSREEMTKNQVSLTCLVKGFYPSDIAVEWESNGQPENNY |
| KTTPPVLDSDGSFFLYSKLTVDKSRWQQGNVFSCSVMHEALHNHYTQKSLSLSPGK |
| SEQ ID NO: 159 |
| CAGGTGCAGCTGGTGCAGTCAGGCGCCGAAGTGAAGAAACCCGGCTCTAGCGTGAAAGTCAGCTGTAAAGCTAG |
| TGGCGGCACCTTCTCTAGCTACGCTATTAGCTGGGTCAGACAGGCCCCAGGTCAGGGCCTGGAGTGGATGGGCAA |
| TATTATCCCTATCACCGGTCAGACCTACTACGCTCAGAAATTTCAGGGTAGAGTGACTATCACCGCCGACGAGTCT |
| ACTAGCACCGCCTATATGGAACTGTCTAGCCTGAGATCAGAGGACACCGCCGTCTACTACTGCGCTAGAGCCGCCT |
| ATCACCCCCTGGTGTTCGATAACTGGGGTCAGGGCACCCTGGTCACCGTGTCTAGCGCTAGCACTAAGGGCCCCTC |
| CGTGTTCCCTCTGGCCCCTTCCAGCAAGTCTACCTCCGGCGGCACAGCTGCTCTGGGCTGCCTGGTCAAGGACTAC |
| TTCCCTGAGCCTGTGACAGTGTCCTGGAACTCTGGCGCCCTGACCTCTGGCGTGCACACCTTCCCTGCCGTGCTGC |
| AGTCCTCCGGCCTGTACTCCCTGTCCTCCGTGGTCACAGTGCCTTCAAGCAGCCTGGGCACCCAGACCTATATCTGC |
| AACGTGAACCACAAGCCTTCCAACACCAAGGTGGACAAGCGGGTGGAGCCTAAGTCCTGCGACAAGACCCACACC |

```
TGTCCTCCCTGCCCTGCTCCTGAAGCTGCTGGCGGCCCTTCTGTGTTCCTGTTCCCTCCAAAGCCCAAGGACACCCT

GATGATCTCCCGGACCCCTGAAGTGACCTGCGTGGTGGTGGACGTGTCCCACGAGGATCCTGAAGTGAAGTTCAA

TTGGTACGTGGACGGCGTGGAGGTGCACAACGCCAAGACCAAGCCTCGGGAGGAACAGTACAACTCCACCTACC

GGGTGGTGTCCGTGCTGACCGTGCTGCACCAGGACTGGCTGAACGGCAAAGAGTACAAGTGCAAAGTCTCCAAC

AAGGCCCTGCCTGCCCCTATCGAAAAGACAATCTCCAAGGCCAAGGGCCAGCCTAGGGAACCCCAGGTGTACACC

CTGCCACCCAGCCGGGAGGAAATGACCAAGAACCAGGTGTCCCTGACCTGTCTGGTCAAGGGCTTCTACCCTTCC

GATATCGCCGTGGAGTGGGAGTCTAACGGCCAGCCTGAGAACAACTACAAGACCACCCCTCCTGTGCTGGACTCC

GACGGCTCCTTCTTCCTGTACTCCAAACTGACCGTGGACAAGTCCCGGTGGCAGCAGGGCAACGTGTTCTCCTGCT

CCGTGATGCACGAGGCCCTGCACAACCACTACACCCAGAAGTCCCTGTCCCTGTCTCCCGGCAAG

SEQ ID NO: 160
QSVLTQPPSASGTPGQRVTISCSGSSSNIGNHYVNWYQQLPGTAPKLLIYRNNHRPSGVPDRFSGSKSGTSASLAISGLQ

SEDEADYYCQSWDYSGFSTVFGGGTKLTVLGQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEKTVAPTECS

SEQ ID NO: 161
CAGTCAGTCCTGACTCAGCCCCCTAGCGCTAGTGGCACCCCTGGTCAGAGAGTGACTATTAGCTGTAGCGGCTCTA

GCTCTAATATCGGTAATCACTACGTGAACTGGTATCAGCAGCTGCCCGGCACCGCCCCTAAGCTGCTGATCTATAG

AAACAATCACCGGCCTAGCGGCGTGCCCGATAGGTTTAGCGGATCTAAGTCAGGGACTAGCGCTAGTCTGGCTAT

TAGCGGCCTGCAGTCAGAGGACGAGGCCGACTACTACTGTCAGTCCTGGGACTATAGCGGCTTTAGCACCGTGTT

CGGCGGAGGCACTAAGCTGACCGTGCTGGGTCAGCCTAAGGCTGCCCCCAGCGTGACCCTGTTCCCCCCCAGCAG

CGAGGAGCTGCAGGCCAACAAGGCCACCCTGGTGTGCCTGATCAGCGACTTCTACCCAGGCGCCGTGACCGTGGC

CTGGAAGGCCGACAGCAGCCCCGTGAAGGCCGGCGTGGAGACCACCACCCCCAGCAAGCAGAGCAACAACAAGT

ACGCCGCCAGCAGCTACCTGAGCCTGACCCCCGAGCAGTGGAAGAGCCACAGGTCCTACAGCTGCCAGGTGACCC

ACGAGGGCAGCACCGTGGAAAAGACCGTGGCCCCAACCGAGTGCAGC

SEQ ID NO: 162
GGSISTGSY

SEQ ID NO: 163
QSPGY

SEQ ID NO: 164
TTRYWMSHILAYGMDY

SEQ ID NO: 165
SSSNIGNHY

SEQ ID NO: 166
ANT

SEQ ID NO: 167
YDGSQSI

SEQ ID NO: 168
EVQLQESGPGLVKPGETLSLTCTVSGGSISTGSYYWNWIRQAPGKGLEWIGEIWHSGPTFYNPSLKSRVTISVDTSKNQF

SLKLSSVTAADTAVYYCARTTRYWMSHILAYGMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNTKVDKRVEPKSCDKTHTCPPCP

APEAAGGPSVFLFPPKPKDTLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLSLSPGK
```

Sequence Listing

SEQ ID NO: 169
GAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATTTGGCATTCTGGTCCTACTTTTTATAATCCTTCTCTTAAGTCTCGGGTGACCATTAGCGTTGATACTTCGA

AAAACCAGTTTAGCCTGAAACTGAGCAGCGTGACGGCGGCGGATACGGCCGTGTATTATTGCGCGCGTACTACTC

GTTATTGGATGTCTCATATTCTTGCTTATGGTATGGATTATTGGGCCAAGGCACCCTGGTGACGGTTAGCTCAGC

CTCCACCAAGGGTCCATCGGTCTTCCCCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACCGTGCCCTCCAGCAGCTTGG

GCACCCAGACCTACATCTGCAACGTGAATCACAAGCCCAGCAACACCAAGGTGGACAAGAGAGTTGAGCCCAAAT

CTTGTGACAAAACTCACACATGCCCACCGTGCCCAGCACCTGAAGCAGCGGGGGACCGTCAGTCTTCCTCTTCCC

CCCAAAACCCAAGGACACCCTCATGATCTCCCGGACCCCTGAGGTCACATGCGTGGTGGTGGACGTGAGCCACGA

AGACCCTGAGGTCAAGTTCAACTGGTACGTGGACGGCGTGGAGGTGCATAATGCCAAGACAAAGCCGCGGGAGG

AGCAGTACAACAGCACGTACCGGGTGGTCAGCGTCCTCACCGTCCTGCACCAGGACTGGCTGAATGGCAAGGAGT

ACAAGTGCAAGGTCTCCAACAAAGCCCTCCCAGCCCCCATCGAGAAAACCATCTCCAAAGCCAAAGGGCAGCCCC

GAGAACCACAGGTGTACACCCTGCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGCAGAAGAGCCTCTCCCTGTC

TCCGGGTAAA

SEQ ID NO: 170
DIVLTQPPSVSGAPGQRVTISCSGSSSNIGNHYVSWYQQLPGTAPKLLIYANTKRPSGVPDRFSGSKSGTSASLAITGLQS

EDEADYYCSSYDGSQSIVFGGGTKLTVLGQPKAAPSVTLFPPSSEELQANKATLVCLISDFYPGAVTVAWKADSSPVKAG

VETTTPSKQSNNKYAASSYLSLTPEQWKSHRSYSCQVTHEGSTVEKTVAPTECS

SEQ ID NO: 171
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTAGGTCAGCCCAAGGCTGCCCCCTCGGTCACTCTGTTCCCGCCCTCCTCTGAGG

AGCTTCAAGCCAACAAGGCCACACTGGTGTGTCTCATAAGTGACTTCTACCCGGGAGCCGTGACAGTGGCCTGGA

AGGCAGATAGCAGCCCCGTCAAGGCGGGAGTGGAGACCACCACACCCTCCAAACAAAGCAACAACAAGTACGCG

GCCAGCAGCTATCTGAGCCTGACGCCTGAGCAGTGGAAGTCCCACAGAAGCTACAGCTGCCAGGTCACGCATGAA

GGGAGCACCGTGGAGAAGACAGTGGCCCCTACAGAATGTTCA

SEQ ID NO: 172
EVQLQESGPGLVKPGETLSLTCTVSGGSISTGSYYWNWIRQAPGKGLEWIGEIHGHGFTFYNPSLKSRVTISVDTSKNQF

SLKLSSVTAADTAVYYCARTTRYWMSHILAYGMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNTKVDKRVEPKSCDKTHTCPPCP

APEAAGGPSVFLFPPKPKDTLMISRTPEVTCVVVDVSHEDPEVKFNWYVDGVEVHNAKTKPREEQYNSTYRVVSVLTVL

-continued

Sequence Listing

HQDWLNGKEYKCKVSNKALPAPIEKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 173
GAGGTGCAATTGCAAGAAAGTGGTCCGGGCCTGGTGAAACCGGGCGAAACCCTGAGCCTGACCTGCACCGTTTCC

GGAGGTAGCATTTCTACTGGTTCTTATTATTGGAATTGGATTCGCCAGGCCCCTGGGAAGGGTCTCGAGTGGATTG

GCGAGATTCATGGTCATGGTTTTACTTTTTATAATCCTTCTCTTAAGTCTCGGGTGACCATTAGCGTTGATACTTCGA

AAAACCAGTTTAGCCTGAAACTGAGCAGCGTGACGGCGGCGGATACGGCCGTGTATTATTGCGCGCGTACTACTC

GTTATTGGATGTCTCATATTCTTGCTTATGGTATGGATTATTGGGGCCAAGGCACCCTGGTGACGGTTAGCTCAGC

CTCCACCAAGGGTCCATCGGTCTTCCCCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACCGTGCCCTCCAGCAGCTTGG

GCACCCAGACCTACATCTGCAACGTGAATCACAAGCCCAGCAACACCAAGGTGGACAAGAGAGTTGAGCCCAAAT

CTTGTGACAAAACTCACACATGCCCACCGTGCCCAGCACCTGAAGCAGCGGGGGGACCGTCAGTCTTCCTCTTCCC

CCCAAAACCCAAGGACACCCTCATGATCTCCCGGACCCCTGAGGTCACATGCGTGGTGGTGGACGTGAGCCACGA

AGACCCTGAGGTCAAGTTCAACTGGTACGTGGACGGCGTGGAGGTGCATAATGCCAAGACAAAGCCGCGGGAGG

AGCAGTACAACAGCACGTACCGGGTGGTCAGCGTCCTCACCGTCCTGCACCAGGACTGGCTGAATGGCAAGGAGT

ACAAGTGCAAGGTCTCCAACAAAGCCCTCCCAGCCCCCATCGAGAAAACCATCTCCAAAGCCAAAGGGCAGCCCC

GAGAACCACAGGTGTACACCCTGCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGCAGAAGAGCCTCTCCCTGTC

TCCGGGTAAA

SEQ ID NO: 174
DIVLTQPPSVSGAPGQRVTISCSGSSSNIGNHYVSWYQQLPGTAPKLLIYANTKRPSGVPDRFSGSKSGTSASLAITGLQS

EDEADYYCSSYDGSQSIVFGGGTKLTVLGQPKAAPSVTLFPPSSEELQANKATLVCLISDFYPGAVTVAWKADSSPVKAG

VETTTPSKQSNNKYAASSYLSLTPEQWKSHRSYSCQVTHEGSTVEKTVAPTECS

SEQ ID NO: 175
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGTCTTGGTACCAGCAGTTGCCCGGGACGGCGCCGAAACTTCTGATTTATG

CTAATACTAAGCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCTCTTCTTATGATGGTTCTCAGTCTATTGTGTTTGGC

GGCGGCACGAAGTTAACCGTCCTAGGTCAGCCCAAGGCTGCCCCCTCGGTCACTCTGTTCCCGCCCTCCTCTGAGG

AGCTTCAAGCCAACAAGGCCACACTGGTGTGTCTCATAAGTGACTTCTACCCGGGAGCCGTGACAGTGGCCTGGA

AGGCAGATAGCAGCCCCGTCAAGGCGGGAGTGGAGACCACCACACCCTCCAAACAAAGCAACAACAAGTACGCG

GCCAGCAGCTATCTGAGCCTGACGCCTGAGCAGTGGAAGTCCCACAGAAGCTACAGCTGCCAGGTCACGCATGAA

GGGAGCACCGTGGAGAAGACAGTGGCCCCTACAGAATGTTCA

SEQ ID NO: 176
EVQLVQSGAEVKKPGSSVKVSCKASGGTFNSYAISWVRQAPGQGLEWMGNIIPHYGFAYYAQKFQGRVTITADESTST

AYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

Sequence Listing

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK

SEQ ID NO: 177
GAGGTGCAATTGGTTCAGTCTGGCGCGGAAGTGAAAAAACCGGGCAGCAGCGTGAAAGTGAGCTGCAAAGCCTC

CGGAGGCACTTTTAATTCTTATGCTATTTCTTGGGTGCGCCAAGCCCCTGGGCAGGGTCTCGAGTGGATGGGCAAT

ATTATTCCTCATTATGGTTTTGCTTATTATGCTCAGAAGTTTCAGGGTCGGGTGACCATTACCGCGGATGAAAGCAC

CAGCACCGCGTATATGGAACTGAGCAGCCTGCGTAGCGAAGATACGGCCGTGTATTATTGCGCGCGTGCTGCTTA

TCATCCTCTTGTTTTTGATAATTGGGGCCAAGGCACCCTGGTGACGGTTAGCTCAGCCTCCACCAAGGGTCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCAGCGGGGGGACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

ACCGGGTGGTCAGCGTCCTCACCGTCCTGCACCAGGACTGGCTGAATGGCAAGGAGTACAAGTGCAAGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGAGGAGATGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTACAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGTAAA

SEQ ID NO: 178
DIVLTQPPSVSGAPGQRVTISCSGSSSNIGNHYVNWYQQLPGTAPKLLIYRNNHRPSGVPDRFSGSKSGTSASLAITGLQ

SEDEADYYCQSWDYSGFSTVFGGGTKLTVLGQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEKTVAPTECS

SEQ ID NO: 179
GATATCGTGCTGACCCAGCCGCCTTCAGTGAGTGGCGCACCAGGTCAGCGTGTGACCATCTCGTGTAGCGGCAGC

AGCAGCAACATTGGTAATCATTATGTGAATTGGTACCAGCAGTTGCCCGGGACGGCGCCGAAACTTCTGATTTATC

GTAATAATCATCGTCCCTCAGGCGTGCCGGATCGTTTTAGCGGATCCAAAAGCGGCACCAGCGCGAGCCTTGCGA

TTACGGGCCTGCAAAGCGAAGACGAAGCGGATTATTATTGCCAGTCTTGGGATTATTCTGGTTTTTCTACTGTGTTT

GGCGGCGGCACGAAGTTAACCGTCCTAGGTCAGCCCAAGGCTGCCCCCTCGGTCACTCTGTTCCCGCCCTCCTCTG

AGGAGCTTCAAGCCAACAAGGCCACACTGGTGTGTCTCATAAGTGACTTCTACCCGGGAGCCGTGACAGTGGCCT

GGAAGGCAGATAGCAGCCCCGTCAAGGCGGGAGTGGAGACCACCACACCCTCCAAACAAAGCAACAACAAGTAC

GCGGCCAGCAGCTATCTGAGCCTGACGCCTGAGCAGTGGAAGTCCCACAGAAGCTACAGCTGCCAGGTCACGCAT

GAAGGGAGCACCGTGGAGAAGACAGTGGCCCCTACAGAATGTTCA

SEQ ID NO: 180
EVQLVQSGAEVKKPGSSVKVSCKASGGTFNSYAISWVRQAPGQGLEWMGNIIPYSGFAYYAQKFQGRVTITADESTST

AYMELSSLRSEDTAVYYCARAAYHPLVFDNWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

SEQ ID NO: 181
GAGGTGCAATTGGTTCAGTCTGGCGCGGAAGTGAAAAAACCGGGCAGCAGCGTGAAAGTGAGCTGCAAAGCCTC
CGGAGGCACTTTTAATTCTTATGCTATTTCTTGGGTGCGCCAAGCCCCTGGGCAGGGTCTCGAGTGGATGGGCAAT
ATTATTCCTTATTCTGGTTTTGCTTATTATGCTCAGAAGTTTCAGGGTCGGGTGACCATTACCGCGGATGAAAGCAC
CAGCACCGCGTATATGGAACTGAGCAGCCTGCGTAGCGAAGATACGGCCGTGTATTATTGCGCGCGTGCTGCTTA
TCATCCTCTTGTTTTTGATAATTGGGGCCAAGGCACCCTGGTGACGGTTAGCTCAGCCTCCACCAAGGGTCCATCG
GTCTTCCCCCTGGCACCCTCCTCCAAGAGCACCTCTGGGGGCACAGCGGCCCTGGGCTGCCTGGTCAAGGACTACT
TCCCCGAACCGGTGACGGTGTCGTGGAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCAAATCTTGTGACAAAACTCACAC
ATGCCCACCGTGCCCAGCACCTGAAGCAGCGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGT
ACCGGGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTACA
CCCTGCCCCCATCCCGGGAGGAGATGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTCTCCGGGTAAA

SEQ ID NO: 182
DIVLTQPPSVSGAPGQRVTISCSGSSSNIGNHYVNWYQQLPGTAPKLLIYRNNHRPSGVPDRFSGSKSGTSASLAITGLQ
SEDEADYYCQSWDYSGFSTVFGGGTKLTVLGQPKAAPSVTLFPPSSEELQANKATLVCLISDFYPGAVTVAWKADSSPV
KAGVETTTPSKQSNNKYAASSYLSLTPEQWKSHRSYSCQVTHEGSTVEKTVAPTECS

SEQ ID NO: 183
GATATCGTGCTGACCCAGCCGCCTTCAGTGAGTGGCGCACCAGGTCAGCGTGTGACCATCTCGTGTAGCGGCAGC
AGCAGCAACATTGGTAATCATTATGTGAATTGGTACCAGCAGTTGCCCGGGACGGCGCCGAAACTTCTGATTTATC
GTAATAATCATCGTCCCTCAGGCGTGCCGGATCGTTTTAGCGGATCCAAAAGCGGCACCAGCGCGAGCCTTGCGA
TTACGGGCCTGCAAAGCGAAGACGAAGCGGATTATTATTGCCAGTCTTGGGATTATTCTGGTTTTTCTACTGTGTTT
GGCGGCGGCACGAAGTTAACCGTCCTAGGTCAGCCCAAGGCTGCCCCCTCGGTCACTCTGTTCCCGCCCTCCTCTG
AGGAGCTTCAAGCCAACAAGGCCACACTGGTGTGTCTCATAAGTGACTTCTACCCGGGAGCCGTGACAGTGGCCT
GGAAGGCAGATAGCAGCCCCGTCAAGGCGGGAGTGGAGACCACCACACCCTCCAAACAAAGCAACAACAAGTAC
GCGGCCAGCAGCTATCTGAGCCTGACGCCTGAGCAGTGGAAGTCCCACAGAAGCTACAGCTGCCAGGTCACGCAT
GAAGGGAGCACCGTGGAGAAGACAGTGGCCCCTACAGAATGTTCA

SEQ ID NO: 184
GGSISTGSY

SEQ ID NO: 185
NHMGI

SEQ ID NO: 186
TTRYWMSHILAYGMDY

| Sequence Listing |
|---|
| SEQ ID NO: 187
SSSNIGNHY

SEQ ID NO: 188
ANT

SEQ ID NO: 189
YDGSQSI

SEQ ID NO: 190
GGSISTGSY

SEQ ID NO: 191
WHSGP

SEQ ID NO: 192
TTRYWMSHILAYGMDY

SEQ ID NO: 193
SSSNIGNHY

SEQ ID NO: 194
ANT

SEQ ID NO: 195
YDGSQSI

SEQ ID NO: 196
EIHGHGFTFYNPSLKS

SEQ ID NO: 197
GGSISTGSY

SEQ ID NO: 198
HGHGF

SEQ ID NO: 199
TTRYWMSHILAYGMDY

SEQ ID NO: 200
SSSNIGNHY

SEQ ID NO: 201
ANT

SEQ ID NO: 202
YDGSQSI

SEQ ID NO: 203
GGTFNSY

SEQ ID NO: 204
IPIYGT

SEQ ID NO: 205
AAYHPLVFDN

SEQ ID NO: 206
SSSNIGNHY

SEQ ID NO: 207
RNN

SEQ ID NO: 208
WDYSGFST

SEQ ID NO: 209
GGTFNSY

SEQ ID NO: 210
NPFYIGE

SEQ ID NO: 211
AAYHPLVFDN

SEQ ID NO: 212
SSSNIGNHY |

Sequence Listing

SEQ ID NO: 213
RNN

SEQ ID NO: 214
WDYSGFST

SEQ ID NO: 215
GGTFNSY

SEQ ID NO: 216
IPHYGF

SEQ ID NO: 217
AAYHPLVFDN

SEQ ID NO: 218
SSSNIGNHY

SEQ ID NO: 219
RNN

SEQ ID NO: 220
WDYSGFST

SEQ ID NO: 221
GGTFNSY

SEQ ID NO: 222
IPYSGF

SEQ ID NO: 223
AAYHPLVFDN

SEQ ID NO: 224
SSSNIGNHY

SEQ ID NO: 225
RNN

SEQ ID NO: 226
WDYSGFST

SEQ ID NO: 227
GGTFNSY

SEQ ID NO: 228
NPFYIGE

SEQ ID NO: 229
AAYHPLVFDN

SEQ ID NO: 230
SSSNIGNHY

SEQ ID NO: 231
RNN

SEQ ID NO: 232
WDYSGFST

SEQ ID NO: 233
GGTFNSY

SEQ ID NO: 234
IPMTGQ

SEQ ID NO: 235
AAYHPLVFDN

SEQ ID NO: 236
SSSNIGNHY

SEQ ID NO: 237
RNN

SEQ ID NO: 238
WDYSGFST

Sequence Listing

SEQ ID NO: 239
NIIPITGQTYYAQKFQG

SEQ ID NO: 240
GGTFSTF

SEQ ID NO: 241
IPIFGT

SEQ ID NO: 242
GGYGGYYYFDY

SEQ ID NO: 243
SQSISNR

SEQ ID NO: 244
KGS

SEQ ID NO: 245
HKVWLT

SEQ ID NO: 246
GGTFSTF

SEQ ID NO: 247
IPIFGT

SEQ ID NO: 248
GGYGGYYYFDY

SEQ ID NO: 249
SQSISNR

SEQ ID NO: 250
KGS

SEQ ID NO: 251
HYVWST

SEQ ID NO: 252
GGTFSTF

SEQ ID NO: 253
IPIFGT

SEQ ID NO: 254
GGYGGYYYFDY

SEQ ID NO: 255
SQSISNR

SEQ ID NO: 256
KGS

SEQ ID NO: 257
HYQWLT

SEQ ID NO: 258
GFTFSSY

SEQ ID NO: 259
QSSGEN

SEQ ID NO: 260
VMIGYGFDY

SEQ ID NO: 261
SQSIFNY

SEQ ID NO: 262
DSS

SEQ ID NO: 263
YSGLLF

The invention claimed is:

1. An isolated antibody or fragment thereof, wherein the isolated antibody or a fragment comprises:
   i) a heavy chain variable region H-CDR1 comprising SEQ ID NO: 3 and
   ii) a heavy chain variable region H-CDR2 comprising SEQ ID NO: 4 or SEQ ID NO: 9 or SEQ ID NO: 10 or SEQ ID NO: 11 or SEQ ID NO: 12 or SEQ ID NO: 13 and
   iii) a heavy chain variable region H-CDR3 comprising SEQ ID NO: 5 and
   iv) a light chain variable region L-CDR1 comprising SEQ ID NO: 6 and
   v) a light chain variable region L-CDR2 comprising SEQ ID NO: 7 and
   vi) a light chain variable region L-CDR3 comprising SEQ ID NO: 8.

2. The isolated antibody or fragment thereof claim 1, wherein the binding molecule inhibits IL-18-dependent interferon gamma (INF-γ) production.

3. The isolated antibody or fragment thereof claim 1, wherein the binding molecule binds IL-18 with a $K_D$ of 100 pM or less.

4. The isolated antibody or fragment thereof claim 1, wherein the binding molecule is an isolated fully human, humanized or chimeric antibody or a fragment thereof.

5. The isolated antibody or fragment thereof according to claim 4, wherein the isolated antibody or fragment comprises a light chain variable domain comprising SEQ ID NO: 16 or SEQ ID NO: 20.

6. The isolated antibody or fragment thereof according to claim 5, wherein the isolated antibody or fragment thereof comprises:
   i) a heavy chain variable domain comprising SEQ ID NO: 14 or SEQ ID NO: 22 or SEQ ID NO: 25 or SEQ ID NO: 28 or SEQ ID NO: 31 or SEQ ID NO: 34 and a light chain variable domain comprising SEQ ID NO: 16 or
   ii) a heavy chain variable domain comprising SEQ ID NO: 18 or SEQ ID NO: 37 or SEQ ID NO: 40 and a light chain variable domain comprising SEQ ID NO: 20.

7. The isolated antibody or fragment thereof according to claim 6, wherein the isolated antibody or fragment thereof comprises a heavy chain variable domain comprising SEQ ID NO: 14 and a light chain variable domain comprising SEQ ID NO: 16.

8. The isolated antibody or fragment thereof according to claim 7, wherein amino acid lysine (Lys; K) in position 30 of SEQ ID NO:14 is replaced by an amino acid selected from asparagine (Asn; N) or serine (Ser; S) or threonine (Thr; T) or alanine (Ala; A) or glutamate (Glu; E) or histidine (His; H) or leucine (Leu; L) or glutamine (Gln; Q) or arginine (Arg; R) or valine (Val; V) or tyrosine (Tyr; Y) or isoleucine (Ile; I).

9. The isolated antibody or fragment thereof claim 1, wherein the binding molecule is an isolated fully human antibody.

10. The isolated antibody or fragment thereof claim 1, wherein the binding molecule is an antibody fragment.

11. The isolated antibody or fragment thereof claim 10, wherein the binding molecule is a Fab, a Fab', a F(ab')$_2$, or a scFv.

12. The isolated antibody or fragment thereof claim 1, wherein the binding molecule is an isolated bispecific antibody or fragment thereof comprising a first specificity to IL-18 and a second specificity to another polypeptide.

13. The isolated antibody or fragment thereof claim 1, wherein the binding molecule is an isolated antibody comprising a mutated or chemically modified amino acid Fc region, wherein the mutated or chemically modified amino acid Fc region prevents or decreases antibody dependent cellular cytotoxic (ADCC) activity and/or increases half-life when compared with a wild type Fc region.

14. The isolated antibody according to claim 13, wherein the mutated or chemically modified amino acid Fc region is a silent IgG1 Fc region.

15. A pharmaceutical composition comprising the isolated antibody or fragment thereof according to claim 4 and a pharmaceutical carrier, wherein the pharmaceutical composition optionally comprises a second therapeutic compound.

16. The pharmaceutical composition of claim 15 in intravenously, inhalable or sub-cutaneously administrable form.

17. A diagnostic kit comprising the isolated antibody or fragment thereof according to claim 4, wherein the kit optionally comprises a first control compound.

18. The diagnostic kit according to claim 17 wherein the first control compound is free IL-18 and wherein the kit optionally comprises a second control compound wherein the second control compound is murine antibody 125-2H.

19. An isolated antibody or antigen binding fragment thereof that binds to IL-18, comprising:
   i) a heavy chain variable region H-CDR1 comprising SEQ ID NO: 3;
   ii) a heavy chain variable region H-CDR2 comprising SEQ ID NO: 9;
   iii) a heavy chain variable region H-CDR3 comprising SEQ ID NO: 5;
   iv) a light chain variable region L-CDR1 comprising SEQ ID NO: 6;
   v) a light chain variable region L-CDR2 comprising SEQ ID NO: 7; and
   vi) a light chain variable region L-CDR3 comprising SEQ ID NO: 8.

20. The antibody or antigen binding fragment thereof of claim 19, wherein the isolated antibody or fragment thereof comprises a heavy chain variable domain comprising SEQ ID NO: 14, and a light chain variable domain comprising SEQ ID NO: 16.

21. The antibody or antigen binding fragment thereof of claim 19, wherein the isolated antibody or fragment thereof comprises a heavy chain comprising SEQ ID NO: 43, and a light chain variable domain comprising SEQ ID NO: 45.

22. A pharmaceutical composition comprising the isolated antibody or fragment thereof according to claim 19 and a pharmaceutical carrier, wherein the pharmaceutical composition optionally comprises a second therapeutic compound.

23. The pharmaceutical composition of claim 22 in intravenously, inhalable, or sub-cutaneously administrable form.

24. A diagnostic kit comprising the isolated antibody or fragment thereof according to claim 19, wherein the kit optionally comprises a first control compound.

25. The diagnostic kit according to claim 24 wherein the first control compound is free IL-18 and wherein the kit optionally comprises a second control compound wherein the second control compound is murine antibody 125-2H.

* * * * *